US009573978B2

(12) United States Patent
Su et al.

(10) Patent No.: US 9,573,978 B2
(45) Date of Patent: Feb. 21, 2017

(54) CYCLOSPORIN DERIVATIVES FOR THE TREATMENT AND PREVENTION OF A VIRAL INFECTION

(75) Inventors: Zhuang Su, Andover, MA (US); Zhengyu Long, Bolton, MA (US); Zhennian Huang, Newton, MA (US); Suizhou Yang, Dracut, MA (US)

(73) Assignee: S&T GLOBAL, INC., Woburn, MA (US)

( * ) Notice: Subject to any disclaimer, the term of this patent is extended or adjusted under 35 U.S.C. 154(b) by 316 days.

(21) Appl. No.: 13/816,393

(22) PCT Filed: Aug. 12, 2011

(86) PCT No.: PCT/US2011/047571
§ 371 (c)(1),
(2), (4) Date: Aug. 26, 2013

(87) PCT Pub. No.: WO2012/021796
PCT Pub. Date: Feb. 16, 2012

(65) Prior Publication Data
US 2014/0005100 A1    Jan. 2, 2014

Related U.S. Application Data

(60) Provisional application No. 61/372,930, filed on Aug. 12, 2010.

(51) Int. Cl.
*A61K 38/12* (2006.01)
*C07K 7/50* (2006.01)
(Continued)

(52) U.S. Cl.
CPC .............. *C07K 7/645* (2013.01); *A61K 38/00* (2013.01)

(58) Field of Classification Search
None
See application file for complete search history.

(56) References Cited

U.S. PATENT DOCUMENTS

| 3,869,448 A | 3/1975 | Earley et al. |
| 4,108,985 A | 8/1978 | Ruegger et al. |

(Continued)

FOREIGN PATENT DOCUMENTS

| CN | 101068829 A | 11/2007 |
| JP | 61-212599 A | 9/1986 |

(Continued)

OTHER PUBLICATIONS

Tang, published Aug. 5, 2010, Viruses, 2, 1621-1634.*

Berge, et al., "Pharmaceutical Salts," Journal of Pharmaceutical Sciences, vol. 66, No. 1, pp. 1-19 (Jan. 1977).
Bouchard, et al., "Activation and Inhibition of Cellular Calcium and Tyrosine Kinase Signaling Pathways Identify Targets of the HBx Protein Involved in Hepatitis B Virus Replication," Journal of Virology, vol. 77, No. 14, pp. 7713-7719, 8 pages (Jul. 2003).
Carry, et al., "Semisynthetic Di- and Tri-Functionalized Non-Immunosuppressive Cyclosporin A Derivatives as Potential Anti-HIV 1 Drugs," *Synlett*, vol. 2, pp. 316-320 (2004).
Castro, et al., "Redistribution of Cyclophilin A to Viral Factories during Vaccinia Virus Infection and Its Incorporation into Mature Particles," Journal of Virology, vol. 77, No. 16, pp. 9052-9068, 18 pages (Aug. 2003).

(Continued)

*Primary Examiner* — Satyanarayana R Gudibande
(74) *Attorney, Agent, or Firm* — Wilmer Cutler Pickering Hale and Dorr LLP

(57) ABSTRACT

The present invention relates to a compound of the formula (I), (II), (III), (IV), (V), or (VI) or pharmaceutically acceptable salt thereof, wherein the symbols are as defined in the specification; a pharmaceutical composition comprising the same, a method for treating or preventing a viral infection using the same.

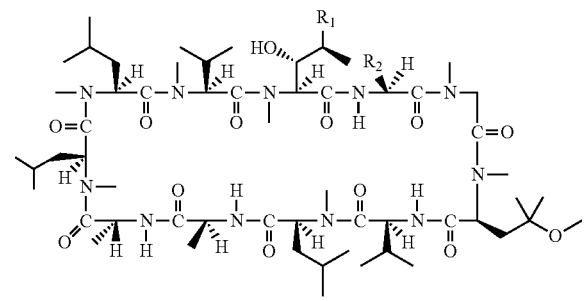

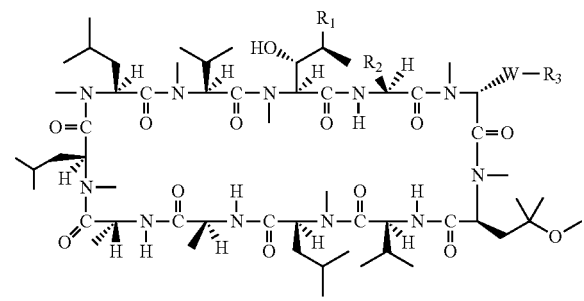

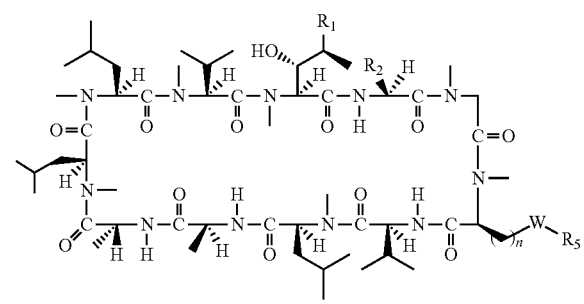

(Continued)

-continued

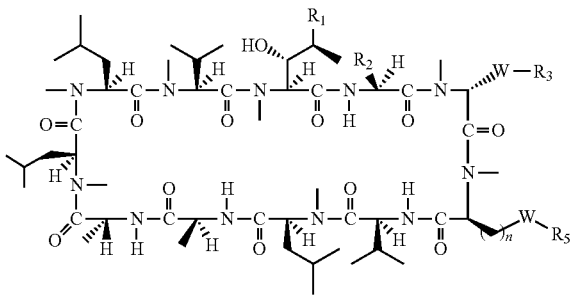
(IV)

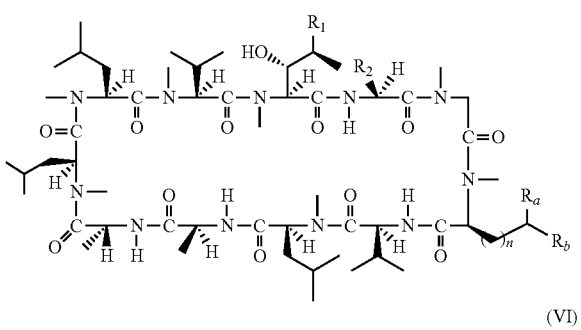

(V)

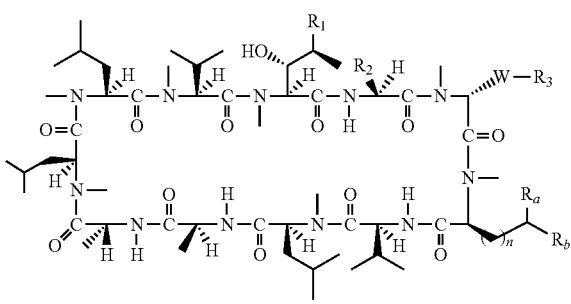

(VI)

35 Claims, No Drawings

(51) Int. Cl.

| | |
|---|---|
| *C07K 14/16* | (2006.01) |
| *A61K 39/29* | (2006.01) |
| *C07K 14/10* | (2006.01) |
| *C07K 7/64* | (2006.01) |
| *A61K 38/00* | (2006.01) |

(56) References Cited

U.S. PATENT DOCUMENTS

| | | | |
|---|---|---|---|
| 4,703,033 | A | 10/1987 | Seebach |
| 5,767,069 | A | 6/1998 | Ko et al. |
| 5,965,527 | A | 10/1999 | Barriere et al. |
| 5,981,479 | A | 11/1999 | Ko et al. |
| 5,994,299 | A | 11/1999 | Barriere et al. |
| 6,583,265 | B1 | 6/2003 | Ellmerer-Muller et al. |
| 6,927,208 | B1 | 8/2005 | Wenger et al. |
| 7,439,227 | B2 | 10/2008 | Scalfaro et al. |
| 7,511,013 | B2 | 3/2009 | Molino et al. |
| 7,696,166 | B2 | 4/2010 | Molino |
| 7,718,767 | B2 | 5/2010 | Fliri et al. |
| 2006/0069015 | A1 | 3/2006 | Molino et al. |
| 2006/0160727 | A1 | 7/2006 | Fliri et al. |
| 2010/0167996 | A1 | 7/2010 | Fliri et al. |
| 2010/0173836 | A1 | 7/2010 | Li et al. |
| 2010/0173837 | A1 | 7/2010 | Hopkins |
| 2010/0196316 | A1* | 8/2010 | Or .................... A61K 38/13 424/85.4 |

FOREIGN PATENT DOCUMENTS

| | | |
|---|---|---|
| JP | 2000-502320 A | 2/2000 |
| RU | 2011127080 A | 2/2013 |
| WO | WO-0001715 A1 | 1/2000 |
| WO | WO-2006/038088 A1 | 4/2006 |
| WO | WO-2006/038119 A1 | 4/2006 |
| WO | WO-2006039164 A2 | 4/2006 |
| WO | WO-2006039668 A2 | 4/2006 |
| WO | WO-2007015824 | 2/2007 |
| WO | WO 2008/143996 * | 11/2008 |
| WO | WO-2010088573 | 8/2010 |
| WO | WO-2012009715 A2 | 1/2012 |
| WO | WO-2012021796 A2 | 2/2012 |
| WO | WO-2012051194 A1 | 4/2012 |
| WO | WO-2012075494 A1 | 6/2012 |

OTHER PUBLICATIONS

Chen, et al., "Function of HAb18G/CD147 in Invasion of Host Cells by Severe Acute Respiratory Syndrome Coronavirus," The Journal of Infectious Diseases, vol. 191, Issue 5, pp. 755-760 (Mar. 1, 2005).
Chokshi, et al., "1104: Characterization of Antiviral Activities of Cyclophilin Inhibitors DEB025 (Alisporivir) and NIM811 on Hepatitis B Virus (HBV) Replication and HBSAG Secretion In Vitro," 07a: Viral Hepatitis B&D: Experimental, Journal of Heptatology, vol. 54, pp. S437-S438 (2011).
Edman, P., et al., "A Protein Sequenator," *Eur. J. Biochem.*, 1, 80-91 (1967).
Edman, P., "Preparation of Phenyl Thiohydantoins from Some Natural Amino Acids," ACTA *Chem. Scand.*, vol. 4, pp. 277-282 (1950).
Evers, et al., "Synthesis of Non-Immunosuppressive Cyclophilin-Binding Cyclosporin A Derivatives as Potential Anti HIV-1 Drugs," Bioorganic & Medicinal Chemistry Letters, vol. 13, pp. 4415-4419 (2003).
Extended European Search Report issued by the European Patent Office for European Patent Application No. 11845460.2 dated Apr. 30, 2014 (11 pgs.).
Fliri, et al., "Cyclosporins. Structure-activity relationships," Ann N.Y. Acad. Sci., vol. 696, pp. 47-53 (Nov. 1993).
Franke, et al., "Specific incorporation of cyclophilin A into HIV-1 virions," Nature, vol. 372, pp. 359-362 (Nov. 24, 1994).
Hopkins, et al., "SCY-635, a Novel Nonimmunosuppressive Analog of Cyclosporine That Exhibits Potent Inhibition of Hepatitis C Virus RNA Replication In Vitro," Antimicrobial Agents and Chemotherapy, vol. 54, No. 2, pp. 660-672 (Feb. 2010).
Hopkins, et al., "SCYNEXIS's SCY-635 Demonstrates Impressive Barrier to Resistance in HCV Treatment," The 45th Annual Meeting of the European Association for the Study of the Liver, Vienna, Austria, 2 pages. (Apr. 15, 2010).
Inoue, et al., "Combined interferon α2b and cyclosporin A in the treatment of chronic hepatitis C: controlled trial," Journal of Gastroenterology, vol. 38, No. 6, pp. 567-572 (Jun. 2003).
Inoue, et al., "IFN combined cyclosporin A therapy," Nippon Rinsho, vol. 59, No. 7, pp. 1326-1330 (Jul. 2001).
International Search Report and Written Opinion issued by the U.S. Patent and Trademark Office as International Searching Authority for International Application No. PCT/US11/047571 mailed Feb. 29, 2012 (13 pgs.).
International Search Report and Written Opinion issued by the U.S. Patent and Trademark Office as International Searching Authority for International Application No. PCT/US11/063295 mailed Apr. 23, 2012 (10 pgs.).
International Search Report and Written Opinion issued by the U.S. Patent and Trademark Office as International Searching Authority for International Application No. PCT/US12/51572 mailed Oct. 16, 2012 (11 pgs.).

(56) References Cited

OTHER PUBLICATIONS

International Search Report and Written Opinion issued by the U.S. Patent and Trademark Office as the International Searching Authority for International Application No. PCT/US11/44362 mailed on Feb. 2, 2012 (10 pages).
International Search Report and Written Opinion issued by the U.S. Patent and Trademark Office as the International Searching Authority for International Application No. PCT/US14/030491 mailed on Nov. 5, 2014 (11 pages).
Klatzmann, et al., "Functional inhibition by cyclosporin A of the lymphocyte receptor for the AIDS virus (HIV)," C.R. Acad. Sci. III, vol. 303, No. 9, (1986) (6 total pages, includes English abstract).
Krieger, et al., "Enhancement of Hepatitis C Virus RNA Replication by Cell Culture-Adaptive Mutations," Journal of Virology, vol. 75, No. 10, pp. 4614-4624, 12 pages. (May 2001).
Kuhnt, et al., "Microbial biotransformation products of cyclosporin A," The Journal of Antibiotics, vol. 49, No. 8, pp. 781-787 (1996).
Lill, et al., "Cyclosporine-Drug Interactions and the Influence of Patient Age," Am. J. Health-Syst. Pharm., vol. 57, pp. 1579-1584 (Sep. 1, 2000).
Liu, et al., "Cyclophilin A interacts with influenza A virus M1 protein and impairs the early stage of the viral replication," Cellular Microbiology, vol. 11, No. 5, pp. 730-741 (Feb. 6, 2009).
Luban, J., "Absconding with the Chaperone: Essential Cyclophilin-Gag Interaction in HIV-1 Virions," Cell, vol. 87, pp. 1157-1159 (Dec. 27, 1996).
Luban,J. et al., "Human immunodeficiency virus type 1 Gag protein binds to cyclophilins A and B," Cell, vol. 73, Issue 6, pp. p1067-p1078 (Jun. 18, 1993).
No Author Listed, "Sandoz Axes Cyclosporine Research," GMHC Treatment Issues, vol. 9, No. 12, (2 total pages) (Dec. 1995).
Office Action issued by the State Intellectual Property Office of China for Application No. 201180035147.9 mailed on Feb. 20, 2014 (16 pages—includes English translation).
Office Action issued by the State Intellectual Property Office of China for Application No. 201280051142.X dated Feb. 25, 2015 (17 total pages).
Papageorgiou, et al., "Calcineurin has a very tight-binding pocket for the side chain of residue 4 of cyclosporin," Bioorganic & Medicinal Chemistry Letters,vol. 4, No. 2, pp. 267-272 (Jan. 1994).
Papageorgiou, et al., "Improved Binding Affinity for Cyclophilin A by a Cyclosporin Derivative Singly Modified at Its effector Domain," Journal of Medicinal Chemistry, vol. 37, No. 22, pp. 3674-3676 (1994).
Pietschmann, et al., "Persistent and Transient Replication of Full-Length Hepatitis C Virus Genomes in Cell Culture," Journal of Virology, vol. 76, No. 8, pp. 4008-4021, 15 pages (Apr. 2002).
Rosenwirth, et al., "Inhibition of human immunodeficiency virus type 1 replication by SDZ NIM 811, a nonimmunosuppressive cyclosporine analog," Antimicrobial Agents and Chemotherapy, vol. 38, No. 8, pp. 1763-1772, 11 pages (Aug. 1994).
Seebach, et al., "Modification of Cyclosporin A (CS): Generation of an enolate at the sarcosine residue and reactions with electrophiles," Helvetica Chimica Acta, vol. 76, Issue 4, pp. 1564-1590 (Jun. 30, 1993).
Tang, H., "Cyclophilin Inhibitors as a Novel HCV Therapy," Viruses, vol. 2, No. 8, pp. 1621-1634 (Aug. 5, 2010).
Thali, et al., "Functional Association of Cyclophilin A with HIV-1 Virions," Nature, vol. 372, pp. 363-365 (1994).
Tian, X. et al., "Hepatitis B Virus (HBV) Surface Antigen Interacts with and Promotes Cyclophilin A Secretion: Possible Link to Pathogenesis of HBV Infection," Journal of Virology, vol. 84, No. 7, pp. 3373-3381, 10 pages (Apr. 2010).
Wainberg, et al., "The effect of cyclosporine A on infection of susceptible cells by human immunodeficiency virus type 1," Blood, vol. 72, No. 6, pp. 1904-1910, 8 pages (Dec. 1988).
Watashi, K. et al., "Chemical genetics approach to hepatitis C virus replication: cyclophilin as a target for anti-hepatitis C virus strategy," Reviews in Medical Virology, vol. 17, Issue 4, pp. 245-252 (Jul./Aug. 2007).
Watashi, K. et al., "Cyclosporine A Suppresses Replication of Hepatitis C Virus Genome in Cultured Hepatocytes," Hepatology, vol. 38, No. 5, pp. 1282-1288 (2003).
Xia, et al., "Inhibitory effect of cyclosporine A on hepatitis B virus replication in vitro and its possible mechanisms," *Hepatobiliary Pancreat Dis Int.*, vol. 4, pp. 18-22 (2005).
Zenke, G. et al., "Molecular mechanisms of Immunosuppression by Cyclosporins," Annals of the New York Academy of Sciences, vol. 685, pp. 330-335 (Jun. 1993).
Papageorgiou, C., et al., "Anti HIV-1 Activity of a Hydrophilic Cyclosporin Derivative with Improved Binding Affinity to Cyclophilin A", Bioorganic & Medicinal Chemistry Letters, 6(1):23-26; including Corrected Figure, published in Bioorganic & Medicinal Chemistry Letters, Additions and Corrections, 6(4):497, 1996 (5 pages).
European Extended Search Report issued in EP14762728.5, dated Sep. 12, 2016 (8 pages).

* cited by examiner

CYCLOSPORIN DERIVATIVES FOR THE TREATMENT AND PREVENTION OF A VIRAL INFECTION

CROSS REFERENCE TO RELATED APPLICATIONS

This application claims the benefit of U.S. Provisional Application No. 61/372,930, filed Aug. 12, 2010, the entire contents of which are hereby incorporated by reference herein.

FIELD OF INVENTION

The invention relates to novel cyclosporine derivatives, their pharmaceutical compositions comprising the same, and methods for treating or preventing a viral infection using the same.

BACKGROUND OF THE INVENTION

Naturally occurring cyclosporins are poly-N-methyl, cyclic undecapeptides, isolated from fungi. Cyclosporin A has an immunosuppressive activity and has been used for almost 40 years to prevent rejection in kidney, heart and liver transplant recipients. It has anti-inflammatory property and is useful for treating rheumatoid arthritis, severe psoriasis, Behget's uveitis and dry eye disease. In addition, it is useful for treating severe ulcerative colitis, Crohn's disease, alopecia greata, aplastic anemia, HSV-1 stromal keratitis, systemic lupus erythematosus, and severe lupus nephritis.

The anti-HIV activity of cyclosporin A was discovered (Klatzmann, D., et al., 1986, *C R Acad. Sci. III,* 303(9):343-8; Wainberg, M. A., et al., 1988, *Blood,* 72, 1904-10; Luban, J., et al., 1993, *Cell,* 73, 1067-1078; each of which is incorporated herein by reference). Its non-immunosuppressive derivative, NIM-811 was reported to have potent anti HIV activity, due to its ability to inhibit cyclophilin A (Franke, E. K., et al., 1994, *Nature,* 372, 359-362; Thali, M., et al., 1994, *Nature,* 372, 363-365; Gamble, T. R., et al., 1996, *Cell,* 87, 1157-1159; Rosenwirth B., et al., 1994, *Antimicrob. Agents Chemother.,* 38, 1763-1772; each of which is incorporated herein by reference).

Cyclosporin A and its non-immunosuppressive derivatives, as such as NIM-811 (N-MeIle-4-Cyclosporin), Debio-025, and SCY-635, inhibit cyclophilin A and B, which interact with HCV protein NS5B and stimulate its RNA-binding activity. As a result, these compounds have an effective anti-HCV activity (Watashi, K., et al., 2007, *Rev. Med. Virol.,* 17:245-252.37; Inoue, K., et al., 2001, *Nippon Rinsho.,* 59, 1326-30; Inoue, K., et al., 2003, *J. Gastroenterol.,* 38, 567-72; Watashi, K., et al., 2003, *Hepatology,* 38, 1282-8; each of which is incorporated herein by reference). Currently, NIM-811, Debio-025, and SCY-635 are undergoing clinical trials for treating HCV.

NIM-811 and Debio-025 have a chemical structure similar to cyclosporine A, and have poor pharmacokinetic profile and poor oral absorption. In addition, they are metabolized by P450 for inducing drug interactions (Lill, J., et al., 2000, *Am J Health-Syst Pharm* 57, 1579; incorporated herein by reference).

SCY-635 has an improved pharmacokinetic profile and low blood serum binding. In addition, it is less metabolized by P450 and has low potential for drug-drug interactions. SCY-635's in vitro anti-HCV activity ($EC_{50}$) was reported to be 0.10 µM, by using the luciferase end point method, by Hopkins, S. et al., 2010, *Antimicrob. Agents Chemother.,* 54, 660-672, incorporated herein by reference. However, SCY-635 is not chemically stable according to testing results in our laboratory. SCY-635 is easily converted to its diastereoisomer by epimerization, which is expected to have poor binding activity with cyclophilin, and therefore has poor anti-viral activity.

Cyclosporin A and its non-immunosuppressive derivatives were also found to possess anti-HBV activity through the inhibition of cyclophilins (Chokshi, S., et al., 2011, Abstract 190 (Poster Presentations), 46th Annual Meeting of the European Association for the Study of the Liver (EASL 2011), Berlin, March 30-April 3; Tian, X. C., et al., 2010, *J. Virol.,* 84, 3373-3381; Xia, W. L., et al., 2004, *Hepatobiliary Pancreat Dis Int.,* 4, 18-22; Michael, J., et al., 2003, *J. Virol.,* 77, 7713-7719; each of which is incorporated herein by reference).

Furthermore, Cyclophilin were reported to regulate life cycles and pathogenesis of several viruses, including influenza A virus, severe acute respiratory syndrome coronavirus, and vaccinia virus (Castro, A. P., et al., 2003, *J. Virol.,* 77, 9052-9068; Chen, Z., L., et al., 2005, *J. Infect. Dis.* 191, 755-760; Liu, X. L., et al., 2009, *Cell Microbiol.,* 11, 730-741; each of which is incorporated herein by reference). Cyclosporin A and its non-immunosuppressive derivative also possess such anti viral-activities.

N-MeVal-4-Cyclosporin (SDZ 220-384), another non-immunosuppressive cyclosporine derivative, has similar chemical structure and similar biological activity compared to NIM-811 (Flirt, H., et al., 1993, *Ann. N Y Acad Sci.* 696, 47-53; Zenke, G., et al., 1993, *Ann N Y Acad. Sci.* 23; 685:330-5).

Hepatitis C virus (HCV) is a small (55-65 nm in size), enveloped, positive sense single strand RNA virus in the family Flaviviridae. HCV has a high rate of replication and has an exceptionally high mutation rate. Most people infected with HCV (about 80%) develop chronic, persistent infection. More than 4 million Americans have been infected with HCV and more than 200 million people are estimated to be infected chronically worldwide. About 35,000 new cases of hepatitis C are estimated to occur in the United States each year. HCV infection is responsible for about 50% of all chronic liver disease, 30% of all liver transplants, and 30% of all cirrhosis, end-stage liver disease, and liver cancer in the U.S. The peg-interferon and ribavirin combination is the standard treatment for chronic hepatitis C but has low efficacy against HCV infection. Recently, the FDA has approved Vertex's Incivek (telaprevir) and Merck's Victrelis (boceprevir) as an add-on to the current interferon/ribavirin therapy for treating HCV. Both drugs are HCV protease inhibitors and target virus to prevent its replication. However, due to the fast mutation of HCV, drug resistance can be developed in a short period of time for the new drugs. There exists a need for an effective therapeutic for HCV treatment.

Hepatitis B virus (HBV) is a 42 nm partially double stranded DNA virus, composed of a 27 nm nucleocapsid core (HBcAg), surrounded by an outer lipoprotein envelope containing the surface antigen (HBsAg). About a quarter of the world's population, more than 2 billion people, have been infected with the hepatitis B virus. This includes 350 million chronic carriers of the virus. The disease has caused epidemics in parts of Asia and Africa, and it is endemic in China. Chronic hepatitis B will cause liver cirrhosis and liver cancer-a fatal disease with very poor response to current chemotherapy. Although the infection is preventable by vaccination and HBV load and replication can be reduced by current antiviral drugs lamivudine (Epivir), adefovir (Hepsera), tenofovir (Viread), telbivudine (Tyzeka) and entecavir (Baraclude) and the two immune system modulators interferon alpha-2a and PEGylated interferon alpha-2a (Pegasys), none of the available drugs can clear the infection. There remains a need for an effective therapeutic for treating or preventing HBV infection.

The non-immunosuppressive Cyclosporins derivatives bind to cyclophilin, a family of host proteins that catalyze cis-tans peptidyl-prolyl isomerization in protein folding, which is crucial for the processing, maturation of the viral proteins for viral replication. It is also different to current anti-HIV and anti-HCV drugs, the advantages of targeting host cofactors—cyclophilins by cyclosporine derivatives is the presumed higher genetic barrier to development of resistance (Rosenwirth, B., et al., 1994, *Antimicrob. Agents Chemother.*, 38, 1763-1772; Tang, H. L. et al., 2010, *Viruses*, 2, 1621-1634; Hopkins, S. et al., 2010, Oral Presentation, Scynexis's SCY-635 Demonstrates Impressive Barrier to Resistance in HCV Treatment, the 45th Annual Meeting of the European Association for the Study of the Liver (EASL 2010), Vienna, Austria, April 14-18; each of which is incorporated herein by reference). Cyclosporine derivatives affect a new target-cyclophilin, and therefore represent a new mechanism of action against HCV viruses.

Cyclophilins are a family of enzymes that assist in the folding and transportation of other proteins synthesized within a cell. Protein folding or misfolding plays a important role in the pathophysiology of a number of serious diseases, such as viral diseases (HIV, HBV, HCV, and herpes simplex virus), central nervous system disorders (mitochondrial protection for stroke, traumatic brain and spinal cord injury, Alzheimer, Parkinson's Disease, and Huntington's Diseases), cancer, cardiovascular diseases (reperfusion injury, heart attack, chronic heart failure), inflammation (respiratory inflammation, asthma, ulcerative colitis, rheumatoid arthritis, dry eye disease), muscular dystrophy, Atopic Dermatitis, anti fungal and anti-parasitic treatment, and hair growth. Cyclosporin derivatives target cyclophilin and can play a crucial role for treatment of such many diseases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

SUMMARY OF THE INVENTION

In one aspect, the present invention provides a compound of the formulae (I), (II), (III), (IV), (V) or (VI):

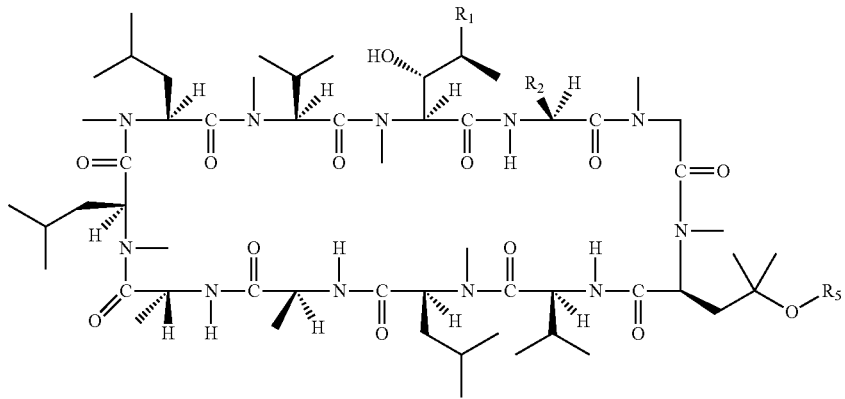

(I)

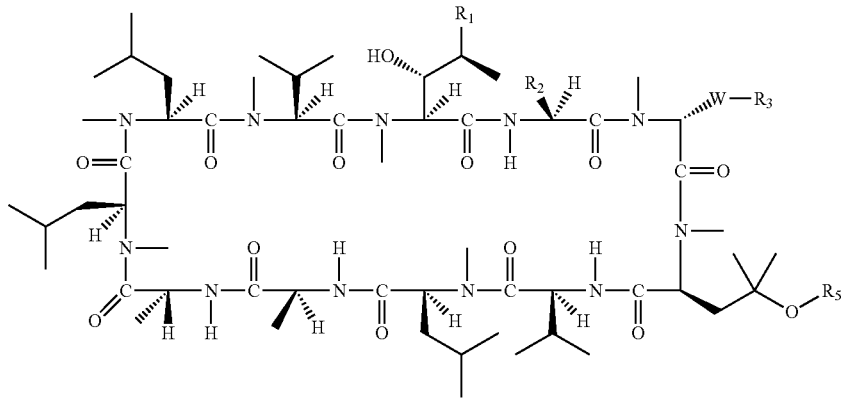

(II)

-continued
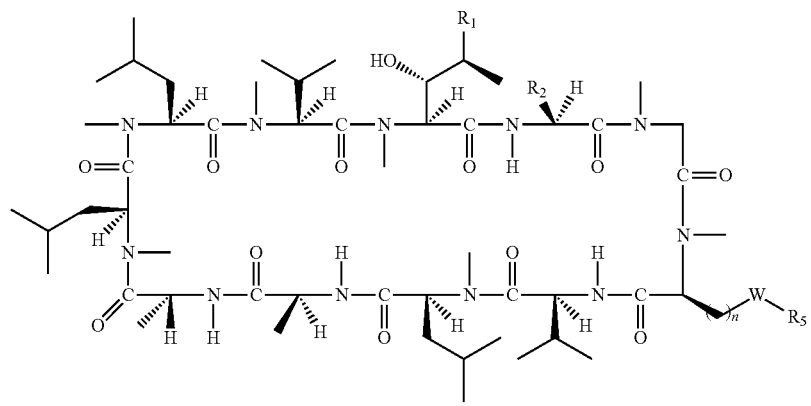
(III)
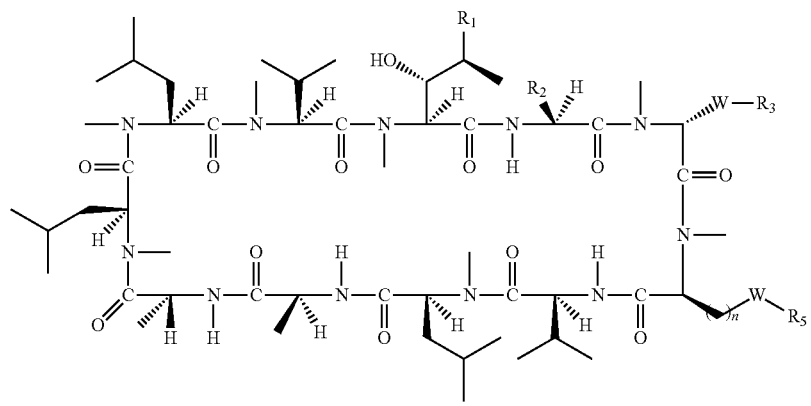
(IV)
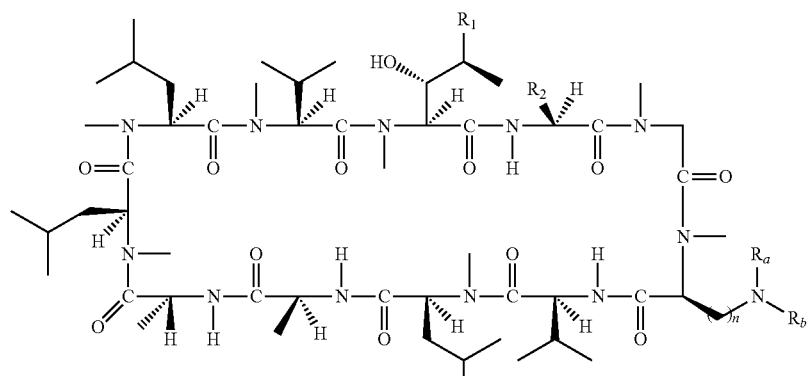
(V)
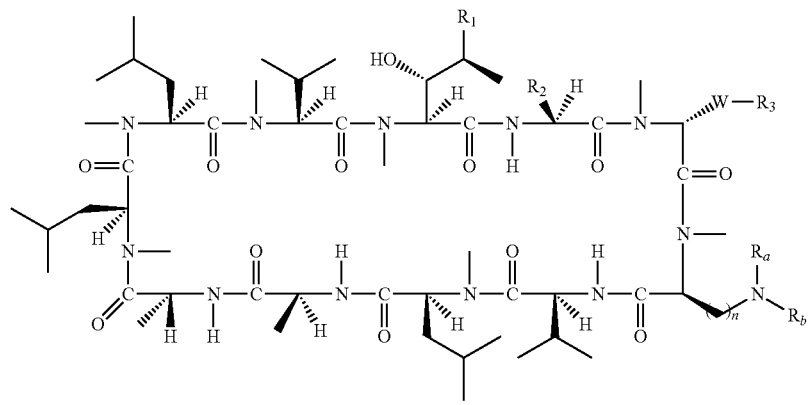
(VI)

or pharmaceutically acceptable salt or solvate thereof, wherein the symbols have the following meanings and are, for each occurrence, independently selected:

$R_1$ is n-butyl or (E)-but-2-enyl;
$R_2$ is ethyl, 1-hydroxyethyl, isopropyl or n-propyl;
W is O, or S;
each occurrence of $R_3$ and $R_5$ is H, alkyl or substituted alkyl, alkenyl or substituted alkenyl, alkynyl or substituted alkynyl, cycloalkyl or substituted cycloalkyl, cycloalkenyl or substituted cycloalkenyl, or aryl or substituted aryl;
each occurrence $R_a$ and $R_b$ is independently H, alkyl or substituted alkyl, alkenyl or substituted alkenyl, alkynyl or substituted alkynyl, cycloalkyl or substituted cycloalkyl, phenyl or substituted phenyl, or $R_a$ and $R_b$, together with the nitrogen atom to which they are attached, form a heterocycle or substituted heterocycle; and
n is an integer of 1, 2, 3, 4, 5, or 6.

In another aspect, the present invention provides a compound of the formulae (I)-(VI) as shown above, or pharmaceutically acceptable salt or solvate thereof, wherein:
$R_1$ is n-butyl or (E)-but-2-enyl;
$R_2$ is ethyl, 1-hydroxyethyl, isopropyl or n-propyl;
W is O, or S;
$R_3$ is:
  H;
  $(C_1-C_6)$alkyl, optionally substituted by one or more groups $R_4$ which may be the same or different;
  $(C_2-C_6)$alkenyl, optionally substituted by one or more groups which may be the same or different selected from halogen, hydroxy, amino, monoalkylamino and dialkylamino;
  $(C_2-C_6)$alkynyl, optionally substituted by one or one or more groups which may be the same or different selected from halogen, hydroxy, amino, monoalkylamino and dialkylamino;
  $(C_3-C_7)$cycloalkyl, optionally substituted by one or more groups which may be the same or different selected from halogen, hydroxy, amino, monoalkylamino and dialkylamino;
  phenyl or $CH_2$-phenyl, optionally substituted by one or more groups which may be the same or different selected from halogen, hydroxy, $(C_1-C_6)$alkyl;
$R_5$ is:
  H;
  $(C_1-C_6)$alkyl, optionally substituted by one or more groups $R_6$ which may be the same or different;
  $(C_2-C_6)$alkenyl, optionally substituted by one or more groups which may be the same or different selected from hydroxy, $(C_1-C_6)$alkyl, aryl (e.g., phenyl), $(CH_2)_p OR_A$, $O(CH_2)_m OH$, $O(CH_2)_m-O-(CH_2)_m H$, $O(CH_2)_m NR_A R_B$, $O(CH_2)_m O(CH_2)_m NR_A R_B$, $(CH_2)_p NR_A R_B$, $(CH_2)_p NR_C(CH_2)_m NR_A R_B$, $(CH_2)_p NR_c (CH_2)_m NR_c(CH_2)_m NR_A R_B$, $(CH_2)_p C(=O)NR_A R_B$, $(CH_2)_p C(=O)OR_A$;
  $(C_2-C_6)$alkynyl, optionally substituted by one or one or more groups which may be the same or different selected from halogen, hydroxy, amino, monoalkylamino and dialkylamino;
  $(C_3-C_7)$cycloalkyl, optionally substituted by one or more groups which may be the same or different selected from halogen, hydroxy, amino, monoalkylamino and dialkylamino;
  phenyl or $CH_2$-phenyl, optionally substituted by one or more groups which may be the same or different selected from halogen, hydroxy, $(C_1-C_6)$alkyl, $(CH_2)_p OR_A$, $(CH_2)_p NR_A R_B$, $(CH_2)_p C(=O)NR_A R_B$, $(CH_2)_p C(=O)OR_A$;

each occurrence $R_a$ and $R_b$ is independently H, $(C_1-C_6)$alkyl, phenyl, $CH_2$-phenyl, $(C_1-C_6)OH$, $(CH_2)_p O(CH_2)_m OH$, $(CH_2)_p-O-(CH_2)_m-O-(CH_2)_m OH$, or $R_a$ and $R_b$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of $(C_1-C_6)$alkyl, phenyl and benzyl;
each occurrence of $R_4$ is independently halogen, hydroxy, aryl (e.g., phenyl), $O(CH_2)_m OH$, $O(CH_2)_m O(CH_2)_m OH$, $C(=O)(C_1-C_6)$alkyl, $C(=O)OH$, $C(=O)O(C_1-C_6)$alkyl, $-NR_A R_B$, or $-NR_C(CH_2)_m NR_A R_B$;
each occurrence of $R_6$ is independently halogen, hydroxy, aryl (e.g., phenyl), $S(C_1-C_6)$alkyl, $SR_A$, $OR_A$, $O(CH_2)_m OH$, $O(CH_2)_m-O-(CH_2)_m OH$, $C(=O)OR_A$, $C(=O)NR_A R_B$, $NR_A R_B$, $O(CH_2)_m NR_A R_B$, $O(CH_2)_m-O-(CH_2)_m NR_A R_B$, $NR_C(CH_2)_m NR_A R_B$, or $NR_C(CH_2)_m NR_C(CH_2)_m NR_A R_B$, wherein said aryl or phenyl is optionally substituted by one or more groups which may be the same or different selected from halogen, hydroxy, $(C_1-C_6)$alkyl, $(CH_2)_p OR_A$, $(CH_2)_p NR_A R_B$, $(CH_2)_p C(=O)NR_A R_B$ and $(CH_2)_p C(=O)OR_A$;
each occurrence of $R_A$ and $R_B$ is independently:
  hydrogen;
  $(C_1-C_6)$alkyl, optionally substituted by one or more groups $R_D$ which may be the same or different;
  $(C_2-C_6)$alkenyl or $(C_2-C_6)$alkynyl;
  $(C_3-C_7)$cycloalkyl optionally substituted with $(C_1-C_6)$ alkyl;
  phenyl optionally substituted with from one to five groups which may be the same or different selected from halogen, $-O(C_1-C_6)$alkyl, $-C(=O)O(C_1-C_6)$alkyl, amino, alkylamino and dialkylamino;
  or a heterocyclic ring which may be saturated or unsaturated containing five or six ring atoms and from one to three heteroatoms which may the same or different selected from nitrogen, sulfur and oxygen;
  or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;
each occurrence of $R_C$ is independently hydrogen or $(C_1-C_6)$alkyl;
p is an integer of 0, 1, 2, 3, 4, or 5; and
m is an integer of 1, 2, 3, 4 or 5.

In yet another aspect, the present invention provides a pharmaceutical composition comprising at least one compound as described herein and a pharmaceutically-acceptable carrier.

In a further aspect, the present invention provides a method for treating or preventing a viral infection in a mammalian species in need thereof, the method comprising administering to the mammalian species a therapeutically effective amount of at least one compound as described herein.

In another aspect, the present invention provides a method for treating or preventing hepatitis C virus infection in a mammalian species in need thereof, the method comprising administering to the mammalian species a therapeutically effective amount of at least one compound as described herein.

DETAILED DESCRIPTION OF THE INVENTION

Definitions

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$(C_1-C_4)$alkyl" refers to a straight or branched chain alkane (hydrocarbon) radical containing from 1 to 4 carbon atoms, such as methyl, ethyl, propyl, isopropyl, n-butyl, t-butyl, and isobutyl. The term "$(C_1-C_6)$alkyl" refers to a straight or branched chain alkane (hydrocarbon) radical containing from 1 to 6 carbon atoms, such as n-hexyl, 2-methylpentyl, 3-methylpentyl, 4-methylpentyl, 2,3-dimethylbutyl, 2,2-dimethylbutyl, in addition to those exemplified for "$(C_1-C_4)$ alkyl." "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, OCF3, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. In the aforementioned exemplary substitutents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplary such groups include ethenyl or allyl. The term "$C_2-C_6$ alkenyl" refers to a straight or branched chain hydrocarbon radical containing from 2 to 6 carbon atoms and at least one carbon-carbon double bond, such as ethylenyl, propenyl, 2-propenyl, (E)-but-2-enyl, (Z)-but-2-enyl, 2-methy(E)-but-2-enyl, 2-methy(Z)-but-2-enyl, 2,3-dimethyl-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. "Substituted alkenyl" refers to an alkenyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, OCF_3, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted.

The term "alkynyl" refers to a straight or branched chain hydrocarbon radical containing from 2 to 12 carbon atoms and at least one carbon to carbon triple bond. Exemplary such groups include ethynyl. The term "$C_2-C_6$ alkynyl" refers to a straight or branched chain hydrocarbon radical containing from 2 to 6 carbon atoms and at least one carbon-carbon triple bond, such as ethynyl, prop-1-ynyl, prop-2-ynyl, but-1-ynyl, but-2-ynyl, pent-1-ynyl, pent-2-ynyl, hex-1-ynyl, hex-2-ynyl, hex-3-ynyl. "Substituted alkynyl" refers to an alkynyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, OCF_3, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted.

The term "cycloalkyl" refers to a fully saturated cyclic hydrocarbon group containing from 1 to 4 rings and 3 to 8 carbons per ring. "$C_3-C_7$ cycloalkyl" refers to cyclopropyl, cyclobutyl, cyclopentyl, cyclohexyl, or cycloheptyl. "Substituted cycloalkyl" refers to a cycloalkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$, together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include spiro-attached or fused cylic substitutents, especially spiro-attached cycloalkyl, spiro-attached cycloalkenyl, spino-attached heterocycle (excluding heteroaryl), fused cycloalkyl, fused cycloalkenyl, fused heterocycle, or fused aryl, where the aforementioned cycloalkyl, cycloalkenyl, heterocycle and aryl substitutents can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substitutents, preferably 1 to 4 substitutents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$, together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include spiro-attached or fused cylic substitutents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substitutents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substitutents, preferably 1 to 3 substitutents, at any available point of attachment. Exemplary substitutents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_a$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include fused cylic groups, especially fused cycloalkyl, fused cycloalkenyl, fused heterocycle, or fused aryl, where the aforementioned cycloalkyl, cycloalkenyl, heterocycle and aryl substitutents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted. Exemplary substituents also include spiro-attached or fused cylic substituents at any available point or points of attachment, especially spiro-attached cycloalkyl, spiro-attached cycloalkenyl, spino-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "alkylamino" refers to a group having the structure —NHR', wherein R' is hydrogen, alkyl or substituted alkyl, cycloalkyl or substituted cyclolakyl, as defined herein. Examples of alkylamino groups include, but are not limited to, methylamino, ethylamino, n-propylamino, isopropylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each independently alkyl or substituted alkyl, cycloalkyl or substituted cycloalkyl, cycloalkenyl or substituted cyclolakenyl, aryl or substituted aryl, heterocylyl or substituted heterocyclyl, as defined herein. R and R' may be the same or different in an dialkyamino moiety. Examples of dialkylamino groups include, but are not limited to, dimethylamino, methyl ethylamino, diethylamino, methylpropylamino, di(n-propyl) amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

The terms "halogen" or "halo" refer to chlorine, bromine, fluorine or iodine.

Unless otherwise indicated, any heteroatom with unsatisfied valences is assumed to have hydrogen atoms sufficient to satisfy the valences.

The compounds of the present invention may form salts which are also within the scope of this invention. Reference to a compound of the present invention is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound of the present invention with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the invention are also contemplated herein. The term "prodrug" asemployed herein denotes a compound that, upon administration to a subject, undergoes chemical conversion by metabolic or chemical processes to yield a compound of the present invention, or a salt and/or solvate thereof. Solvates of the compounds of the present invention include, for example, hydrates.

Compounds of the present invention, and salts or solvates thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 90%, for example, equal to greater than 95%, equal to or greater than 99% compound of the present invention ("substantially pure"), which is then used or formulated as described herein. Such "substantially pure" compounds of the present invention are also contemplated herein as part of the present invention.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

Compounds

Surprisingly it has been found that the novel cyclosporin derivatives of the present invention are potent inhibitors of viruses such as HIV, HBV and HCV.

In one aspect, the present invention provides a compound of the formulae (I), (II), (III), (IV), (V) or (VI):

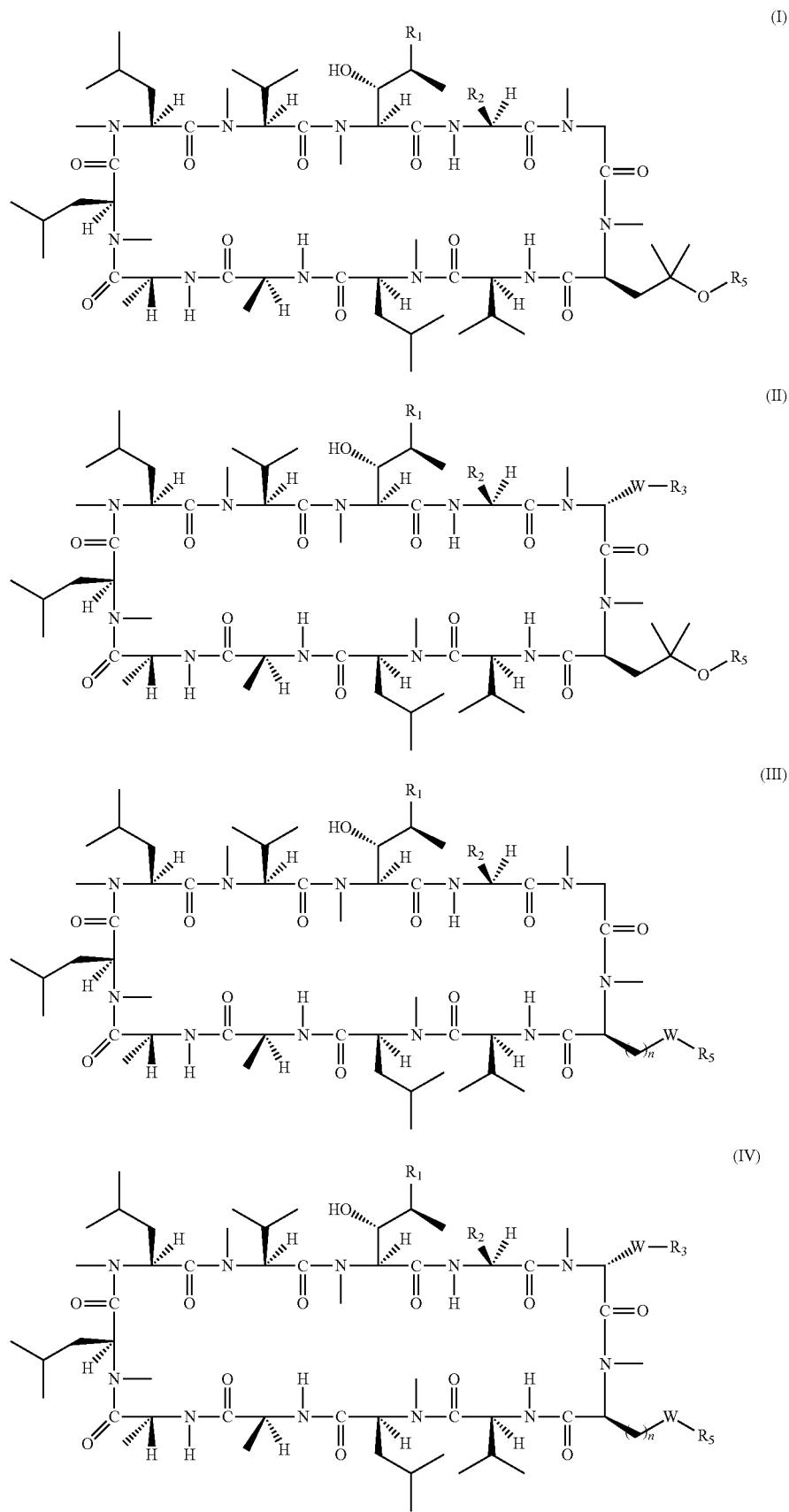

-continued

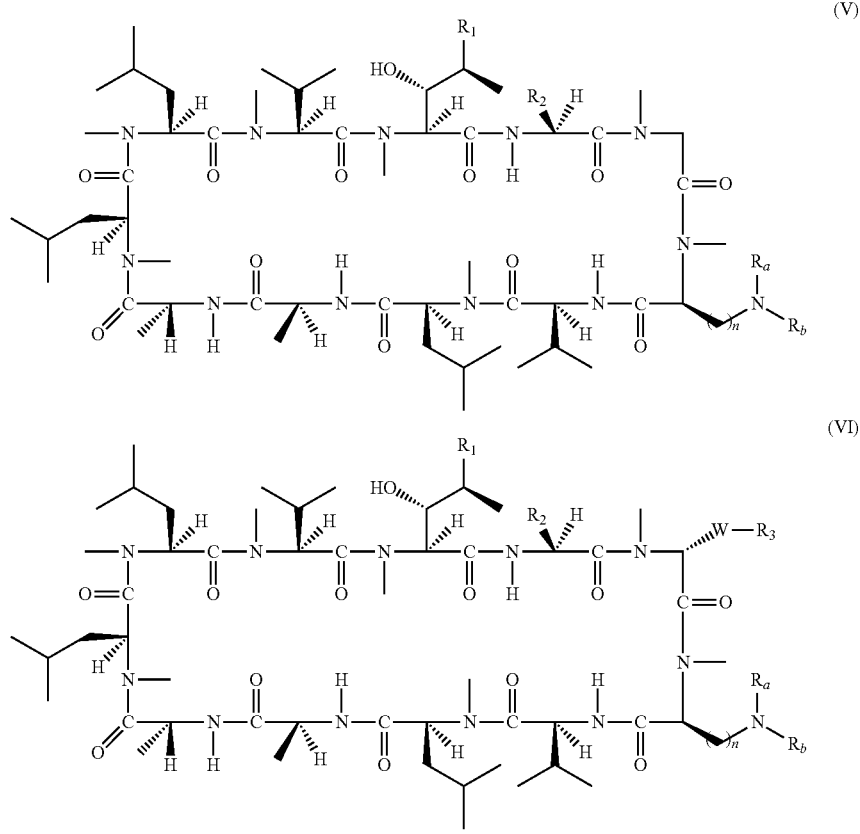

or pharmaceutically acceptable salt or solvate thereof, wherein the symbols have the following meanings and are, for each occurrence, independently selected:

$R_1$ is n-butyl or (E)-but-2-enyl;
$R_2$ is ethyl, 1-hydroxyethyl, isopropyl or n-propyl;
W is O, or S;
each occurrence of $R_3$ and $R_5$ is H, alkyl or substituted alkyl, alkenyl or substituted alkenyl, alkynyl or substituted alkynyl, cycloalkyl or substituted cycloalkyl, cycloalkenyl or substituted cycloalkenyl, or aryl or substituted aryl;
each occurrence $R_a$ and $R_b$ is independently H, alkyl or substituted alkyl, alkenyl or substituted alkenyl, alkynyl or substituted alkynyl, cycloalkyl or substituted cycloalkyl, phenyl or substituted phenyl, or $R_a$ and $R_b$, together with the nitrogen atom to which they are attached, form a heterocycle or substituted heterocycle; and
n is an integer of 1, 2, 3, 4, 5, or 6.

In another aspect, the present invention provides a compound of formulae (I)-(VI) as shown above, or pharmaceutically acceptable salt or solvate thereof, wherein:
$R_1$ is n-butyl or (E)-but-2-enyl;
$R_2$ is ethyl, 1-hydroxyethyl, isopropyl or n-propyl;
W is O, or S;
$R_3$ is:
H;
$(C_1-C_6)$alkyl, optionally substituted by one or more groups $R_4$ which may be the same or different;
$(C_2-C_6)$alkenyl, optionally substituted by one or more groups which may be the same or different selected from halogen, hydroxy, amino, monoalkylamino and dialkylamino;
$(C_2-C_6)$alkynyl, optionally substituted by one or one or more groups which may be the same or different selected from halogen, hydroxy, amino, monoalkylamino and dialkylamino;
$(C_3-C_7)$cycloalkyl, optionally substituted by one or more groups which may be the same or different selected from halogen, hydroxy, amino, monoalkylamino and dialkylamino;
phenyl or $CH_2$-phenyl, optionally substituted by one or more groups which may be the same or different selected from halogen, hydroxy, $(C_1-C_6)$alkyl;

$R_5$ is:
H;
$(C_1-C_6)$alkyl, optionally substituted by one or more groups $R_6$ which may be the same or different;
$(C_2-C_6)$alkenyl, optionally substituted by one or more groups which may be the same or different selected from hydroxy, $(C_1-C_6)$alkyl, aryl (e.g., phenyl), $(CH_2)_p OR_A$, $O(CH_2)_m OH$, $O(CH_2)_m-O-(CH_2)_m OH$, $O(CH_2)_m NR_A R_B$, $O(CH_2)_m-O-(CH_2)_m NR_A R_B$, $(CH_2)_p NR_A R_B$, $(CH_2)_p NR_C (CH_2)_m NR_A R_B$, $(CH_2)_p NR_C (CH_2)_m NR_C (CH_2)_m NR_A R_B$, $(CH_2)_p C(=OC) NR_A R_B$, $(CH_2)_p C(=O)OR_A$;
$(C_2-C_6)$alkynyl, optionally substituted by one or one or more groups which may be the same or different selected from halogen, hydroxy, amino, monoalkylamino and dialkylamino;
$(C_3-C_7)$cycloalkyl, optionally substituted by one or more groups which may be the same or different selected from halogen, hydroxy, amino, monoalkylamino and dialkylamino;

phenyl or CH$_2$-phenyl, optionally substituted by one or more groups which may be the same or different selected from halogen, hydroxy, (C$_1$-C$_6$)alkyl, (CH$_2$)$_p$OR$_A$, (CH$_2$)$_p$NR$_A$R$_B$, (CH$_2$)$_p$C(=O)NR$_A$R$_B$, (CH$_2$)$_p$C(=O)OR$_A$;

each occurrence R$_a$ and R$_b$ is independently H, (C$_1$-C$_6$)alkyl, phenyl, CH$_2$-phenyl, (C$_1$-C$_6$)OH, (CH$_2$)$_p$O(CH$_2$)$_m$OH, (CH$_2$)$_p$—O—(CH$_2$)$_m$—O—(CH$_2$)$_m$OH, or R$_a$ and R$_b$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of (C$_1$-C$_6$)alkyl, phenyl and benzyl;

each occurrence of R$_4$ is independently halogen, hydroxy, aryl (e.g., phenyl), O(CH$_2$)$_m$OH, O(CH$_2$)$_m$O(CH$_2$)$_m$OH, C(=O)(C$_1$-C$_6$)alkyl, C(=O)OH, C(=O)O(C$_1$-C$_6$)alkyl, —NR$_A$R$_B$, or —NR$_C$(CH$_2$)$_m$NR$_A$R$_B$;

each occurrence of R$_6$ is independently halogen, hydroxy, aryl (e.g., phenyl), S(C$_1$-C$_6$)alkyl, SR$_A$, OR$_A$, O(CH$_2$)$_m$OH, O(CH$_2$)$_m$—O—(CH$_2$)$_m$OH, C(=O)OR$_A$, C(=O)NR$_A$R$_B$, NR$_A$R$_B$, O(CH$_2$)$_m$NR$_A$R$_B$, O(CH$_2$)$_m$—O—(CH$_2$)$_m$ NR$_A$R$_B$, NR$_C$(CH$_2$)$_m$NR$_A$R$_B$, or NR$_C$(CH$_2$)$_m$NR$_C$(CH$_2$)$_m$NR$_A$R$_B$, wherein said aryl or phenyl is optionally substituted by one or more groups which may be the same or different selected from halogen, hydroxy, (C$_1$-C$_6$)alkyl, (CH$_2$)$_p$OR$_A$, (CH$_2$)$_p$NR$_A$R$_B$, (CH$_2$)$_p$C(=O)NR$_A$R$_B$ and (CH$_2$)$_p$C(=O)OR$_A$;

each occurrence of R$_A$ and R$_B$ is independently:
hydrogen;
(C$_1$-C$_6$)alkyl, optionally substituted by one or more groups R$_D$ which may be the same or different;
(C$_2$-C$_6$)alkenyl or (C$_2$-C$_6$)alkynyl;
(C$_3$-C$_7$)cycloalkyl optionally substituted with (C$_1$-C$_6$)alkyl;
phenyl optionally substituted with from one to five groups which may be the same or different selected from halogen, —O(C$_1$-C$_6$)alkyl, —C(=O)O(C$_1$-C$_6$)alkyl, amino, alkylamino and dialkylamino;
or a heterocyclic ring which may be saturated or unsaturated containing five or six ring atoms and from one to three heteroatoms which may the same or different selected from nitrogen, sulfur and oxygen;
or R$_A$ and R$_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;

each occurrence of R$_c$ is independently hydrogen or (C$_1$-C$_6$)alkyl;
p is an integer of 0, 1, 2, 3, 4, or 5; and
m is an integer of 1, 2, 3, 4 or 5.

In certain embodiments, R$_1$ is n-butyl or

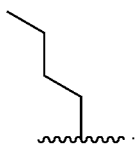 [SMILES: *CCCC]

In certain other embodiments, R$_1$ is (E)-but-2-enyl or

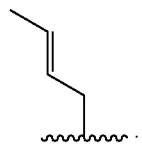 [SMILES: *C/C=C/C]

In certain embodiments, R$_2$ is ethyl. In certain other embodiments, R$_2$ is 1-hydroxyethyl. In yet other embodiments, R$_2$ is isopropyl. In yet other embodiments, R$_2$ is n-propyl.

In certain embodiments, W is O. In certain other embodiments, W is S.

In certain embodiments, R$_5$ is H. In certain other embodiments, R$_5$ is methyl. In yet other embodiments, R$_5$ is CH$_2$—S—(C$_1$-C$_6$)alky, e.g., CH$_2$—S—CH$_3$. In yet other embodiments, R$_5$ is CH$_2$—O—(C$_1$-C$_6$)alkyl, e.g., CH$_2$—O—CH$_2$—CH$_3$. In yet other embodiments, R$_5$ is (C$_2$-C$_6$)alkenyl, e.g., CH$_2$—CH=CH$_2$. In yet other embodiments, R$_5$ is benzyl. In yet other embodiments, R$_5$ is (C$_2$-C$_6$)OH. In yet other embodiments, R$_5$ is (C$_1$-C$_6$)-monoalkyl amine, e.g., CH$_2$—NH-Me. In yet other embodiments, R$_5$ is (C$_1$-C$_6$)-dialkyl amine, e.g., CH$_2$—CH$_2$—N(Et)$_2$. In yet other embodiments, R$_5$ is (C$_1$-C$_6$)-cyclic amine, e.g., CH$_2$—CH$_2$-morpholine.

In certain embodiments, m is 1. In certain other embodiments, m is 2. In yet other embodiments, m is 3. In yet other embodiments, m is 4 or 5.

In certain embodiments, p is 0. In certain other embodiments, p is 1. In yet other embodiments, m is 2. In yet other embodiments, m is 3, 4 or 5.

In certain embodiments, R$_3$ is —(CH$_2$)$_n$NR$_A$R$_B$, wherein n is an integer of 2, 3, 4, 5, or 6; and wherein each occurrence of R$_A$ and R$_B$ is independently hydrogen; (C$_1$-C$_4$)alkyl, optionally substituted by one or more groups R$_D$ which may be the same or different, in which each occurrence of R$_D$ is independently halogen, hydroxy, O(C$_1$-C$_4$)alkyl, C(=O)(C$_1$-C$_4$)alkyl, C(=O)O(C$_1$-C$_4$)alkyl; or R$_A$ and R$_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from (C$_1$-C$_4$)alkyl, phenyl and benzyl.

In certain embodiments, R$_3$ is —(CH$_2$)$_n$NR$_A$R$_B$, wherein n is an integer of 2, 3, 4, 5, or 6; and wherein R$_A$ and R$_B$, together with the nitrogen atom to which they are attached, form a saturated or unsaturated heterocyclic ring containing from three to seven ring atoms, which ring may optionally contain another heteroatom selected from nitrogen, oxygen and sulfur and may be optionally substituted by from one to four groups which may be the same or different selected from (C$_1$-C$_4$)alkyl, phenyl and benzyl.

In certain embodiments, n is 2. In certain other embodiments, n is 3. In yet other embodiments, n is 4, 5, or 6.

In certain embodiments, R$_3$ is 2-aminoethyl, 2-aminopropyl, 3-aminopropyl, 2-monoalkylaminoethyl, 2-monoalkylaminopropyl, 3-monoalkylaminopropyl, 2-dialkylaminoethyl, 2-dialkylaminopropyl, or 3-dialkylaminopropyl, wherein said alkyl is (C$_1$-C$_4$)alkyl.

In certain embodiments, R$_3$ is 2-aminoethyl, 2-aminopropyl, 3-aminopropyl, 2-monoalkylaminoethyl, 2-monoalkylaminopropyl, 3-monoalkylaminopropyl, 2-dialkylaminoethyl, 2-dialkylaminopropyl, or 3-dialkylaminopropyl, wherein said alkyl is (C$_1$-C$_4$)alkyl. wherein R$_3$ is dimethylaminoethyl, diethylaminoethyl, methylethylaminoethyl, methyl-iso-butylaminoethyl, ethyl-iso-butylaminoethyl, methyl-tert-butylaminoethyl, or ethyl-tert-butylaminoethyl.

In certain embodiments, R$_3$ is in which n is an integer of 2, 3, 4, 5, or 6. In certain embodiments, n is 2. In certain other embodiments, n is 3. In yet other embodiments, n is 4, or 5, or 6.

In one aspect, the present invention provides a compound of formula (VII):

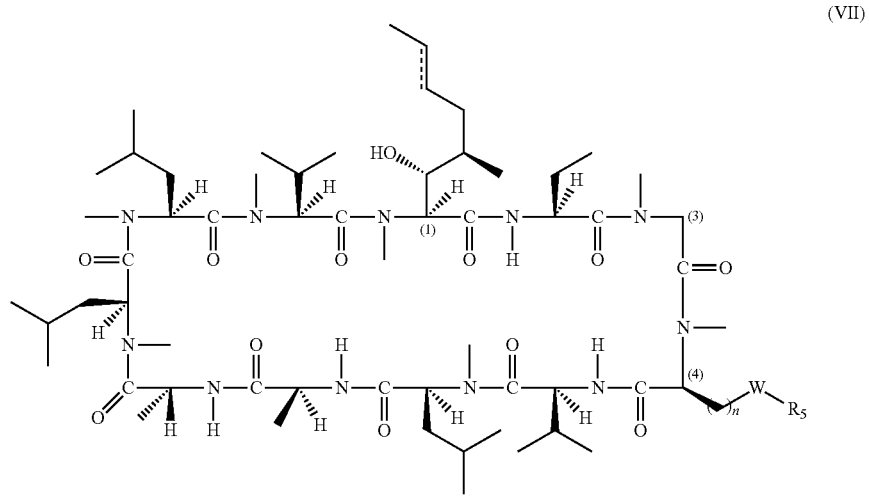

(VII)

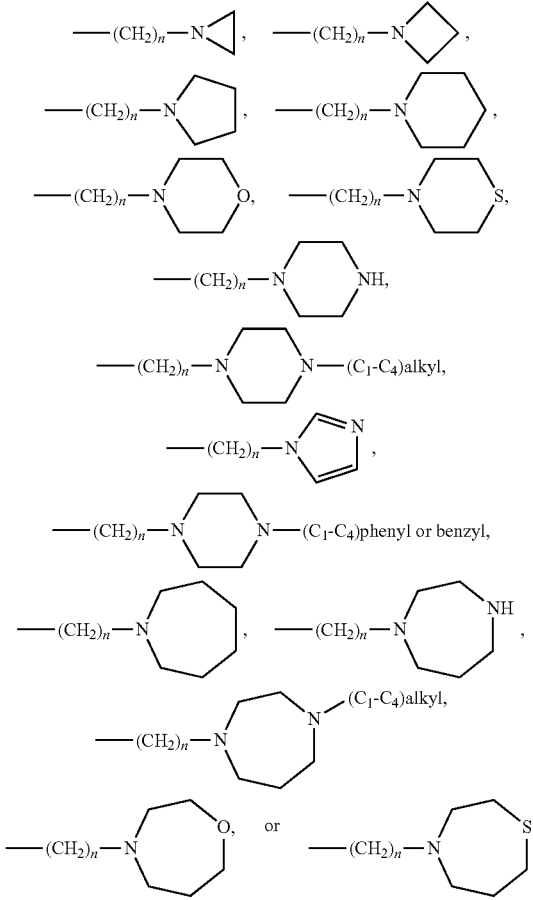

wherein ∥ represents a single bond or a double bond;
W is O or S;

R$_5$ is H, methyl, ethyl, n-propyl, i-propyl, n-butyl, i-butyl, t-butyl, CH$_2$CMe$_3$, phenyl, CH$_2$-phenyl,

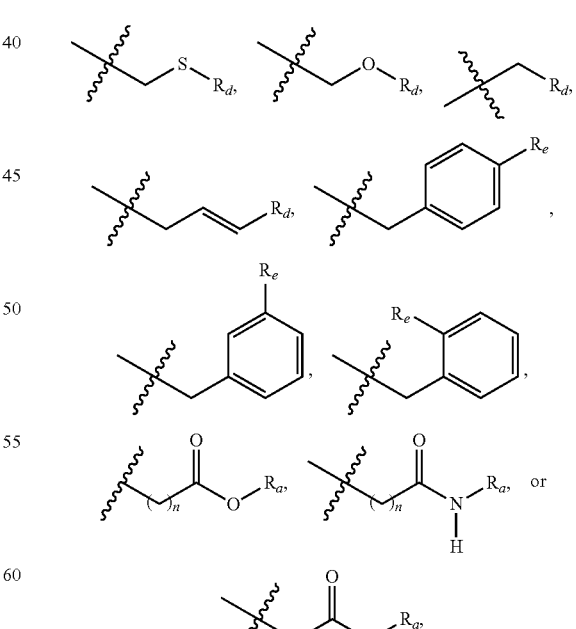

each R$_d$ is independently R$_a$, OR$_a$, CH$_2$OR$_a$,

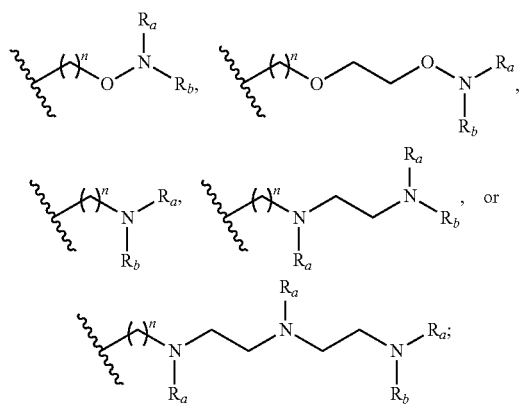

each $R_e$ is independently H, Me, Et, $OR_a$, $CH_2OR_a$, $CH_2CH_2OR_a$,

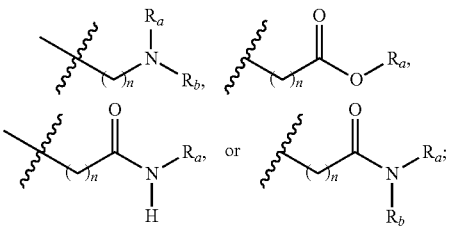

each of $R_a$ and $R_b$ is independently H, methyl, ethyl, n-propyl, propyl, n-butyl, i-butyl, t-butyl, $CH_2CMe_3$, phenyl, $CH_2$-phenyl,

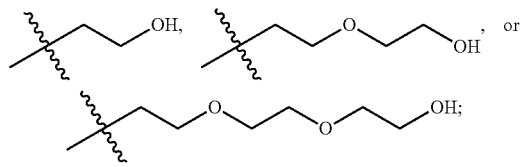

or $R_a$ and $R_b$, together with the nitrogen atom to which they are attached

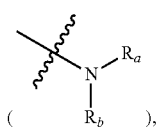

form a heterocycle selected from

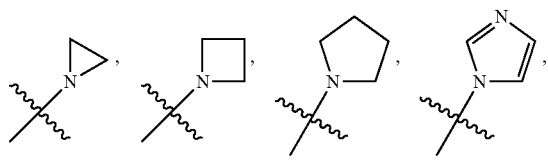

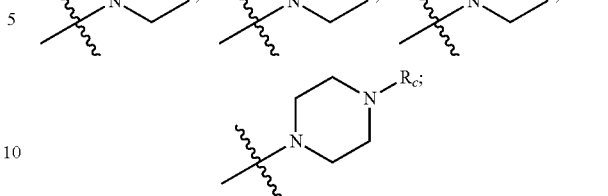

$R_c$ is H, methyl, ethyl, n-propyl, i-propyl, n-butyl, i-butyl, t-butyl, $CH_2CMe_3$, phenyl, or $CH_2$-phenyl; and each n is independently 1, 2, 3, 4, 5 or 6.

In certain embodiments, $R_5$ is H, methyl, ethyl, n-propyl, i-propyl, n-butyl, butyl, t-butyl, $CH_2CMe_3$, phenyl, or $CH_2$-phenyl. In certain other embodiments, $R_5$ is

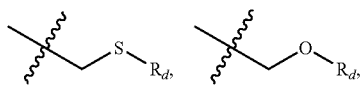

in which each $R_d$ is independently H, $C_1$-$C_4$alkyl, phenyl, $CH_2$-phenyl, $CH_2OH$, $CH_2$—O—$C_1$-$C_4$alkyl, $CH_2$—O—$CH_2$—OH, $CH_2$—O—$CH_2$—O—$C_1$-$C_4$alkyl, $CH_2$—O-phenyl, or $CH_2$—O—$CH_2$-phenyl.

In certain other embodiments, $R_5$ is

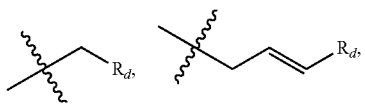

in which each $R_d$ is independently H, $C_1$-$C_4$alkyl, OH, O—$C_1$-$C_4$alkyl, phenyl, $CH_2$-phenyl, O-phenyl, O—$CH_2$-phenyl, $CH_2OH$, $CH_2$—O—$C_1$-$C_4$alkyl, $CH_2$—O—$CH_2$—$C_1$-$C_4$alkyl, $CH_2$—O-phenyl, or $CH_2$—O—$CH_2$-phenyl.

In certain embodiments, each of $R_a$ and $R_b$ is independently H, methyl, ethyl, n-propyl, i-propyl, n-butyl, i-butyl, t-butyl, or $CH_2CMe_3$; or $R_a$ and $R_b$, together with the nitrogen atom to which they are attached

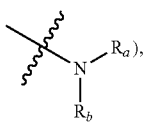

form a heterocycle selected from

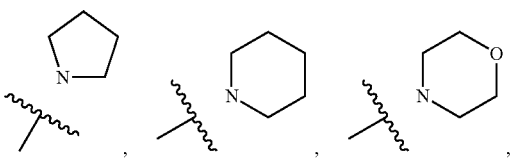

-continued

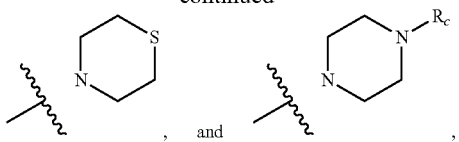  and  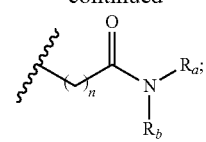, in which $R_c$ is H, methyl, ethyl, n-propyl, i-propyl, n-butyl, i-butyl, t-butyl, $CH_2CMe_3$, phenyl, or $CH_2$-phenyl.

In certain embodiments, n is 2, 3 or 4.

In another aspect, the present invention provides a compound of formula (IX):

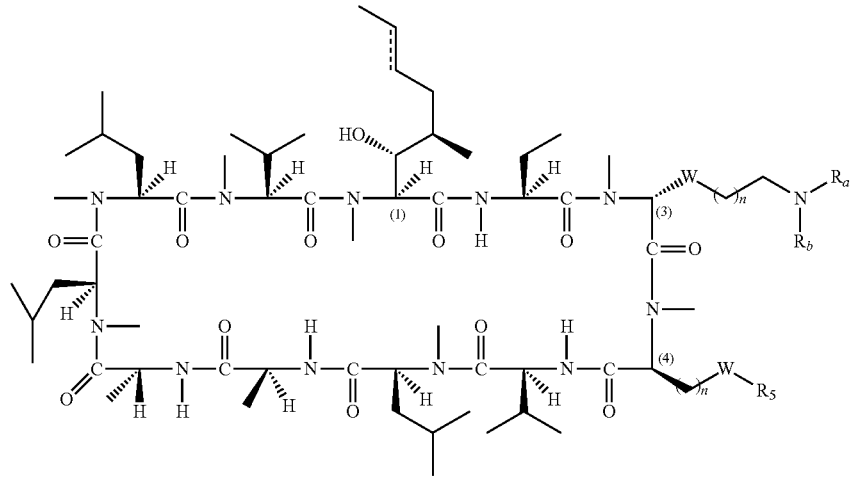

(IX)

wherein ∥ represents a single bond or a double bond;

W is O or S;

$R_5$ is H, methyl, ethyl, n-propyl, i-propyl, n-butyl, i-butyl, t-butyl, $CH_2CMe_3$, phenyl, $CH_2$-phenyl,

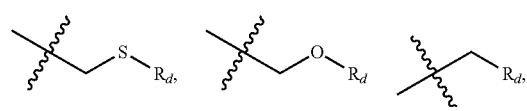

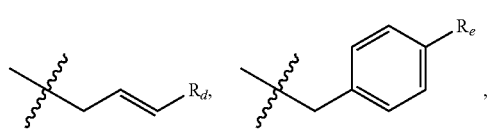

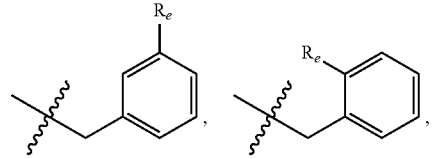

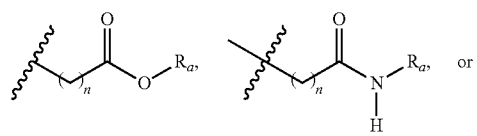

each $R_d$ is independently $R_a$, $OR_a$, $CH_2OR_a$,

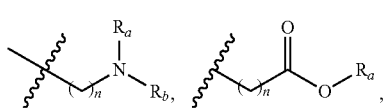

each $R_e$ is independently H, Me, Et, $OR_a$, $CH_2OR_a$, $CH_2CH_2OR_a$,

-continued

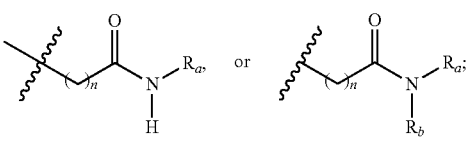

each of $R_a$ and $R_b$ is independently H, methyl, ethyl, n-propyl, propyl, n-butyl, i-butyl, t-butyl, $CH_2CMe_3$, phenyl, $CH_2$-phenyl,

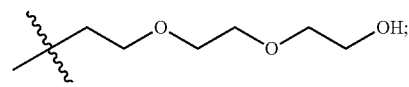

or $R_a$ and $R_b$, together with the nitrogen atom to which they are attached

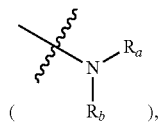

form a heterocycle selected from

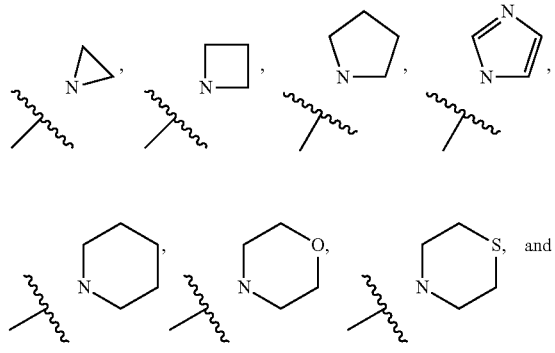

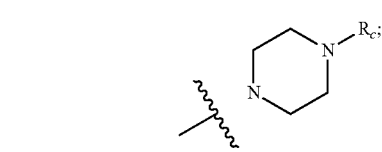

$R_c$ is H, methyl, ethyl, n-propyl, i-propyl, n-butyl, i-butyl, t-butyl, $CH_2CMe_3$, phenyl, or $CH_2$-phenyl; and
each n is independently 1, 2, 3, 4, 5 or 6.

In certain embodiments, $R_5$ is H, methyl, ethyl, n-propyl, i-propyl, n-butyl, butyl, t-butyl, $CH_2CMe_3$, phenyl, or $CH_2$-phenyl. In certain other embodiments, $R_5$ is

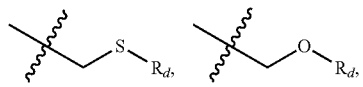

in which each $R_d$ is independently H, $C_1$-$C_4$alkyl, phenyl, $CH_2$-phenyl, $CH_2OH$, $CH_2$—O—$C_1$-$C_4$alkyl, $CH_2$—O—$CH_2$—OH, $CH_2$—O—$CH_2$—O—$C_1$-$C_4$alkyl, $CH_2$—O-phenyl, or $CH_2$—O—$CH_2$-phenyl.

In certain other embodiments, $R_5$ is

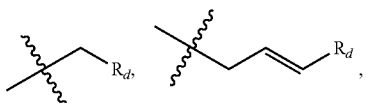

in which each $R_d$ is independently H, $C_1$-$C_4$alkyl, OH, O—$C_1$-$C_4$alkyl, phenyl, $CH_2$-phenyl, O-phenyl, O—$CH_2$-phenyl, $CH_2OH$, $CH_2$—O—$C_1$-$C_4$alkyl, $CH_2$—O—$CH_2$—$C_1$-$C_4$alkyl, $CH_2$—O-phenyl, or $CH_2$—O—$CH_2$-phenyl.

In certain embodiments, each of $R_a$ and $R_b$ is independently H, methyl, ethyl, n-propyl, propyl, n-butyl, i-butyl, t-butyl, or $CH_2CMe_3$; or $R_a$ and $R_b$, together with the nitrogen atom to which they are attached

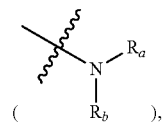

form a heterocycle selected from

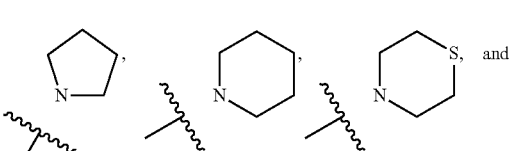

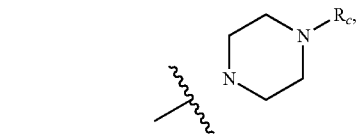

in which $R_c$ is H, methyl, ethyl, n-propyl, i-propyl, n-butyl, i-butyl, t-butyl, $CH_2CMe_3$, phenyl, or $CH_2$-phenyl.

In certain embodiments, n is 2, 3 or 4.

In yet another aspect, the present invention provides a compound of formula (X):

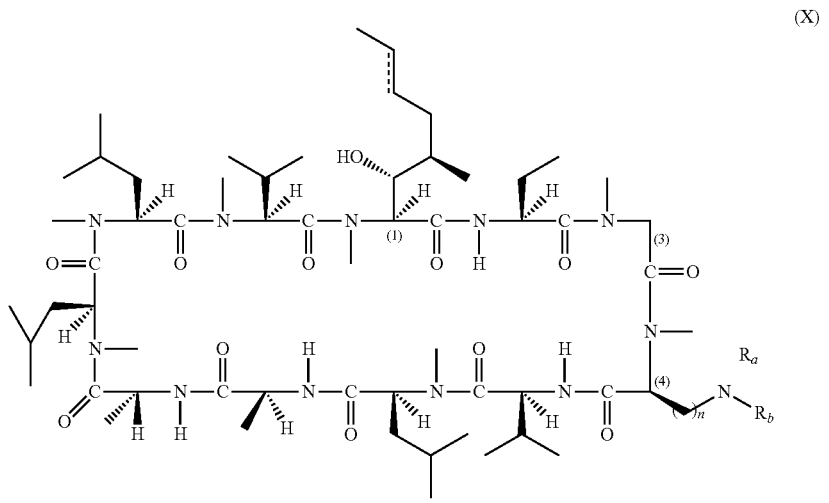

(X)

wherein ∥ represents a single bond or a double bond;

each of $R_a$ and $R_b$ is independently H, methyl, ethyl, n-propyl, propyl, n-butyl, i-butyl, t-butyl, $CH_2CMe_3$, phenyl, $CH_2$-phenyl

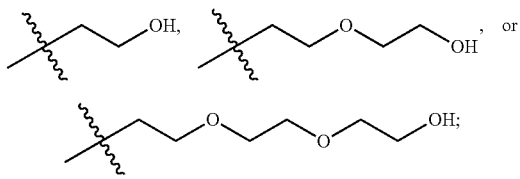

or $R_a$ and $R_b$, together with the nitrogen atom to which they are attached

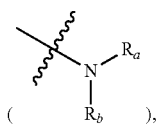

form a heterocycle selected from

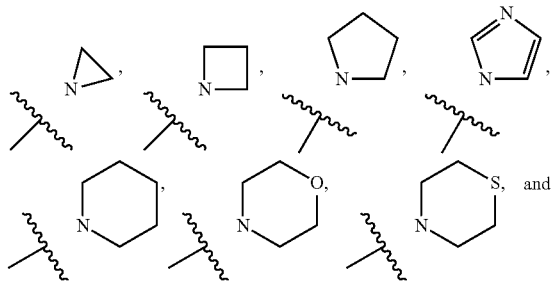

-continued

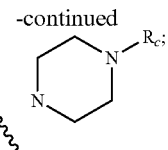

$R_c$ is H, methyl, ethyl, n-propyl, i-propyl, n-butyl, i-butyl, t-butyl, $CH_2CMe_3$, phenyl, or $CH_2$-phenyl; and n is independently 1, 2, 3, 4, 5 or 6.

In certain embodiments, each of $R_a$ and $R_b$ is independently H, methyl, ethyl, n-propyl, propyl, n-butyl, i-butyl, t-butyl, or $CH_2CMe_3$; or $R_a$ and $R_b$, together with the nitrogen atom to which they are attached

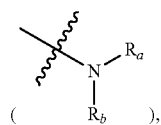

form a heterocycle selected from

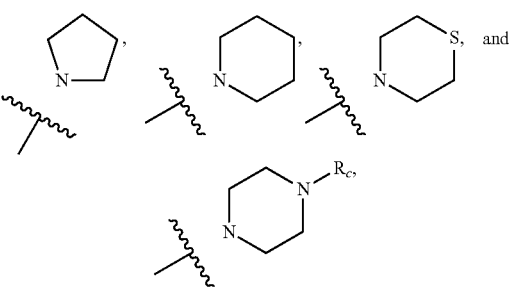

in which $R_c$ is H, methyl, ethyl, n-propyl, i-propyl, n-butyl, i-butyl, t-butyl, $CH_2CMe_3$, phenyl, or $CH_2$-phenyl.

In certain embodiments, n is 2, 3 or 4.

In yet another aspect, the present invention provides a compound of formula (XI):

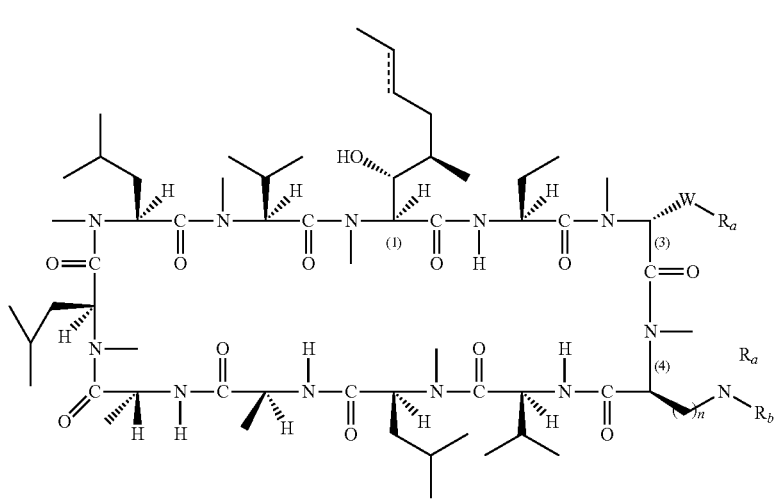

(XI)

wherein ∥ represents a single bond or a double bond;
W is O or S;
each of $R_a$ and $R_b$ is independently H, methyl, ethyl, n-propyl, i-propyl, n-butyl, i-butyl, t-butyl, $CH_2CMe_3$, phenyl, $CH_2$-phenyl,

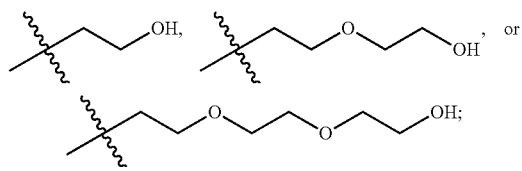

or $R_a$ and $R_b$, together with the nitrogen atom to which they are attached

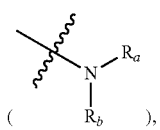

form a heterocycle selected from

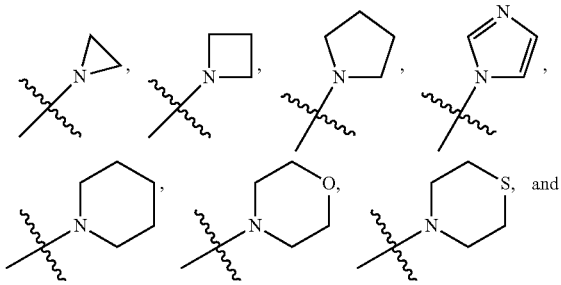

-continued

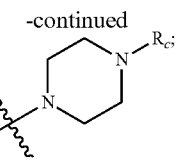

$R_c$ is H, methyl, ethyl, n-propyl, i-propyl, n-butyl, i-butyl, t-butyl, $CH_2CMe_3$, phenyl, or $CH_2$-phenyl; and
each n is independently 1, 2, 3, 4, 5 or 6.

In certain embodiments, each of $R_a$ and $R_b$ is independently H, methyl, ethyl, n-propyl, i-propyl, n-butyl, i-butyl, t-butyl, or $CH_2CMe_3$; or $R_a$ and $R_b$, together with the nitrogen atom to which they are attached

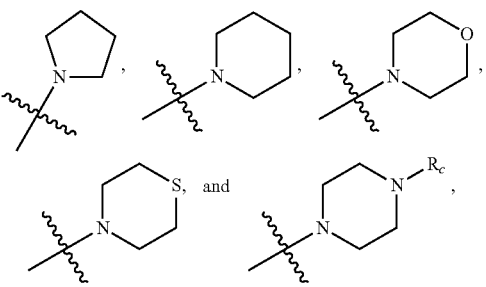

form a heterocycle selected from in which $R_c$ is H, methyl, ethyl, n-propyl, i-propyl, n-butyl, i-butyl, t-butyl, $CH_2CMe_3$, phenyl, or $CH_2$-phenyl.

In certain embodiments, n is 2, 3 or 4.

In yet another aspect, the present invention provides a compound of formula (XII):

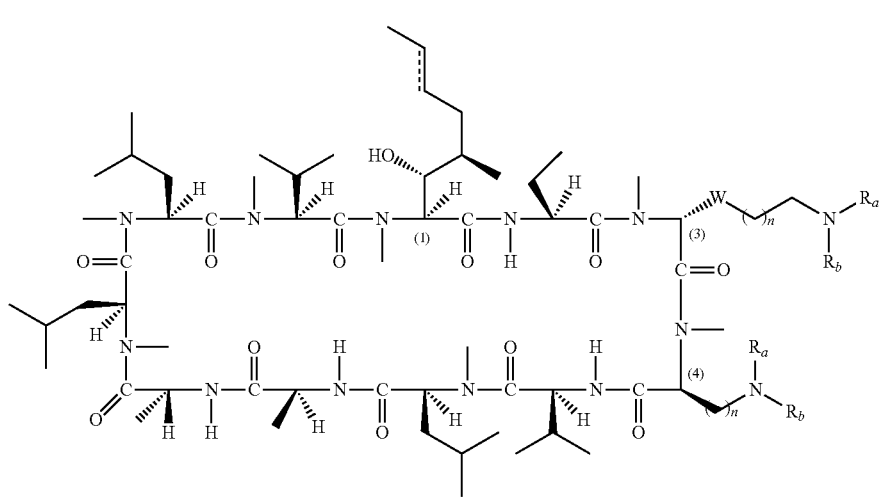

(XII)

wherein ∥ represents a single bond or a double bond;
W is O or S;
each of $R_a$ and $R_b$ is independently H, methyl, ethyl, n-propyl, i-propyl, n-butyl, i-butyl, t-butyl, $CH_2CMe_3$, phenyl, $CH_2$-phenyl,

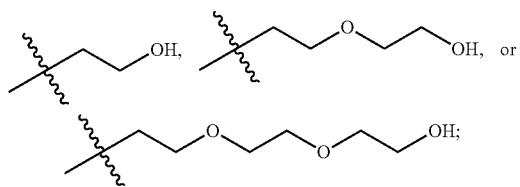

or $R_a$ and $R_b$, together with the nitrogen atom to which they are attached

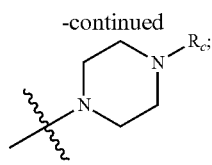

form a heterocycle selected from

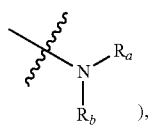

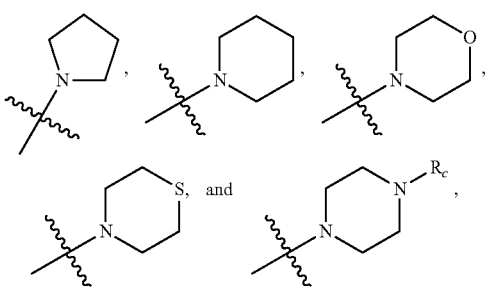

$R_c$ is H, methyl, ethyl, n-propyl, i-propyl, n-butyl, i-butyl, t-butyl, $CH_2CMe_3$, phenyl, or $CH_2$-phenyl; and
each n is independently 1, 2, 3, 4, 5 or 6.

In certain embodiments, each of $R_a$ and $R_b$ is independently H, methyl, ethyl, n-propyl, i-propyl, n-butyl, i-butyl, t-butyl, or $CH_2CMe_3$; or $R_a$ and $R_b$, together with the nitrogen atom to which they are attached form a heterocycle selected from in which $R_c$ is H, methyl, ethyl, n-propyl, i-propyl, n-butyl, i-butyl, t-butyl, $CH_2CMe_3$, phenyl, or $CH_2$-phenyl.

In certain embodiments, n is 2, 3 or 4.

In yet another aspect, the present invention provides a compound of formula (XIII):

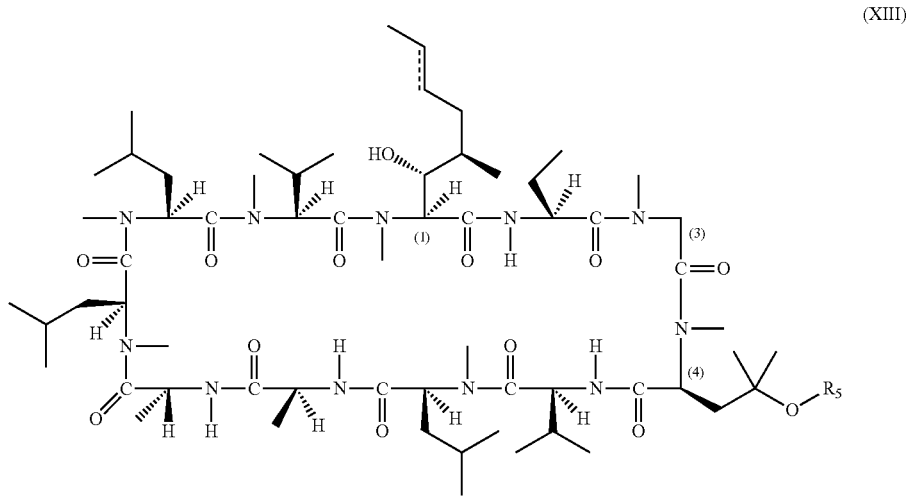

(XIII)

wherein ‖ represents a single bond or a double bond;
$R_5$ is H, methyl, ethyl, n-propyl, i-propyl, n-butyl, i-butyl, t-butyl, $CH_2CMe_3$, phenyl, $CH_2$-phenyl,

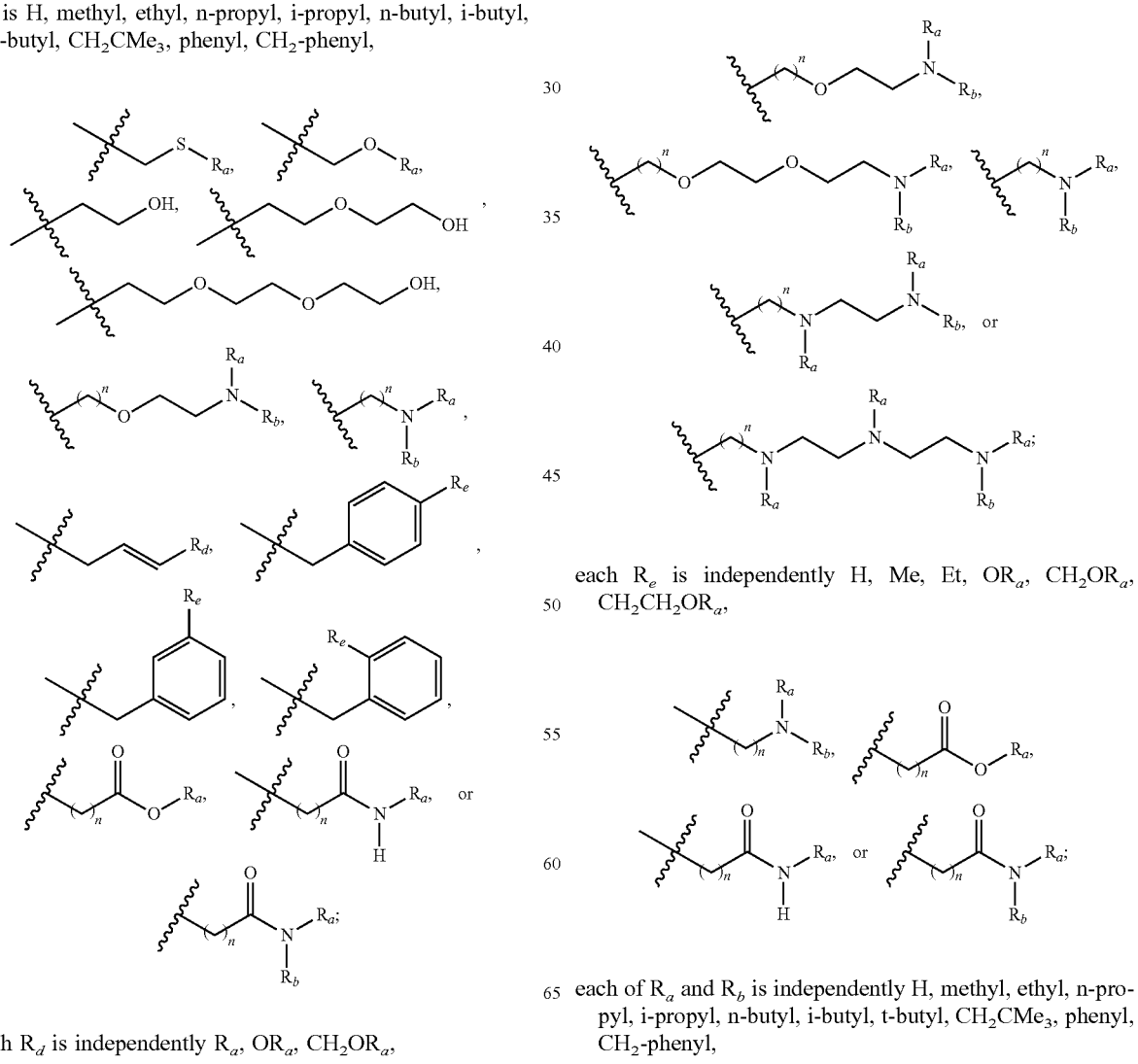

each $R_d$ is independently $R_a$, $OR_a$, $CH_2OR_a$, each $R_e$ is independently H, Me, Et, $OR_a$, $CH_2OR_a$, $CH_2CH_2OR_a$, each of $R_a$ and $R_b$ is independently H, methyl, ethyl, n-propyl, i-propyl, n-butyl, i-butyl, t-butyl, $CH_2CMe_3$, phenyl, $CH_2$-phenyl,

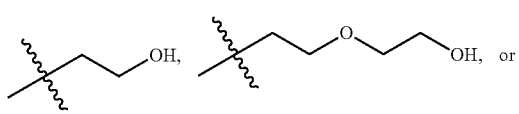

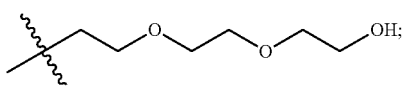

or $R_a$ and $R_b$, together with the nitrogen atom to which they are attached

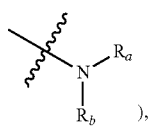

form a heterocycle selected from

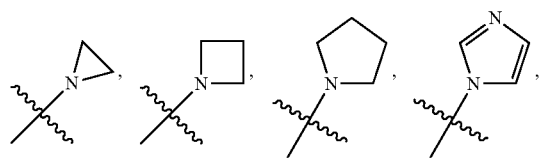

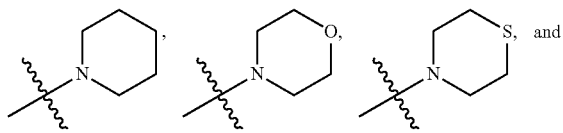

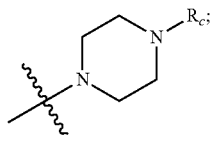

$R_c$ is H, methyl, ethyl, n-propyl, i-propyl, n-butyl, i-butyl, t-butyl, $CH_2CMe_3$, phenyl, or $CH_2$-phenyl; and
each n is independently 1, 2, 3, 4, 5 or 6.

In certain embodiments, $R_5$ is H, methyl, ethyl, n-propyl, i-propyl, n-butyl, i-butyl, t-butyl, $CH_2CMe_3$, phenyl, or $CH_2$-phenyl. In certain other embodiments, $R_5$ is

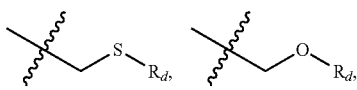

in which each $R_d$ is independently H, $C_1$-$C_4$alkyl, phenyl, $CH_2$-phenyl, $CH_2OH$, $CH_2$—O—$C_1$-$C_4$alkyl, $CH_2$—O—$CH_2$—OH, $CH_2$—O—$CH_2$—O—$C_1$-$C_4$alkyl, $CH_2$—O-phenyl, or $CH_2$—O—$CH_2$-phenyl.

In certain other embodiments, $R_5$ is

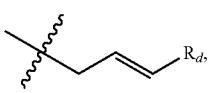

in which each $R_d$ is independently H, $C_1$-$C_4$alkyl, OH, O—$C_1$-$C_4$alkyl, phenyl, $CH_2$-phenyl, O-phenyl, O—$CH_2$-phenyl, $CH_2OH$, $CH_2$—O—$C_1$-$C_4$alkyl, $CH_2$—O—$CH_2$—$C_1$-$C_4$alkyl, $CH_2$—O-phenyl, or $CH_2$—O—$CH_2$-phenyl.

In certain embodiments, each of $R_a$ and $R_b$ is independently H, methyl, ethyl, n-propyl, i-propyl, n-butyl, i-butyl, t-butyl, or $CH_2CMe_3$; or $R_a$ and $R_b$, together with the nitrogen atom to which they are attached

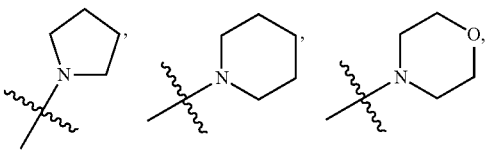

form a heterocycle selected from

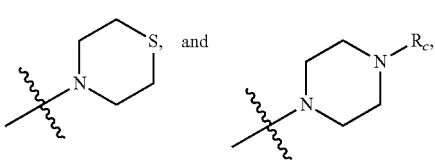

in which $R_c$ is H, methyl, ethyl, n-propyl, i-propyl, n-butyl, i-butyl, t-butyl, $CH_2CMe_3$, phenyl, or $CH_2$-phenyl.

In certain embodiments, n is 2, 3 or 4.

In yet another aspect, the present invention provides a compound of formula (XIV):

(XIV)
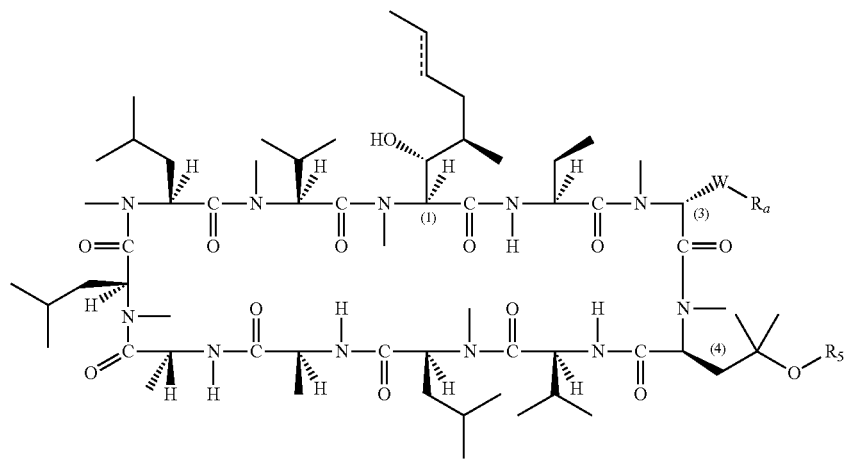
wherein ∥ represents a single bond or a double bond;
W is O or S;
$R_5$ is H, methyl, ethyl, n-propyl, i-propyl, n-butyl, i-butyl, t-butyl, $CH_2CMe_3$, phenyl, $CH_2$-phenyl,
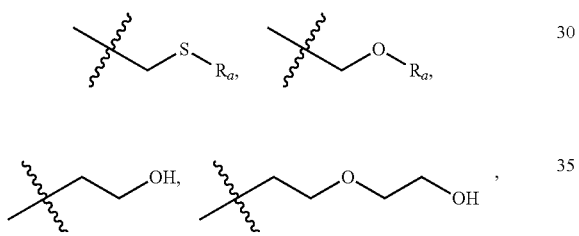
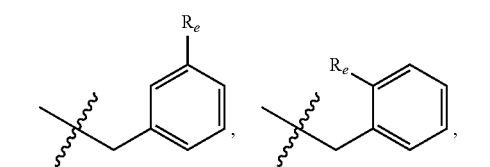
-continued
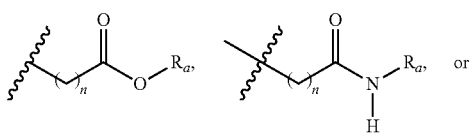
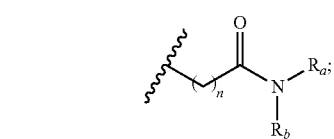
each $R_d$ is independently $R_a$, $OR_a$, $CH_2OR_a$,
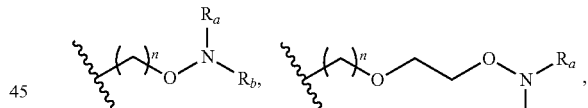
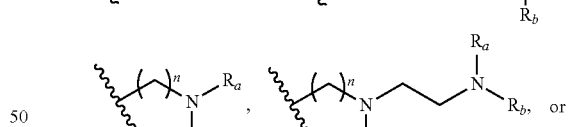
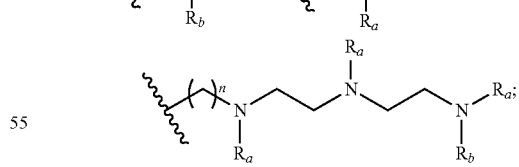
each $R_e$ is independently H, Me, Et, $OR_a$, $CH_2OR_a$, $CH_2CH_2OR_a$,
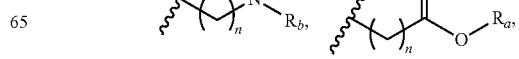

-continued

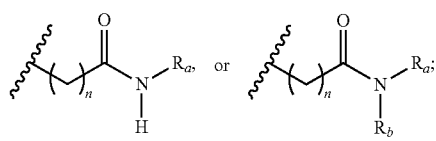

each of $R_a$ and $R_b$ is independently H, methyl, ethyl, n-propyl, i-propyl, n-butyl, i-butyl, t-butyl, $CH_2CMe_3$, phenyl, $CH_2$-phenyl,

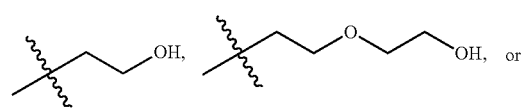

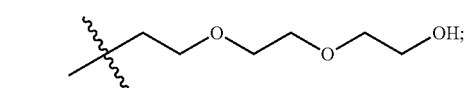

or $R_a$ and $R_b$, together with the nitrogen atom to which they are attached

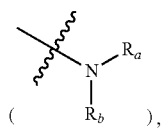

form a heterocycle selected from

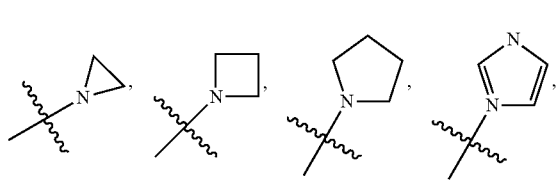

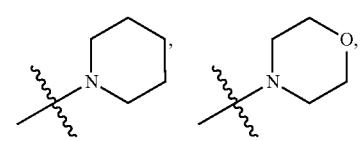

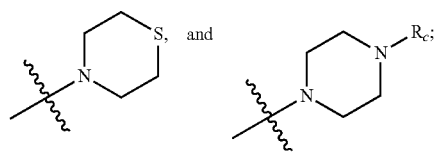

$R_c$ is H, methyl, ethyl, n-propyl, i-propyl, n-butyl, i-butyl, t-butyl, $CH_2CMe_3$, phenyl, or $CH_2$-phenyl; and
each n is independently 1, 2, 3, 4, 5 or 6.

In certain embodiments, $R_5$ is H, methyl, ethyl, n-propyl, i-propyl, n-butyl, i-butyl, t-butyl, $CH_2CMe_3$, phenyl, or $CH_2$-phenyl. In certain other embodiments, $R_5$ is

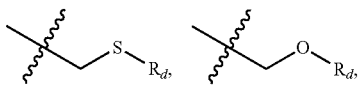

in which each $R_d$ is independently H, $C_1$-$C_4$alkyl, phenyl, $CH_2$-phenyl, $CH_2OH$, $CH_2$—O—$C_1$-$C_4$alkyl, $CH_2$—O—$CH_2$—OH, $CH_2$—O—$CH_2$—O—$C_1$-$C_4$alkyl, $CH_2$—O-phenyl, or $CH_2$—O—$CH_2$-phenyl.

In certain other embodiments, $R_5$ is

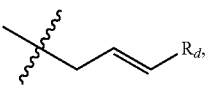

in which each $R_d$ is independently H, $C_1$-$C_4$alkyl, OH, O—$C_1$-$C_4$alkyl, phenyl, $CH_2$-phenyl, O-phenyl, O—$CH_2$-phenyl, $CH_2OH$, $CH_2$—O—$C_1$-$C_4$alkyl, $CH_2$—O—$CH_2$—$C_1$-$C_4$alkyl, $CH_2$—O-phenyl, or $CH_2$—O—$CH_2$-phenyl.

In certain embodiments, each of $R_a$ and $R_b$ is independently H, methyl, ethyl, n-propyl, i-propyl, n-butyl, i-butyl, t-butyl, or $CH_2CMe_3$; or $R_a$ and $R_b$, together with the nitrogen atom to which they are attached

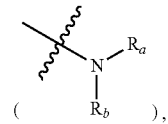

form a heterocycle selected from

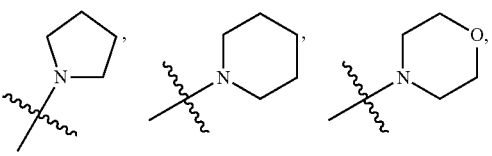

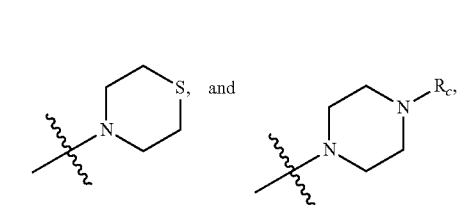

in which $R_c$ is H, methyl, ethyl, n-propyl, i-propyl, n-butyl, i-butyl, t-butyl, $CH_2CMe_3$, phenyl, or $CH_2$-phenyl.

In certain embodiments, n is 2, 3 or 4.

In yet another aspect, the present invention provides a compound of formula (XV):

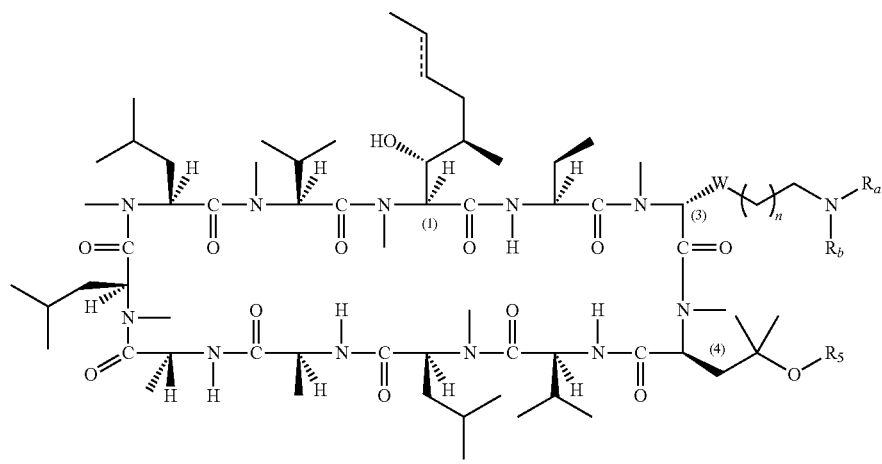

(XV)

wherein ∥ represents a single bond or a double bond;
W is O or S;
$R_5$ is H, methyl, ethyl, n-propyl, i-propyl, n-butyl, i-butyl, t-butyl, $CH_2CMe_3$, phenyl, $CH_2$-phenyl,

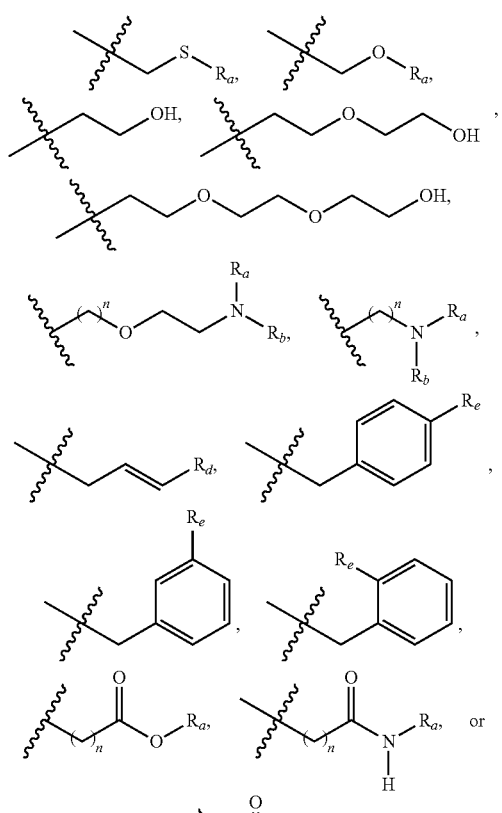

each $R_d$ is independently $R_a$, $OR_a$, $CH_2OR_a$, each $R_e$ is independently H, Me, Et, $OR_a$, $CH_2OR_a$, $CH_2CH_2OR_a$, each of $R_a$ and $R_b$ is independently H, methyl, ethyl, n-propyl, i-propyl, n-butyl, i-butyl, t-butyl, $CH_2CMe_3$, phenyl, $CH_2$-phenyl, -continued

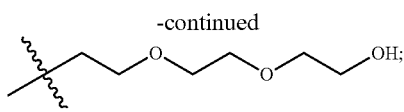

or $R_a$ and $R_b$, together with the nitrogen atom to which they are attached

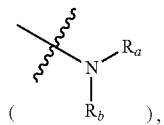

form a heterocycle selected from

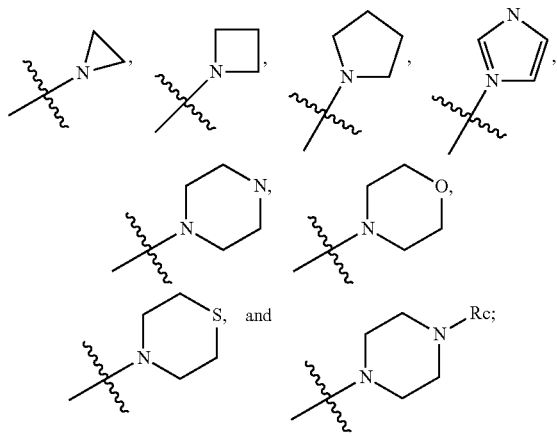

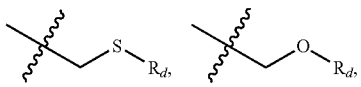

$R_c$ is H, methyl, ethyl, n-propyl, i-propyl, n-butyl, i-butyl, t-butyl, $CH_2CMe_3$, phenyl, or $CH_2$-phenyl; and
each n is independently 1, 2, 3, 4, 5 or 6.

In certain embodiments, $R_5$ is H, methyl, ethyl, n-propyl, i-propyl, n-butyl, i-butyl, t-butyl, $CH_2CMe_3$, phenyl, or $CH_2$-phenyl. In certain other embodiments, $R_5$ is

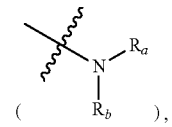

in which each $R_d$ is independently H, $C_1$-$C_4$alkyl, phenyl, $CH_2$-phenyl, $CH_2OH$, $CH_2$—O—$C_1$-$C_4$alkyl, $CH_2$—O—$CH_2$—OH, $CH_2$—O—$CH_2$—O—$C_1$-$C_4$alkyl, $CH_2$—O-phenyl, or $CH_2$—O—$CH_2$-phenyl.

In certain other embodiments, $R_5$ is

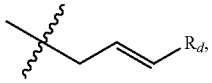

in which each $R_d$ is independently H, $C_1$-$C_4$alkyl, OH, O—$C_1$-$C_4$alkyl, phenyl, $CH_2$-phenyl, O-phenyl, O—$CH_2$-phenyl, $CH_2OH$, $CH_2$—O—$C_1$-$C_4$alkyl, $CH_2$—O—$CH_2$—$C_1$-$C_4$alkyl, $CH_2$—O-phenyl, or $CH_2$—O—$CH_2$-phenyl.

In certain embodiments, each of $R_a$ and $R_b$ is independently H, methyl, ethyl, n-propyl, i-propyl, n-butyl, i-butyl, t-butyl, or $CH_2CMe_3$; or $R_a$ and $R_b$, together with the nitrogen atom to which they are attached

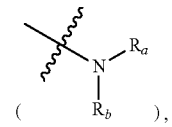

form a heterocycle selected from

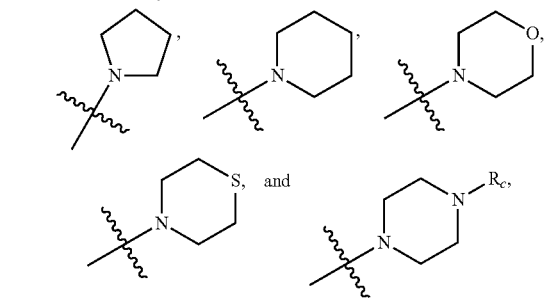

in which $R_c$ is H, methyl, ethyl, n-propyl, i-propyl, n-butyl, i-butyl, t-butyl, $CH_2CMe_3$, phenyl, or $CH_2$-phenyl.

In certain embodiments, n is 2, 3 or 4.

In yet another aspect, the present invention provides a compound of formula (XVI):

(XVI)

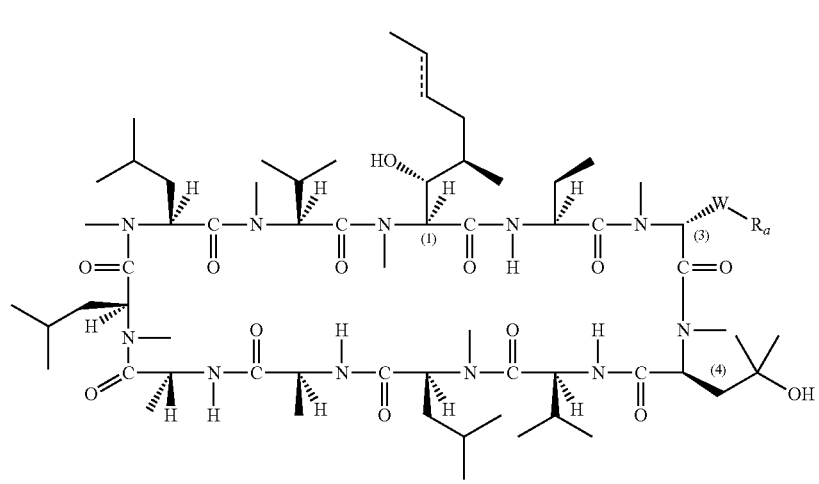

wherein ||| represents a single bond or a double bond;
W is O or S; and
$R_a$ is methyl, ethyl, n-propyl, i-propyl, n-butyl, i-butyl, t-butyl, $CH_2CMe_3$, phenyl, $CH_2$-phenyl,

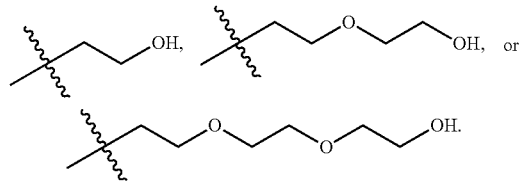

In yet another aspect, the present invention provides a compound of formula (XVII):

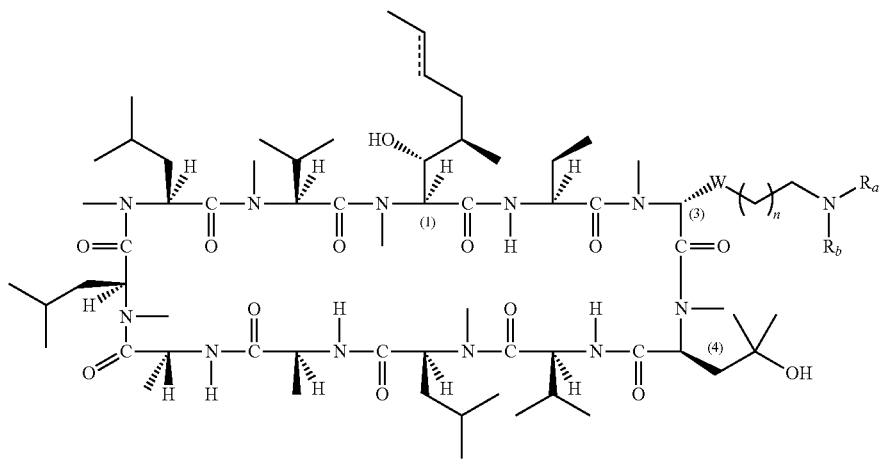

(XVII)

wherein ||| represents a single bond or a double bond;

W is S or O;

each of $R_a$ and $R_b$ is independently H, methyl, ethyl, n-propyl, i-propyl, n-butyl, i-butyl, t-butyl, $CH_2CMe_3$, phenyl, or $CH_2$-phenyl; or $R_a$ and $R_b$, together with the nitrogen atom to which they are attached

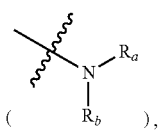

form a heterocycle selected from

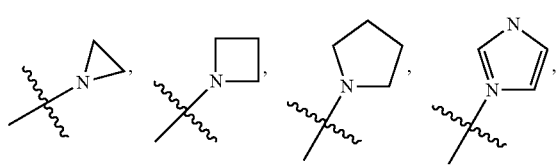

$R_c$ is H, methyl, ethyl, n-propyl, i-propyl, n-butyl, i-butyl, t-butyl, $CH_2CMe_3$, phenyl, or $CH_2$-phenyl; and each n is independently 1, 2, 3, 4, 5 or 6.

In certain embodiments, n is 2, 3 or 4. In certain other embodiments, each of $R_a$ and $R_b$ is independently H, methyl, ethyl, n-propyl, i-propyl, n-butyl, i-butyl, or t-butyl, provided that when $R_a$ is H or methyl, then $R_b$ is n-propyl, i-propyl, n-butyl, i-butyl, or t-butyl. In yet other embodiments,

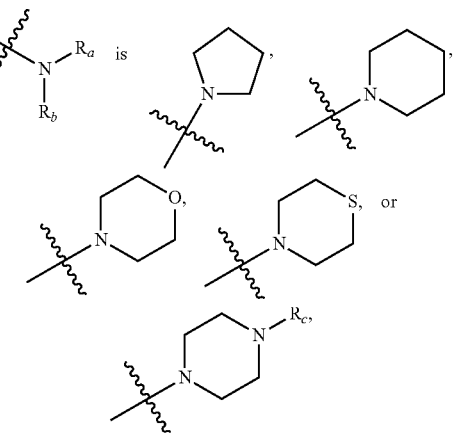

in which $R_c$ is H, methyl, ethyl, n-propyl, i-propyl, n-butyl, i-butyl, or t-butyl.

In yet another aspect, the present invention provides a compound of formula (XVIII):

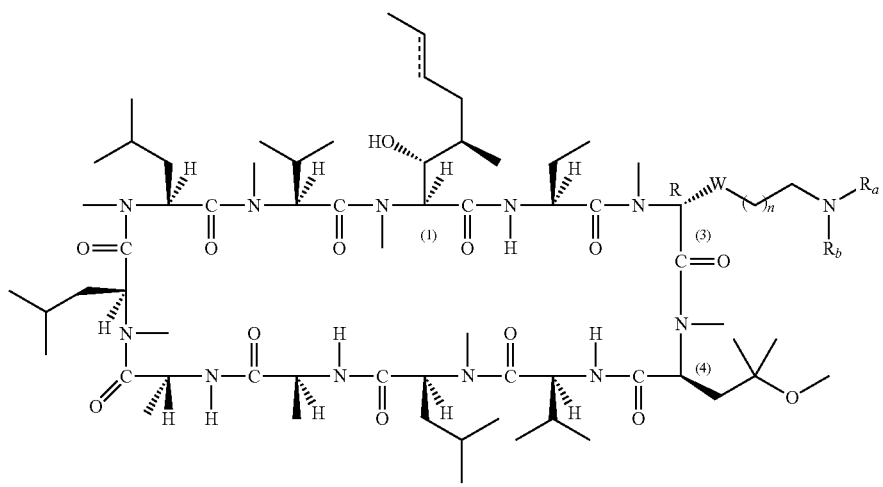

(XVIII)

wherein ∥ represents a single bond or a double bond;

W is S or O;

each of $R_a$ and $R_b$ is independently H, methyl, ethyl, n-propyl, i-propyl, n-butyl, i-butyl, t-butyl, $CH_2CMe_3$, phenyl, or $CH_2$-phenyl; or $R_a$ and $R_b$, together with the nitrogen atom to which they are attached

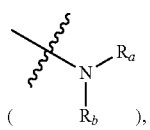

form a heterocycle selected from

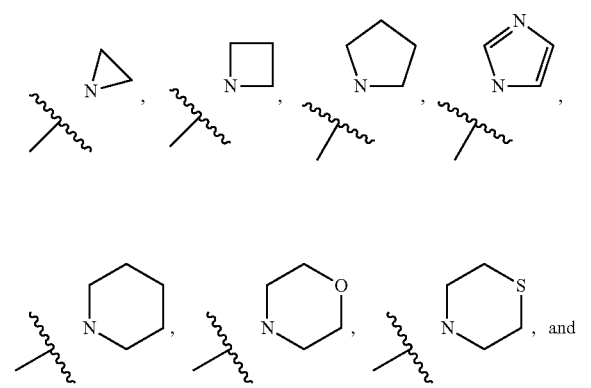

-continued

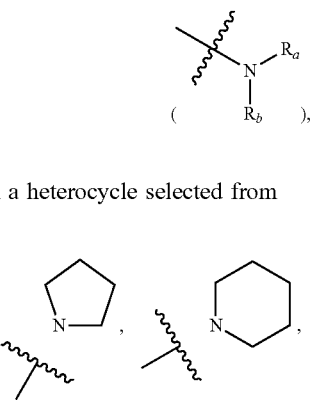

$R_c$ is H, methyl, ethyl, n-propyl, i-propyl, n-butyl, i-butyl, t-butyl, $CH_2CMe_3$, phenyl, or $CH_2$-phenyl; and each n is independently 1, 2, 3, 4, 5 or 6.

In certain embodiments, each of $R_a$ and $R_b$ is independently H, methyl, ethyl, n-propyl, i-propyl, n-butyl, i-butyl, t-butyl, or $CH_2CMe_3$; or $R_a$ and $R_b$, together with the nitrogen atom to which they are attached

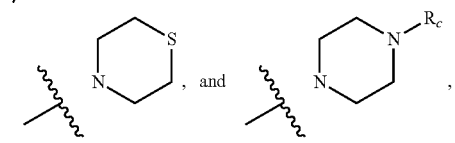

form a heterocycle selected from in which $R_c$ is H, methyl, ethyl, n-propyl, i-propyl, n-butyl, i-butyl, t-butyl, $CH_2CMe_3$, phenyl, or $CH_2$-phenyl.

In yet another aspect, the present invention provides a compound of formula (XIX):

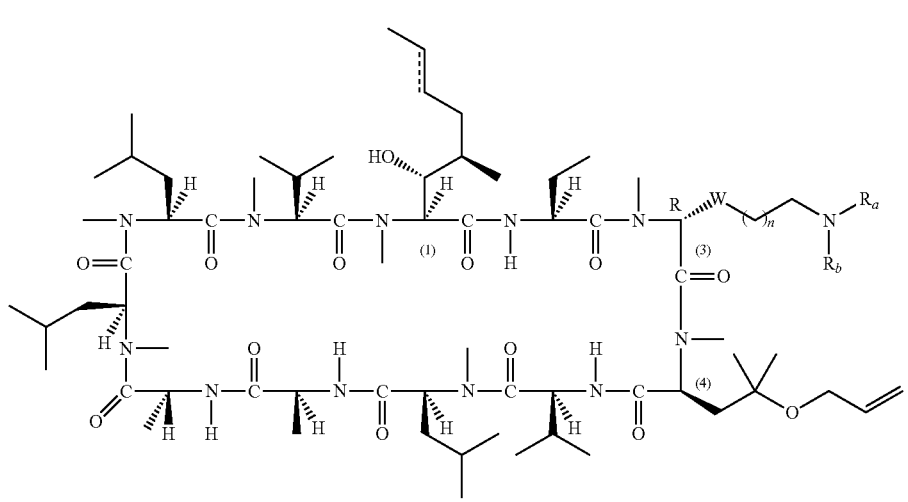

(XIX)

wherein ‖ represents a single bond or a double bond;
W is S or O;
each of $R_a$ and $R_b$ is independently H, methyl, ethyl, n-propyl, propyl, n-butyl, i-butyl, t-butyl, $CH_2CMe_3$, phenyl, or $CH_2$-phenyl; or $R_a$ and $R_b$, together with the nitrogen atom to which they are attached

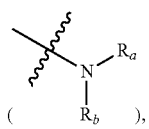

form a heterocycle selected from

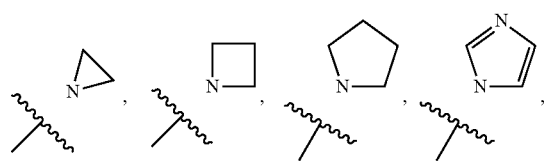

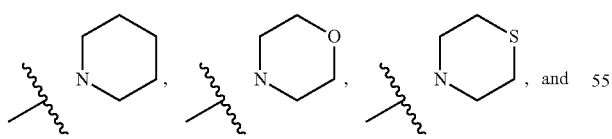

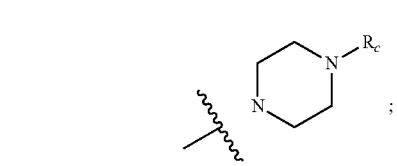

each n is independently 1, 2, 3, 4, 5 or 6.

$R_c$ is H, methyl, ethyl, n-propyl, i-propyl, n-butyl, i-butyl, t-butyl, $CH_2CMe_3$, phenyl, or $CH_2$-phenyl; and In certain embodiments, each of $R_a$ and $R_b$ is independently H, methyl, ethyl, n-propyl, propyl, n-butyl, i-butyl, t-butyl, or $CH_2CMe_3$; or $R_a$ and $R_b$, together with the nitrogen atom to which they are attached

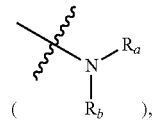

form a heterocycle selected from

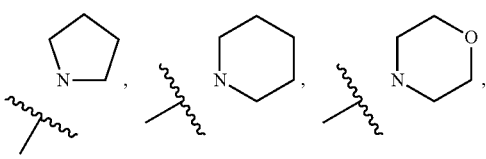

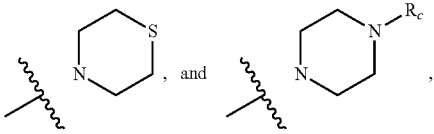

in which $R_c$ is H, methyl, ethyl, n-propyl, i-propyl, n-butyl, i-butyl, t-butyl, $CH_2CMe_3$, phenyl, or $CH_2$-phenyl.

In yet another aspect, the present invention provides a compound of formula (XX):

(XIX)

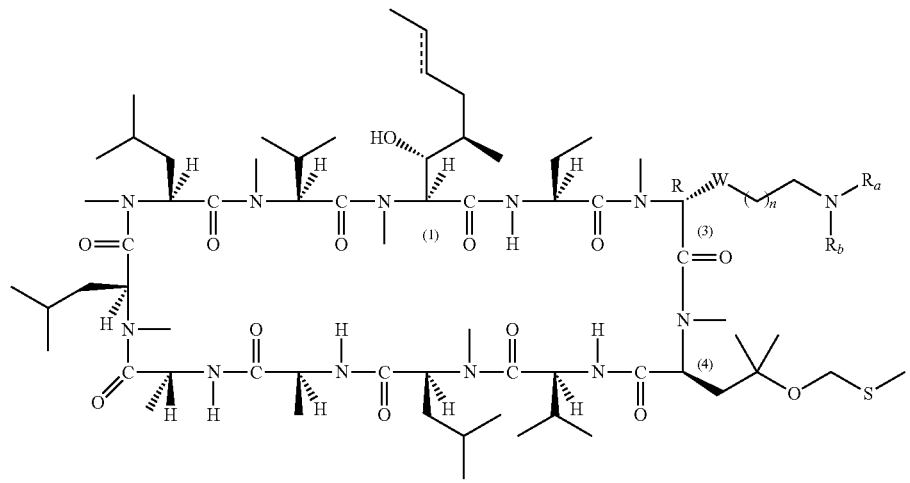

wherein ∥ represents a single bond or a double bond;
W is S or O;
each of $R_a$ and $R_b$ is independently H, methyl, ethyl, n-propyl, propyl, n-butyl, i-butyl, t-butyl, $CH_2CMe_3$, phenyl, or $CH_2$-phenyl; or $R_a$ and $R_b$, together with the nitrogen atom to which they are attached

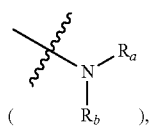

form a heterocycle selected from

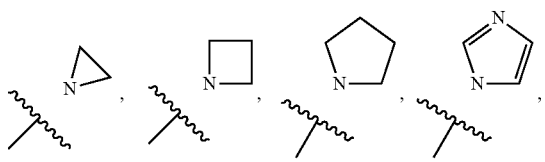

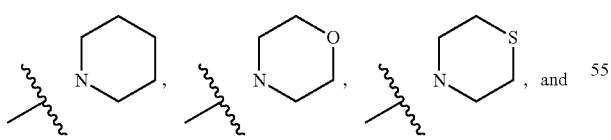

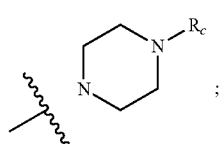

;

$R_c$ is H, methyl, ethyl, n-propyl, i-propyl, n-butyl, i-butyl, t-butyl, $CH_2CMe_3$, phenyl, or $CH_2$-phenyl; and
each n is independently 1, 2, 3, 4, 5 or 6.

In certain embodiments, each of $R_a$ and $R_b$ is independently H, methyl, ethyl, n-propyl, propyl, n-butyl, i-butyl, t-butyl, or $CH_2CMe_3$; or $R_a$ and $R_b$, together with the nitrogen atom to which they are attached

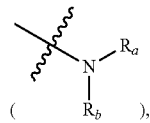

form a heterocycle selected from

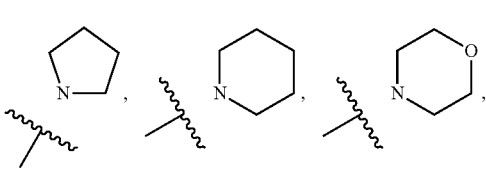

in which $R_c$ is H, methyl, ethyl, n-propyl, i-propyl, n-butyl, i-butyl, t-butyl, $CH_2CMe_3$, phenyl, or $CH_2$-phenyl.

In yet another aspect, the present invention provides a compound of formula (XXI):

(XXI)

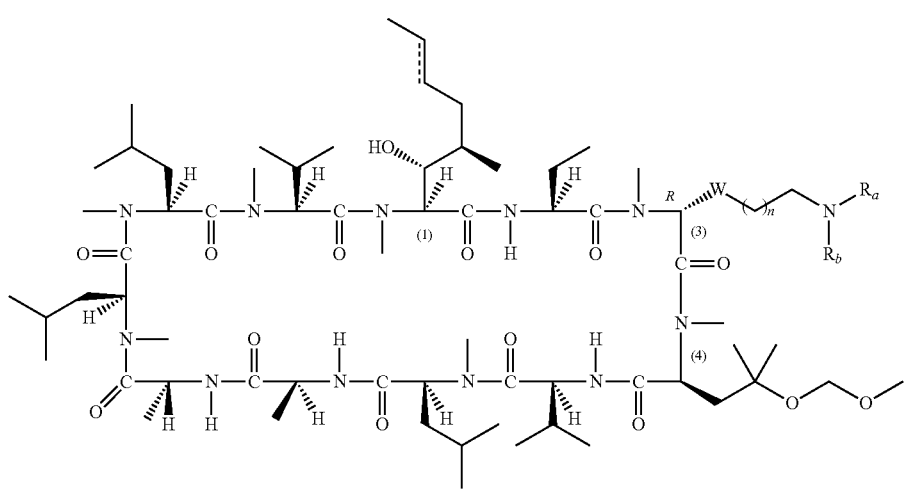

wherein ‖ represents a single bond or a double bond;
W is S or O;
each of $R_a$ and $R_b$ is independently H, methyl, ethyl, n-propyl, propyl, n-butyl, i-butyl, t-butyl, $CH_2CMe_3$, phenyl, or $CH_2$-phenyl; or $R_a$ and $R_b$, together with the nitrogen atom to which they are attached

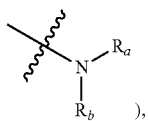

form a heterocycle selected from

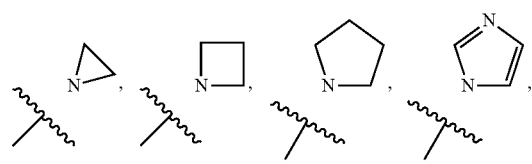

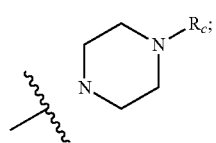

$R_c$ is H, methyl, ethyl, n-propyl, i-propyl, n-butyl, i-butyl, t-butyl, $CH_2CMe_3$, phenyl, or $CH_2$-phenyl; and
each n is independently 1, 2, 3, 4, 5 or 6.

In certain embodiments, each of $R_a$ and $R_b$ is independently H, methyl, ethyl, n-propyl, propyl, n-butyl, i-butyl, t-butyl, or $CH_2CMe_3$; or $R_a$ and $R_b$, together with the nitrogen atom to which they are attached

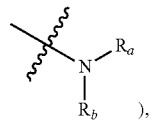

form a heterocycle selected from

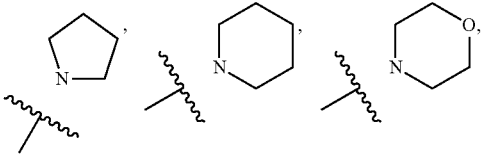

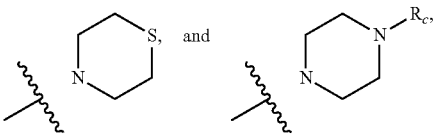

in which $R_c$ is H, methyl, ethyl, n-propyl, i-propyl, n-butyl, i-butyl, t-butyl, $CH_2CMe_3$, phenyl, or $CH_2$-phenyl.

In yet another aspect, the present invention provides a compound of formula (XXII):

(XXII)

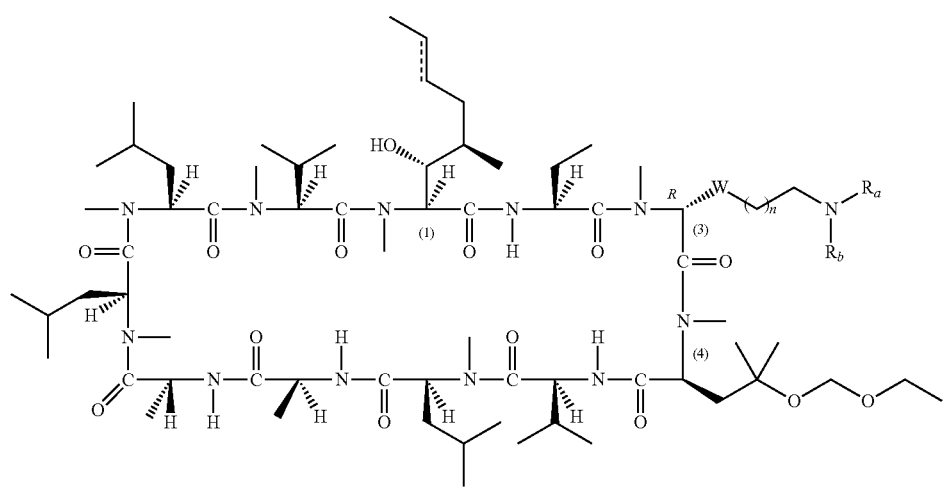

wherein ∥ represents a single bond or a double bond;
W is S or O;
each of $R_a$ and $R_b$ is independently H, methyl, ethyl, n-propyl, i-propyl, n-butyl, i-butyl, t-butyl, $CH_2CMe_3$, phenyl, or $CH_2$-phenyl; or $R_a$ and $R_b$, together with the nitrogen atom to which they are attached form a heterocycle selected from

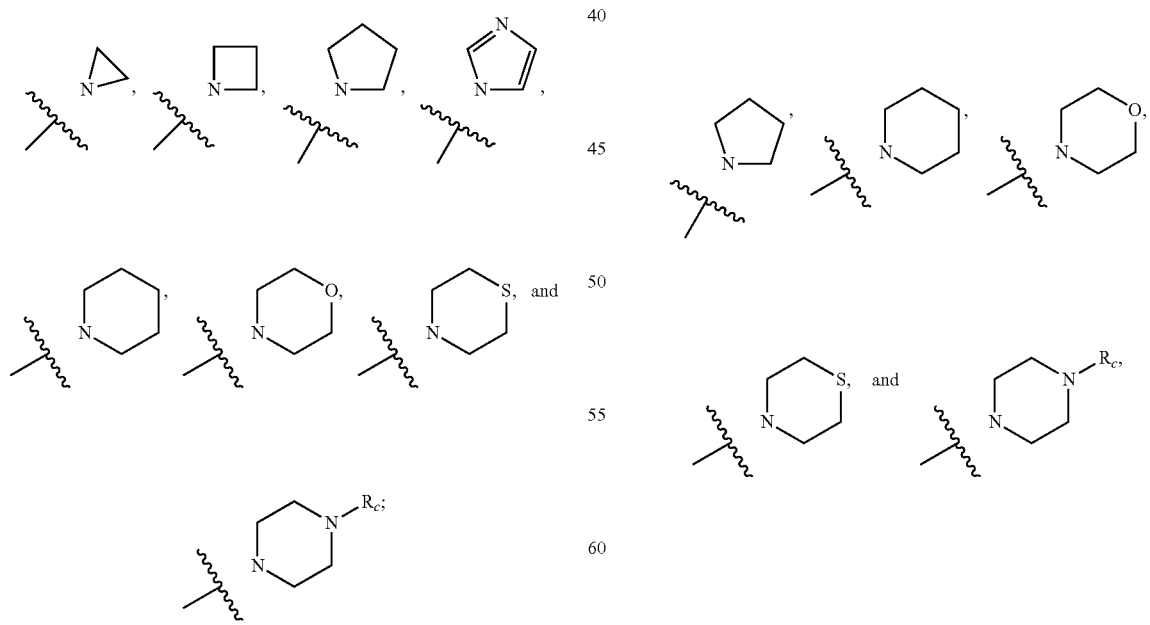

$R_c$ is H, methyl, ethyl, n-propyl, i-propyl, n-butyl, i-butyl, t-butyl, $CH_2CMe_3$, phenyl, or $CH_2$-phenyl; and
each n is independently 1, 2, 3, 4, 5 or 6.

In certain embodiments, each of $R_a$ and $R_b$ is independently H, methyl, ethyl, n-propyl, i-propyl, n-butyl, i-butyl, t-butyl, or $CH_2CMe_3$; or $R_a$ and $R_b$, together with the nitrogen atom to which they are attached form a heterocycle selected from in which $R_c$ is H, methyl, ethyl, n-propyl, i-propyl, n-butyl, i-butyl, t-butyl, $CH_2CMe_3$, phenyl, or $CH_2$-phenyl.

In yet another aspect, the present invention provides a compound of formula (XXIII):

(XXIII)

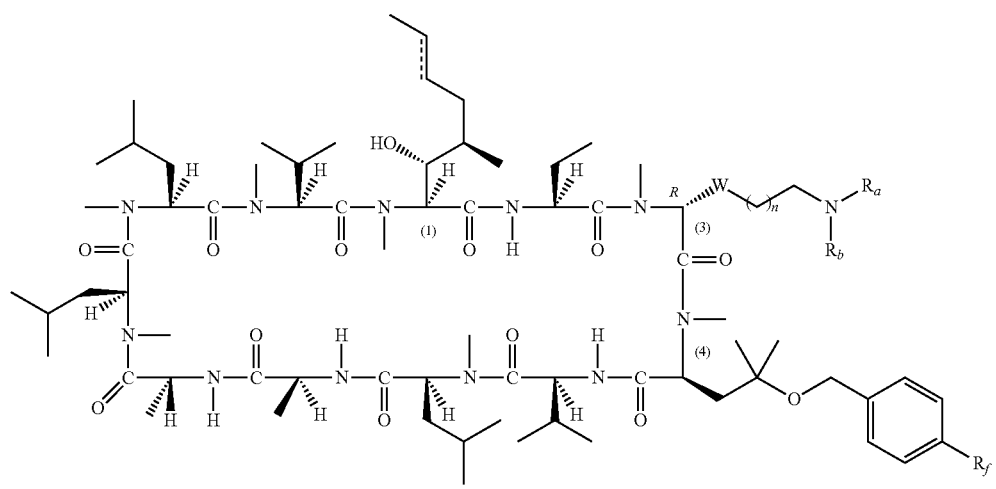

wherein ∥ represents a single bond or a double bond;
W is S or O;
each of $R_a$ and $R_b$ is independently H, methyl, ethyl, n-propyl, i-propyl, n-butyl, i-butyl, t-butyl, $CH_2CMe_3$, phenyl, or $CH_2$-phenyl; or $R_a$ and $R_b$, together with the nitrogen atom to which they are attached form a heterocycle selected from

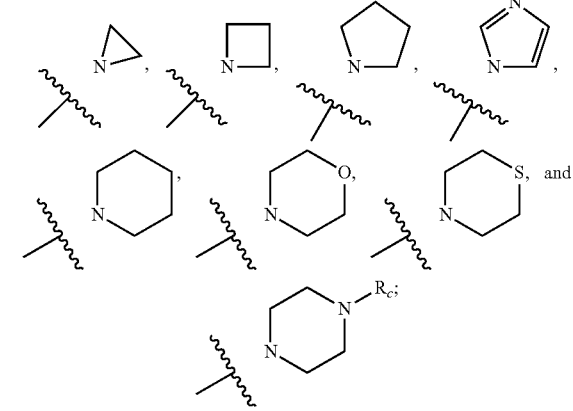

$R_c$ is H, methyl, ethyl, n-propyl, i-propyl, n-butyl, i-butyl, t-butyl, $CH_2CMe_3$, phenyl, or $CH_2$-phenyl;
$R_f$ is H or OMe; and
each n is independently 1, 2, 3, 4, 5 or 6.

In certain embodiments, each of $R_a$ and $R_b$ is independently H, methyl, ethyl, n-propyl, i-propyl, n-butyl, i-butyl, t-butyl, or $CH_2CMe_3$; or $R_a$ and $R_b$, together with the nitrogen atom to which they are attached

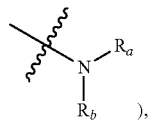

form a heterocycle selected from

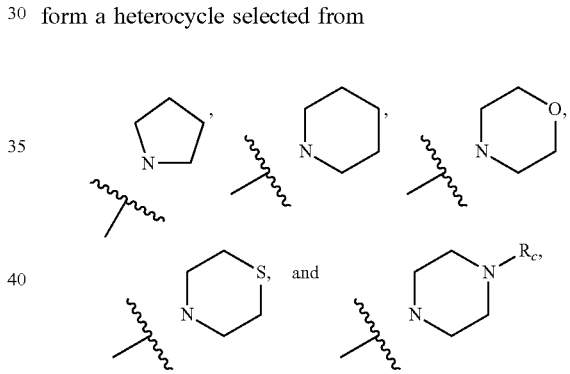

in which $R_c$ is H, methyl, ethyl, n-propyl, i-propyl, n-butyl, i-butyl, t-butyl, $CH_2CMe_3$, phenyl, or $CH_2$-phenyl.

In one aspect, the present invention provides a compound as described in the Examples.

In another aspect, the present invention provides a pharmaceutical composition comprising at least one compound described herein and a pharmaceutically-acceptable carrier or diluent.

In a further aspect, the present invention provides a method for treating or preventing a viral infection in a mammalian species in need thereof, the method comprising administering to the mammalian species a therapeutically effective amount of at least one compound described herein. In certain embodiments, the viral infection is HIV infection. In certain other embodiments, the viral infection is HBV infection. In yet other embodiments, the viral infection is HCV infection. In yet other embodiments, the viral infection is influenza A virus infection, severe acute respiratory syndrome coronavirus infection or vaccinia virus infection. In yet other embodiments, the viral infection is herpes simplex virus.

In another aspect, the present invention provides a method for treating or preventing hepatitis C virus infection or hepatitis B virus infection in a mammalian species in need thereof, the method comprising administering to the mammalian species a therapeutically effective amount of at least one compound described herein.

In another aspect, the present invention provides a method for treating or preventing a central nervous system disorder in a mammalian species in need thereof, the method comprising administering to the mammalian species a therapeutically effective amount of at least one compound described herein. In certain embodiments, the central nervous system disorder is mitochondrial protection for stroke, traumatic brain and spinal cord injury, Alzheimer, Parkinson's Disease, or Huntington's Diseases.

In yet another aspect, the present invention provides a method for treating or preventing a cardiovascular disease in a mammalian species in need thereof, the method comprising administering to the mammalian species a therapeutically effective amount of at least one compound described herein. In certain embodiments, the cardiovascular disease is reperfusion injury, heart attack, or chronic heart failure.

In yet another aspect, the present invention provides a method for treating or preventing an inflammation disease in a mammalian species in need thereof, the method comprising administering to the mammalian species a therapeutically effective amount of at least one compound described herein. In certain embodiments, the inflammation disease is respiratory inflammation, asthma, ulcerative colitis, rheumatoid arthritis, or dry eye disease.

Methods of Preparation

In certain embodiments, cyclosporine derivatives can be prepared by treating cyclosporin A or an analog thereof with a base (e.g., LDA) to form the sarcosine enolate at the 3-position, and then a side chain is introduced by addition of an electrophile (Seebach, D., et al., 1993, *Modification of Cyclosporin A* (CS): Generation of an Enolate at the Sercosine Residue and Reactions with Electrophiles, *Helv. Chim. Acta,* 76, 1564-1590; see also U.S. Pat. Nos. 5,965,527, 5,994,299, 6,583,265, and 7,718,767; each of which is incorporated herein by reference). In certain embodiments, the resulting enolate can be alkylated as follows:

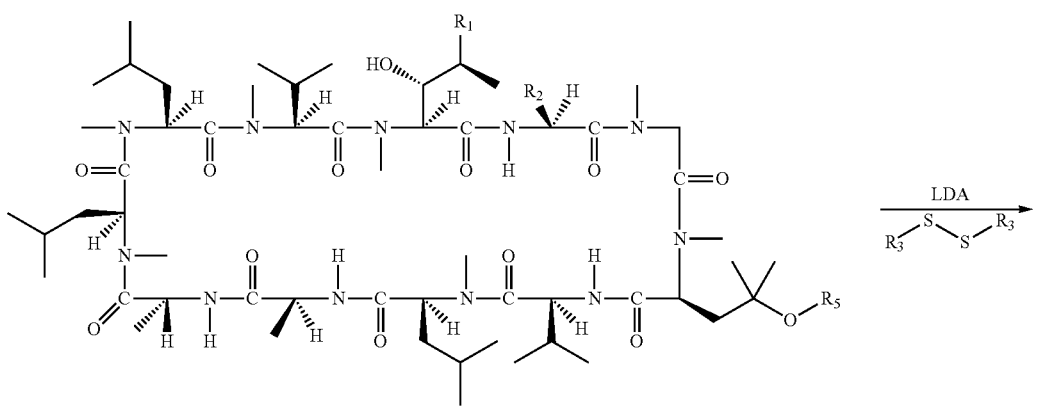

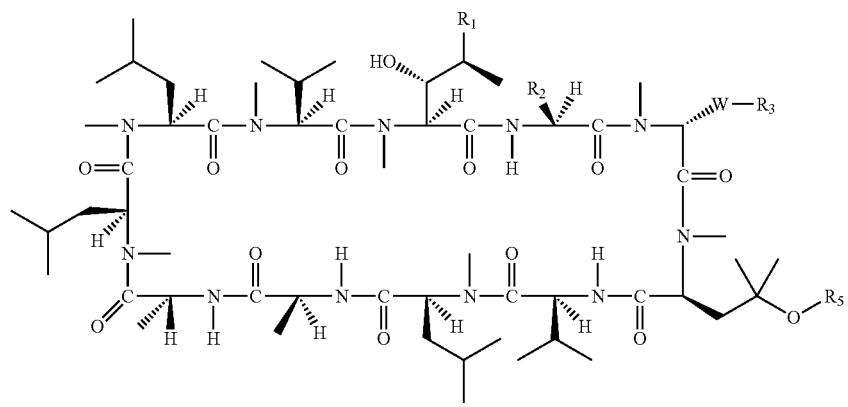

-continued

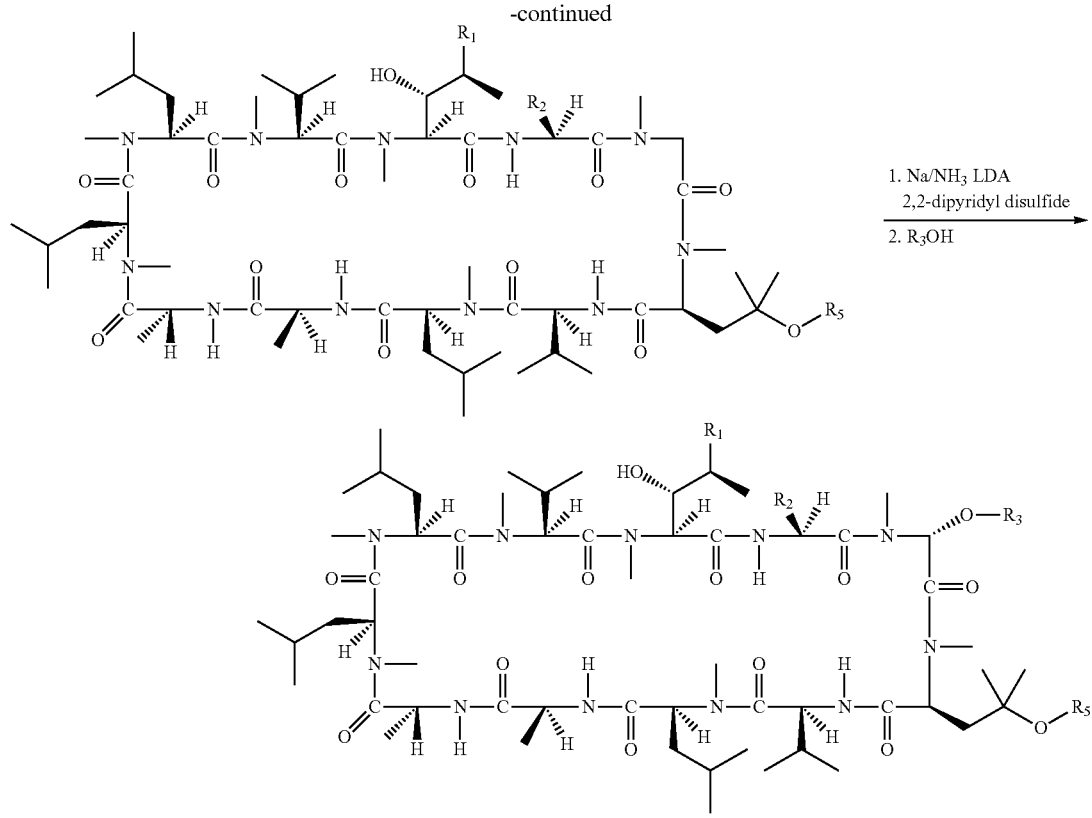

In certain other embodiments, cyclosporine derivatives can be obtained by the selective ring-opening reaction between position 3 and 4, developed by Dr. Zhuang Su in 1992, followed by Edman degradation (Edman, P., 1950, *Chem. Scand.*, 4, 277; Edman, P., 1967, *Eur. J. Biochem.*, 1, 80; incorporated herein by reference) to yielded cyclosporine decapeptide, which can be incorporated with aminoacid to form undecapeptide, deprotected and cyclized to produce a cyclosporine derivatives modified in position 4 (Papageorgiou, C., et al., 1994, *J. Med. Chem.*, 37, 3674-3676 and its reference 11: Su, Z., Wenger, R., Unpublished results; Papageorgiou, C., et al., 1994, *Bioorg & Med Chem Lett*, 4, 267-272 and its reference 14: Su, Z., Wenger, R., Unpublished results; Wenger, R., 1996, Peptide, Ramage, R.; Epton, R., Eds.; The European Peptides Society, 1996, 173 and its reference 36: Su, Z., Ko, S., and Wenger, R., Unpublished results; each of which is incorporated herein by reference).

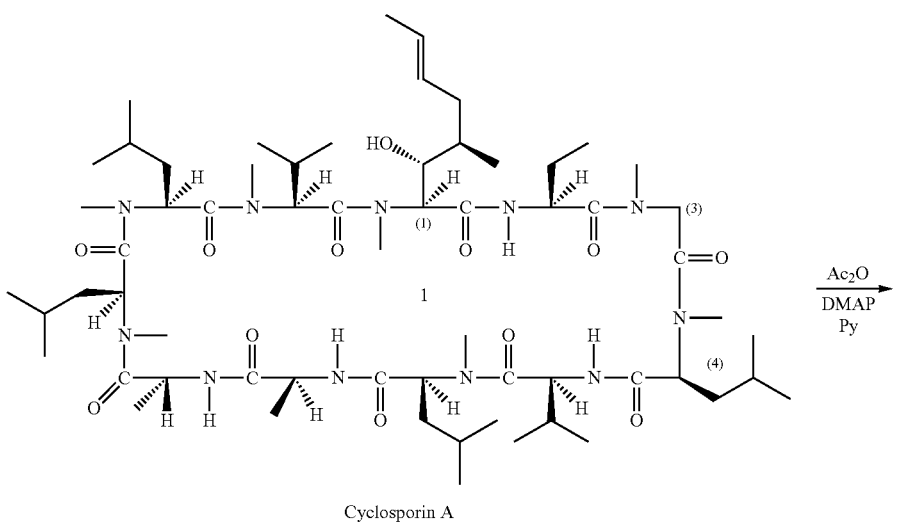

Cyclosporin A

-continued
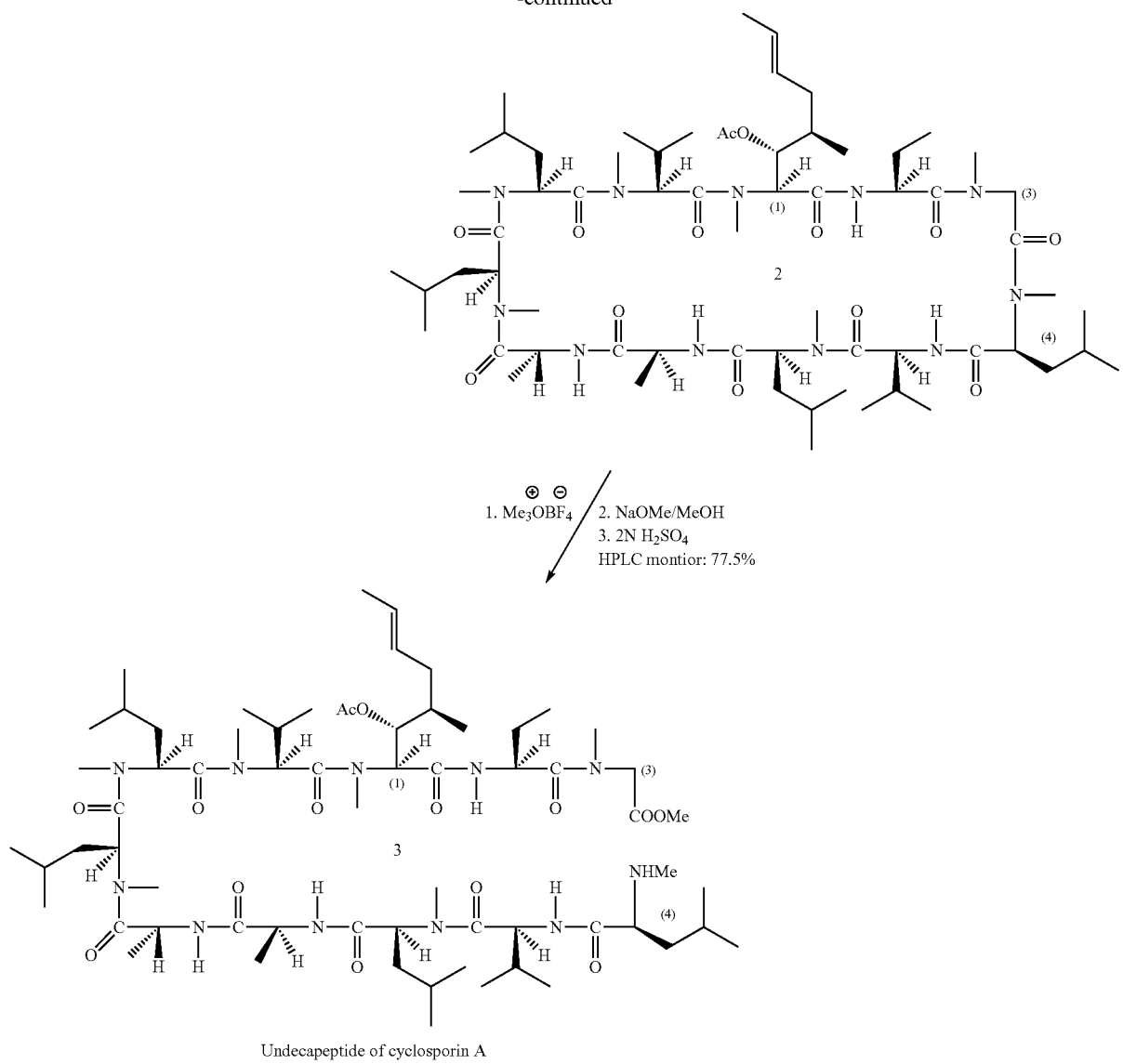
1. Me₃OBF₄  2. NaOMe/MeOH
3. 2N H₂SO₄
HPLC montior: 77.5%
Undecapeptide of cyclosporin A
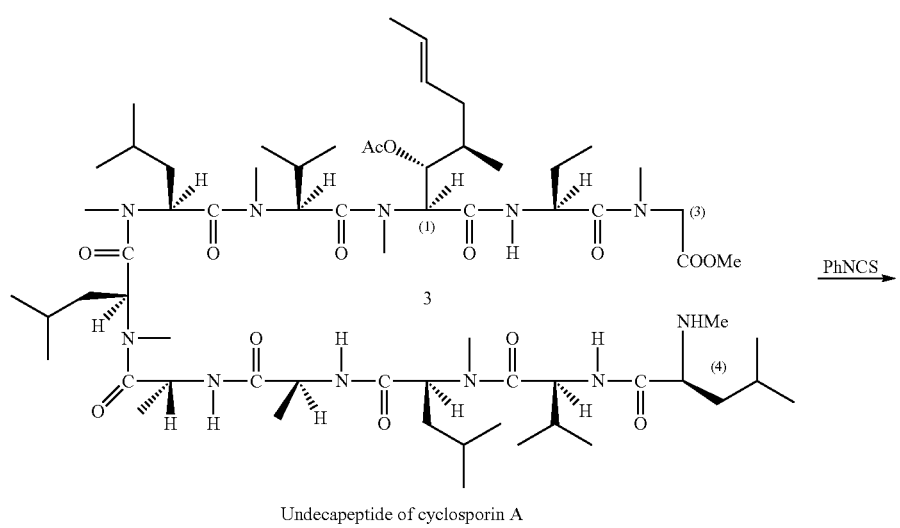
PhNCS →
Undecapeptide of cyclosporin A -continued
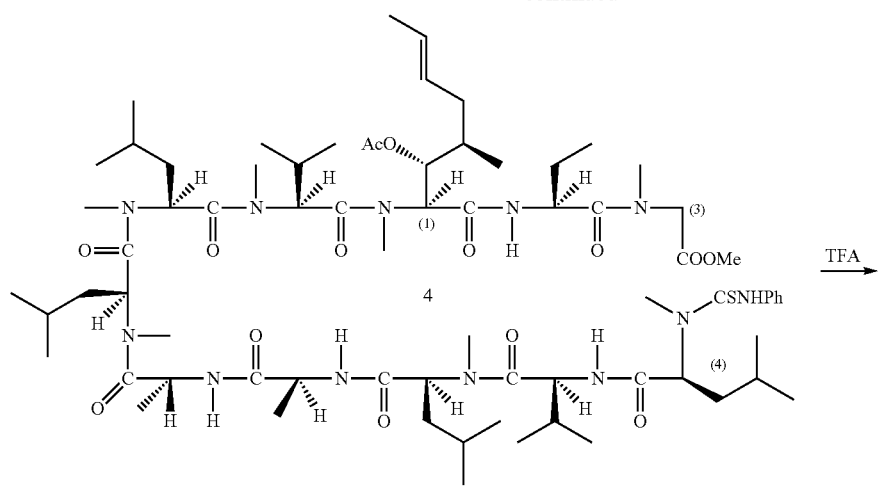
4
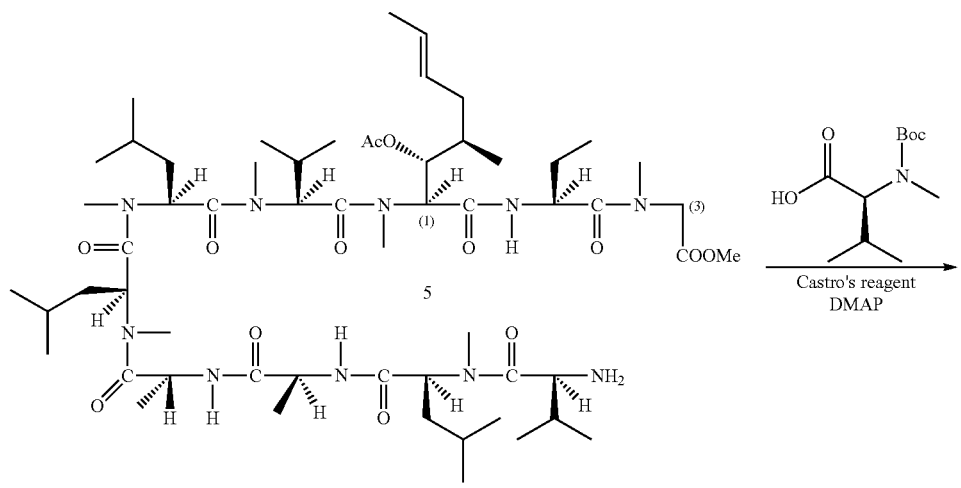
5
Decapeptide of cyclosporin A
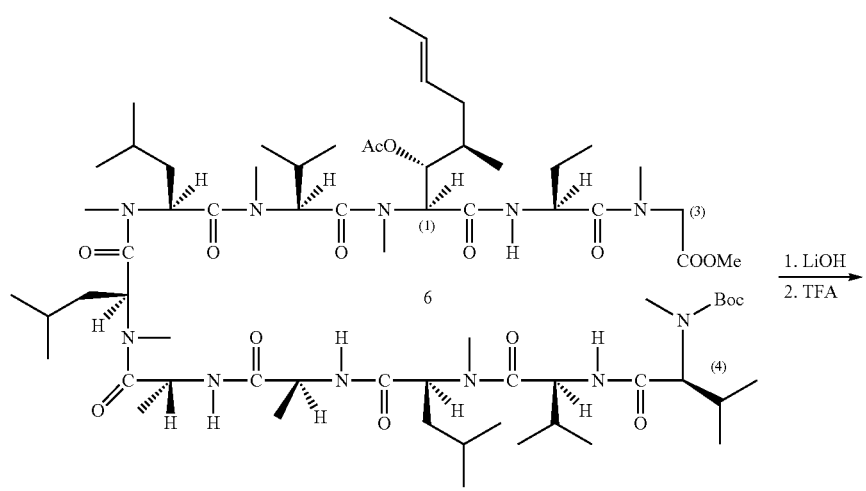
6

-continued

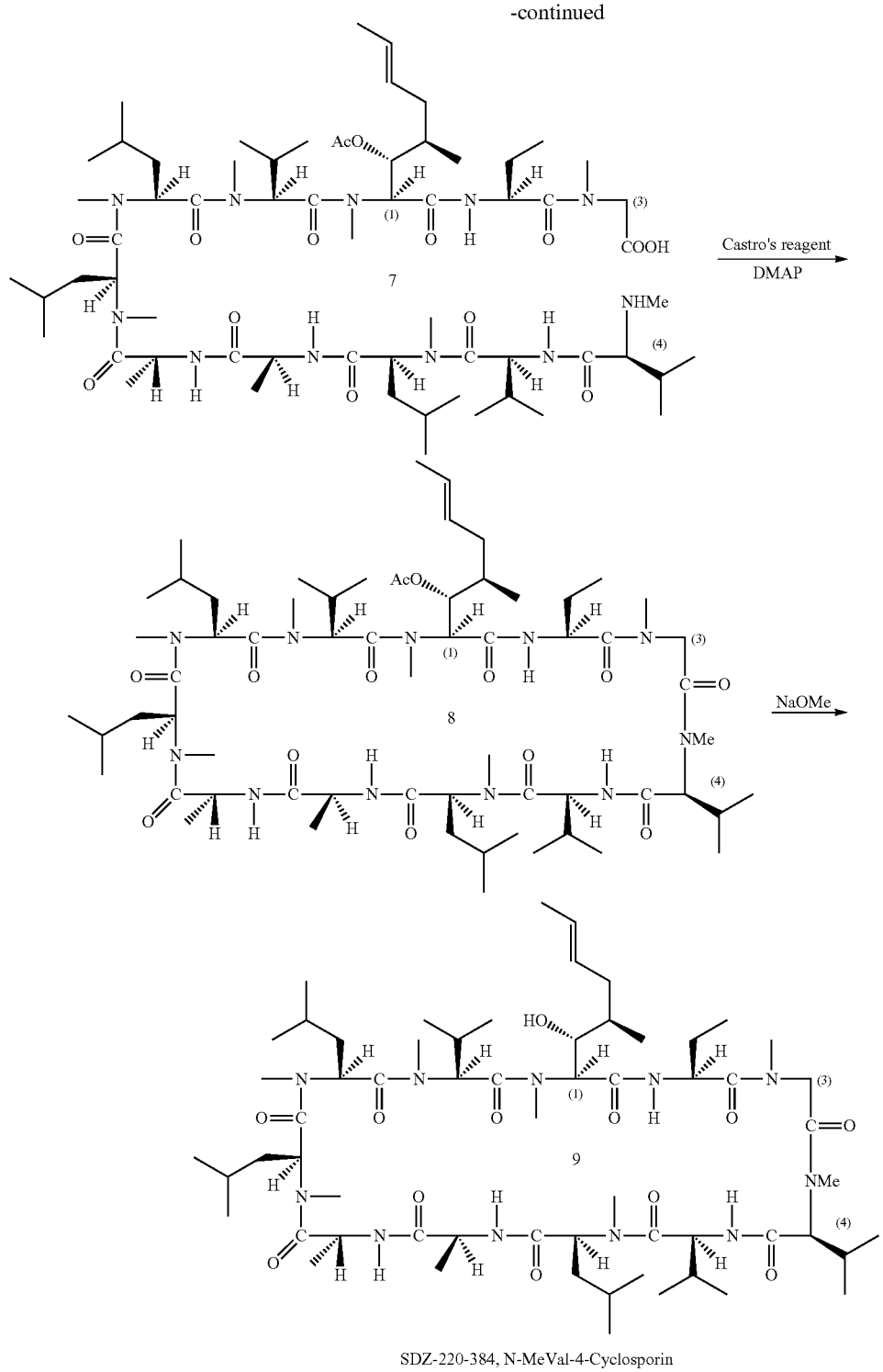

SDZ-220-384, N-MeVal-4-Cyclosporin

The hydrogenation of the double bond of MeBmt at position 1 of cyclosporine can provide (Dihydro-MeBmt)-1-cyclosporin by using a method described by U.S. Pat. Nos. 4,108,985, 5,767,069, and 5,981,479, each of which is incorporated herein by reference.

Pharmaceutical Compositions

This invention also provides a pharmaceutical composition comprising at least one of the compounds as described herein or a pharmaceutically-acceptable salt or solvate thereof, and a pharmaceutically-acceptable carrier.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present pharmaceutical agents may be provided in the form of pharmaceutically-acceptable salts. The term "pharmaceutically-acceptable salt", in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., (1977) "Pharmaceutical Salts", J. Pharm. Sci. 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, butionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate, magnesium stearate, and polyethylene oxide-polybutylene oxide copolymer as well as coloring agents, release agents, coating agents, sweetening, flavoring and perfuming agents, preservatives and antioxidants can also be present in the compositions.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polybutylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxybutylmethyl cellulose), lubricant, inert diluent, preservative, disintegrant (for example, sodium starch glycolate or cross-linked sodium carboxymethyl cellulose), surface-active or dispersing agent. Molded tablets, may be, made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxybutylmethyl cellulose in varying butortions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if apbutriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxybutyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention.

Formulations of the present invention which are suitable for vaginal administration also include pessaries, tampons, creams, gels, pastes, foams or spray formulations containing such carriers as are known in the art to be apbutriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or butellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary butellants, such as chlorofluorohydrocarbons and volatile unsubstituted hydrocarbons, such as butane and butane.

Transdermal patches have the added advantage of providing controlled delivery of a compound of the present invention to the body. Such dosage forms can be made by dissolving, or dispersing the pharmaceutical agents in the buter medium. Absorption enhancers can also be used to increase the flux of the pharmaceutical agents of the invention across the skin. The rate of such flux can be controlled, by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form.

Alternatively, delayed absorption of a parenterally-administered drug form is accomplished by dissolving or suspending the drug in an oil vehicle. One strategy for depot injections includes the use of polyethylene oxide-polybutylene oxide copolymers wherein the vehicle is fluid at room temperature and solidifies at body temperature.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions, which are compatible with body tissue.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another anti-HCV agent), or they may achieve different effects (e.g., control of any adverse effects).

The compounds of the invention may be administered intravenously, intramuscularly, intraperitoneally, subcutaneously, topically, orally, or by other acceptable means. The compounds may be used to treat arthritic conditions in mammals (i.e., humans, livestock, and domestic animals), birds, lizards, and any other organism, which can tolerate the compounds.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and equivalents thereof.

EXAMPLES

Example 1

[(R)-3-(N-Morphlino)propylthio-Sar]-3-[(γ-Hydroxy)-NMeLeu]-4-cyclosporin

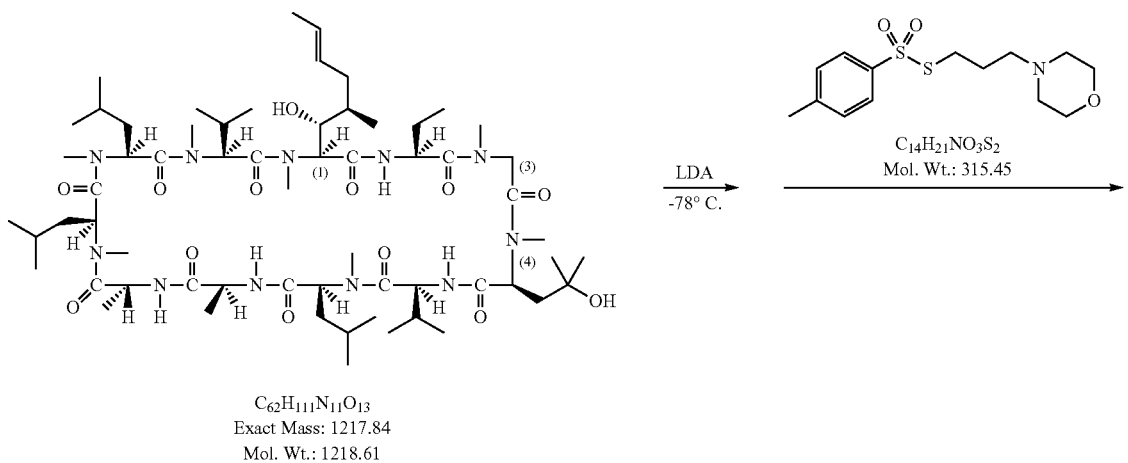

-continued

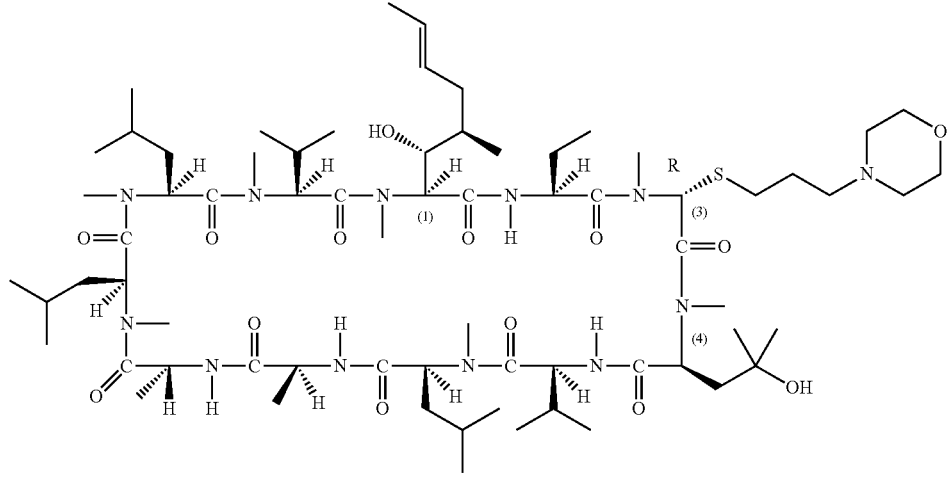

C$_{69}$H$_{124}$N$_{12}$O$_{14}$S
Exact Mass: 1376.91
Mol. Wt.: 1377.86 n-Butyllithium (2.87 M, 9.02 mmol, 3.14 ml, 11 equiv) was added into a solution of diisopropylamine (FW 101.19, d 0.722, 1.27 ml, 9.02 mmol, 11 equiv) in 40 ml of THF under nitrogen at −78° C. over 30 minutes, and the resulting LDA solution was stirred at −78° C. for one hour. A solution of [(γ-hydroxy)-NMeLeu]-4-cyclosporin (FW 1218.61, 1.0 g, 0.82 mmol) in 10 ml of THF was dropwise added over 5 minutes below −65° C. After the mixture was stirred for 2 hours at −78° C., p-toluenesulphonic acid (3-morphorlino)propylthioester (FW 315.45, 1.64 g, 5.2 mmol) in 5 ml of THF was added over 5 minutes at −70° C., and the reaction mixture was stirred for 3 hours at −78° C. Then the reaction mixture was allowed to warm to room temperature and stirred for another two hours. The pH of the reaction mixture was adjusted to 7 by adding citric acid solution, and then the most of THF was evaporated under reduced pressure. 50 ml of ethyl acetate and 30 ml of water were added and layers were separated. The aqueous layer was extracted with ethyl acetate (3×50 mL). The organic layers were combined, washed with brine, dried over MgSO$_4$, filtered, and evaporated under vacuum. The residue was subjected to chromatography on silica gel using ethyl acetate/methanol (5/1), followed by DCM/methanol (10:1) to give the product [Molecular formula: C$_{69}$H$_{124}$N$_{12}$O$_{14}$S; Exact Mass: 1376.91; MS (m/z): 1377.90 (M+1)$^+$, 1399.9 (M+Na)$^+$; TLC R$_f$: 0.37 (ethyl acetate/methanol=5/1); HPLC RT: 19.53 minutes (C8 reverse phase column, 250 mm, acetonitrile/0.077% NH$_4$OAc in water, operation temperature: 64° C.; Detector: 210 nm)].

[(γ-Hydroxy)-NMeLeu]-4-cyclosporin was prepared by *Sebekia benihana* biotransformation according to a method described by Kuhnt M. et al., 1996, Microbial Biotransformation Products of Cyclosporin A, *J. Antibiotics*, 49 (8), 781.

p-Toluene sulphonic acid (3-Morphlino)propylthioester was prepared by the following procedure.

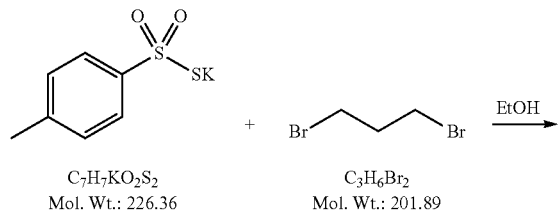

C$_7$H$_7$KO$_2$S$_2$
Mol. Wt.: 226.36

C$_3$H$_6$Br$_2$
Mol. Wt.: 201.89

-continued

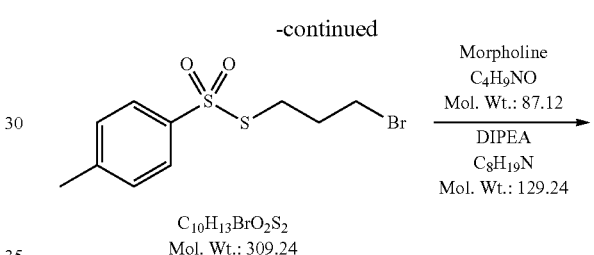

C$_{10}$H$_{13}$BrO$_2$S$_2$
Mol. Wt.: 309.24

Morpholine
C$_4$H$_9$NO
Mol. Wt.: 87.12

DIPEA
C$_8$H$_{19}$N
Mol. Wt.: 129.24

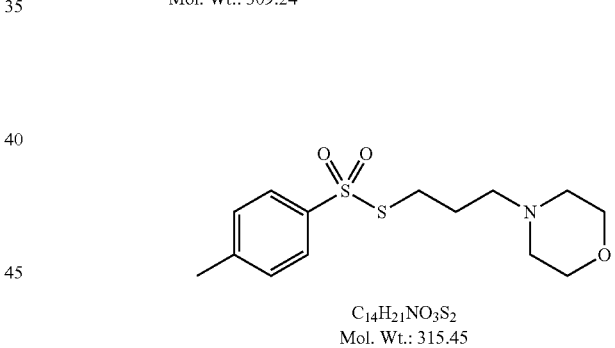

C$_{14}$H$_{21}$NO$_3$S$_2$
Mol. Wt.: 315.45 p-Toluenethiosulfonic acid potassium salt (FW 226.36, 10.00 g, 44.18 mmol) and 1,3-dibromopropane (FW 201.89, 44.67 g, 221.26 mmol) were added into 150 ml of ethanol. The reaction mixture was heated to reflux for 3 hours with stirring. Removal of ethanol under vacuum yielded the residue, which was mixed with 50 ml of ethyl acetate, washed with brine, dried over MgSO$_4$ and evaporated under reduced pressure. The resulting residue was purified by column on silica gel using hexane/ethyl acetate (5:1) to give 12.40 g of p-toluene sulphonic acid 3-bromopropylthioester. This intermediate (9.67 g, 31.27 mmol), morpholine (FW 87.12, 4.10 g, 47.10 mmol), and DIPEA (FW 129.25, d 0.742, 15.65 ml, 11.61 g, 89.72 mmol) were mixed in 125 ml of DCM at room temperature. The reaction mixture was stirred for 48 hours and then was washed with 1N NaOH solution (2×15 ml). The DCM solution was dried over MgSO$_4$ and evaporated to give 8.90 g of product.

Example 2

[(R)-3-(N,N-Diethylamino)propylthio-Sar]-3-[(γ-Hydroxy)-NMeLeu]-4-cyclosporin

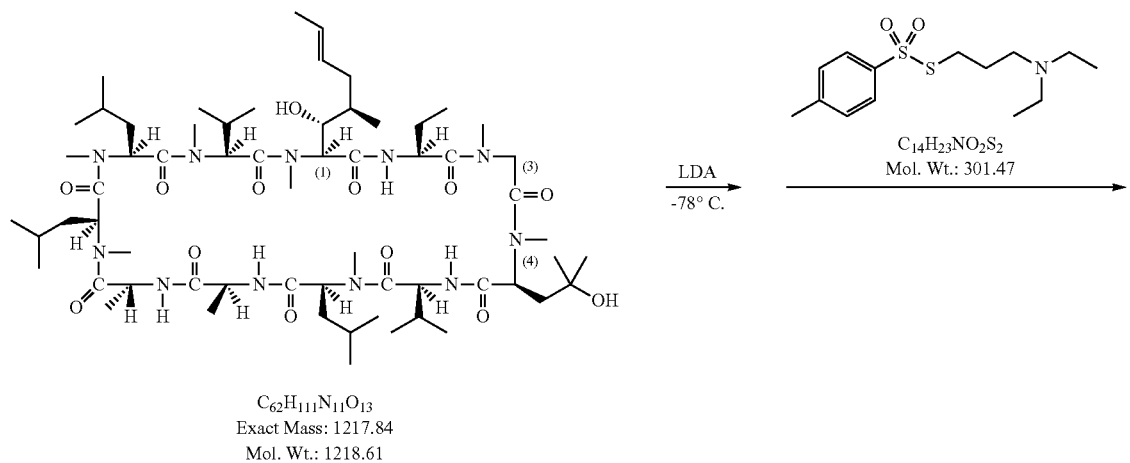

$C_{62}H_{111}N_{11}O_{13}$
Exact Mass: 1217.84
Mol. Wt.: 1218.61

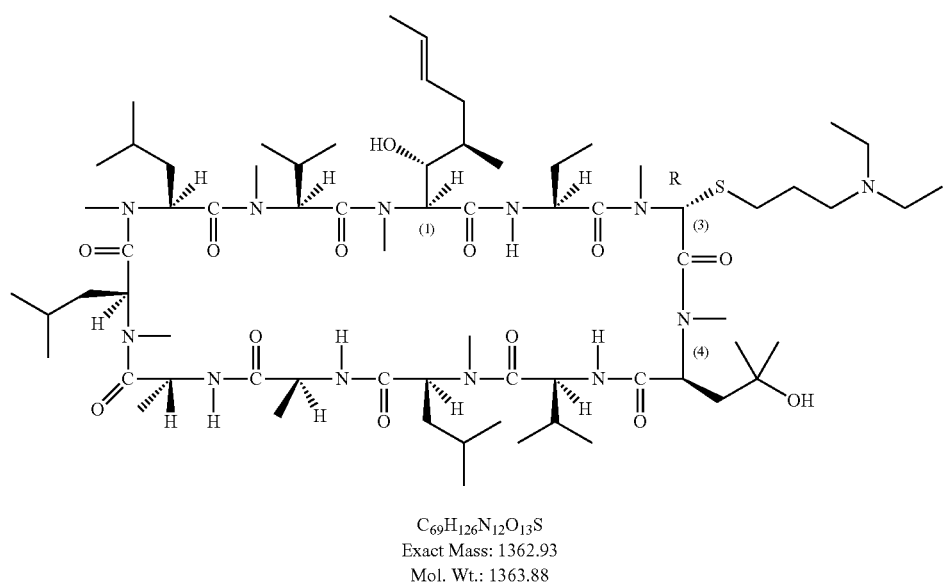

$C_{69}H_{126}N_{12}O_{13}S$
Exact Mass: 1362.93
Mol. Wt.: 1363.88

[(R)-3-(N,N-Diethylamino)propylthio-Sar]-3-[(γ-Hydroxy)-NMeLeu]-4-cyclosporin was prepared according to the method described in Example 1. Molecular formula: $C_{69}H_{126}N_{12}O_{13}S$; Exact Mass: 1362.93; MS (m/z): 1363.90 (M+H)$^+$; TLC $R_f$: 0.30 (DCM/MeOH=94/6); HPLC RT: 16.96 minutes (C8 reverse phase column, 250 mm, acetonitrile/0.077% $NH_4OAc$ in water, operation temperature: 64° C.; Detector: 210 nm).

p-Toluene sulphonic acid (3-N,N-diethylamino)propylthioester was prepared according to the similar method described in Example 1.

Example 3

[(R)-3-(N-iso-Propyl-N-ethylamino)propylthio-Sar]-
3-[(γ-Hydroxy)-NMeLeu]-4-cyclosporin

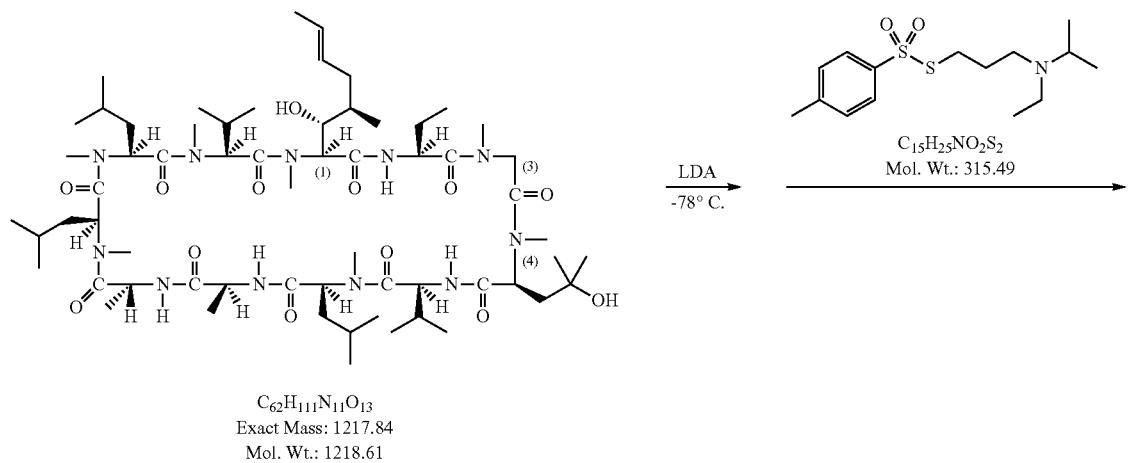

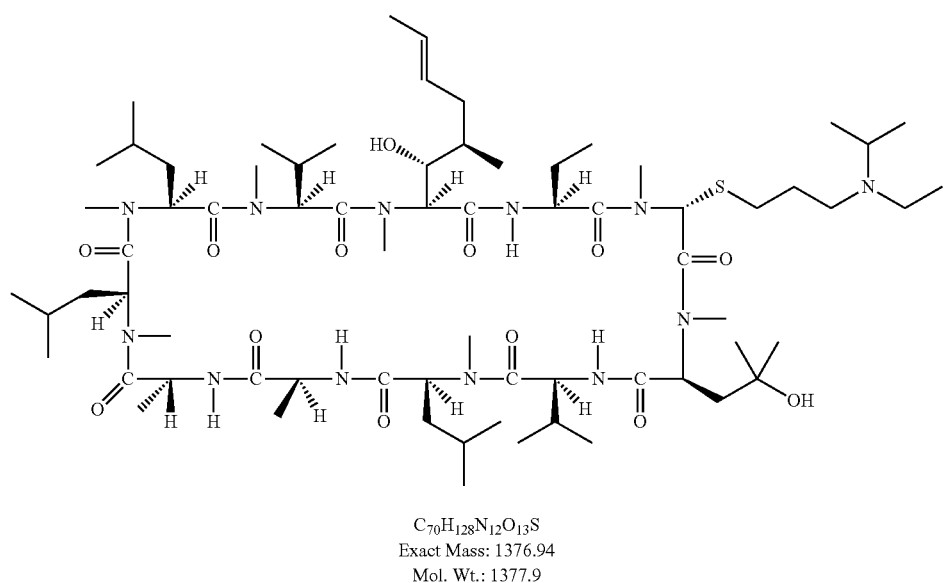

[(R)-3-(N-isoPropyl-N-ethylamino)propylthio-Sar]-3-[(γ-Hydroxy)-NMeLeu]-4-cyclosporin was prepared according to the method described in Example 1. Molecular formula: $C_{69}H_{128}N_{12}O_{13}S$; Exact Mass: 1376.94; MS (m/z): 1377.75 (M+H)$^+$; TLC $R_f$: 0.45 (DCM/MeOH=95/5); HPLC RT: 17.32 minutes (C8 reverse phase column, 250 mm, acetonitrile/0.077% NH$_4$OAc in water, operation temperature: 64° C.; Detector: 210 nm).

p-Toluene sulphonic acid (3-N-isopropyl-N-ethylamino) propylthioester was prepared according to the similar method described in Example 1.

Example 4

[(R)-3-(N-Morphlino)propylthio-Sar]-3-[(γ-Methyl-thio)methoxy-NMeLeu]-4-cyclosporin

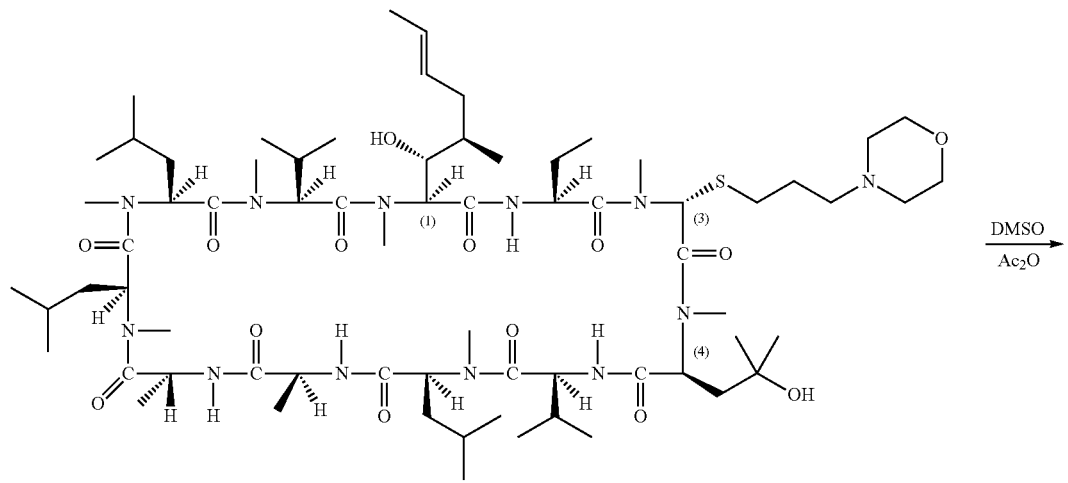

$C_{69}H_{124}N_{12}O_{14}S$
Exact Mass: 1376.91
Mol. Wt.: 1377.86

DMSO
Ac₂O

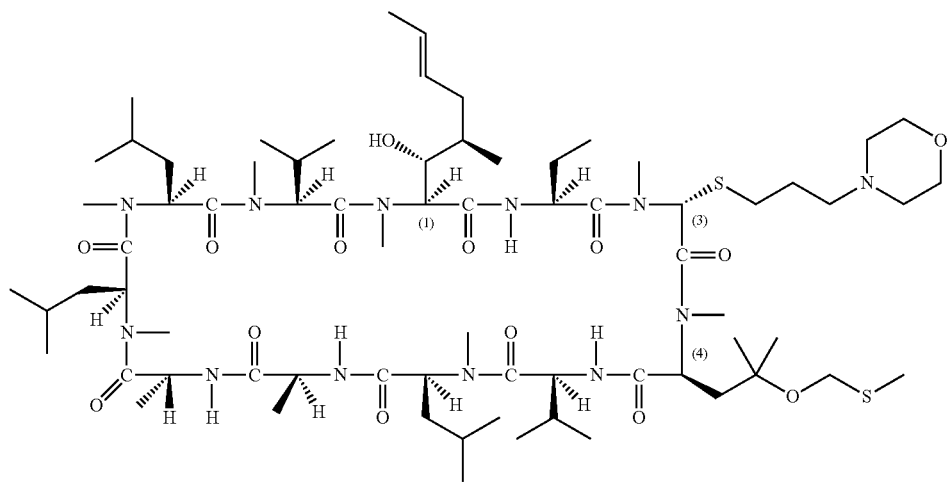

$C_{71}H_{128}N_{12}O_{14}S_2$
Exact Mass: 1436.91
Mol. Wt.: 1437.98

To a solution of [(R)-3-(N-Morphlino)propylthio-Sar]-3-[(γ-Hydroxy)-NMeLeu]-4-cyclosporin (FW 1377.86, 100 mg, 0.073 mmol) in 0.6 ml of DMSO was added dropwise 0.4 ml of acetic anhydride by syringe. The mixture was stirred overnight at room temperature and TLC was used to monitor the completion of the reaction. After diluted with 20 mL of ethyl acetate, the mixture was washed with saturated NaHCO₃ water solution, brine, and dried over MgSO₄. Removal of solvent afforded a yellowish oil, which was subjected to chromatography on silica gel using ethyl acetate/methanol (10:1), followed by methylene chloride/methanol (10:1) as eluents to yield the desired product [Molecular formula: $C_{71}H_{128}N_{12}O_{14}S_2$; Exact Mass: 1436.91; MS (m/z): 1437.90 (M+H)⁺, 1459.90 (M+Na)⁺; TLC $R_f$: 0.29 (EtOAc/MeOH=10/1); HPLC RT: 23.21 minutes (C8 reverse phase column, 250 mm, acetonitrile/0.077% NH₄OAc in water, operation temperature: 64° C.; Detector: 210 nm)].

Example 5

[(γ-Methylthio)methoxy-NMeLeu]-4-cyclosporin

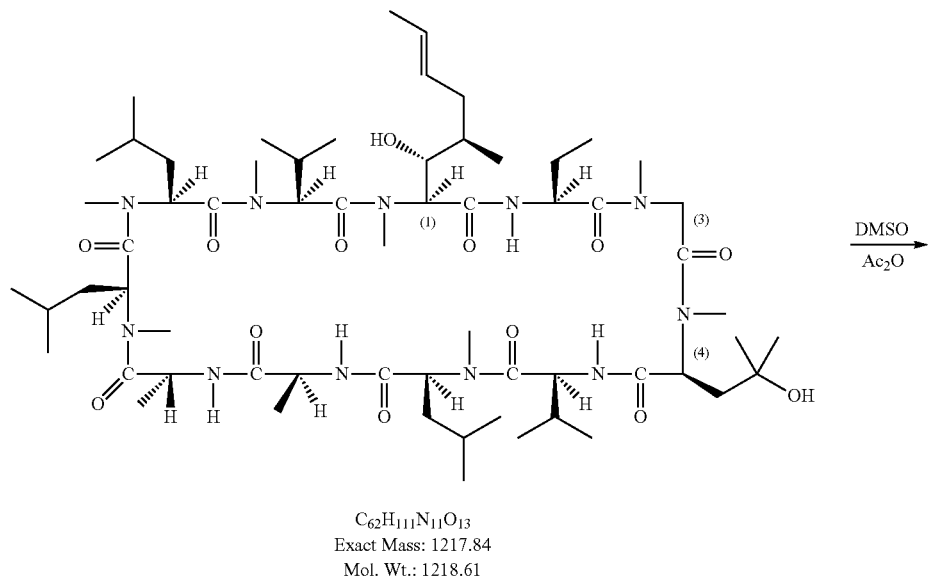

C$_{62}$H$_{111}$N$_{11}$O$_{13}$
Exact Mass: 1217.84
Mol. Wt.: 1218.61

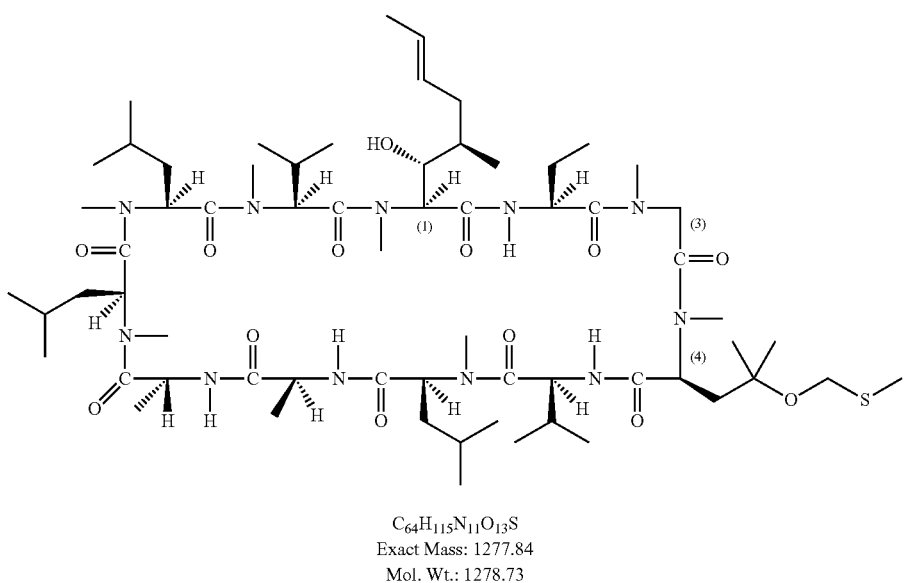

C$_{64}$H$_{115}$N$_{11}$O$_{13}$S
Exact Mass: 1277.84
Mol. Wt.: 1278.73

To a solution of [(γ-Hydroxy)-NMeLeu]-4-cyclosporin (FW 1218.61, 4.5 g, 3.7 mmol) in 25 ml of anhydrous DMSO was added 15 ml of acetic anhydride at room temperature, then the reaction mixture was stirred for 17 hs, the LC-MS/HPLC was used to monitor the reaction. After diluted with ethyl acetate, the mixture was washed with saturated NaHCO$_3$ water solution, and brine. The organic layer was dried over MgSO$_4$ and filtered. After evaporation in vacuum, the residue was purified on silica gel chromatography by eluant with DCM/MeOH (98/2) to give (γ-Methylthio)methoxy-NMeLeu-4-cyclosporin [Molecular formula: C$_{64}$H$_{115}$N$_{11}$O$_{13}$S; Exact Mass: 1277.84; MS (m/z): 1300.70 (M+Na)$^+$; TLC R$_f$: 0.30 (DCM/MeOH=95/5); HPLC RT: 19.57 minutes (C8 reverse phase column, 250 mm, acetonitrile/0.077% NH$_4$OAc in water, operation temperature: 64° C.; Detector: 210 nm)].

Example 6

[(R)-2-(N,N-Diethylamino)ethylthio-Sar]-3-[(γ-Methylthio)methoxy-NMeLeu]-4-cyclosporin

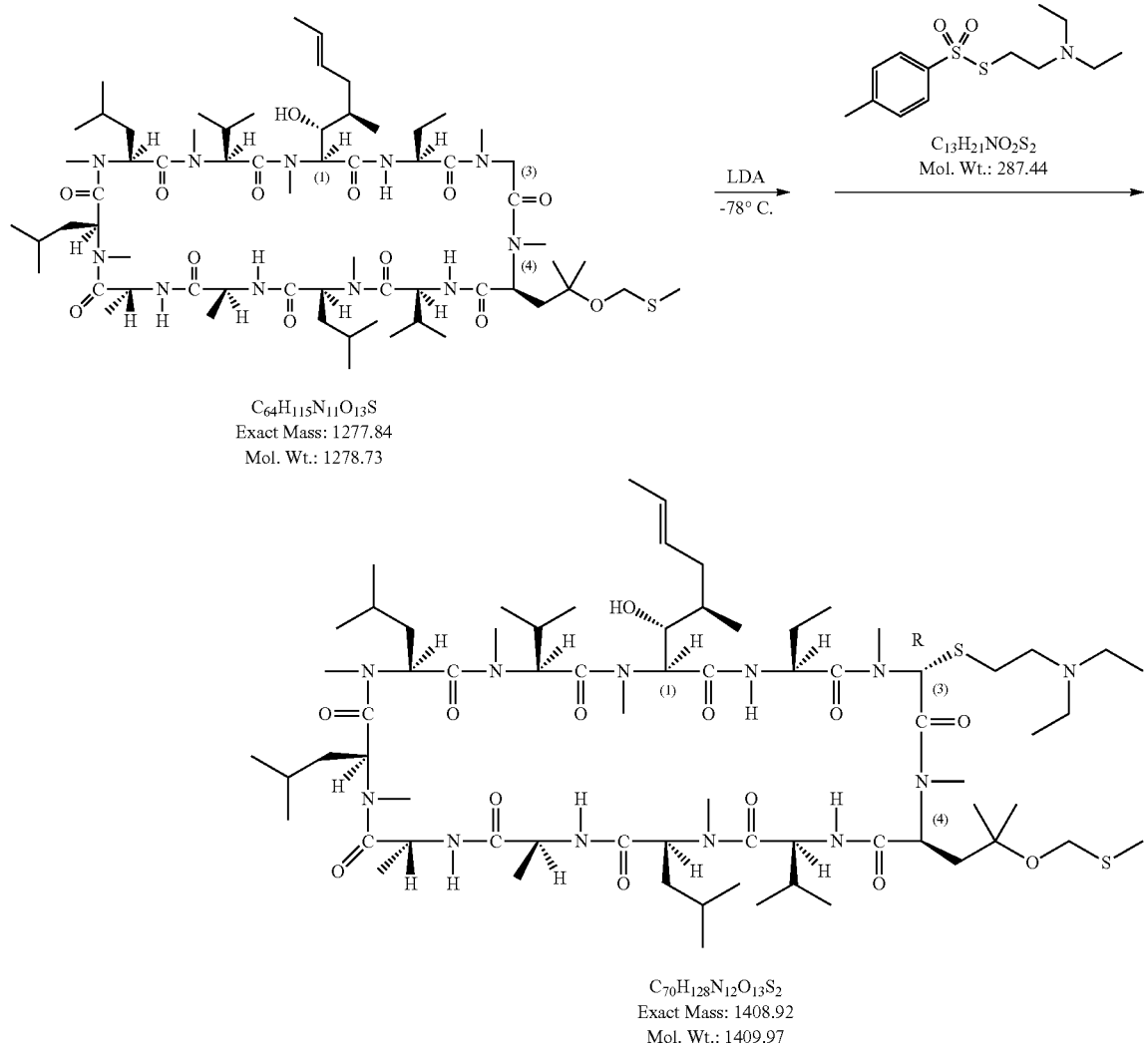

n-Butyllithium (2.87 M, 10.0 mmol, 3.48 ml, 10 equiv) was added into the solution of diisopropylamine (FW 101.19, d 0.722, 1.40 ml, 10.0 mmol, 10 equiv) in 40 ml of THF under nitrogen at −78° C. over 30 minutes, and the resulting LDA solution was stirred for one hour at −78° C. A solution of [(γ-Methylthio)methoxy-NMeLeu]-4-cyclosporin (FW 1278.73, 1.28 g, 1.0 mmol) in 10 ml of THF was dropwise added over 5 minutes below −65° C. After the mixture was stirred for 2 hours at −78° C., p-toluene sulphonic acid (2-N,N-diethylamino) ethylthioester (FW 287.44, 0.98 g, 3.4 mmol) in 5 ml of THF was added over 5 minutes at −70° C. The reaction mixture was stirred for 3 hours at −78° C., and then was allowed to warm to room temperature and stirred for another two hours. The pH of the reaction mixture was adjusted to 7 by adding citric acid solution, and then the most of THF was evaporated under reduced pressure. Then 50 ml of ethyl acetate and 30 ml of water were added and separated. The aqueous layer was extracted with ethyl acetate (3×50 mL). The organic layers were combined, washed with brine, dried over $MgSO_4$, filtered, and evaporated under vacuum. The residue was subjected to chromatography on silica gel using ethyl acetate/methanol (5/1) to give the product [Molecular formula: $C_{70}H_{128}N_{12}O_{13}S_2$; Exact Mass: 1408.92; MS (m/z): 1409.90 $(M+H)^+$; TLC $R_f$: 0.27 (DCM/MeOH=10/1.5); HPLC RT: 24.06 minutes (C8 reverse phase column, 250 mm, acetonitrile/0.077% $NH_4OAc$ in water, operation temperature: 64° C.; Detector: 210 nm)].

p-Toluene sulphonic acid (3-N,N-diethylamino)ethylthioester was prepared by the following procedure.

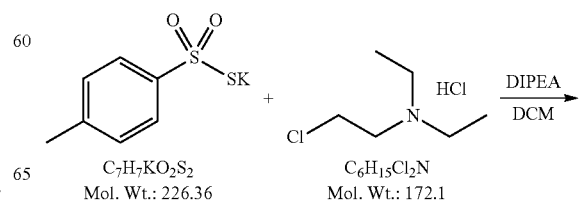

91

-continued

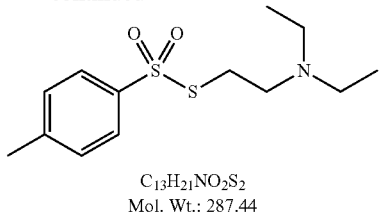

C₁₃H₂₁NO₂S₂
Mol. Wt.: 287.44

2-Chloro-N,N-diethylethanamine hydrochloride (15. 22 g, 88.44 mmol) was dissolved in 333 ml H₂O. p-Toluenethiosulfonic acid potassium salt (20.00 g, 88.35 mmol),

92

KOH (4.96 g, 88.50 mmol) and 220 ml of DCM were added. The reaction mixture was stirred at room temperature for 48 hours. The organic phase was separated, and the aqueous layer was extracted with DCM (100 ml×3). The combined DCM layers were washed with saturated NaHCO₃ solution, brine and dried over MgSO₄. The solvent was evaporated under vacuum to give 22.80 g product.

Example 7

[(γ-Ethoxy)methoxy-NMeLeu]-4-cyclosporin

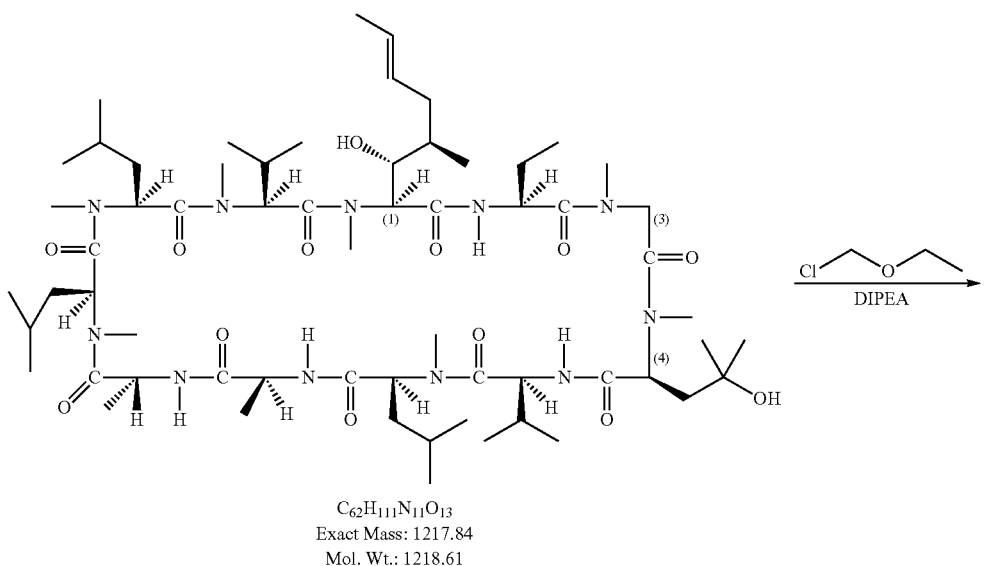

C₆₂H₁₁₁N₁₁O₁₃
Exact Mass: 1217.84
Mol. Wt.: 1218.61

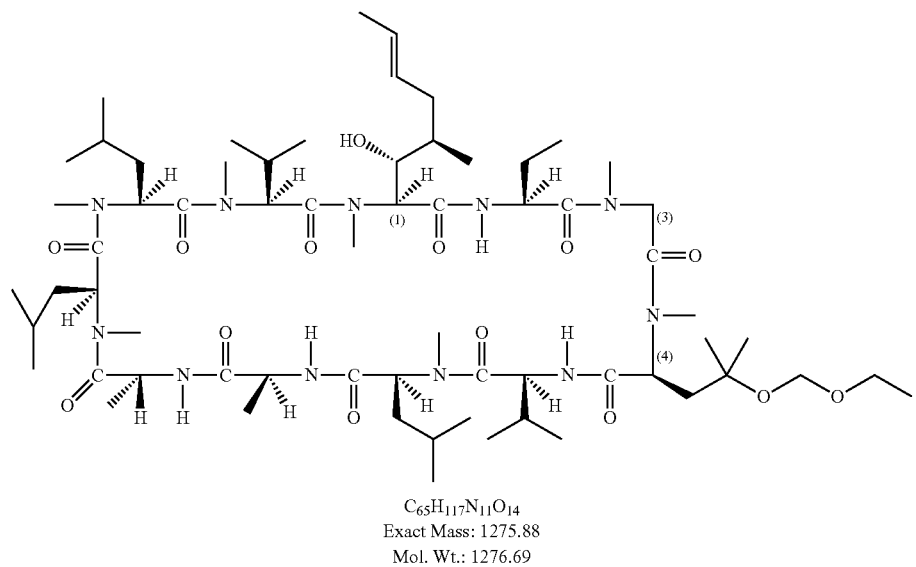

C₆₅H₁₁₇N₁₁O₁₄
Exact Mass: 1275.88
Mol. Wt.: 1276.69

To a solution of [(γ-Hydroxy)-NMeLeu]-4-cyclosporin (FW 1218.61, 1.2 g, 1 mmol) in 80 ml of dichloromethane was added DIPEA (FW 129.25, d 0.742, 1.32 ml, 0.98 g, 7.60 mmol), followed by addition of chloromethyl ethyl ether (FW 94.54, d 1.019, 2.32 ml, 2.27 g, 24 mmol) dropwise. The mixture was stirred overnight and TLC was used to monitor the completion of the reaction. The reaction mixture was washed with 1N HCl, saturated NaHCO$_3$ water solution, brine, and dried over MgSO$_4$. Removal of solvent afforded a yellowish oil, which was further purified by flash chromatography using dichloromethane/methanol to give the product [Molecular formula: C$_{65}$H$_{117}$N$_{11}$O$_{14}$; Exact Mass: 1275.88; MS (m/z): 1276.70 (M+H)$^+$, 1298.70 (M+Na)$^+$; TLC R$_f$: 0.37 (EtOAc)].

Example 8

[(R)-3-(N-Morphlino)propylthio-Sar]-3-[(γ-Ethoxy)methoxy-NMeLeu]-4-cyclosporin

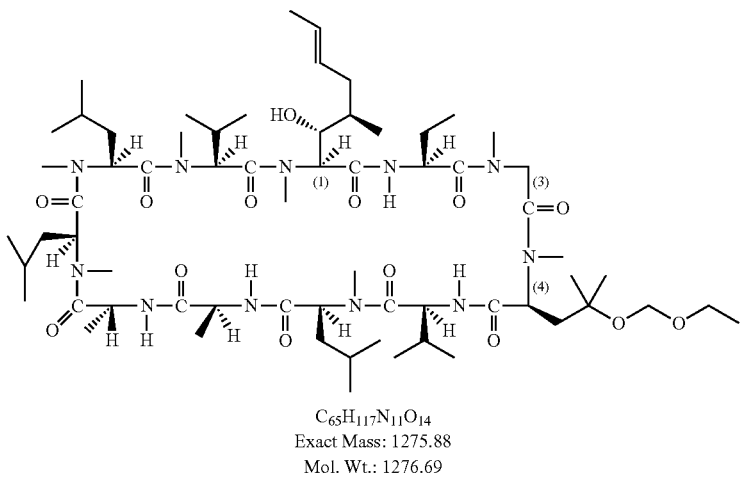

C$_{65}$H$_{117}$N$_{11}$O$_{14}$
Exact Mass: 1275.88
Mol. Wt.: 1276.69

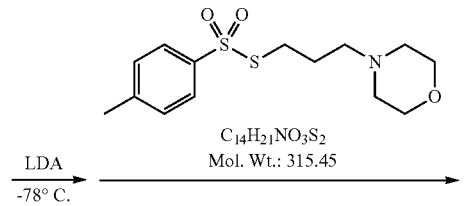

C$_{14}$H$_{21}$NO$_3$S$_2$
Mol. Wt.: 315.45

LDA
-78° C.

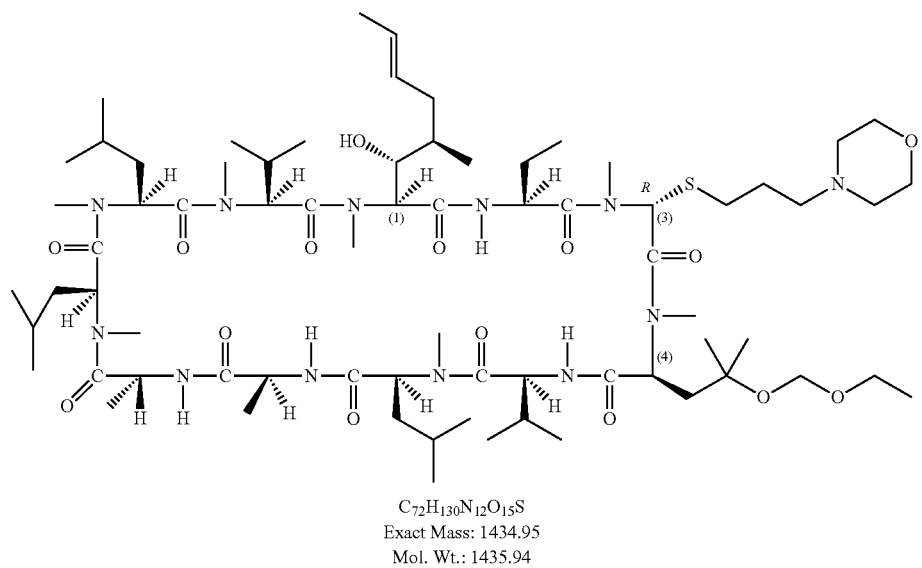

C$_{72}$H$_{130}$N$_{12}$O$_{15}$S
Exact Mass: 1434.95
Mol. Wt.: 1435.94

According to the method of example 6, [(R)-3-(Morphlino)propylthio-Sar]-3-[(γ-Ethoxy)methoxy-NMeLeu]-4-cyclosporin was prepared. Molecular formula: C$_{72}$H$_{130}$N$_{12}$O$_{15}$S; Exact Mass: 1434.95; MS (m/z): 1435.70 (M+H)$^+$; TLC R$_f$: 0.45 (EtOAc/MeOH=10/1); HPLC RT: 24.23 minutes (C8 reverse phase column, 250 mm, acetonitrile/0.077% NH$_4$OAc in water, operation temperature: 64° C.; Detector: 210 nm).

Example 9

[(γ-Methoxy)-NMeLeu]-4-dihydrocyclosporin

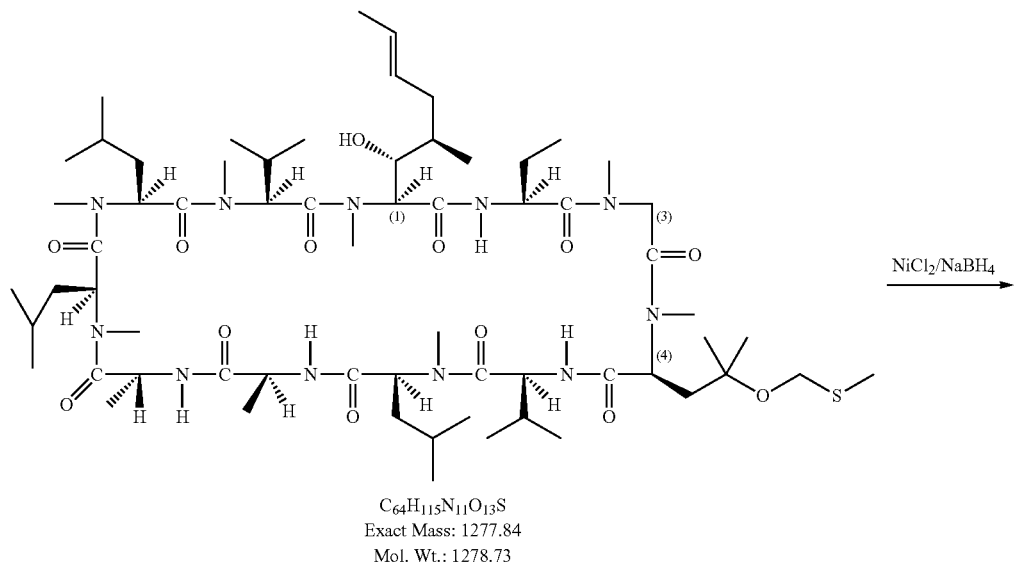

To a suspension of [(γ-Methylthio)methoxy-NMeLeu]-4-cyclosporin (FW 1278.73, 2.5 g, 2 mmol) and $NiCl_2 \cdot 6H_2O$ (FW 237.71, 10.6 g, 45 mmol) in 130 ml of methanol was added $NaBH_4$ (FW 37.83, 5.0 g, 131 mmol) in portions over 20 min under an ice-water cooling bath. After finishing addition, the cooling bath was removed and the mixture was continued to stir at room temperature for 2 hours. The black mixture was filtered through celite pad, and the filter cake was washed with methanol. The filtrate was evaporated under vacuum. The residue was diluted with DCM. The resulting solution was washed with aqueous citric acid to PH~7, brine, dried over $MgSO_4$ and filtered. After concentration under vacuum, the residue was purified by chromatography by eluant of DCM/MeOH (97.5:2.5) to give the product [Molecular formula: $C_{63}H_{115}N_{11}O_{13}$; Exact Mass: 1233.87; MS (m/z): 1234.90 $(M+H)^+$; TLC $R_f$: 0.46 (DCM/MeOH=95/5); HPLC RT: 22.59 minutes (C8 reverse phase column, 250 mm, acetonitrile/0.077% $NH_4OAc$ in water, operation temperature: 64° C.; Detector: 210 nm)].

Example 10

[(R)-3-(N-Morphlino)propylthio-Sar]-3-[(γ-Methoxy)-NMeLeu]-4-Dihydrocyclosporin

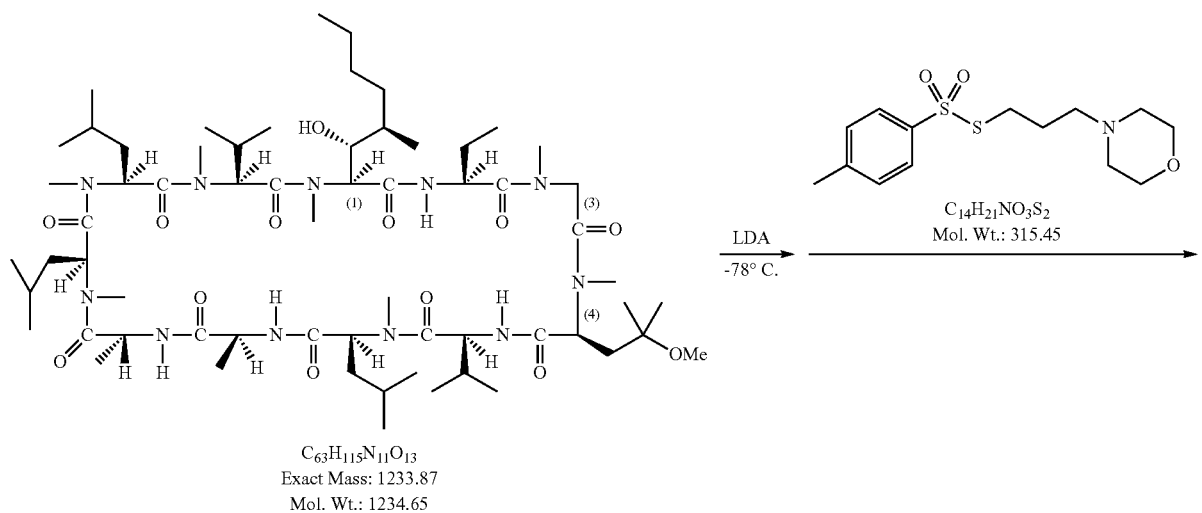

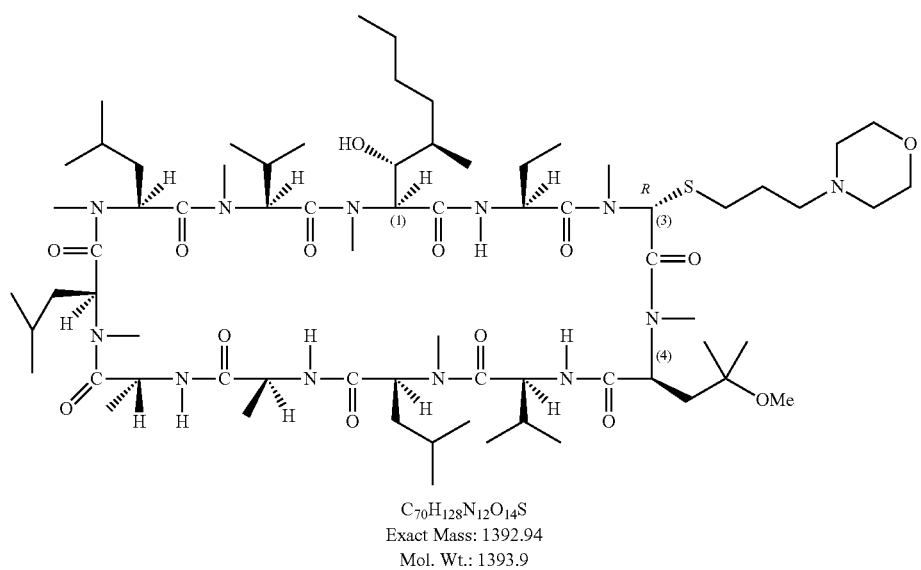

[(R)-3-(N-Morphlino)propylthio-Sar]-3-[(γ-Methoxy)-NMeLeu]-4-dihydrocyclosporin was prepared according to the method described in Example 6. Molecular formula: $C_{70}H_{128}N_{12}O_{14}S$; Exact Mass: 1392.94; MS (m/z): 1393.90 (M+H)$^+$; TLC$_{Rf}$: 0.41 (DCM/MeOH=95/5); HPLC RT: 21.96 minutes (C8 reverse phase column, 250 mm, acetonitrile/0.077% $NH_4OAc$ in water, operation temperature: 64° C.; Detector: 210 nm).

Example 11

[(γ-Methoxy)-NMeLeu]-4-cyclosporin

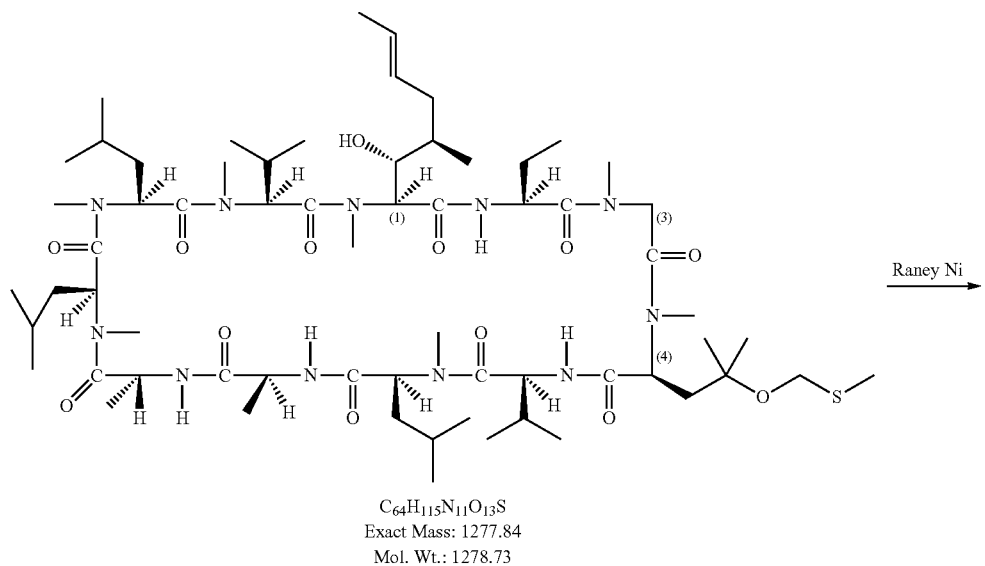

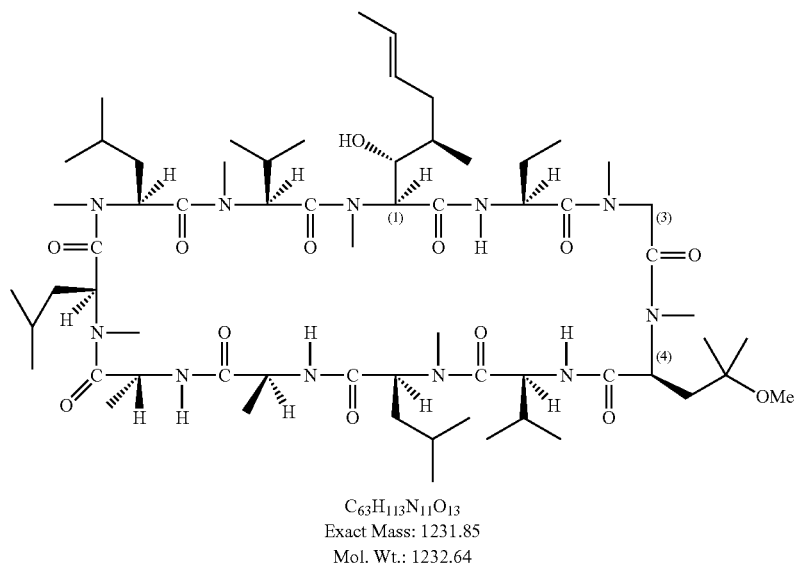

To a solution of [(γ-Methylthio)methoxy-NMeLeu]-4-cyclosporin (FW 1278.73, 1.2 g, 0.94 mmol) in 40 ml of anhydrous THF was added Raney Ni (~2 g). The resulting suspension was heated at 60° C. for 30 minutes and the reaction was monitored by LC-MS. The reaction mixture was filtered and the filter cake was washed with THF. The filtrate was evaporated under vacuum. The residue was purified by chromatography using eluant of EtOAc/MeOH (97.5/2.5) to give product [Molecular formula: $C_{63}H_{113}N_{11}O_{13}$; Exact Mass: 1231.85; MS (m/z): 1232.70 (M+H)$^+$; TLC $R_f$: 0.46 (DCM/MeOH=95/5); HPLC RT: 20.63 minutes (C8 reverse phase column, 250 mm, acetonitrile/0.077% NH$_4$OAc in water, operation temperature: 64° C.; Detector: 210 nm)].

Example 12

[(R)-3-(N-Morphlino)propylthio-Sar]-3-[(γ-Methoxy)-NMeLeu]-4-cyclosporin

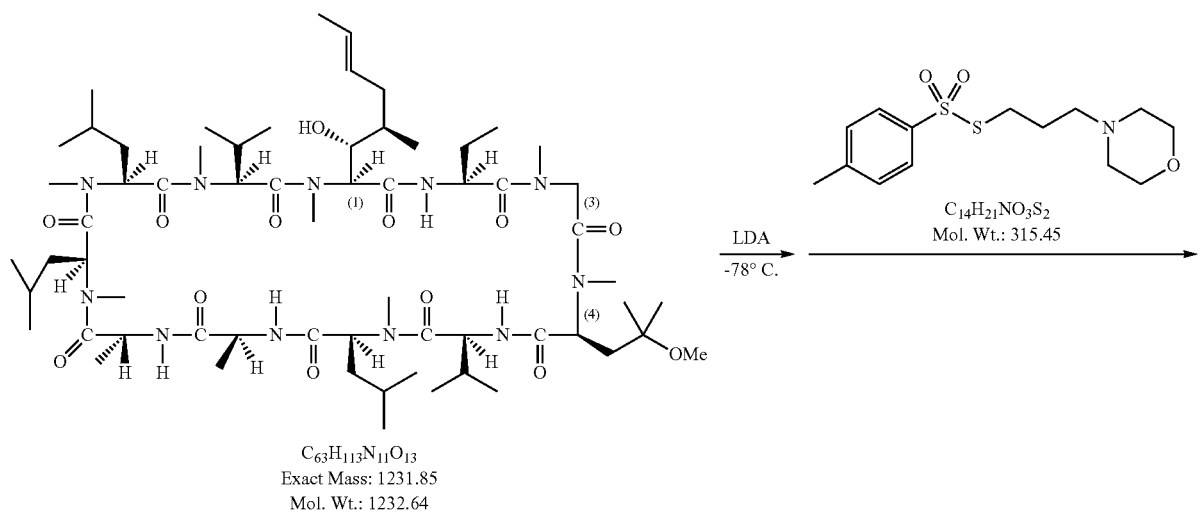

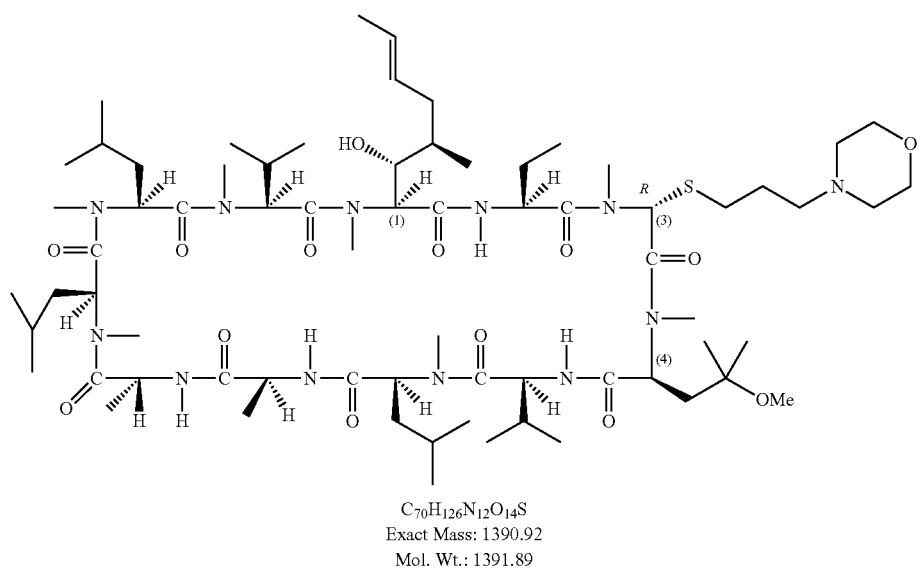

[(R)-3-(N-Morphlino)propylthio-Sar]-3-[(γ-Methoxy)-NMeLeu]-4-cyclosporin was prepared according to the method described in Example 6. Molecular formula: $C_{70}H_{126}N_{12}O_{14}S$; Exact Mass: 1390.92; MS (m/z): 1391.80 $(M+H)^+$; TLC $R_f$: 0.42 (DCM/MeOH=95/5); HPLC RT: 22.93 minutes (C8 reverse phase column, 250 mm, acetonitrile/0.077% $NH_4OAc$ in water, operation temperature: 64° C.; Detector: 210 nm).

Example 13

[(R)-3-(N-Pyrrolidinyl)propylthio-Sar]-3-[(γ-Methoxy)-NMeLeu]-4-cyclosporin

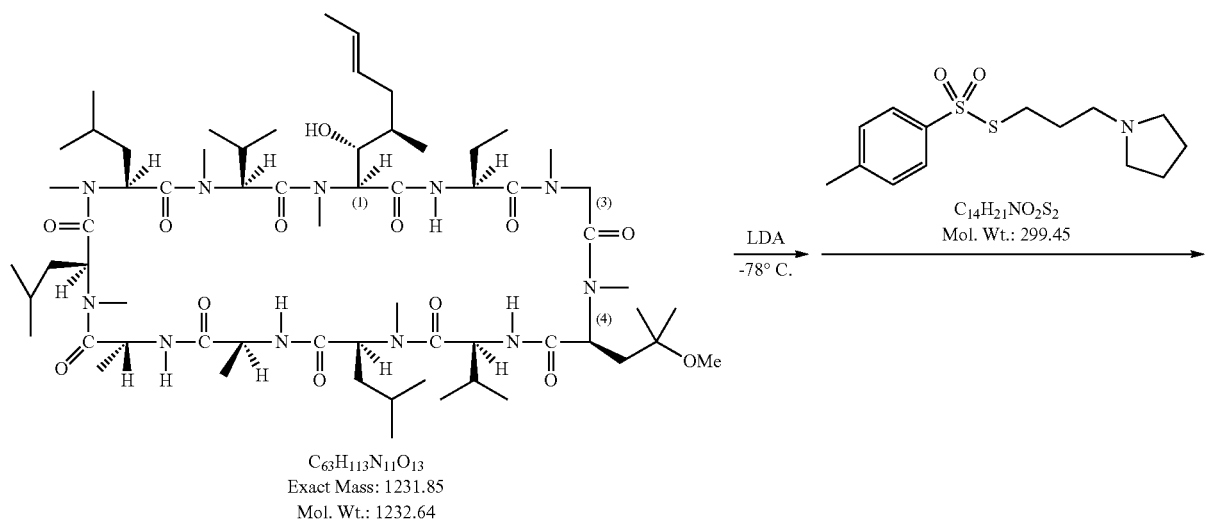

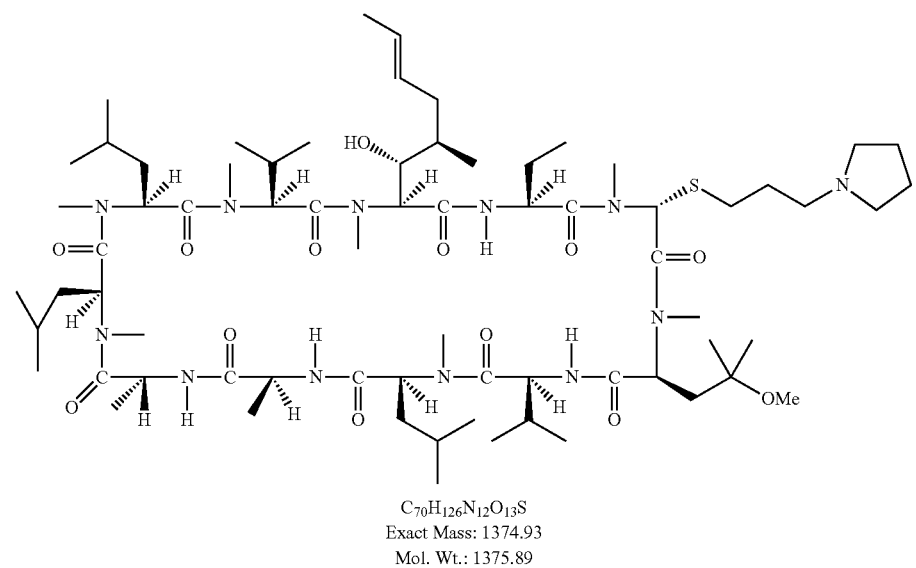

[(R)-3-(N-Pyrrolidinyl)propylthio-Sar]-3-[(γ-Methoxy)-NMeLeu]-4-cyclosporin was prepared according to the method described in Example 6. Molecular formula: $C_{70}H_{126}N_{12}O_{13}S$; Exact Mass: 1374.93; MS (m/z): 1375.57 (M+H)$^+$, 1397.70 (M+Na)$^+$; TLC $R_f$: 0.24 (DCM/MeOH=9/1); HPLC RT: 13.3 minutes (C8 reverse phase column, 250 mm, acetonitrile/0.05% TFA in water, operation temperature: 64° C.; Detector: 210 nm).

Example 14

[(R)-3-(N,N-Diethylamino)propylthio-Sar]-3-[(γ-Methoxy)-NMeLeu]-4-cyclosporin

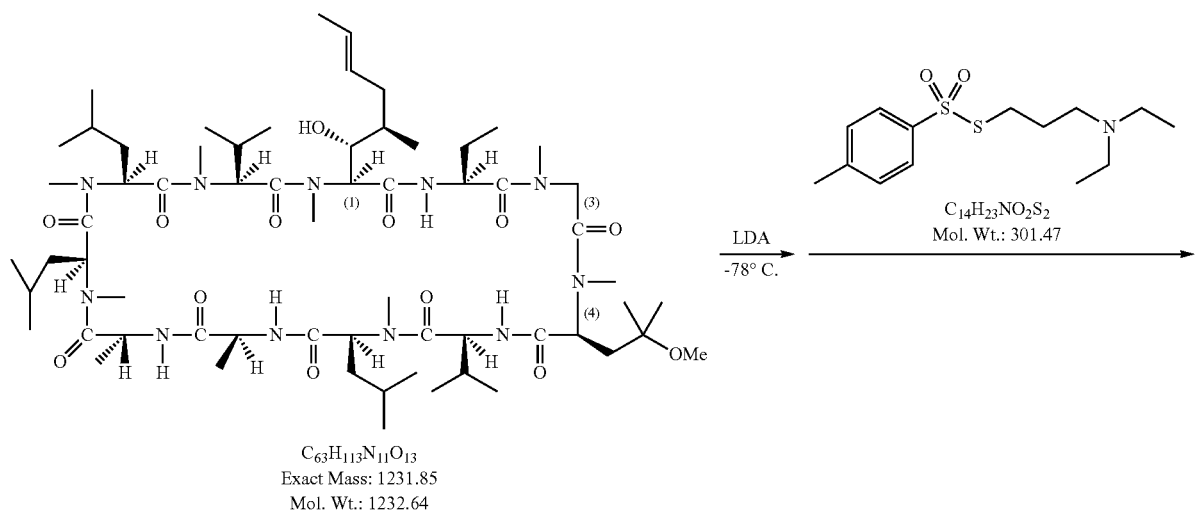

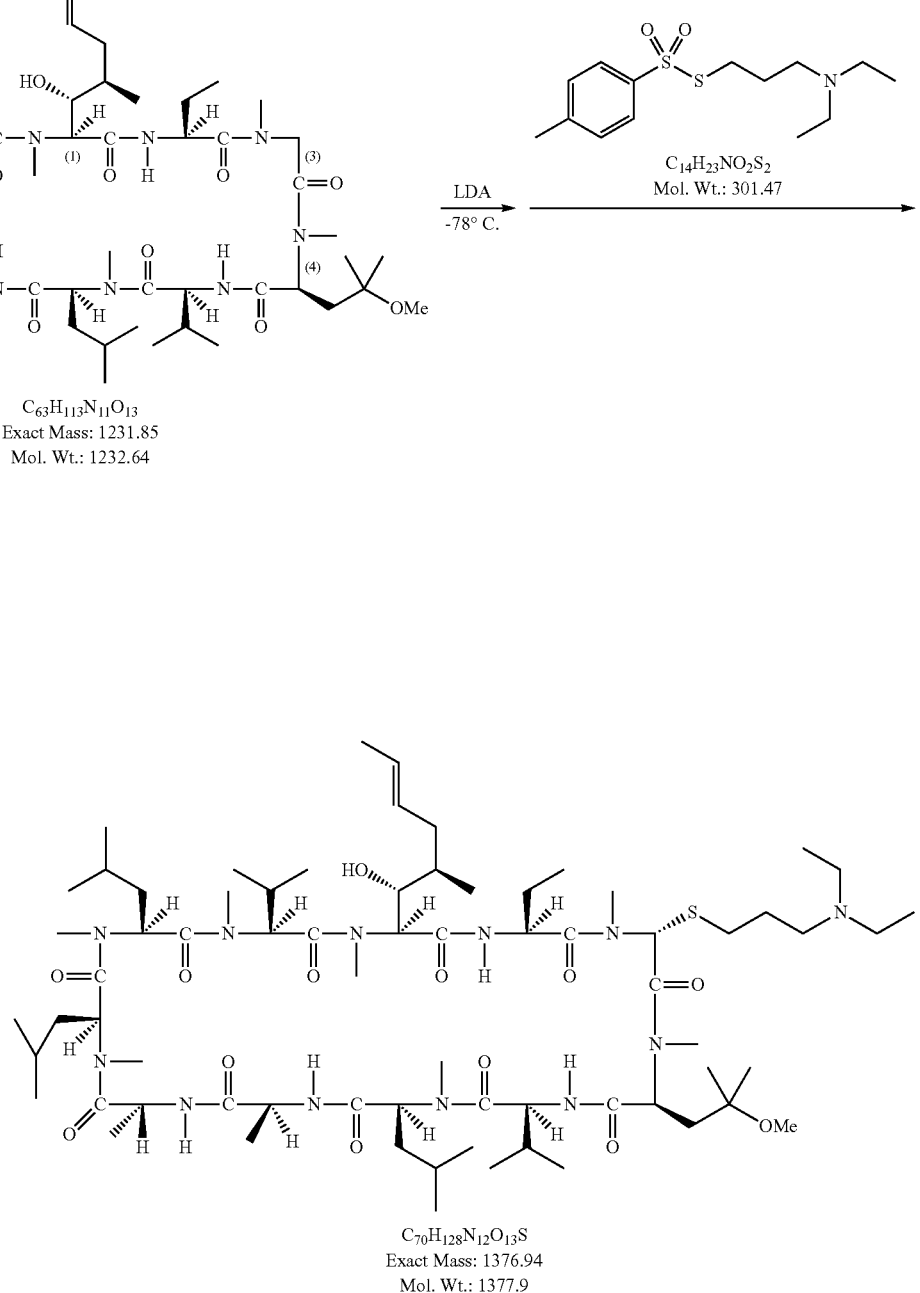

[(R)-3-(N,N-Diethylamino)propylthio-Sar]-3-[(γ-Methoxy)-NMeLeu]-4-cyclosporin was prepared according to the method described in Example 6. Molecular formula: $C_{70}H_{128}N_{12}O_{13}S$; Exact Mass: 1376.94; MS (m/z): 1377.66 (M+H)$^+$; TLC $R_f$: 0.44 (DCM/MeOH=95/5); HPLC RT: 19.00 minutes (C8 reverse phase column, 250 mm, acetonitrile/0.077% NH$_4$OAc in water, operation temperature: 64° C.; Detector: 210 nm).

Example 15

[(R)-3-(N,N-Dimethylamino)propylthio-Sar]-3-[(γ-Methoxy)-NMeLeu]-4-cyclosporin

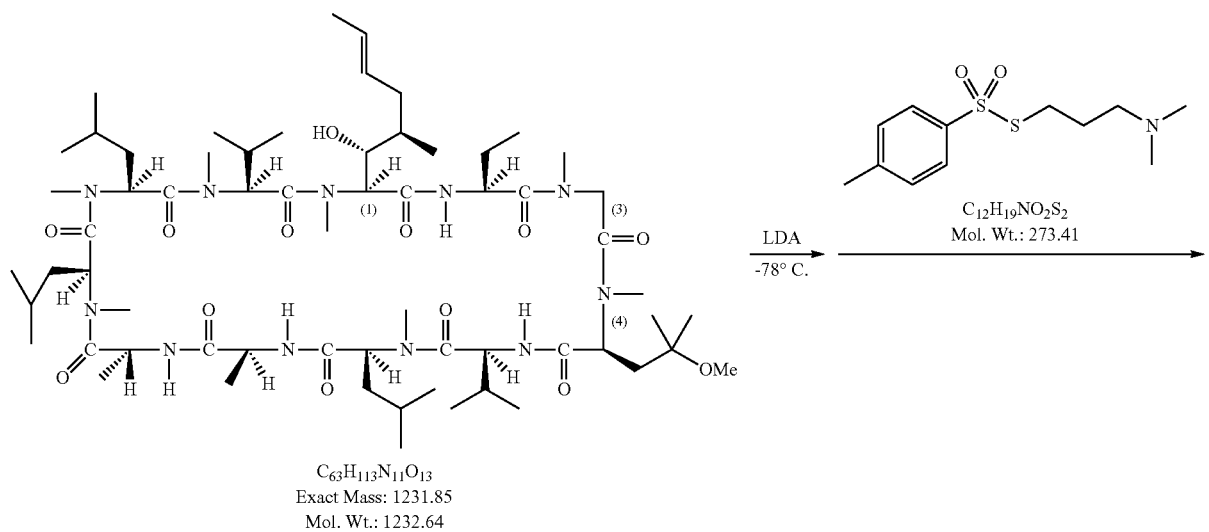

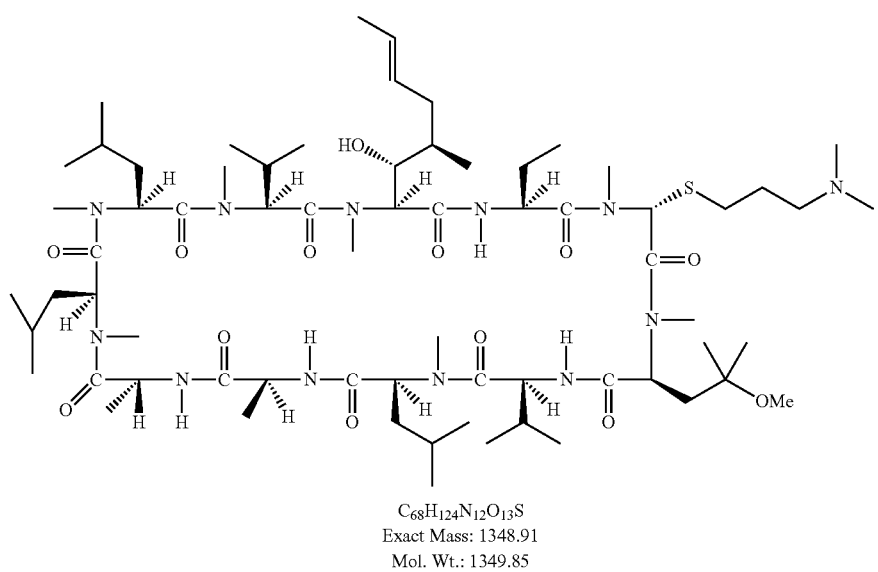

[(R)-3-(N,N-Dimethylamino)propylthio-Sar]-3-[(γ-Methoxy)-NMeLeu]-4-cyclosporin was prepared according to the method described in Example 6. Molecular formula: $C_{68}H_{124}N_{12}O_{13}S$; Exact Mass: 1348.91; MS (m/z): 1349.75 (M+H)$^+$; TLC $R_f$: 0.38 (DCM/MeOH=95/5); HPLC RT: 18.33 minutes (C8 reverse phase column, 250 mm, acetonitrile/0.077% NH$_4$OAc in water, operation temperature: 64° C.; Detector: 210 nm).

Example 16

[(R)-3-(N-iso-Propyl-N-ethylamino)propylthio-Sar]-3-[(γ-Methoxy)-NMeLeu]-4-cyclosporin

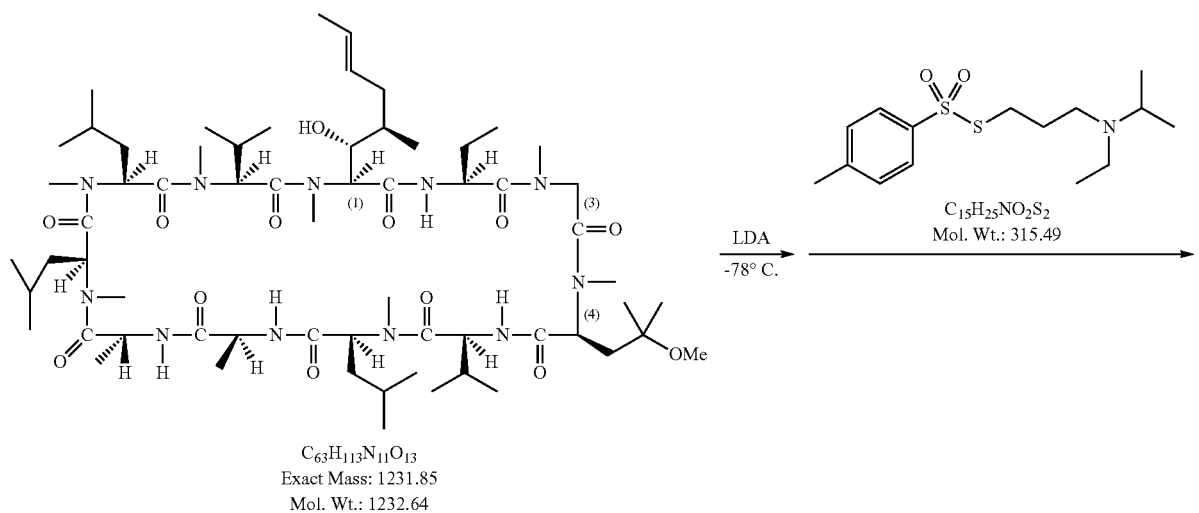

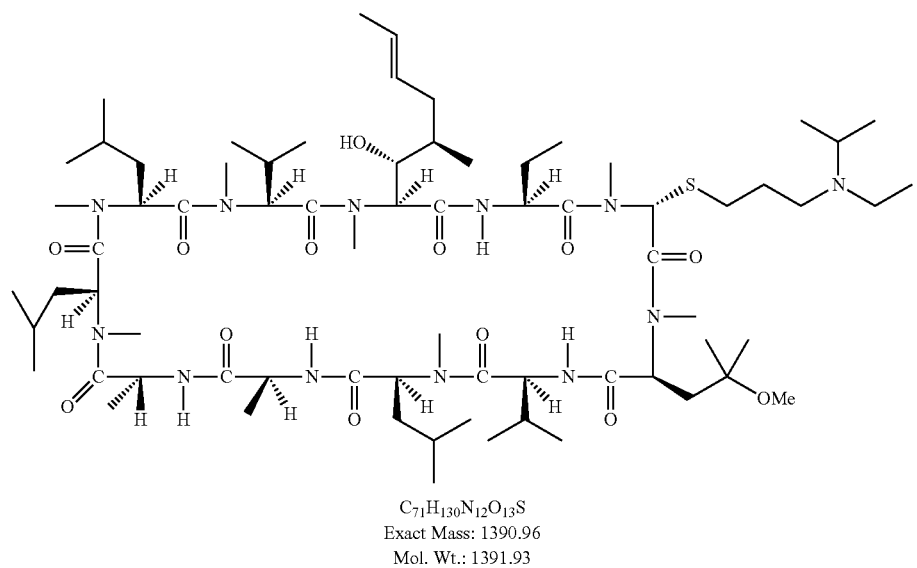

[(R)-3-(N-iso-Propyl-N-ethylamino)propylthio-Sar]-3-[(γ-Methoxy)-NMeLeu]-4-cyclosporin was prepared according to the method described in Example 6. Molecular formula: $C_{71}H_{130}N_{12}O_{13}S$; Exact Mass: 1390.96; MS (m/z): 1391.72 (M+H)$^+$, 1413.81 (M+Na)$^+$; TLC $R_f$: 0.36 (DCM/MeOH=9/1); HPLC RT: 14.0 minutes (C8 reverse phase column, 250 mm, acetonitrile/0.05% TFA in water, operation temperature: 64° C.; Detector: 210 nm).

Example 17

[(R)-3-(N-Piperidinyl)propylthio-Sar]-3-[(γ-Methoxy)-NMeLeu]-4-cyclosporin

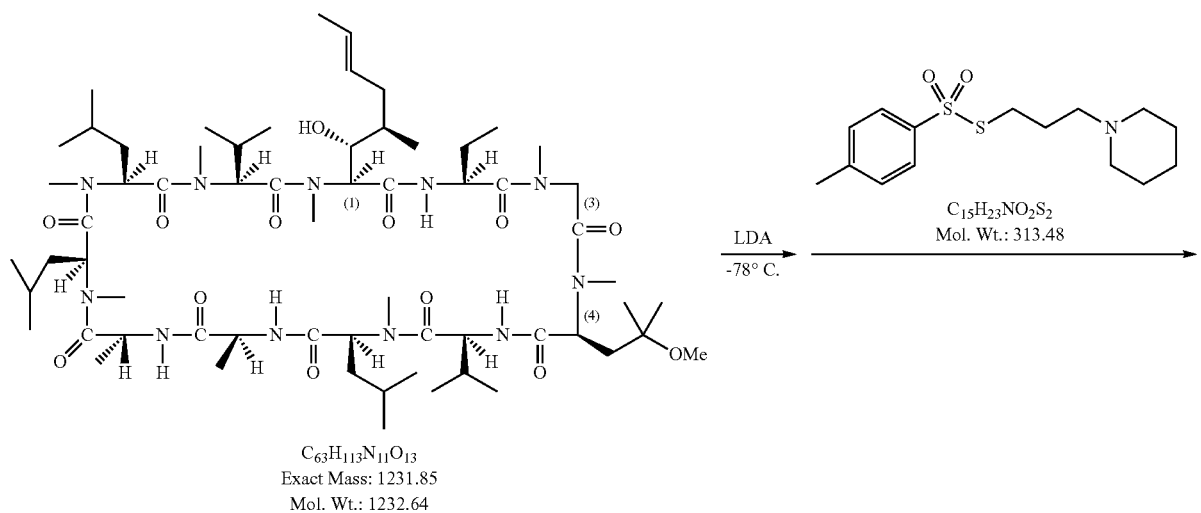

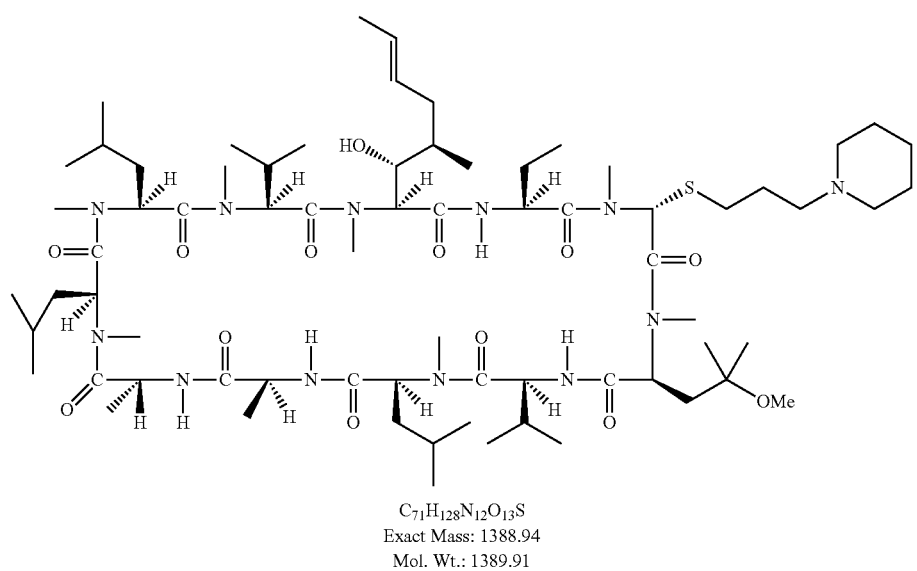

[(R)-3-(N-Piperidinyl)propylthio-Sar]-3-[(γ-Methoxy)-NMeLeu]-4-cyclosporin was prepared according to the method described in Example 6. Molecular formula: $C_{71}H_{128}N_{12}O_{13}S$; Exact Mass: 1388.94; MS (m/z): 1389.78 (M+H)$^+$, 1411.82 (M+Na)$^+$; TLC $R_f$: 0.30 (DCM/MeOH=9/1); HPLC RT: 13.8 minutes (C8 reverse phase column, 250 mm, acetonitrile/0.05% TFA in water, operation temperature: 64° C.; Detector: 210 nm).

Example 18

[(R)-2-(N,N-Diethylamino)ethylthio-Sar]-3-[(γ-Methoxy)-NMeLeu]-4-cyclosporin

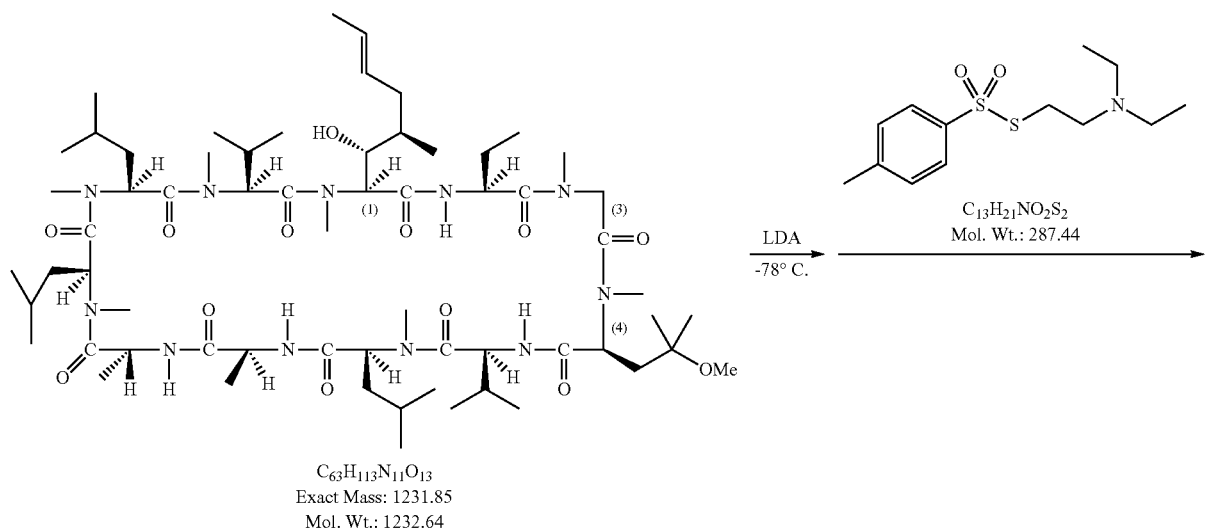

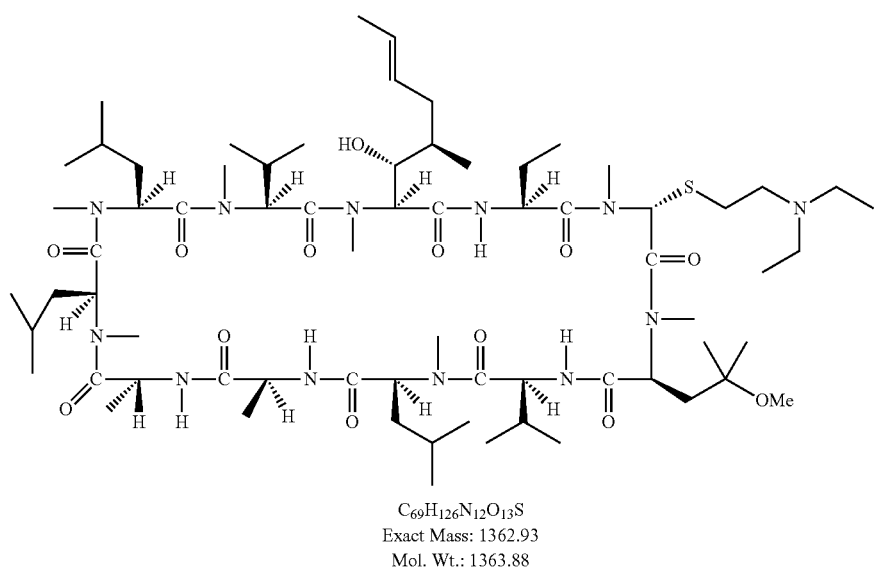

[(R)-2-(N,N-Diethylamino)ethylthio-Sar]-3-[(γ-Methoxy)-NMeLeu]-4-cyclosporin was prepared according to the method described in Example 6. Molecular formula: $C_{69}H_{126}N_{12}O_{13}S$; Exact Mass: 1362.93; MS (m/z): 1363.81 (M+H)$^+$, 1385.94 (M+Na)$^+$; TLC R$_f$: 0.38 (DCM/MeOH=9/1); HPLC RT: 13.2 minutes (C8 reverse phase column, 250 mm, acetonitrile/0.05% TFA in water, operation temperature: 64° C.; Detector: 210 nm).

Example 19

[(R)-2-(N-Morpholino)ethylthio-Sar]-3-[(γ-Methoxy)-NMeLeu]-4-cyclosporin

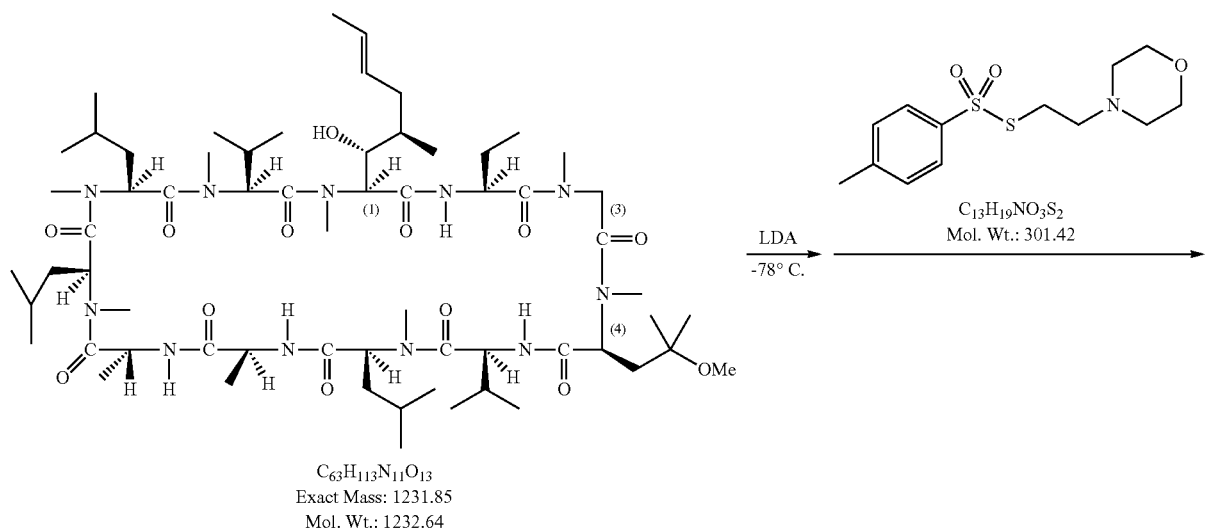

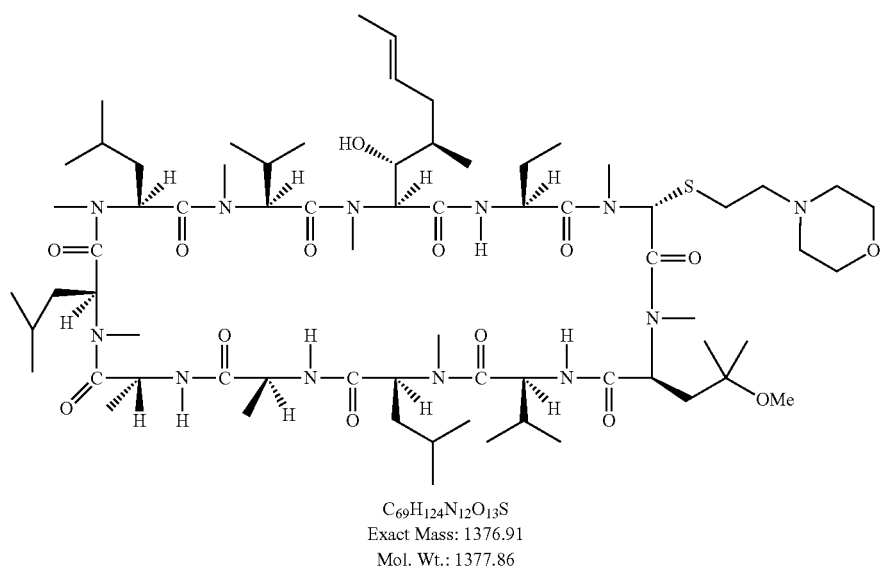

[(R)-2-(N-Morpholino)ethylthio-Sar]-3-[(γ-Methoxy)-NMeLeu]-4-cyclosporin was prepared according to the method described in Example 6. Molecular formula: $C_{69}H_{124}N_{12}O_{14}S$; Exact Mass: 1376.91; MS (m/z): 1377.76 $(M+H)^+$; TLC $R_f$: 0.46 (DCM/MeOH=95/5); HPLC RT: 15.06 minutes (C8 reverse phase column, 250 mm, acetonitrile/0.05% TFA in water, operation temperature: 64° C.; Detector: 210 nm).

Example 20

[(R)-2-(N-Piperidinyl)ethylthio-Sar]-3-[(γ-Methoxy)-NMeLeu]-4-cyclosporin

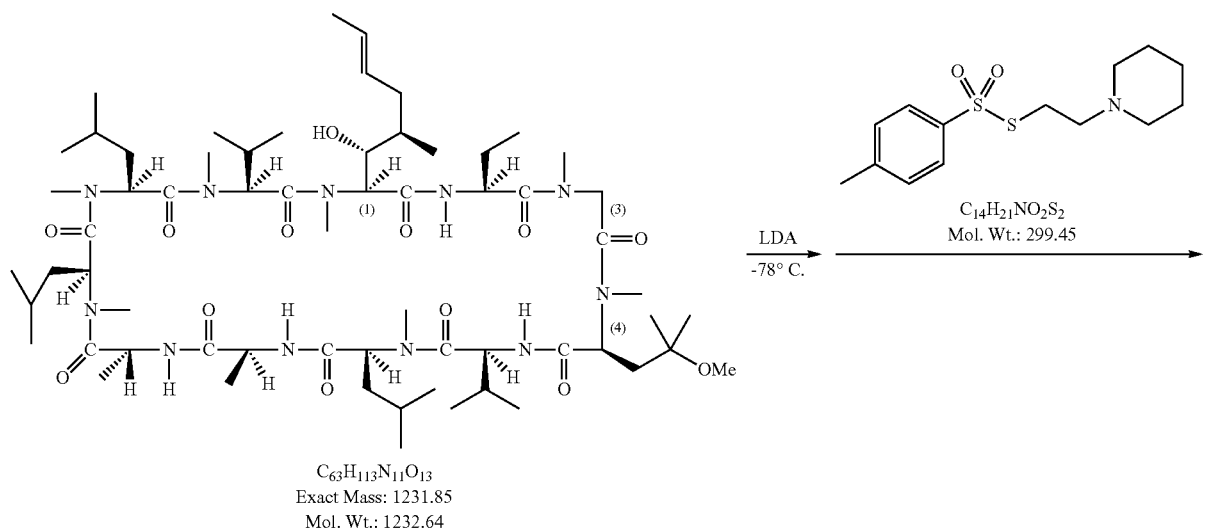

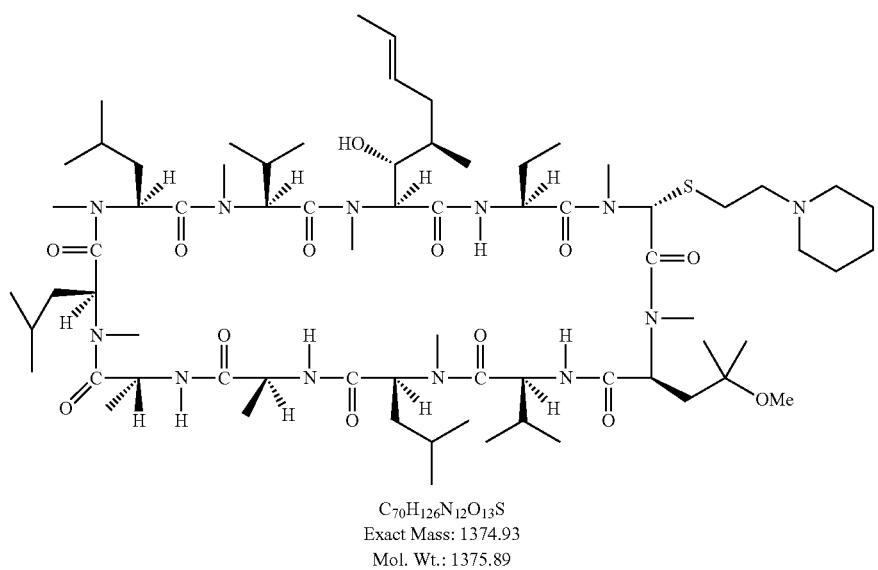

[(R)-2-(N-Piperidinyl)ethylthio-Sar]-3-[(γ-Methoxy)-NMeLeu]-4-cyclosporin was prepared according to the method described in Example 6. Molecular formula: $C_{70}H_{126}N_{12}O_{13}S$; Exact Mass: 1374.93; MS (m/z): 1375.82 (M+H)$^+$, 1397.82 (M+Na)$^+$; TLC $R_f$: 0.28 (DCM/MeOH=9/1); HPLC RT: 13.3 minutes (C8 reverse phase column, 250 mm, acetonitrile/0.05% TFA in water, operation temperature: 64° C.; Detector: 210 nm).

Example 21

[(R)-2-(N-Pyrrolidinyl)ethylthio-Sar]-3-[(γ-Methoxy)-NMeLeu]-4-cyclosporin

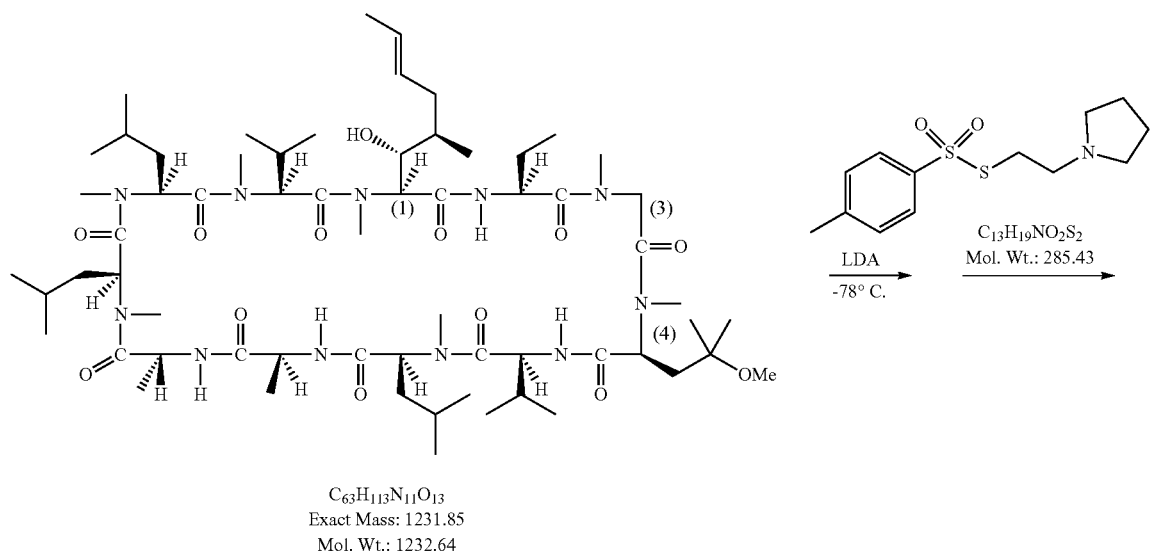

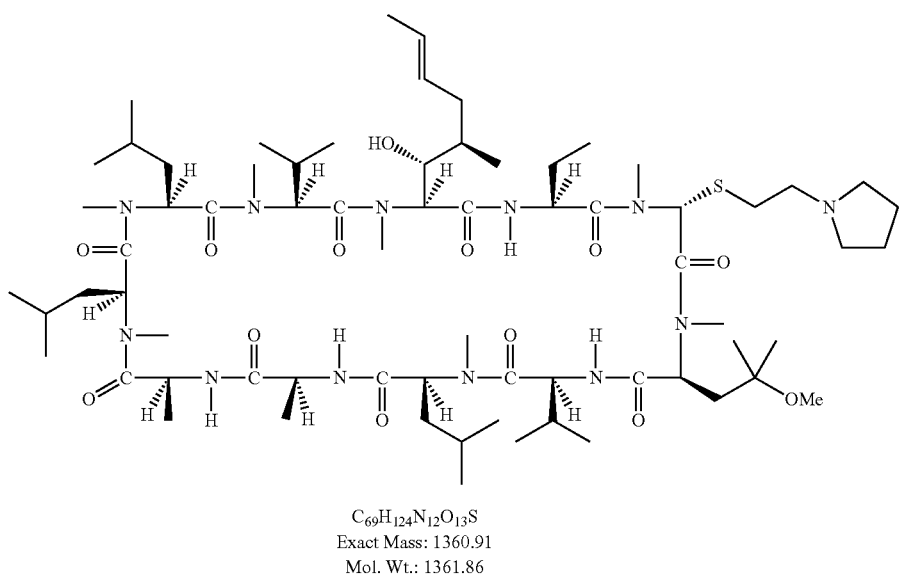

[(R)-2-(N-Pyrrolidinyl)ethylthio-Sar]-3-[(γ-Methoxy)-NMeLeu]-4-cyclosporin was prepared according to the method described in Example 6. Molecular formula: $C_{69}H_{124}N_{12}O_{13}S$; Exact Mass: 1360.91; MS (m/z): 1361.65 $(M+H)^+$, 1383.79 $(M+Na)^+$; TLC $R_f$: 0.27 (DCM/MeOH=9/1); HPLC RT: 12.8 minutes (C8 reverse phase column, 250 mm, acetonitrile/0.05% TFA in water, operation temperature: 64° C.; Detector: 210 nm).

Example 22

[(R)-2-(N,N-Dimethyl)ethylthio-Sar]-3-[(γ-Methoxy)-NMeLeu]-4-cyclosporin

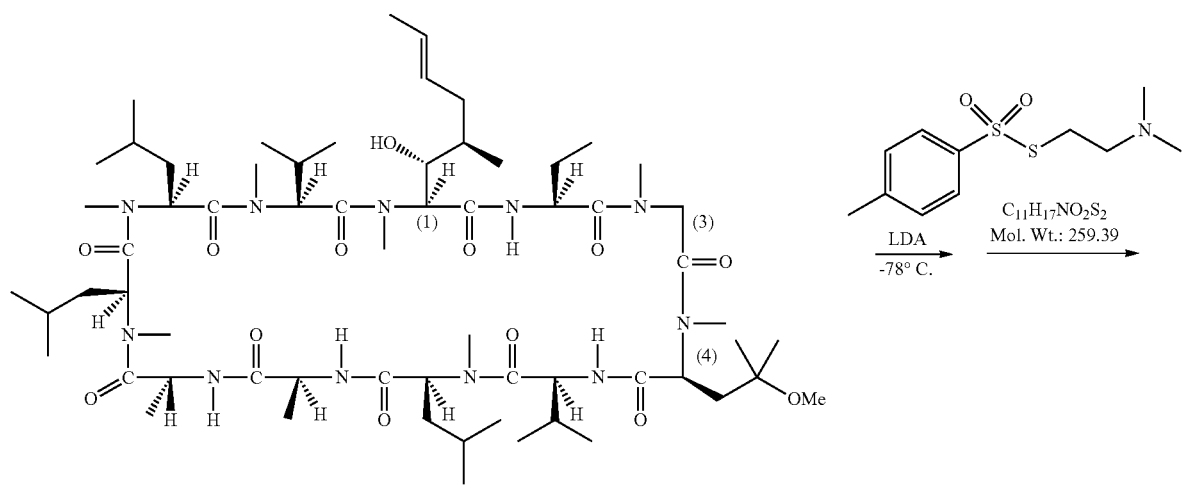

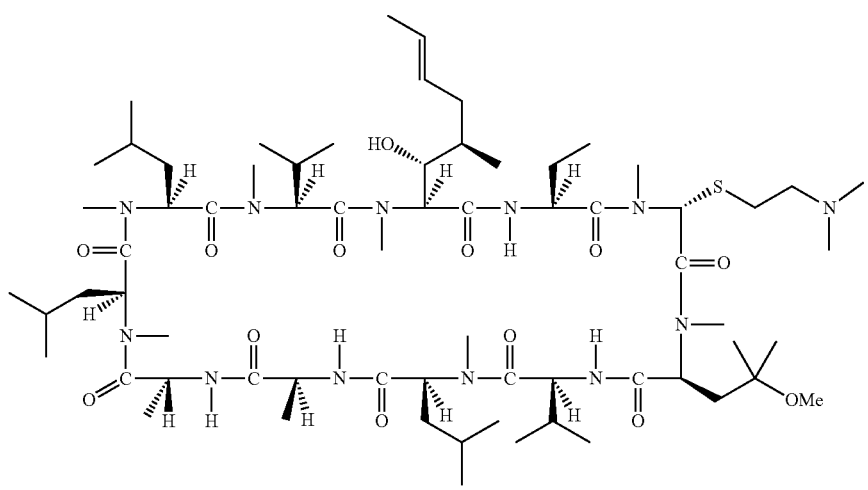

[(R)-2-(N,N-Dimethyl)ethylthio-Sar]-3-[(γ-Methoxy)-NMeLeu]-4-cyclosporin was prepared according to the method described in Example 6. Molecular formula: $C_{67}H_{122}N_{12}O_{13}S$; Exact Mass: 1334.90; MS (m/z): 1335.76 $(M+H)^+$, 1357.82 $(M+Na)^+$; TLC $R_f$: 0.21 (DCM/MeOH=9/1); HPLC RT: 12.1 minutes (C8 reverse phase column, 250 mm, acetonitrile/0.05% TFA in water, operation temperature: 64° C.; Detector: 210 nm).

Example 23

[(R)-2-(N-4-Methylpiperazinyl)ethylthio-Sar]-3-[(γ-Methoxy)-NMeLeu]-4-cyclosporin

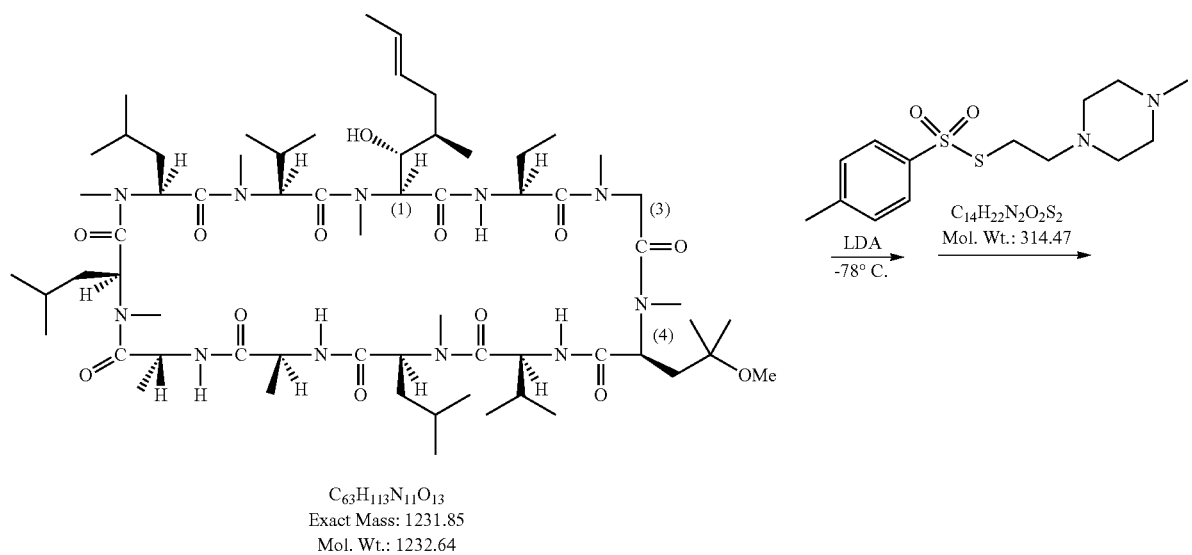

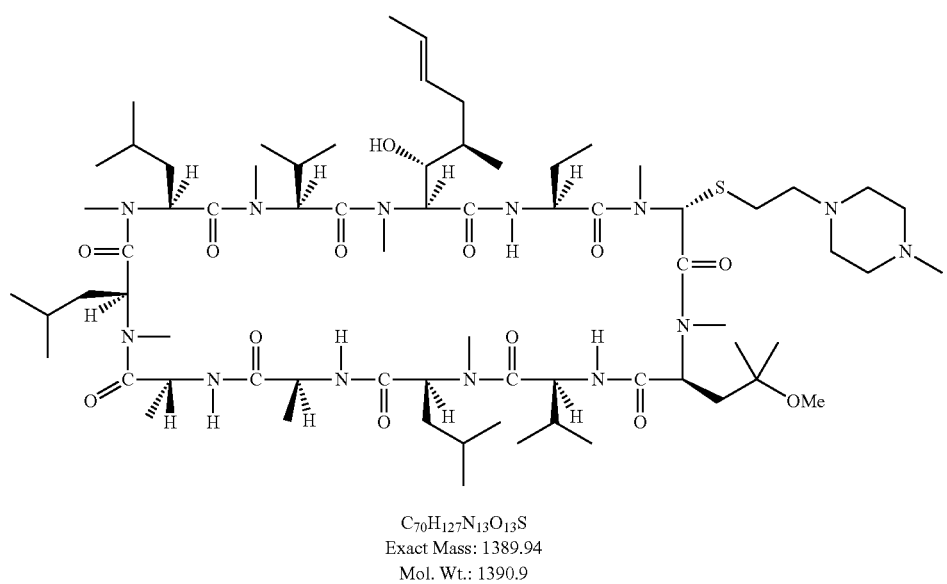

[(R)-2-(N-4-Methylpiperazinyl)ethylthio-Sar]-3-[(γ-Methoxy)-NMeLeu]-4-cyclosporin was prepared according to the method described in Example 6. Molecular formula: $C_{70}H_{127}N_{13}O_{13}S$; Exact Mass: 1389.94; MS (m/z): 1390.71 $(M+H)^+$, 1412.81 $(M+Na)^+$; TLC $R_f$: 0.23 (DCM/MeOH=9/1); HPLC RT: 12.3 minutes (C8 reverse phase column, 250 mm, acetonitrile/0.05% TFA in water, operation temperature: 64° C.; Detector: 210 nm).

Example 24

[(R)-2-(N-iso-Propyl-N-ethylamino)ethylthio-Sar]-3-[(γ-Methoxy)-NMeLeu]-4-cyclosporin

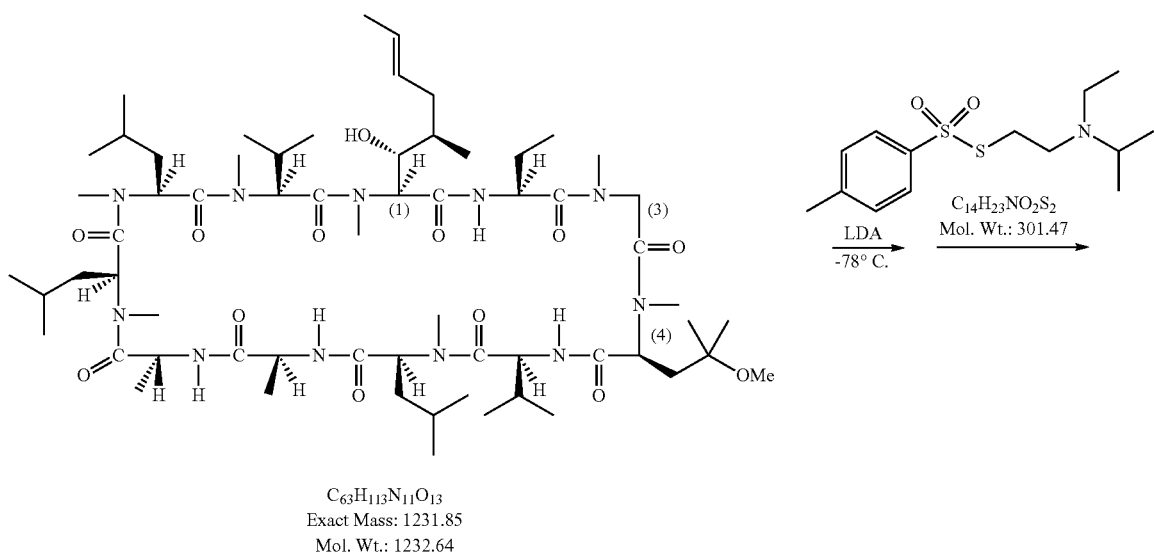

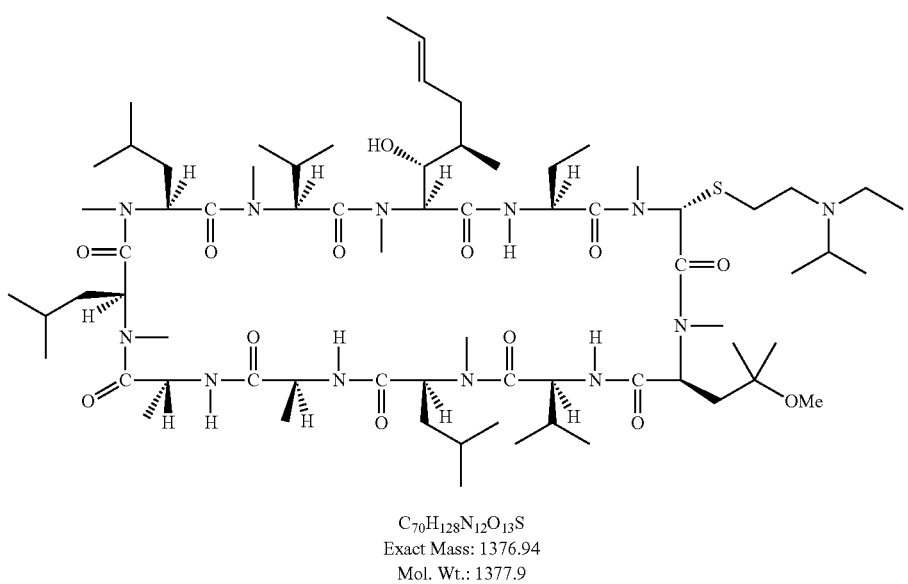

[(R)-2-(N-iso-Propyl-N-ethylamino)ethylthio-Sar]-3-[(γ-Methoxy)-NMeLeu]-4-cyclosporin was prepared according to the method described in Example 6. Molecular formula: $C_{70}H_{128}N_{12}O_{13}S$; Exact Mass: 1376.94; MS (m/z): 1377.67 $(M+H)^+$, 1399.81 $(M+Na)^+$; TLC $R_f$: 0.38 (DCM/MeOH=9/1); HPLC RT: 13.7 minutes (C8 reverse phase column, 250 mm, acetonitrile/0.05% TFA in water, operation temperature: 64° C.; Detector: 210 nm).

Example 25

[(γ-Allyloxy)-NMeLeu]-4-cyclosporin

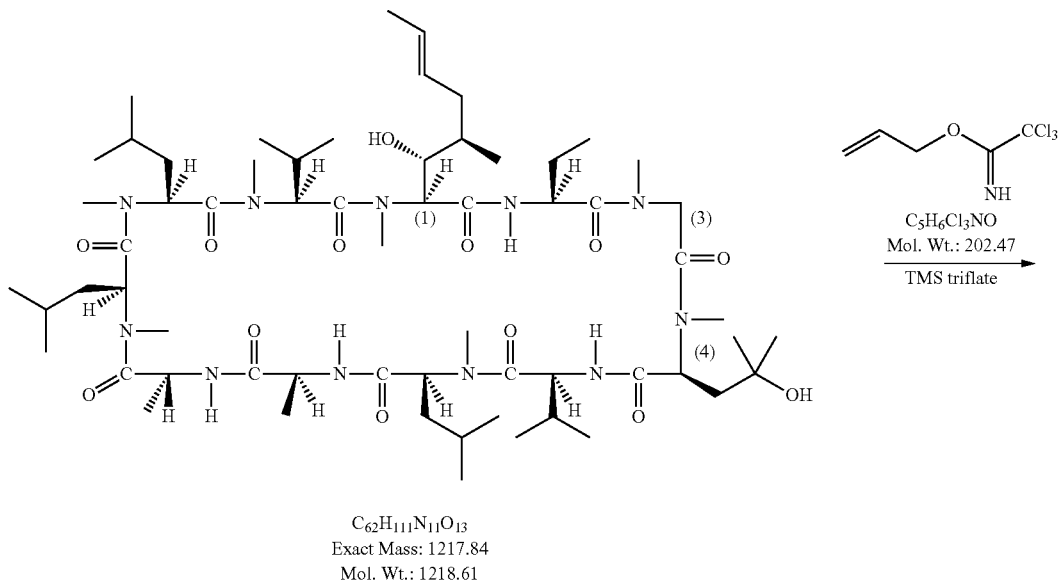

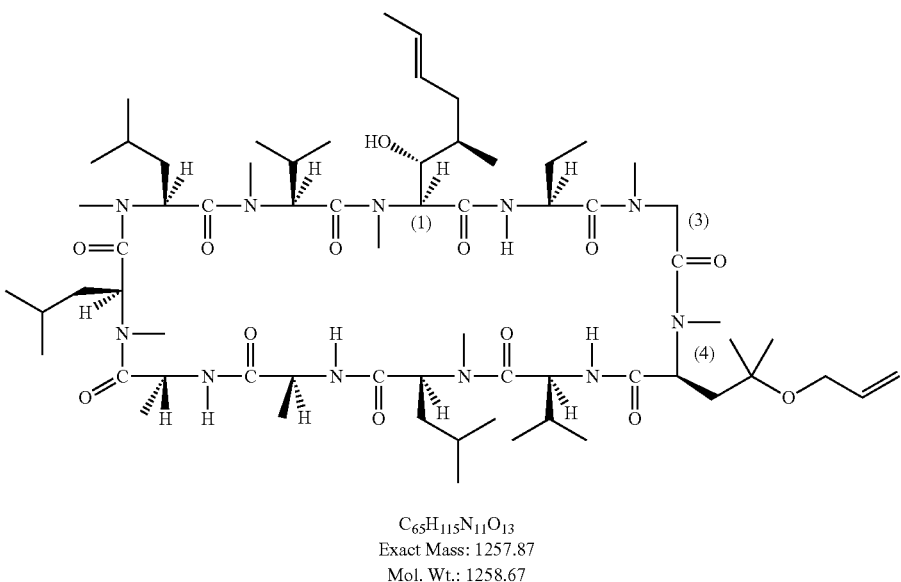

Under nitrogen atmosphere, to a mixture of [(γ-Hydroxy)-NMeLeu]-4-cyclosporin (FW 1218.61, 800 mg, 0.66 mmol) and ally 2,2,2-trichloroacetimidate (FW 202.47, 930 mg, 4.6 mmol) in 150 ml of DCM was added trimethylsily trifluoromethanesulfonate (FW 222.26, d 1.228, 250 mg, 1.12 mmol) at 0° C. The resulting mixture was allowed to warm to room temperature and stirred for overnight. Then the mixture was washed with saturated $NaHCO_3$ water solution and brine. The organic layer was separated, dried over $MgSO_4$ and evaporated under vacuum. The residue was purified by column chromatography using DCM/MeOH (98/2) to give product [Molecular formula: $C_{65}H_{115}N_{11}O_{13}$; Exact Mass: 1257.87; MS (m/z): 1280.7 $(M+Na)^+$; TLC $R_f$: 0.46 (DCM/MeOH=95/5); HPLC RT: 16.45 minutes (C8 reverse phase column, 250 mm, acetonitrile/0.05% TFA in water, operation temperature: 64° C.; Detector: 210 nm)].

Example 26

[(R)-3-(N-Morphlino)propylthio-Sar]-3-[(γ-Allyloxy)-NMeLeu]-4-cyclosporin

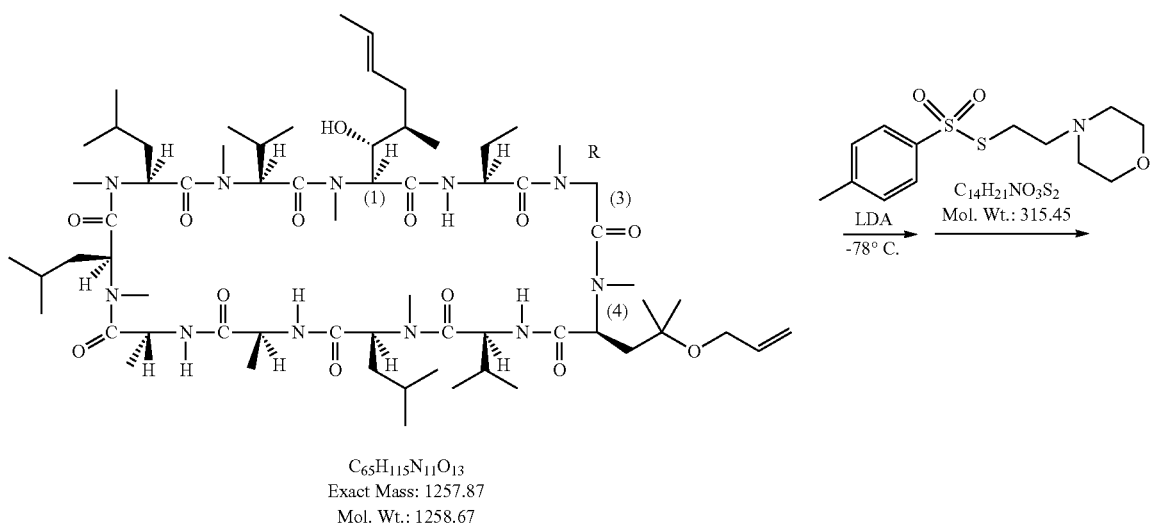

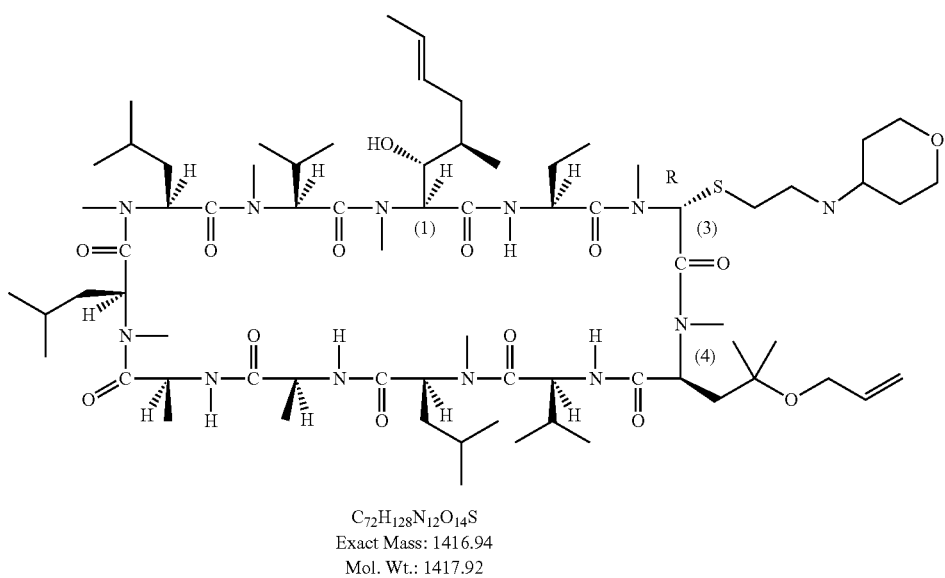

[(R)-3-(N-Morphlino)propylthio-Sar]-3-[(γ-Allyloxy)-NMeLeu]-4-cyclosporin was prepared according to the method described in Example 6. Molecular formula: $C_{72}H_{128}N_{12}O_{14}S$; Exact Mass: 1416.94; MS (m/z): 1417.80 (M+H)$^+$; TLC $R_f$: 0.41 (DCM/MeOH=95/5); HPLC RT: 14.31 minutes (C8 reverse phase column, 250 mm, acetonitrile/0.05% TFA in water, operation temperature: 64° C.; Detector: 210 nm).

Example 27

[(γ-Benzyloxy)-NMeLeu]-4-cyclosporin

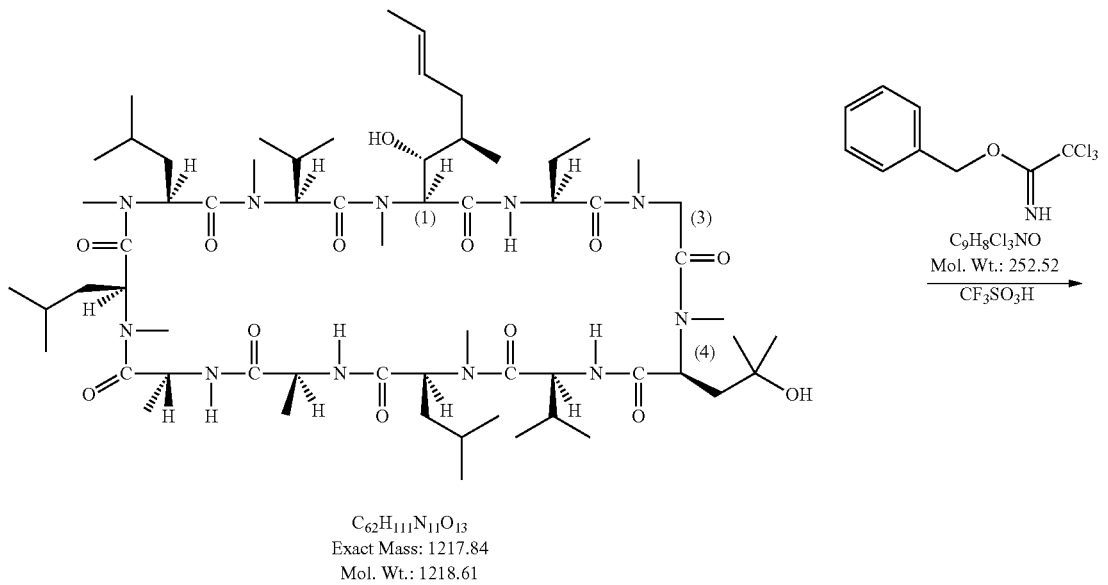

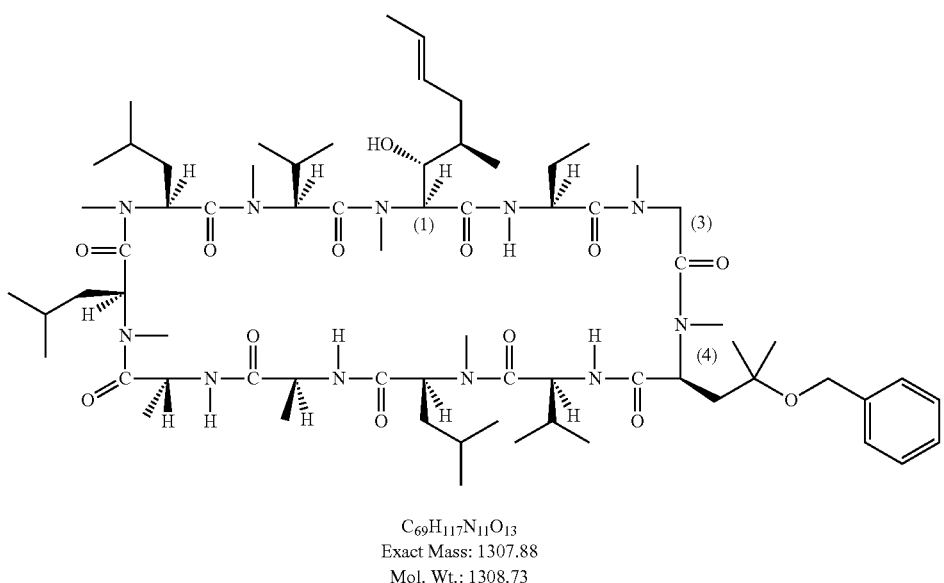

Under nitrogen atmosphere, to a mixture of [(γ-Hydroxy)-NMeLeu]-4-cyclosporin (FW 1218.61, 250 mg, 0.2 mmol) and benzyl 2,2,2-trichloroacetimidate (FW 252.52, 260 mg, 1.0 mmol) in 10 ml of DCM was added trifluoromethanesulfonic acid (FW 150.07, d 1.696, 86 mg, 0.57 mmol) at 0° C. The resulting mixture was allowed to warm to room temperature and stirred for overnight. Then the mixture was washed with saturated $NaHCO_3$ water solution and brine. The organic layer was separated, dried over $MgSO_4$ and evaporated under vacuum. The residue was purified by column chromatography using DCM/MeOH (98/2) to give product [Molecular formula: $C_{69}H_{117}N_{11}O_{13}$; Exact Mass: 1307.88; MS (m/z): 1308.80 (M+H)$^+$; TLC $R_f$: 0.40 (DCM/MeOH=95/5); HPLC RT: 17.41 minutes (C8 reverse phase column, 250 mm, acetonitrile/0.05% TFA in water, operation temperature: 64° C.; Detector: 210 nm)].

Example 28

[(R)-3-(N-Morphlino)propylthio-Sar]-3-[(γ-Benzyloxy)-NMeLeu]-4-cyclosporin

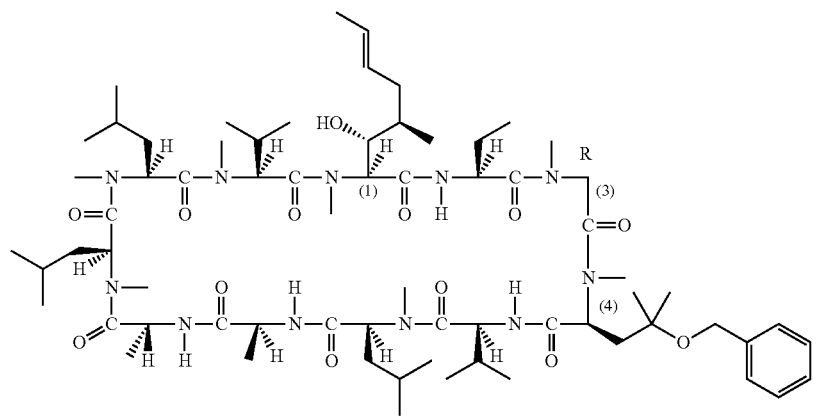

$C_{69}H_{117}N_{11}O_{13}$
Exact Mass: 1307.88
Mol. Wt.: 1308.73

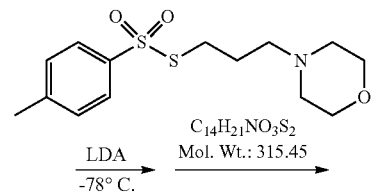

$C_{14}H_{21}NO_3S_2$
Mol. Wt.: 315.45

LDA
-78° C.

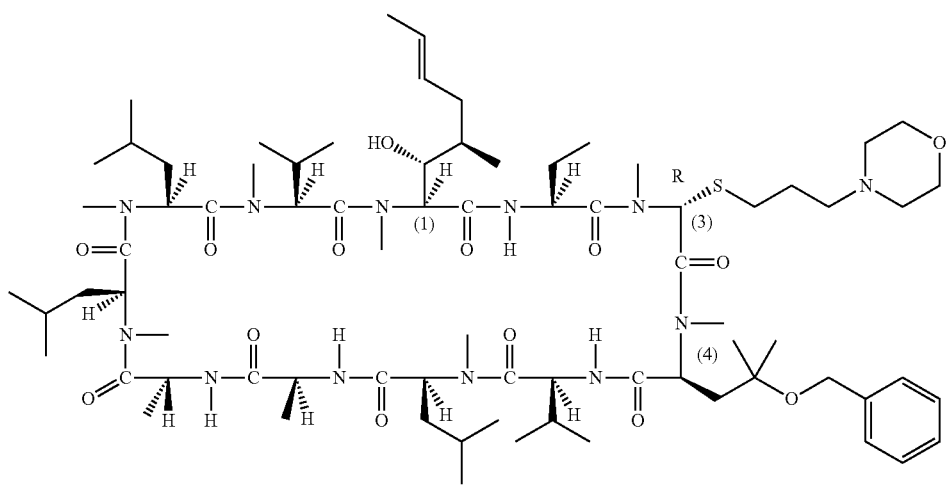

$C_{76}H_{130}N_{12}O_{14}$
Exact Mass: 1466.96
Mol. Wt.: 1467.98

[(R)-3-(N-Morphlino)propylthio-Sar]-3-[(γ-Benzyloxy)-NMeLeu]-4-cyclosporin was prepared according to the method described in Example 6. Molecular formula: $C_{76}H_{130}N_{12}O_{14}S$; Exact Mass: 1466.96; MS (m/z): 1467.90 (M+H)$^+$; TLC $R_f$: 0.42 (DCM/MeOH=95/5); HPLC RT: 16.45 minutes (C8 reverse phase column, 250 mm, acetonitrile/0.05% TFA in water, operation temperature: 64° C.; Detector: 210 nm).

Example 29
[(γ-(4-Methoxy)Benzyloxy)-NMeLeu]-4-cyclosporin
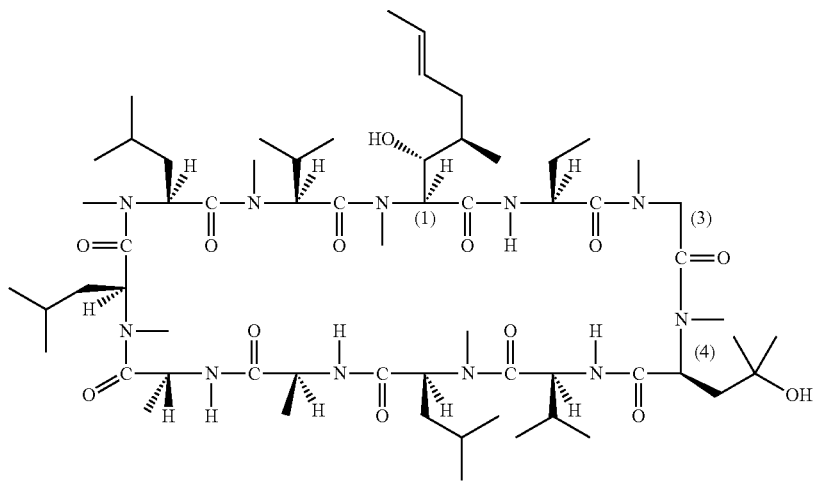
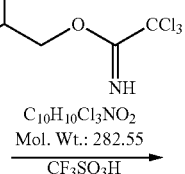
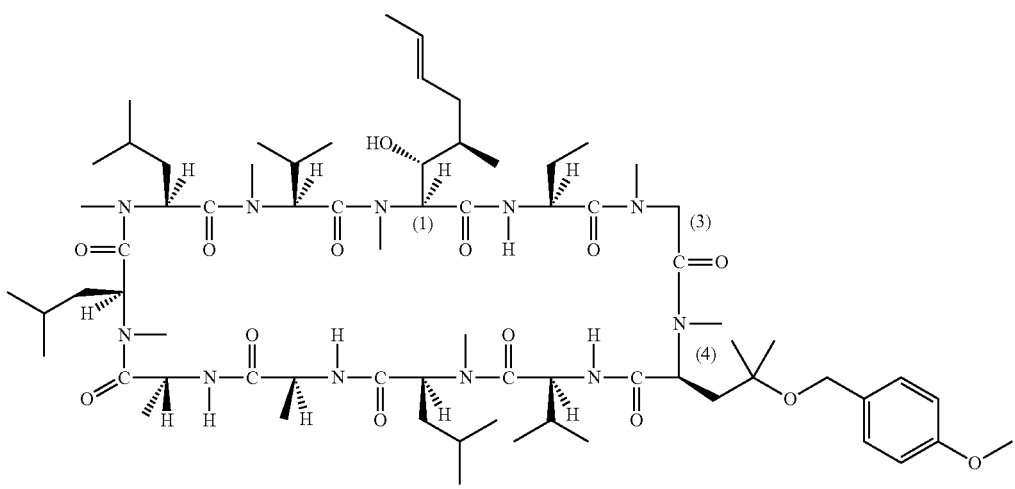
[(γ-(4-Methoxy)Benzyloxy)-NMeLeu]-4-cyclosporin was prepared according to the method described in Example 27. Molecular formula: $C_{70}H_{119}N_{11}O_{14}$; Exact Mass: 1337.89; MS (m/z): 1338.87 (M+H)$^+$; TLC R$_f$: 0.31 (DCM/MeOH=95/5); HPLC RT: 17.23 minutes (C8 reverse phase column, 250 mm, acetonitrile/0.05% TFA in water, operation temperature: 64° C.; Detector: 210 nm).

Example 30

[(R)-3-(N-Morphlino)propylthio-Sar]-3-[(γ-(4-Methoxy)Benzyloxy)-NMeLeu]-4-cyclosporin

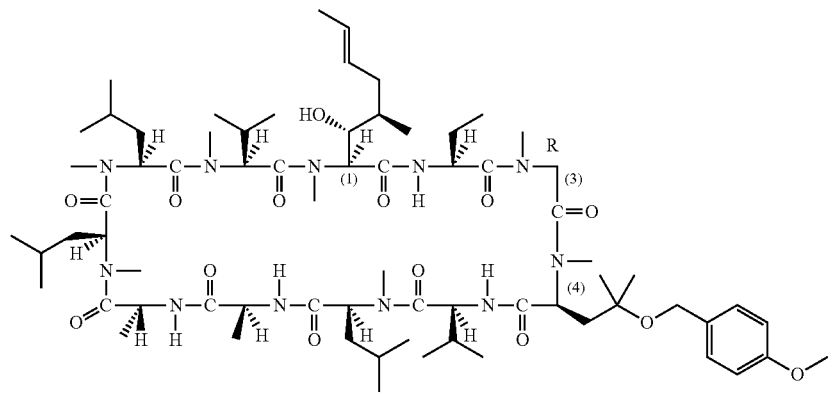

$C_{70}H_{119}N_{11}O_{14}$
Exact Mass: 1337.89
Mol. Wt.: 1338.76

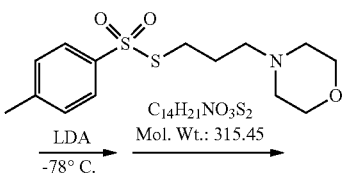

$C_{14}H_{21}NO_3S_2$
Mol. Wt.: 315.45

LDA
-78° C.

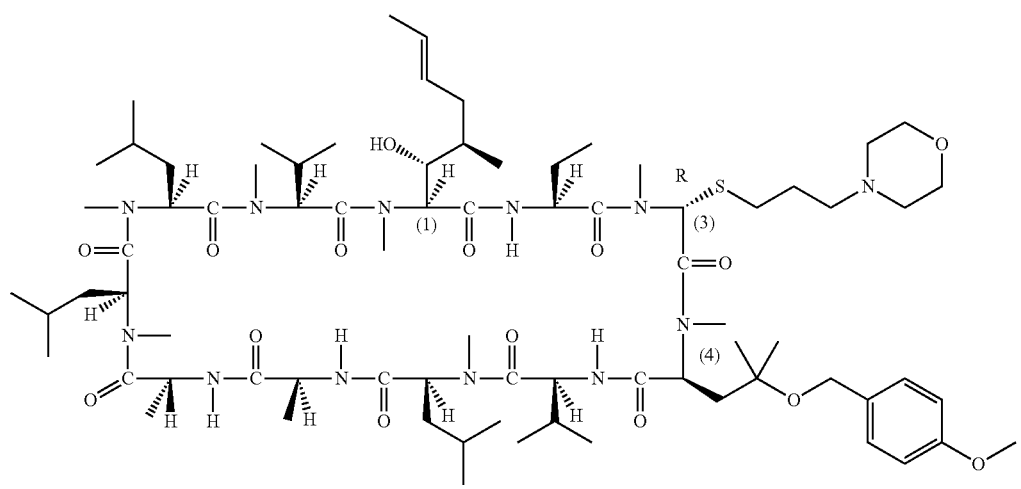

$C_{77}H_{132}N_{12}O_{15}S$
Exact Mass: 1496.97
Mol. Wt.: 1498.01

[(R)-3-(N-Morphlino)propylthio-Sar]-3-[(γ-(4-Methoxy)Benzyloxy)-NMeLeu]-4-cyclosporin was prepared according to the method described in Example 6. Molecular formula: $C_{77}H_{132}N_{12}O_{15}S$; Exact Mass: 1496.97; MS (m/z): 1519.94 (M+Na)$^+$; TLC R$_f$: 0.38 (DCM/MeOH=95/5); HPLC RT: 14.76 minutes (C8 reverse phase column, 250 mm, acetonitrile/0.05% TFA in water, operation temperature: 64° C.; Detector: 210 nm).

Example 31

[(3R,4R)-Hydroxy-N,4-dimethyl-L-2-aminooctanic acid]-1-[(γ-hydroxy)-NMeLeu]-4-cyclosporin

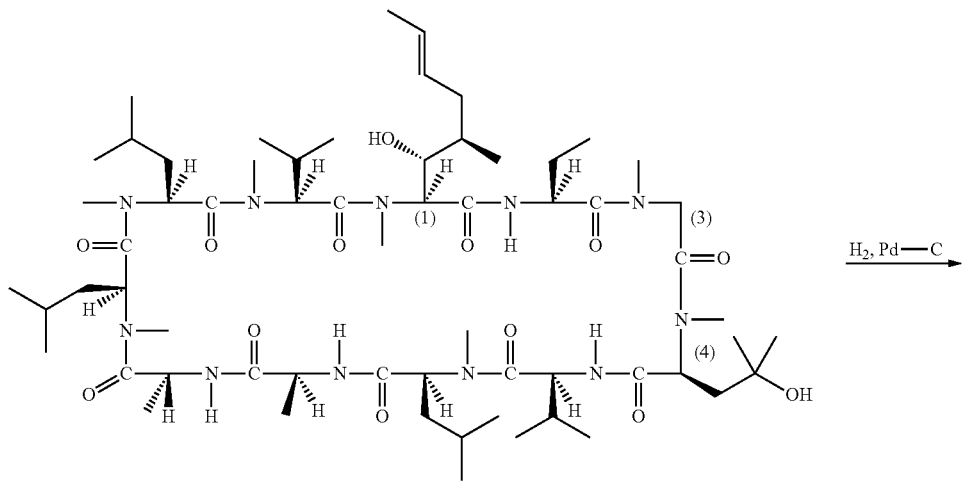

$C_{62}H_{111}N_{11}O_{13}$
Exact Mass: 1217.84
Mol. Wt.: 1218.61

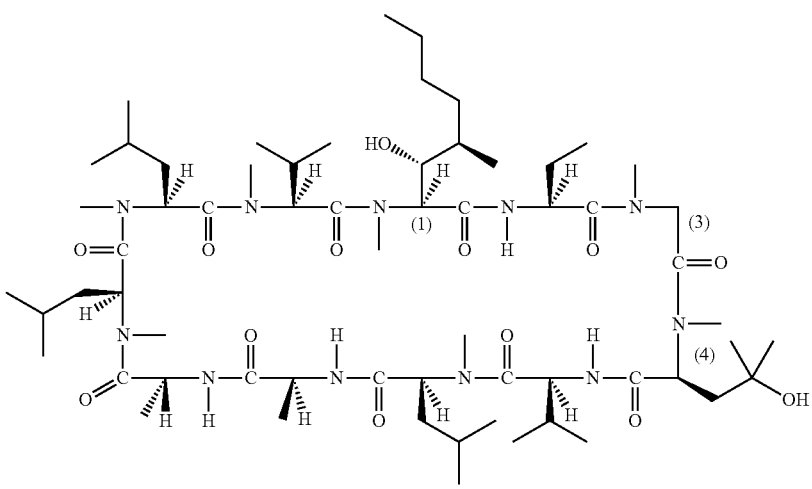

$C_{62}H_{113}N_{11}O_{13}$
Exact Mass: 1219.85
Mol. Wt.: 1220.63

To a solution of [(γ-Hydroxy)-NMeLeu]-4-cyclosporin (FW 1218.61, 1.0 g, 0.82 mmol) in 35 ml of methanol was added Pd—C (10%, 300 mg). The reactor was charged $H_2$ (1 atm) and the mixture was stirred at room temperature for overnight. The mixture was filtered through a pad of celite and the filtrate was evaporated in vacuum. The residue was dissolved in DCM. The solution was dried over $MgSO_4$ and evaporated in vacuum to give product [Molecular formula: $C_{62}H_{113}N_{11}O_{13}$; Exact Mass: 1219.85; MS (m/z): 1242.70 (M+Na)$^+$; TLC $R_f$: 0.43 (DCM/MeOH=95/5); HPLC RT: 14.90 minutes (C8 reverse phase column, 250 mm, acetonitrile/0.077% $NH_4OAc$ in water, operation temperature: 64° C.; Detector: 210 nm)].

Example 32

[(4R)-3-Keto-4-Methyl-N-methyl-L-2-aminooctanic acid)]-1-[(γ-Hydroxy)-NMeLeu]-4-cyclosporin

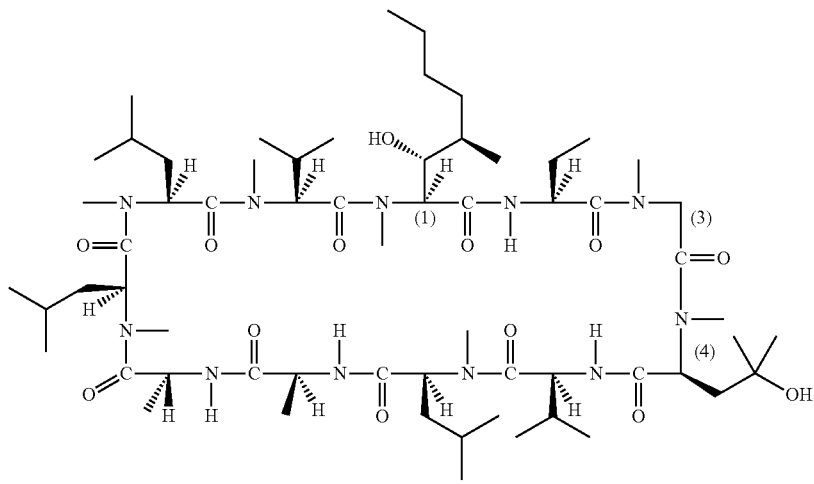

C₆₂H₁₁₁N₁₁O₁₃
Exact Mass: 1219.85
Mol. Wt.: 1220.63

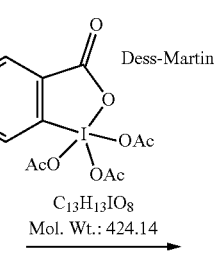

Dess-Martin

C₁₃H₁₃IO₈
Mol. Wt.: 424.14

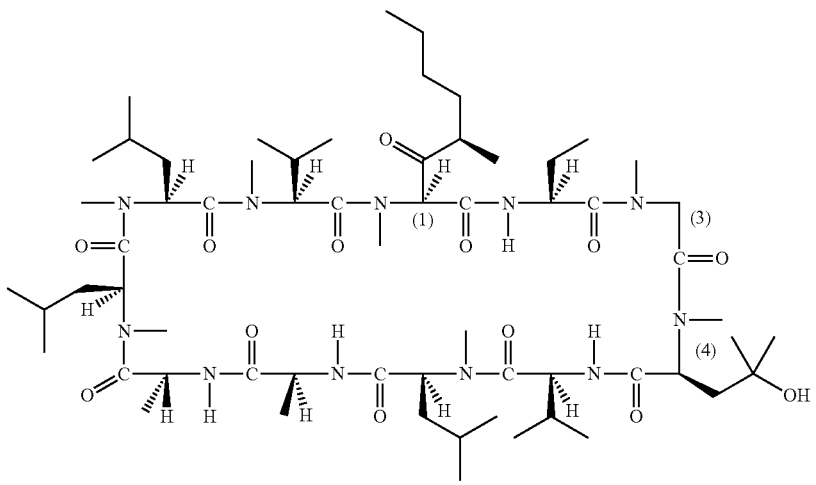

C₆₂H₁₁₁N₁₁O₁₃
Exact Mass: 1217.84
Mol. Wt.: 1218.61

To a solution of [(3R,4R)-Hydroxy-N,4-dimethyl-L-2-aminooctanic acid]-1-[(γ-Hydroxy)-NMeLeu]-4-cyclosporin (FW 1220.63, 0.9 g, 0.74 mmol) in 80 ml of DCM was added Dess-Martin periodinane (FW 424.14, 490 mg, 1.15 mmol). The resulting mixture was stirred at room temperature 2.5 hours. Then 15 ml of the saturated NaHCO$_3$ water solution and the 10 ml of water solution of the saturated Na$_2$SO$_3$ were added. The organic layer was separated, washed with brine, dried over MgSO$_4$, filtered and evaporated to give product [Molecular formula: C$_{62}$H$_{111}$N$_{11}$O$_{13}$; Exact Mass: 1217.84; MS (m/z): 1240.70 (M+Na)$^+$; TLC R$_f$: 0.44 (DCM/MeOH=95/5); HPLC RT: 15.30 minutes (C8 reverse phase column, 250 mm, acetonitrile/0.077% NH$_4$OAc in water, operation temperature: 64° C.; Detector: 210 nm)].

Example 33

[(4R)-3-Keto-4-Methyl-N-methyl-L-2-aminooctanic acid)]-1-[(γ-allyloxy)-NMeLeu]-4-cyclosporin

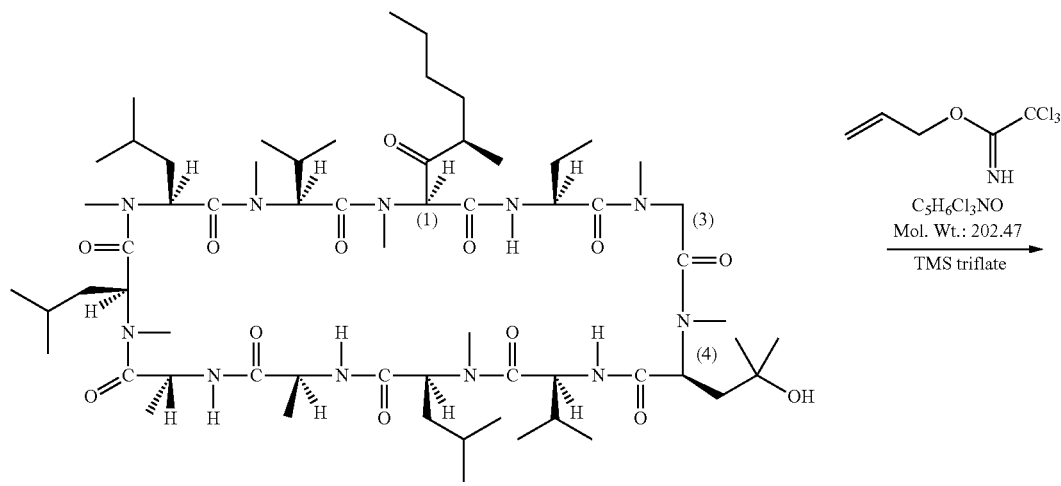

C₆₂H₁₁₁N₁₁O₁₃
Exact Mass: 1217.84
Mol. Wt.: 1218.61

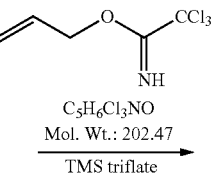

C₅H₆Cl₃NO
Mol. Wt.: 202.47

TMS triflate

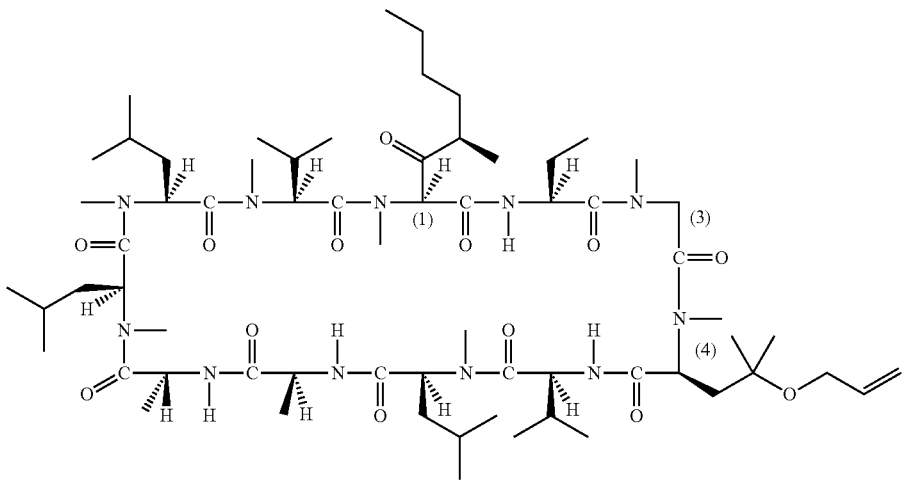

C₆₅H₁₁₅N₁₁O₁₃
Exact Mass: 1257.87
Mol. Wt.: 1258.67

Under nitrogen atmosphere, to a mixture of [(4R)-3-Keto-4-Methyl-N-methyl-L-2-aminooctanic acid)]-1-[(γ-Hydroxy)-NMeLeu]-4-cyclosporin (FW 1218.61, 800 mg, 0.65 mmol) and ally 2,2,2-trichloroacetimidate (FW 202.47, 930 mg, 4.6 mmol) in 150 ml of DCM was added trimethylsily trifluoromethanesulfonate (FW 222.26, d 1.228, 250 mg, 1.12 mmol) at 0° C. The resulting mixture was allowed to warm to room temperature and stirred at for overnight. Then the mixture was washed with the water solution of the saturated NaHCO₃ and brine. The organic layer was dried over MgSO₄ and evaporated under vacuum. The residue was purified by column chromatography with eluent of DCM/MeOH (98/2) to give product [Molecular formula: C₆₅H₁₁₅N₁₁O₁₃; Exact Mass: 1257.87; MS (m/z): 1280.70 (M+Na)⁺; TLC R_f: 0.47 (DCM/MeOH=95/5); HPLC RT: 20.45 minutes (C8 reverse phase column, 250 mm, acetonitrile/0.077% NH₄OAc in water, operation temperature: 64° C.; Detector: 210 nm)].

Example 34

[(γ-Allyloxy)-NMeLeu]-4-dihydrocyclosporin

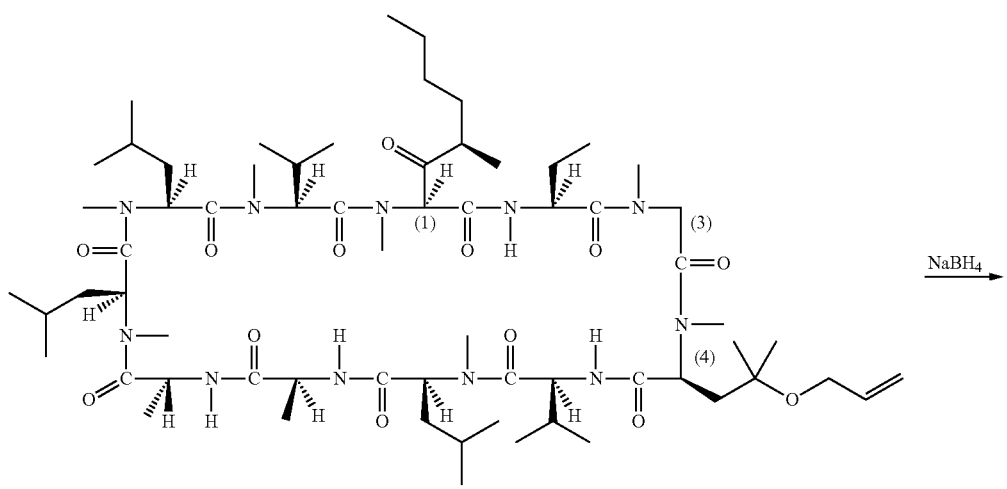

C₆₅H₁₁₅N₁₁O₁₃
Exact Mass: 1257.87
Mol. Wt.: 1258.67

NaBH₄ →

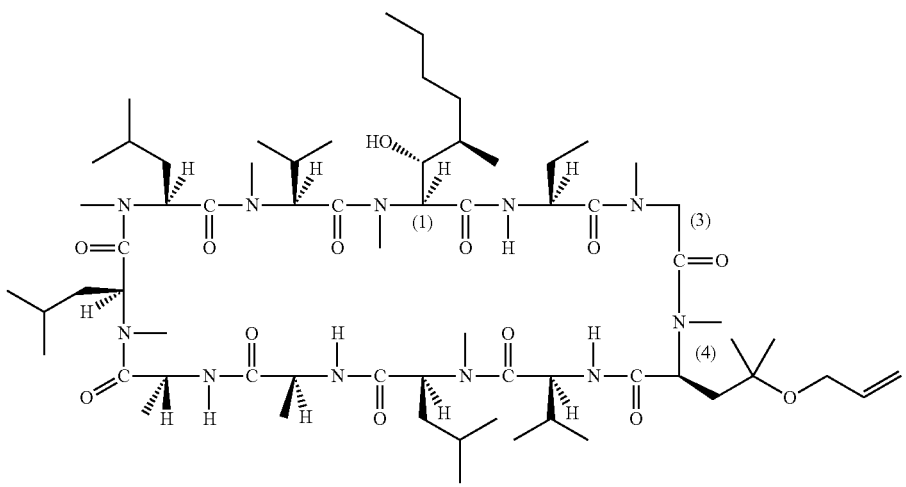

C₆₅H₁₁₇N₁₁O₁₃
Exact Mass: 1259.88
Mol. Wt.: 1260.69

To a solution of [(4R)-3-Keto-4-Methyl-N-methyl-L-2-aminooctanic acid)]-1-[(γ-allyloxy)-NMeLeu]-4-cyclosporin (FW 1258.67, 540 mg, 0.43 mmol) in 50 ml of methanol was added NaBH₄ (FW 37.83, 170 mg, 4.4 mmol) in three portions over 10 minutes at room temperature with stirring. Then the reaction mixture was stirred for 1.5 hours, concentrated under reduced pressure, diluted with DCM, washed with brine, and dried over MgSO₄. The solution was filtered and concentrated under vacuum to provide product [Molecular formula: C₆₅H₁₁₇N₁₁O₁₃; Exact Mass: 1259.88; MS (m/z): 1282.70 (M+Na)⁺; TLC R$_f$: 0.45 (DCM/MeOH=95/5); HPLC RT: 16.95 minutes (C8 reverse phase column, 250 mm, acetonitrile/0.077% NH₄OAc in water, operation temperature: 64° C.; Detector: 210 nm)].

Example 35

[(γ-Formylmethoxy)-NMeLeu]-4-Dihydrocyclosporin

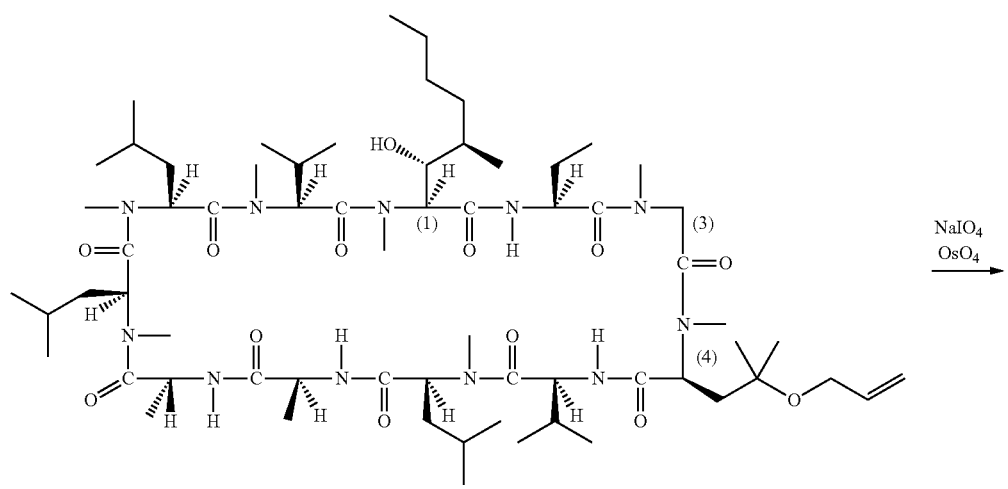

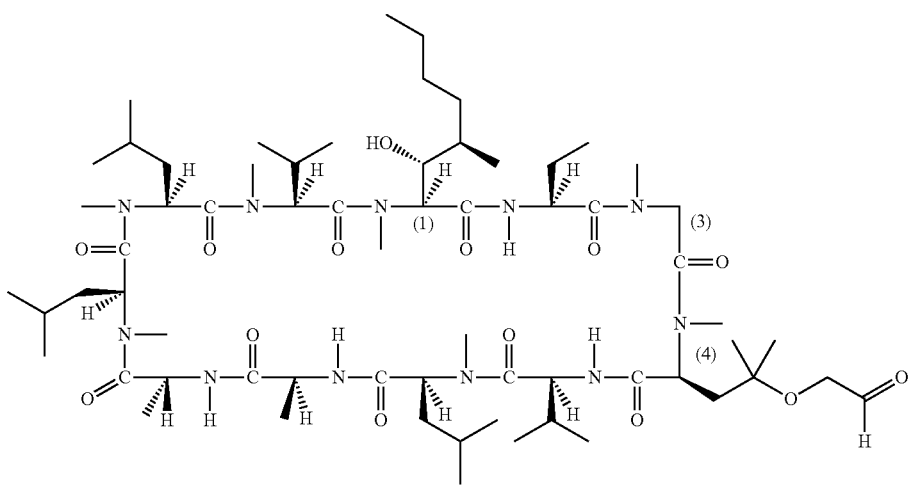

To a mixture of [(γ-Allyloxy)-NMeLeu}-4-Dihydrocyclosporin (FW 1260.69, 480 mg, 0.38 mmol) in 30 ml of THF/H$_2$O (1/1) were added NaIO$_4$ (FW 213.90, 260 mg, 1.2 mmol) and OsO$_4$ (FW 254.10, 1 ml, 4% in H$_2$O). The mixture was stirred at room temperature for overnight, and then 15 ml of the water solution of the saturated NaHCO$_3$ and 2 ml of the saturated water solution of Na$_2$SO$_3$ were added. After stirred for 1 hour, the mixture was extracted with DCM (3×50 ml). The combined organic layers were washed with brine, dried over MgSO$_4$, and evaporated under vacuum to give product [Molecular formula: C$_{64}$H$_{115}$N$_{11}$O$_{14}$; Exact Mass: 1261.86; MS (m/z): 1284.70 (M+Na)$^+$; TLC R$_f$: 0.44 (DCM/MeOH=95/5)].

Example 36

[(γ-(2-(N,N-Diethylamino)ethoxy)-NMeLeu]-4-di-hydrocyclosporin

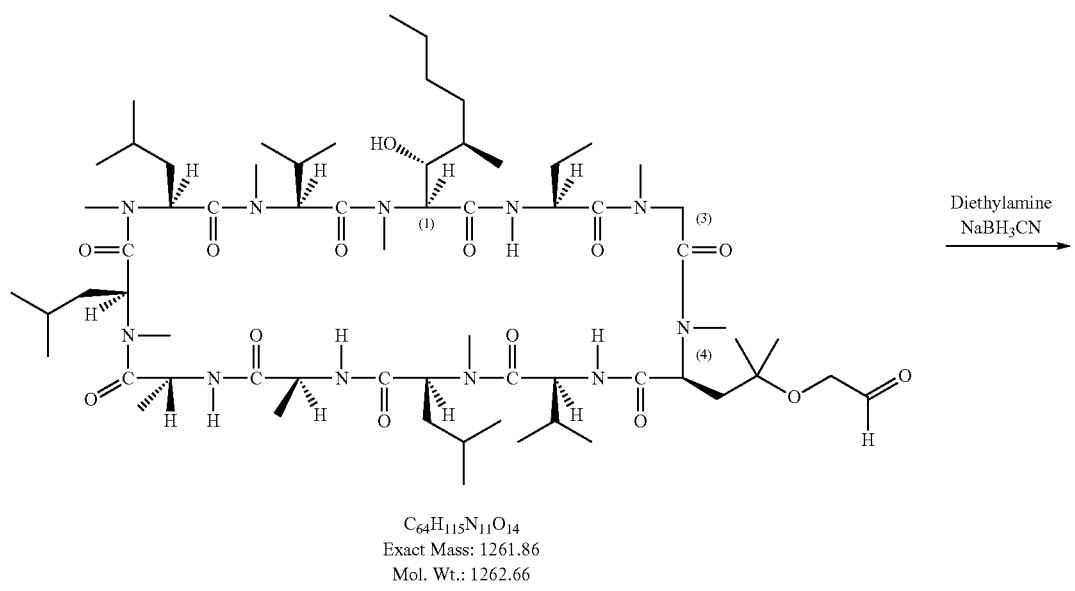

C_{64}H_{115}N_{11}O_{14}
Exact Mass: 1261.86
Mol. Wt.: 1262.66

Diethylamine
NaBH$_3$CN
→

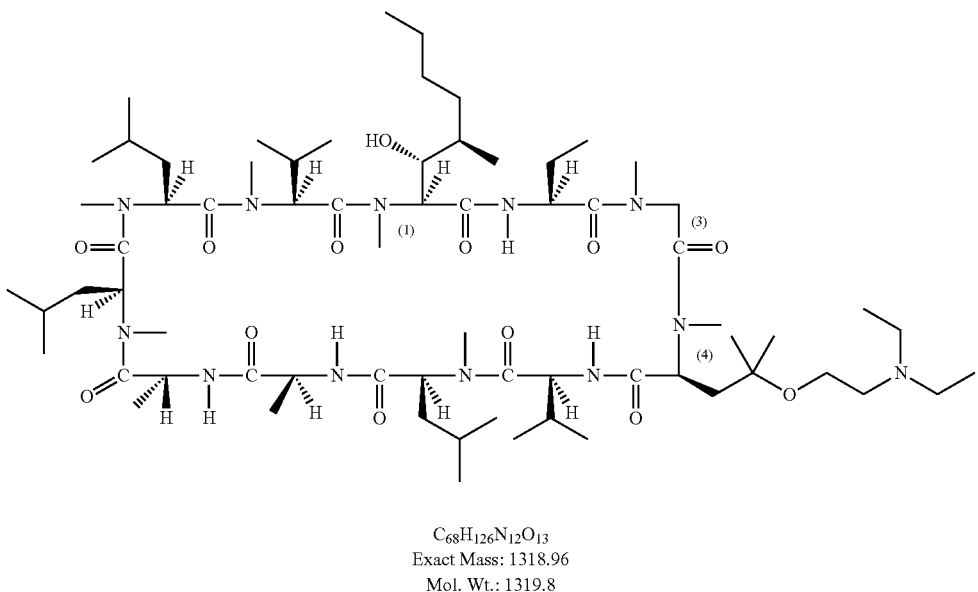

C_{68}H_{126}N_{12}O_{13}
Exact Mass: 1318.96
Mol. Wt.: 1319.8

A mixture of [(γ-Formylmethoxy)-NMeLeu]-4-Dihydro-cyclosporin (FW 1262.66, 400 mg, 0.31 mmol) and diethylamine (FW 73.14, d 0.706, 188 mg, 2.6 mmol) in 50 ml of THF was stirred at room temperature, then NaBH$_3$CN (FW 62.84, 160 mg, 2.54 mmol) was added. The mixture was stirred for overnight, concentrated under reduced pressure, diluted with the 50 ml of DCM and washed with water and brine. The solution was dried over MgSO$_4$ and evaporated under vacuum. The residue was purified by column chromatography with eulant of DCM/MeOH/Et$_3$N (96.5/3.5/0.3) to give product [Molecular formula: C$_{68}$H$_{126}$N$_{12}$O$_{13}$; Exact Mass: 1318.96; MS (m/z): 1341.90 (M+Na)$^+$; TLC R$_f$: 0.31 (DCM/MeOH=94/6); HPLC RT: 13.50 minutes (C8 reverse phase column, 250 mm, acetonitrile/0.077% NH$_4$OAc in water, operation temperature: 64° C.; Detector: 210 nm)].

Example 37

[γ-(2-Hydroxyethoxy)-NMeLeu]-4-dihydrocyclosporin

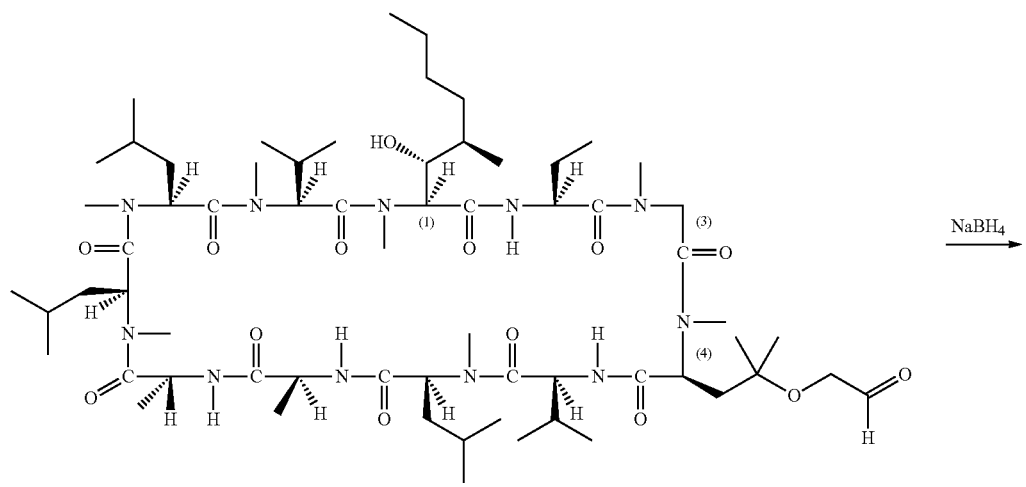

$C_{64}H_{115}N_{11}O_{14}$
Exact Mass: 1261.86
Mol. Wt.: 1262.66

NaBH₄ →

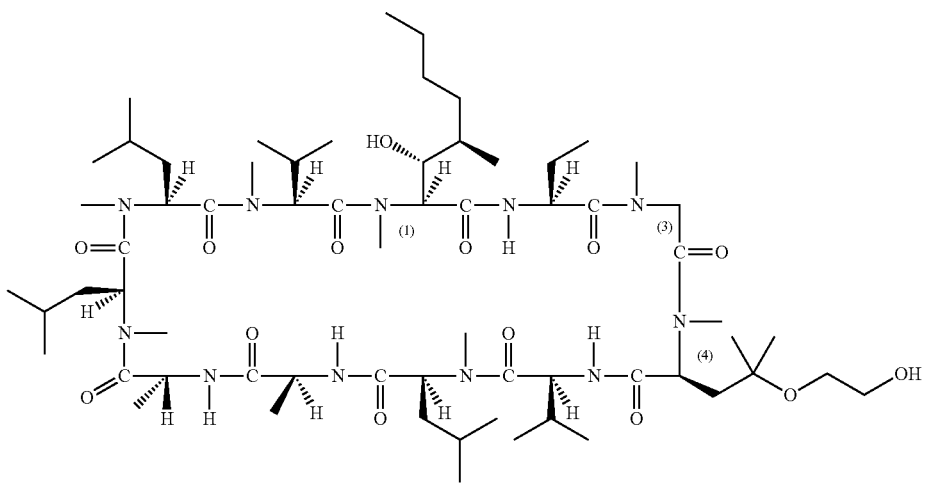

$C_{68}H_{117}N_{11}O_{14}$
Exact Mass: 1263.88
Mol. Wt.: 1264.68

To a solution of [(γ-Formylmethoxy)-NMeLeu]-4-Dihydrocyclosporin (FW 1262.66, 75 mg, 0.06 mmol) in 3 ml of methanol was added NaBH₄ (FW 37.83, 25 mg, 0.66 mmol) with stirring, and then the mixture was stirred at room temperature for 30 minutes. The mixture was concentrated under reduced pressure, diluted with 30 ml of DCM and washed with water, aqueous NH₄Cl solution and brine. The organic layer was separated, dried over MgSO₄, and evaporated under vacuum. The residue was purified by column chromatography with eluent of DCM/MeOH (97.5/2.5) to give product [Molecular formula: $C_{64}H_{117}N_{11}O_{14}$; Exact Mass: 1263.88; MS (m/z): 1264.90 (M+H)⁺; TLC $R_f$: 0.48 (DCM/MeOH=95/5); HPLC RT: 16.60 minutes (C8 reverse phase column, 250 mm, acetonitrile/0.077% NH₄OAc in water, operation temperature: 64° C.; Detector: 210 nm)].

Example 38

Cyclosporin-Trifluoroacetate

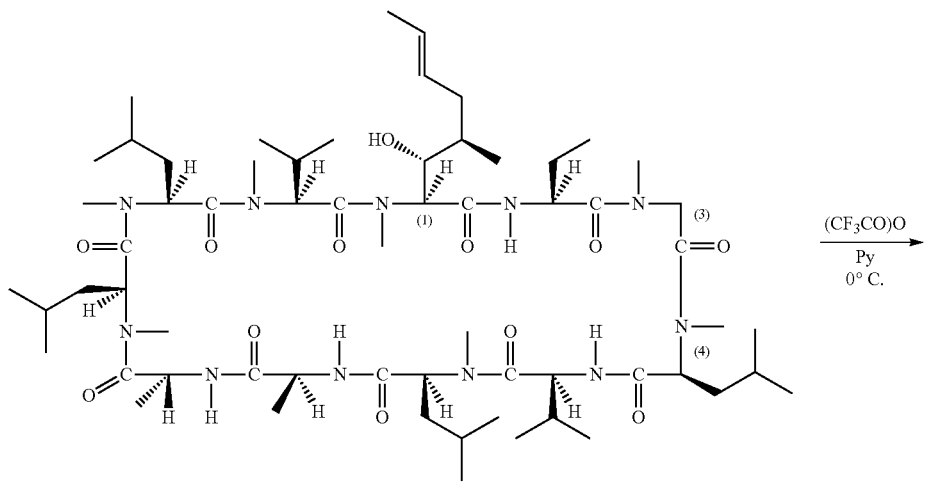

$C_{62}H_{111}N_{11}O_{12}$
Exact Mass: 1201.84
Mol. Wt.: 1202.61

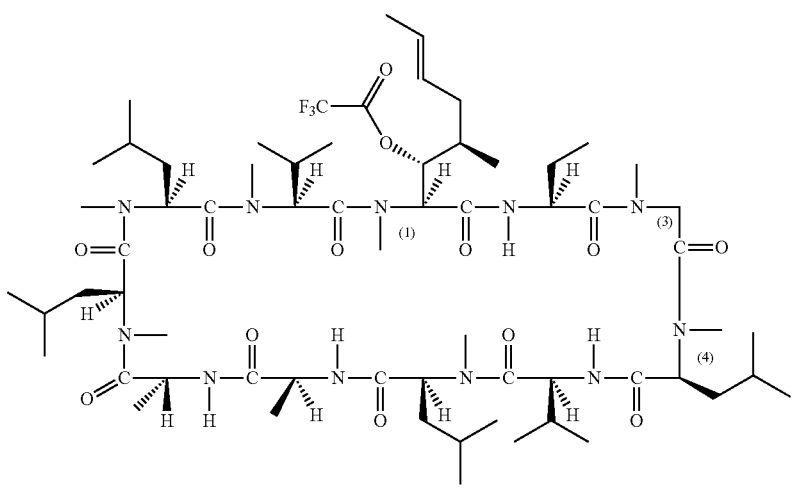

$C_{64}H_{110}N_{11}O_{13}$
Exact Mass: 1297.82
Mol. Wt.: 1298.62

To a solution of Cyclosporin A (MW 1202,16, 12 g, 10 mmol) and 4.8 ml of pyridine (FW 79.01, d 0.978, 4.8 ml, 4.69 g, 59.4 mmol) in 200 ml of methylene chloride was added trifluoroacetic anhydride (FW 210.03, d 1.487, 2.82 ml, 4.20 g, 2.0 equiv.) dropwise at 0° C. with stirring. The TLC was used to monitor the completion of the reaction. After the reaction was completed, 100 ml of water was added to quench the reaction. The organic layer was separated, washed with saturated $NaHCO_3$ solution, brine and dried over magnesium sulfate. Evaporation of methylene chloride under reduced pressure yielded 11.8 g (9.1 mmol, 91%) of Cyclosporin-trifluoroacetate, which was used for next step reaction without purification [TLC $R_f$: 0.55 (EtOAc)].

Example 39

MeLeuValMeLeuAlaDAlaMeLeuMeLeuMe-
ValMeBmt(O—COCF₃)AbuSar-OMe

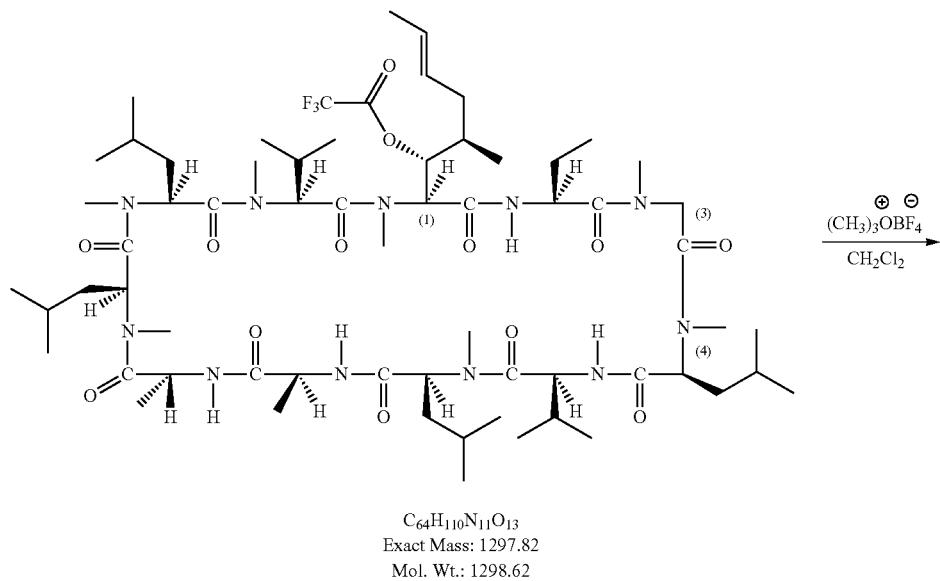

C$_{64}$H$_{110}$N$_{11}$O$_{13}$
Exact Mass: 1297.82
Mol. Wt.: 1298.62

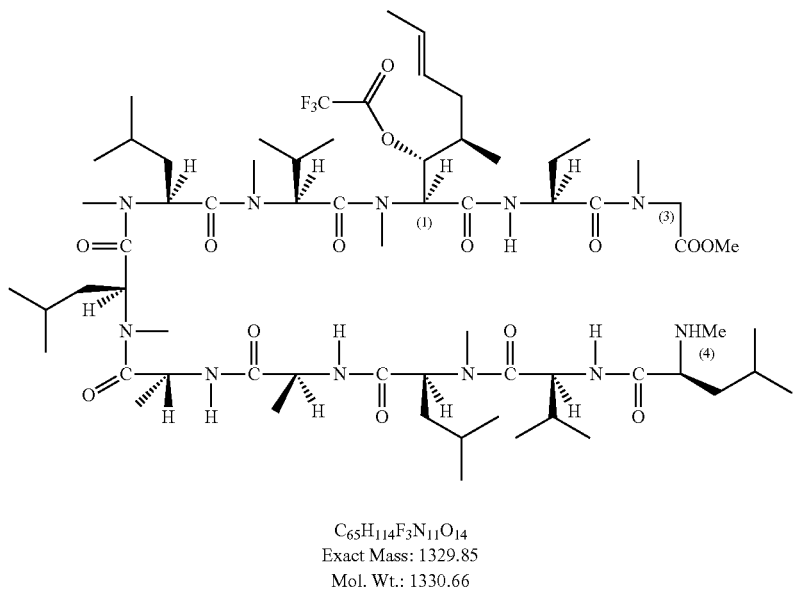

C$_{65}$H$_{114}$F$_3$N$_{11}$O$_{14}$
Exact Mass: 1329.85
Mol. Wt.: 1330.66

To a suspension of trimethyloxonium-fluoroborate (FW 147.91, 2.96 g, 20 mmol, 2.5 equiv.) in 80 ml dichloromethane was added cyclosporine trifluoroacetate (FW 1298.62, 10 g, 7.70 mmol) at room temperature. The suspension was stirred for 18 hours, and then sodium methoxide (FW 54.02, 9.9 mmol) in 40 ml methanol was added. The mixture was stirred for another 30 minutes and then 40 ml of 2 N sulfuric acid in 40 ml of MeOH was then added. The mixture was stirred for 20 minutes, and neutralized with 15% of potassium bicarbonate solution. The mixture was extracted twice with 700 ml of ethyl acetate. The combined organic layers were washed with brine, dried over sodium sulphate, filtered, and evaporated under reduced pressure. The crude product was purified by flash chromatography on a silica gel (100-200 mesh) with eluent of methanol in methyl t-butyl ether to give the 7.15 g (FW 1330.66, 5.37 mmol, 70%) of linear cyclosporine trifluoroacetate undecapeptide [MeLeu-ValMeLeuAlaDAlaMeLeu-MeLeuMeValMeBmt(O—COCF₃)AbuSar-OMe, TLC R$_f$: 0.40 (EtOAc/MeOH=10/1); Exact Mass: 1329.85. found: 1330.70].

Example 40

Phenylthiourea-MeLeuValMeLeuAlaDAlaMeLeu-MeLeuMeValMeBmt(O—COCF$_3$)AbuSar-OMe

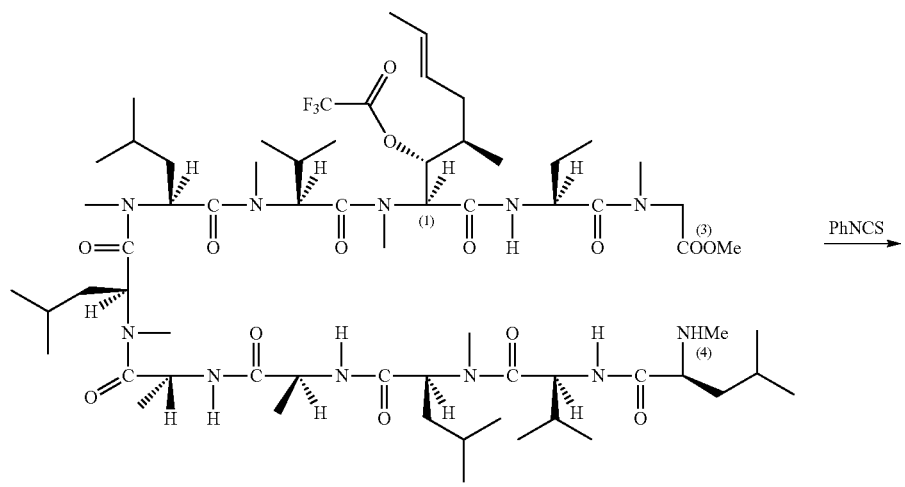

C$_{65}$H$_{114}$F$_3$N$_{11}$O$_{14}$
Exact Mass: 1329.85
Mol. Wt.: 1330.66

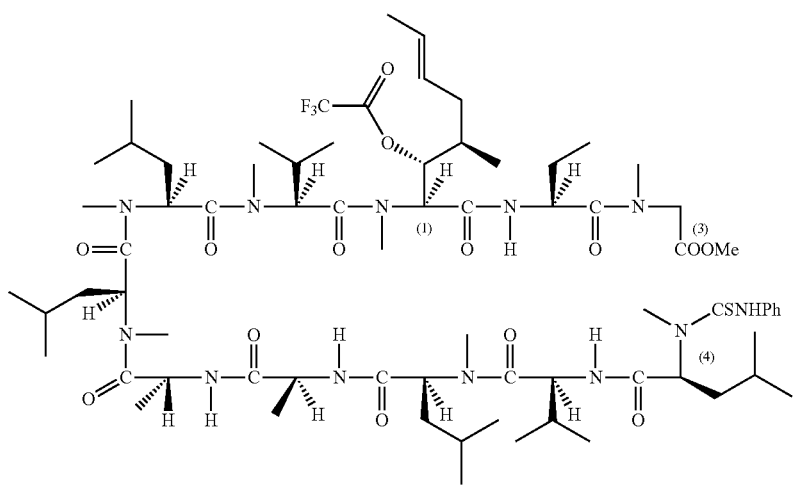

C$_{72}$H$_{119}$F$_3$N$_{12}$O$_{14}$S
Exact Mass: 1464.86
Mol. Wt.: 1465.85

To a solution of linear undecapeptide (FW 1330.66, 7.0 g, 5.3 mmol) in 80 ml of tetrahydrofuran was added phenyl isothiocyanate (MW 135.19, d 1.130, 0.855 ml, 7.15 mmol, 0.966 g, 1.35 equiv.) at room temperature. The solution was stirred for 3 hours and the solvent was evaporated under reduced pressure. The residue was purified by flash chromatography on a silica gel (100-200 mesh) with eluent of acetone in hexane (1/5) to give the 6.99 g (FW 1465.85, 4.75 mmol, 90%) of linear phenylthiourea undecapeptide (phenylthiourea-MeLeuValMeLeuAlaDAlaMeLeuMeLeuMeValMeBmt(O—COCF$_3$)AbuSar-OMe, Exact Mass: 1464.86. found: 1465.70 [M+H]$^+$).

Example 41

ValMeLeuAlaDAlaMeLeuMeLeuMeValMeBmt
(O—COCF₃)AbuSar-OMe

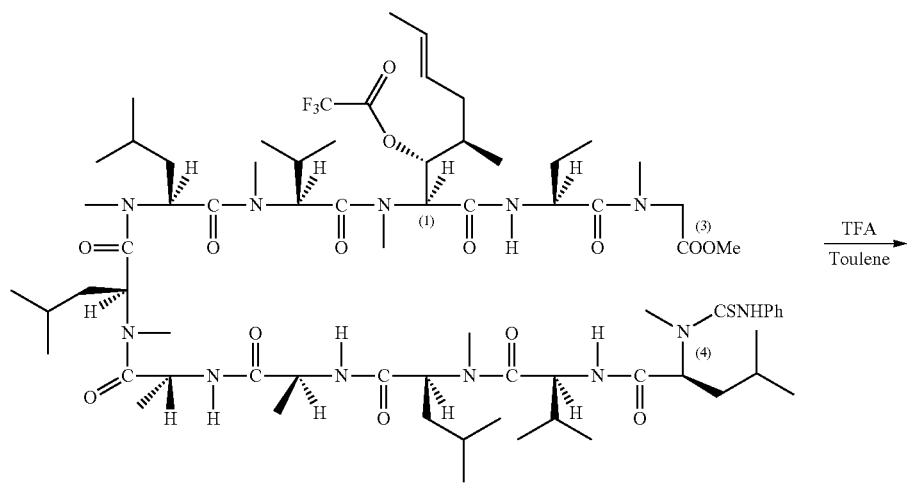

$C_{72}H_{119}F_3N_{12}O_{14}S$
Exact Mass: 1464.86
Mol. Wt.: 1465.85

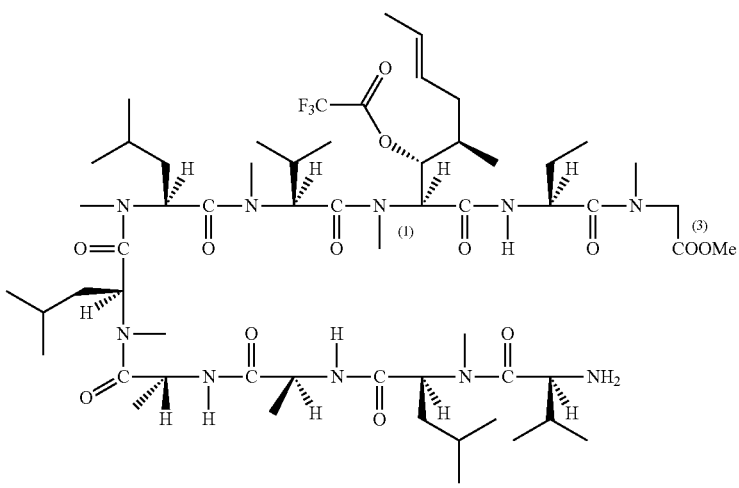

$C_{58}H_{101}F_3N_{10}O_{13}$
Exact Mass: 1202.75
Mol. Wt.: 1203.48

To a solution of linear phenylthiourea undecapeptide (FW 1465.85, 6.80 g, 4.64 mmol) in 300 ml of toluene, trifluoroacetic acid (MW 114.02, d 1.480, 8 ml, 11.84 g, 103.84 mmol) was added at room temperature and the mixture was stirred for 1.5-2 hours. The reaction was quenched by adding sodium bicarbonate slurry. The mixture was separated. The aqueous phase was extracted twice with 100 ml of toluene and 100 ml of ethyl acetate. The combined organic layers were dried and evaporated under reduced pressure. The residue was purified by flash chromatography on a silica gel (100-200 mesh) with eluent of acetone in hexane (3/1) to give the 3.88 g (70% yield) of linear trifluoroacetate decapeptide (ValMeLeuAlaDAla-MeLeuMeLeuMeValMeBmt (O—COCF₃)AbuSar-OMe, TLC $R_f$: 0.30 (EtOAc/MeOH=10/1), FW 1203.48, Exact Mass: 1202.75. found: 1203.60 [M+1]).

Example 42

ValMeLeuAlaDAlaMeLeuMeLeuMeValMeBmtAbuSar-
OH

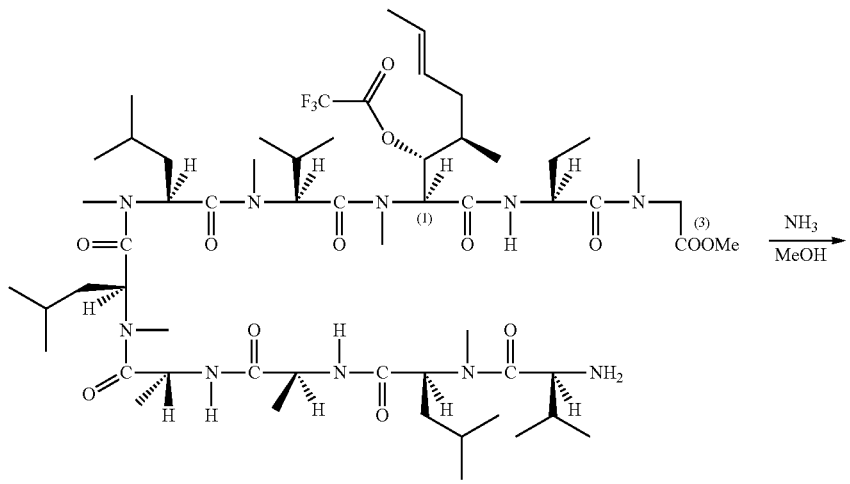

C₅₈H₁₀₁F₃N₁₀O₁₃
Exact Mass: 1202.75
Mol. Wt.: 1203.48

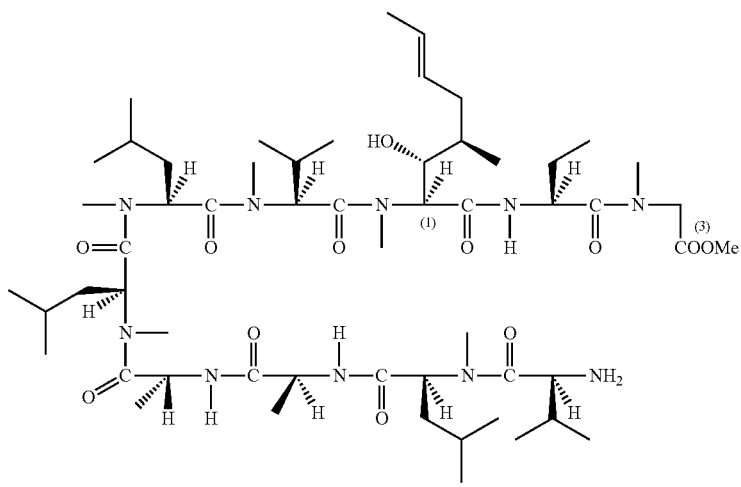

C₅₆H₁₀₂N₁₀O₁₂
Exact Mass: 1106.77
Mol. Wt.: 1107.47

To a solution of linear trifluoroacetate decapeptide (FW 1203.48, 1.0 g, 0.83 mmol) in 15 ml of MeOH was added 5 ml of 50% of ammonia solution at room temperature. After stirred for two days, the mixture was evaporated to remove MeOH under reduced pressure. The residue was dissolved in 60 ml of EtOAc. The organic layer was washed with 2 N NaHCO₃ solution for 3 times and brine, dried over MgSO₄, and filtered. Removal of solvent gave 0.9 g of the linear decapeptide as an important intermediate (TLC $R_f$: 0.16 (EtOAc/MeOH=10/1), Exact Mass: 1106.77. found: 1107.67).

Example 43

BocNMeSerValMeLeuAlaDAlaMeLeuMeLeuMe-
ValMeBmt(O—COCF$_3$)AbuSar-OMe

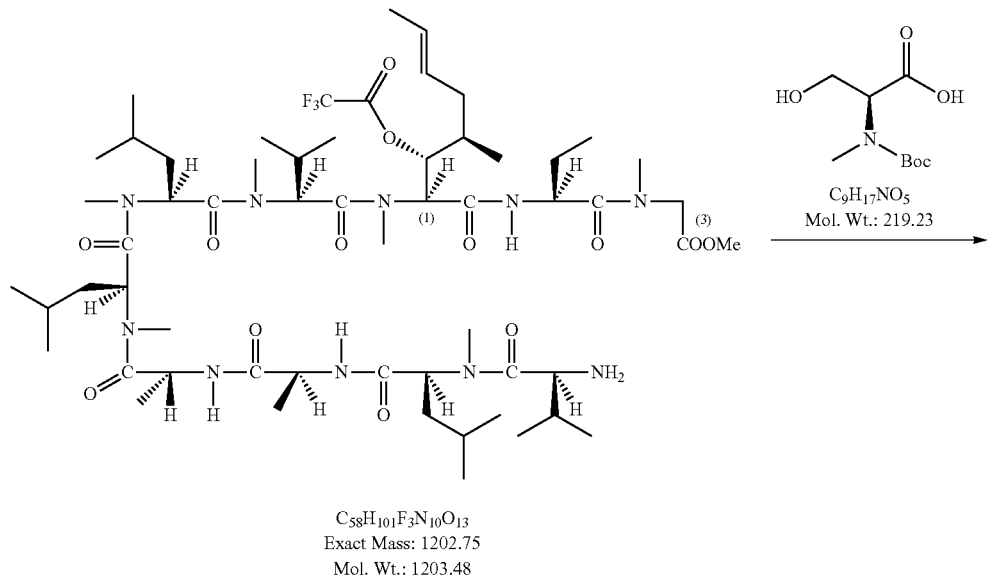

C$_{58}$H$_{101}$F$_3$N$_{10}$O$_{13}$
Exact Mass: 1202.75
Mol. Wt.: 1203.48

C$_9$H$_{17}$NO$_5$
Mol. Wt.: 219.23

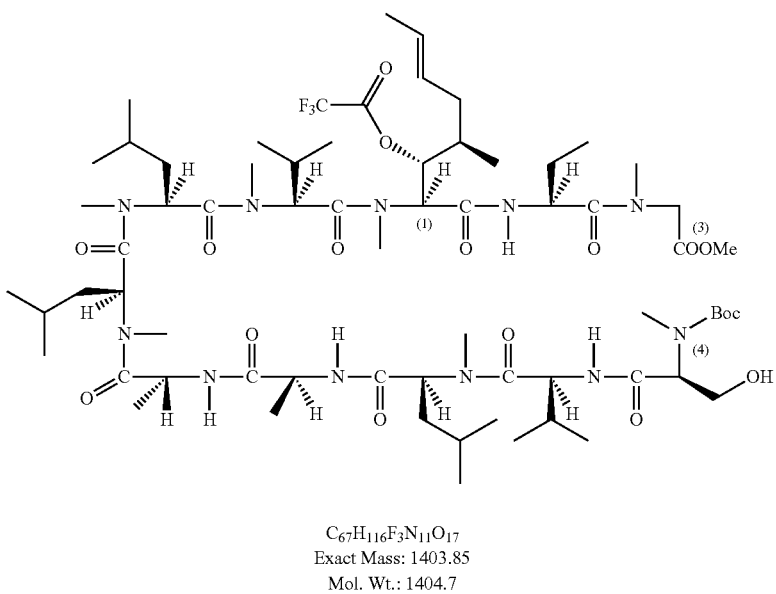

C$_{67}$H$_{116}$F$_3$N$_{11}$O$_{17}$
Exact Mass: 1403.85
Mol. Wt.: 1404.7

To a solution of linear decapeptide (FW 1203.48, 2.40 g, 2.0 mmol) in 50 ml of dichloromethane was added N-Boc-N-methyl-serine (FW 219.23, 1.10 g, 5.02 mmol, 2.5 equiv.), followed by addition of HATU (FW 380.20, 1.9 gram, 5 mmol) and DIPEA (FW 129.25, d 0.742, 1.05 ml, 0.776 g, 6.0 mmol). The mixture was stirred for overnight, the reaction was quenched with 1N HCl. The organic layer was washed with 2 N NaHCO$_3$ solution, brine, dried over magnesium sulfate, and filtered. The solvent was evaporated under reduced pressure, the residue was purified by chromatography on silica gel to give 1.6 g (1.14 mmol, 57%) of pure product (BocNMeSerValMeLeuAlaDAlaMeLeu-MeLeuMeVal-MeBmt(O—COCF$_3$)AbuSar-OMe, TLC R$_f$: 0.51 (ethyl acetate/methanol=20:1); Exact Mass: 1403.85. found: 1404.88 (M+H)$^+$, 1426.80 (M+Na)$^+$.

Example 44

NMeSerValMeLeuAlaDAlaMeLeuMeLeuMeValMe-
BmtAbuSarOH

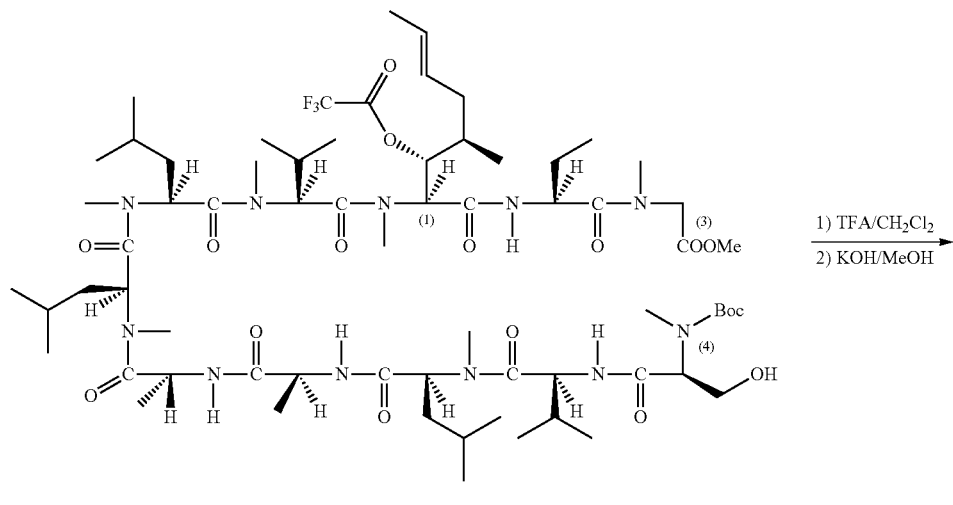

$C_{67}H_{116}F_3N_{11}O_{17}$
Exact Mass: 1403.85
Mol. Wt.: 1404.7

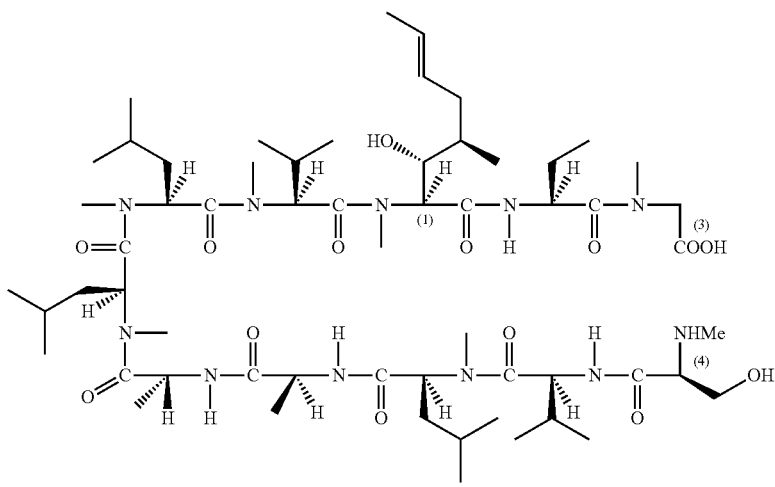

$C_{59}H_{107}N_{11}O_{14}$
Exact Mass: 1193.8
Mol. Wt.: 1194.55

The undecapeptide (BocNMeSerValMeLeuAlaDAlaMeLeuMeLeuMeValMeBmt(O—COCF$_3$)AbuSar-OMe, FW 1404.70, 0.76 g, 0.54 mmol) was dissolved in 10 ml of mixed solvent of dichloromethane/TFA (1:1) and then the mixture was stirred for 2.0 hours. After removal of solvent under reduced pressure, the residue was dissolved in 100 ml of ethyl acetate, washed with saturated NaHCO$_3$ solution and brine. The resulting de-Boc product, which was subsequently dissolved in 25 ml of methanol and 5 ml of 1 N NaOH. The mixture was stirred for overnight at room temperature. After removal of solvents, the mixture was neutralized with 1 N HCl and extracted with ethyl acetate. Removal of solvent gave 0.61 g of the final product (Exact Mass: 1193.80. found: 1194.7 (M+H)$^+$. found: 1216.9 (M+Na)$^+$.

Example 45

[NMeSer]-4-Cyclosporin

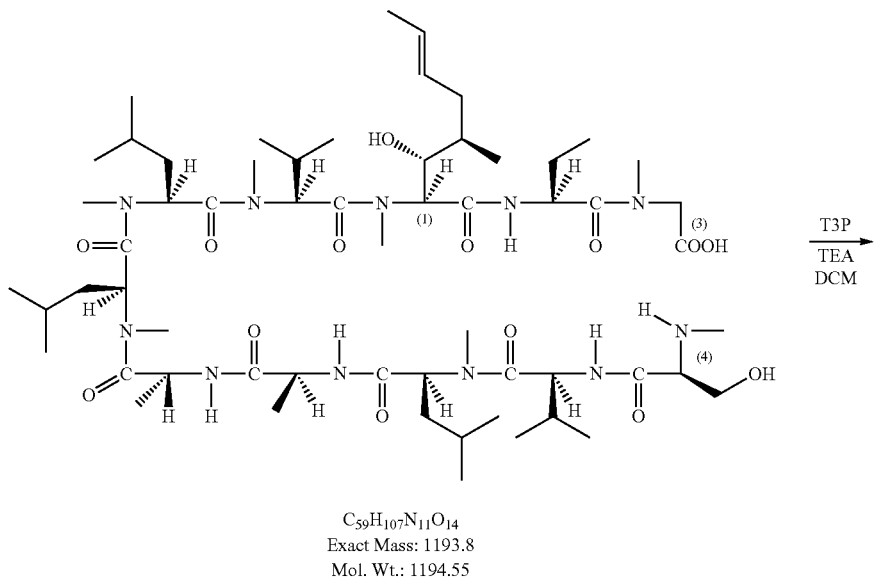

$C_{59}H_{107}N_{11}O_{14}$
Exact Mass: 1193.8
Mol. Wt.: 1194.55

T3P
TEA
DCM

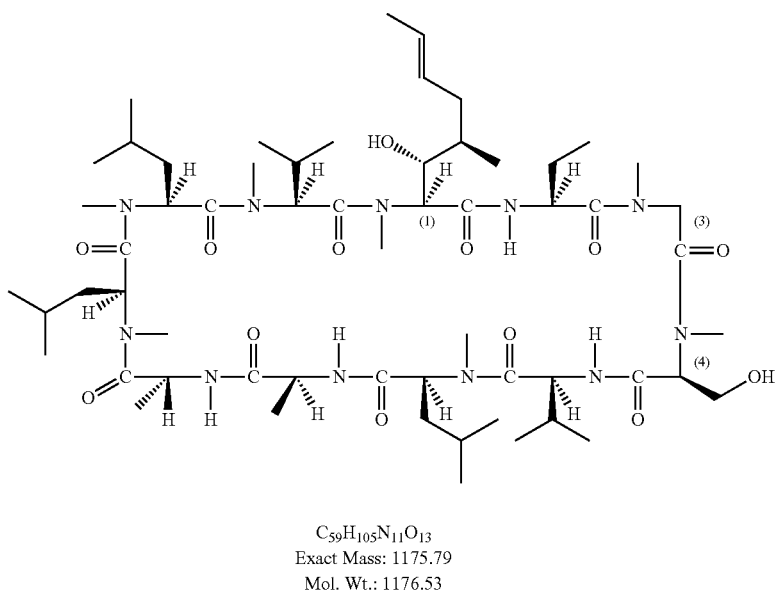

$C_{59}H_{105}N_{11}O_{13}$
Exact Mass: 1175.79
Mol. Wt.: 1176.53

To a solution of the undecapeptide (FW 1194.55, 204 mg, 0.17 mmol) in 100 ml of dichloromethane was added 1-propanephosphoric acid cyclic anhydride (FW 318.19, 50% in EtOAc, 0.2 ml), followed by addition of the triethyl amine (FW 101.19, d 0.726, 0.23 ml, 1.71 mmol). The mixture was stirred for overnight and TLC showed the completion of the reaction. The reaction mixture was diluted with 50 ml of DCM, washed with 1N HCl, aqueous NaHCO$_3$, brine, and then dried over MgSO$_4$. After filtration, the solvent was evaporated under reduced pressure, the residue was purified by chromatography on silica gel using ethyl acetate/methanol to gave product [Molecular formula: $C_{59}H_{105}N_{11}O_{13}$; Exact Mass: 1175.79; MS (m/z): 1176.70 (M+H)$^+$, 1198.7 (M+Na)$^+$; TLC R$_f$: 0.22 (EtOAc/MeOH=10/1); HPLC RT: 12.24 minutes (C8 reverse phase column, 250 mm, acetonitrile/0.077% NH$_4$OAc in water, operation temperature: 64° C.; Detector: 210 nm)].

Example 46

[(S)-2-(N-Boc)-ethylamino-NMeGly]-4-Cyclosporin

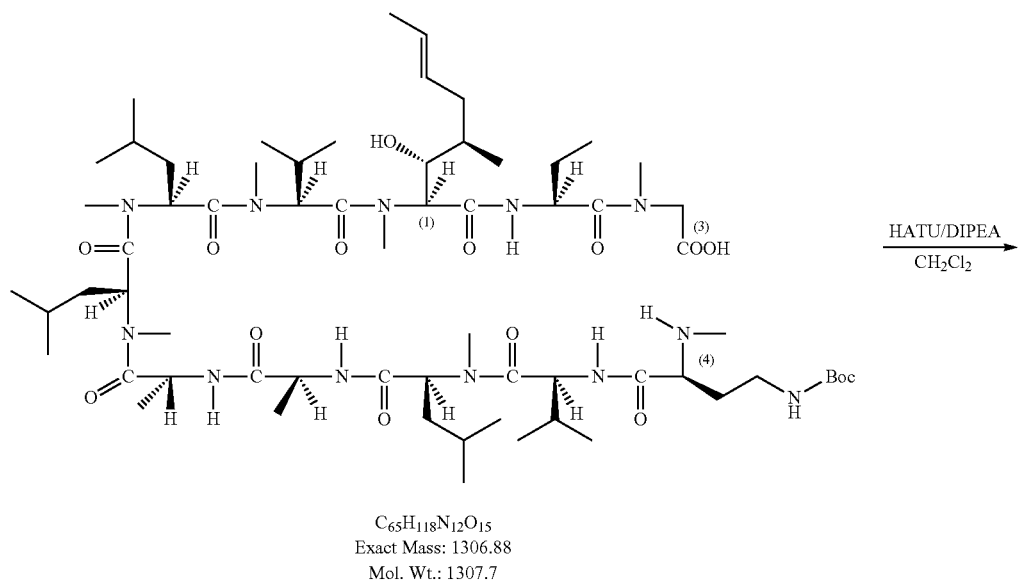

To a solution of the undecapeptide (FW 1307.70, 1.20 g, 0.92 mmol) in 800 ml of DCM were added HATU (FW 380.20, 1.05 g, 2.75 mmol) and diisopropylethylamine (FW 129.25, d 0.747, 0.48 ml, 0.36 g, 2.75 mmol). The mixture was stirred at room temperature for 3 hours, and then was washed with 120 ml of 1N HCl, 120 ml of aqueous $NaHCO_3$ solution, brine (3×150 ml), dried over $MgSO_4$, and evaporated under reduced pressure. The residue was purified by Combi-flash on silica gel with eluent of DCM/MeOH from the ratio of 10:0 to 9:1 and to give the product [Molecular formula: $C_{65}H_{116}N_{12}O_{14}$; Exact Mass: 1288.87; MS (m/z): 1289.90 $(M+H)^+$].

The undecapeptide was prepared according to a similar method described in Examples 38, 39, 40, 41, 43, and 44. The (S)-γ-N-methyl-N-Boc-2,4-diaminobutyric acid was prepared according to WO 2007/015824.

Example 47

[(S)-(2-aminoethyl)-NMeGly]-4-Cyclosporin

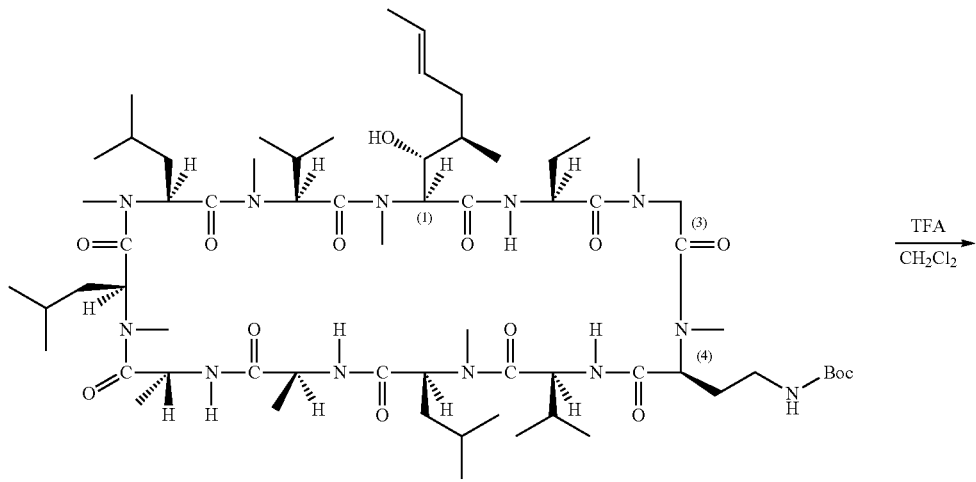

C$_{65}$H$_{116}$N$_{12}$O$_{14}$
Exact Mass: 1288.87
Mol. Wt.: 1289.69

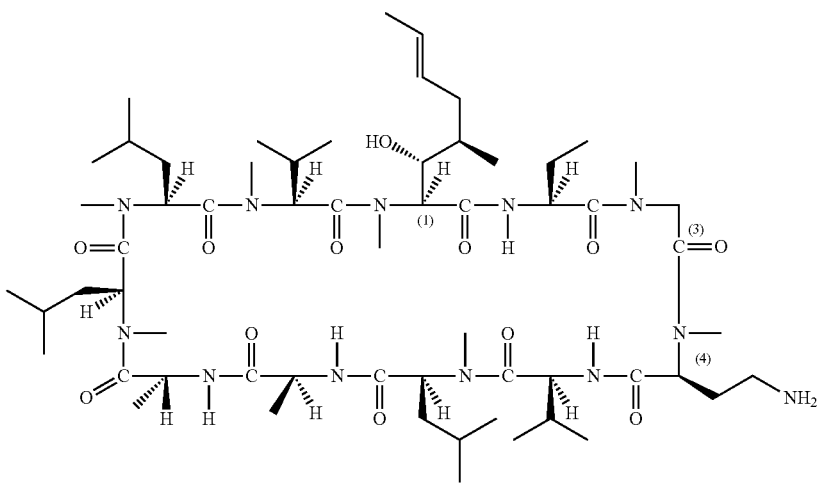

C$_{60}$H$_{108}$N$_{12}$O$_{12}$
Exact Mass: 1188.82
Mol. Wt.: 1189.57

[(S)—N-Boc-ethylamino)-NMeGly]-4-Cyclosporin (FW 1289.69, 580 mg, 0.45 mmol) and 5 ml of TFA were added into 20 ml of DCM at room temperature. The mixture was stirred at room temperature for 3 hours. After removal of the solvent and TFA under reduced pressure, 40 ml of toluene was added and the solution was evaporated under vacuum. Then the residue was diluted with 150 ml of EtOAc, washed with 40 ml of the saturated NaHCO$_3$ water solution, brine, dried over MgSO$_4$ and evaporated under reduced pressure to give the product for next step without purification. The product was confirmed by MS (m/e): 1189.7 (M+H)$^+$, 1211.7 (M+Na)$^+$.

Example 48

[(S)-2-(N,N-Diethylamino)ethyl)-NMeGly]-4-Cyclosporin

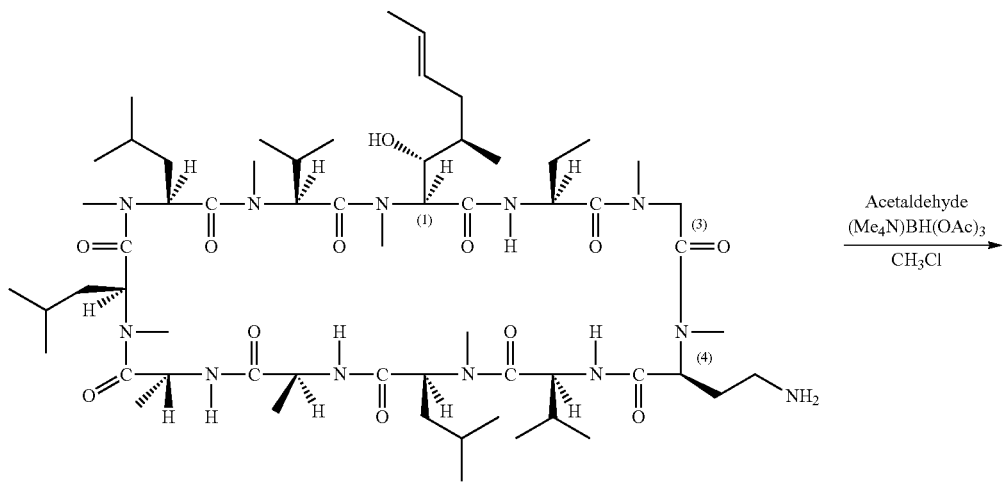

$C_{60}H_{108}N_{12}O_{12}$
Exact Mass: 1188.82
Mol. Wt.: 1189.57

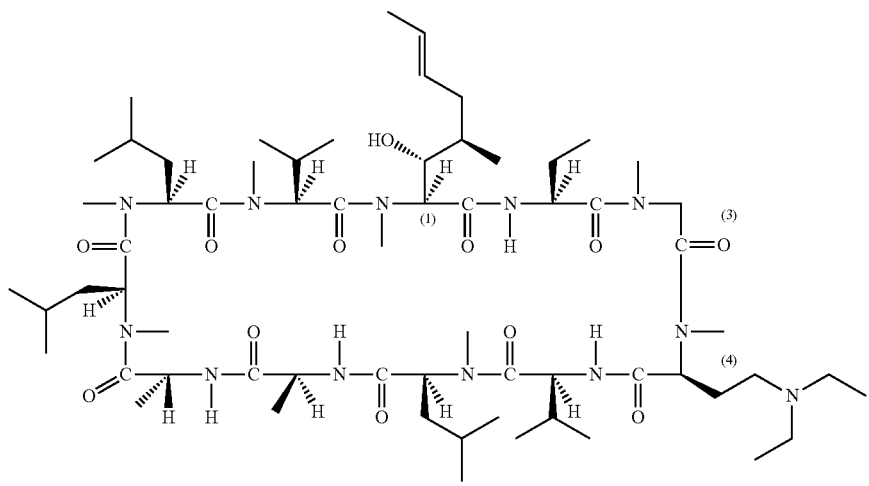

$C_{64}H_{116}N_{12}O_{12}$
Exact Mass: 1244.88
Mol. Wt.: 1245.68

[(S)-(2-aminoethyl)-NMeGly]-4-Cyclosporin (FW 1189.57, 300 mg, 0.25 mmol) was dissolved in 10 ml of chloroform. Acetaldehyde (FW 44.06, d 0.780, 27.5 mg, 0.63 mmol) was added and stirred at room temperature for 10 minutes. Tetramethylammonium triacetoxyborohydride (FW 263.10, 329 mg, 1.25 mmol) was added in three portions over 30 minutes. The reaction mixture was stirred at room temperature for additional 2 hours. The solvent was evaporated under reduced pressure, then 40 ml of DCM was added. The mixture was washed with the 30 ml of the saturated $NaHCO_3$ water solution, brine, dried over $MgSO_4$, and evaporated under reduced pressure. The residue was purified on silica gel with eluent of EtOAc/MeOH from the ratio of 10:0 to 9:1, and to give the product [Molecular formula: $C_{64}H_{116}N_{12}O_{12}$; Exact Mass: 1244.88; MS (m/z): 1245.90 (M+H)$^+$; TLC R$_f$: 0.25 (DCM/MeOH=10/1); HPLC RT: 11.87 minutes (C8 reverse phase column, 250 mm, acetonitrile/0.05% TFA in water, operation temperature: 64° C.; Detector: 210 nm)].

Example 49

Stability Testing of [(R)-3-(N,N-Dimethylamino)ethylthio-Sar]-3-[(γ-Hydroxy)-NMeLeu]-4-cyclosporin (SCY-635) and Cyclosporin Derivatives Stability of Cyclosporin derivatives was evaluated in methanol at 65° C. and 50° C., and HPLC was used to monitor possible degradation of these compounds.

It was found that SCY-635 is not stable and can easily degrade to form its corresponding epimer, which is expected to have low or no anti-viral activity.

Epimerization of SCY-635* in MeOH at 65° C.

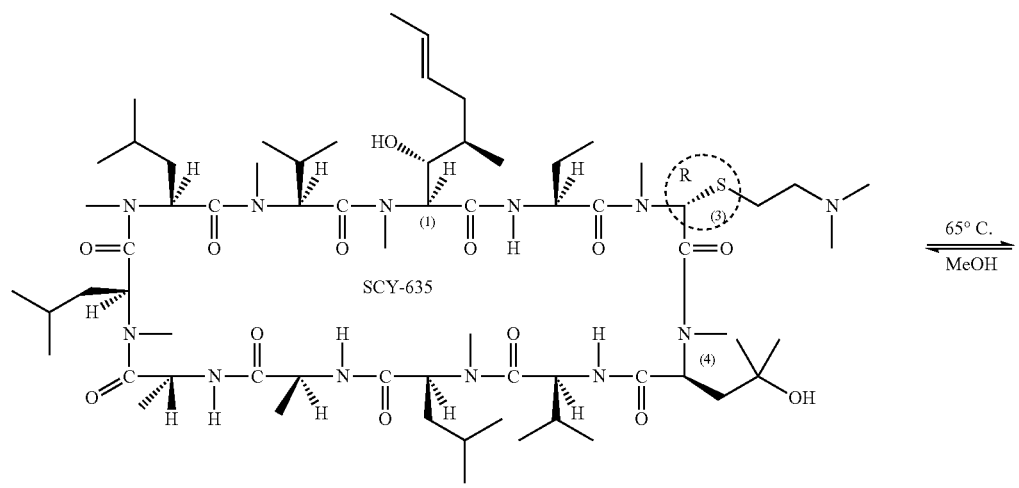

SCY-635
HPLC RT: 14.60 min
The equilibrium endpoint: ~ 58%

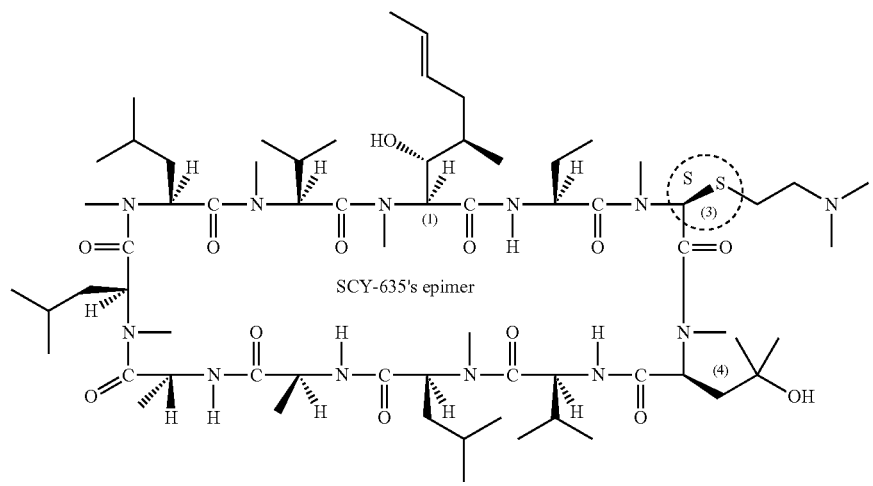

SCY-635's epimer
HPLC RT: 15.01 min
The equilibrium endpoint: ~ 42%

| Epimerization | SCY-635's epimer % | | | | |
|---|---|---|---|---|---|
| | 2 hours | 4 hours | 6 hours | 8 hours | 10 hours |
| SCY-635 ⇌ SCY-635's epimer | 24% | 35% | 39% | 41% | 43% |

*SCY-635 was prepared according to a method described by: Evans, M., et al, 2003, *Bioorg. Med. Chem. Lett.*, 4, 4415-4419; Carry, J., et al, 2004, Synlett. 2, 316-320; or U.S. Pat. No. 5,994,299 (each of which is incorporated herein by reference).

Epimerization of SCY-635's epimer* in MeOH at 65° C.

| Epimerization | SCY-635% | | |
|---|---|---|---|
| | 3 hours | 6 hours | 10 hours |
| SCY-635's epimer ⇌ SCY-635 | 51% | 58% | 58% |

*During the stability study, it was found that SCY-635 transformed into its epimer, which was separated as a pure compound. HPLC RT for SCY-635: 14.60 minutes, and for its epimer: 15.01 minutes (C8 reverse phase column, 250 mm, acetonitrile/0.077% NH₄OAc in water, operation temperature: 64° C.; Detector: 210 nm).

When the epimer was treated within MeOH at 65° C., it also was found that transformed to SCY-635. At the endpoint of the equilibrium in methanol, the solution contained about 58% of SCY-635 and about 42% of its epimer.

Epimerization of [(R)-2-(N,N-dimethylamino)ethyl-thio-Sar]-3-cyclosporin in MeOH at 65° C.

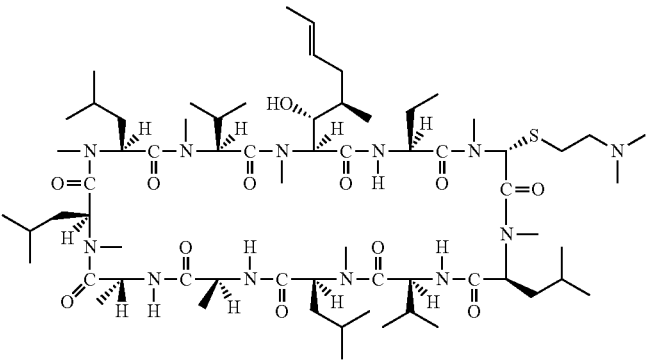 [SMILES: C/C=C/C[C@@H](C)[C@@H](O)[C@H]1C(=O)N[C@@H](CC)C(=O)N(C)[C@H](SCCN(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

| Compound | Epimerization % | | |
|---|---|---|---|
| | 2 hours | 4 hours | 6 hours |
| [(R)-2-(N,N-Dimethylamino)ethylthio-Sar]-3-cyclosporin | ~12% | ~19% | ~23% |

Epimerization of [(R)-3-(N-Morpholino)propylthio-Sar]-3-[(γ-hydroxy)-NMeLeu]-4-cyclosporin in MeOH at 65° C.

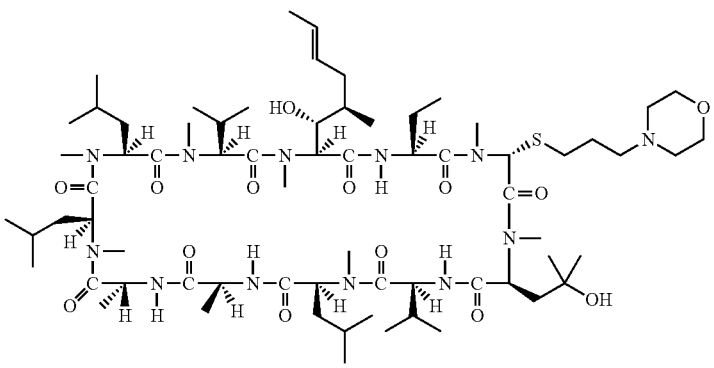 [SMILES: C/C=C/C[C@@H](C)[C@@H](O)[C@H]1C(=O)N[C@@H](CC)C(=O)N(C)[C@H](SCCCN2CCOCC2)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

| Compound | Epimerization % in MeOH at 65° C. | | | | |
|---|---|---|---|---|---|
| | 2 hours | 4 hours | 6 hours | 8 hours | 10 hours |
| [(R)-3-(Morpholino)propylthio-Sar]-3-[(γ-hydroxy)-NMeLeu]-4-cyclosporin | 0% | 0% | 0% | Less than 1% | ~10% |

Epimerization of [(R)-3-(N-Morpholino)propylthio-Sar]-3-[(γ-Methoxy)-NMeLeu]-4-cyclosporin in MeOH at 65° C.

| Compound | Epimerization % in MeOH at 65° C. | | | | | |
|---|---|---|---|---|---|---|
| | 2 hours | 4 hours | 10 hours | 22 hours | 30 hours | 38 hours |
| 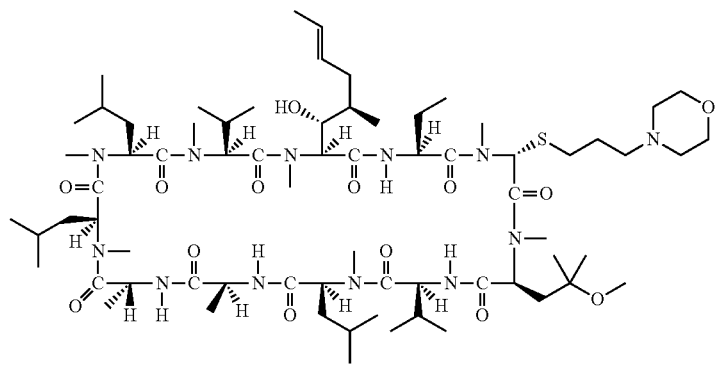 [SMILES: C/C=C/C[C@@H](C)[C@@H](O)[C@H]1C(=O)N[C@@H](CC)C(=O)N(C)[C@H](SCCCN2CCOCC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] [(R)-3-(N-Morpholino)propylthio-Sar]-3-[(γ-methoxy)-NMeLeu]-4-cyclosporin | 0% | 0% | 0% | 0% | 0% | 0% |

Epimerization of Cyclosporin Derivatives in MeOH at 50° C.

| Compounds | Epimerization % | | |
|---|---|---|---|
| | 29 hours | 77 hours | 125 hours |
| 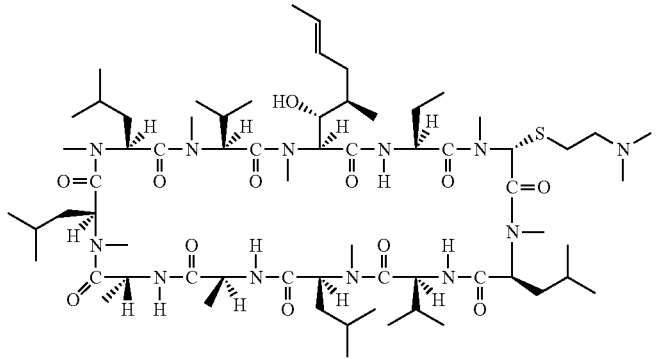 [SMILES: C/C=C/C[C@@H](C)[C@@H](O)[C@H]1C(=O)N[C@@H](CC)C(=O)N(C)[C@H](SCCN(C)C)C(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] [(R)-2-(N,N-Dimethylamino)ethylthio-Sar]-3-cyclosporin | ~26% | ~32% | ~35% |

-continued

| Compounds | Epimerization % | | |
|---|---|---|---|
| | 29 hours | 77 hours | 125 hours |
| [(R)-3-(N,N Diethylamino)propylthio-Sar]-3-[(γ-hydroxy)-NMeLeu]-4-cyclosporin | 0% | Less than 1% | ~12% |
| [(R)-3-(N,N-Diethylamino)propylthio-Sar]-3-[(γ-methoxy)-NMeLeu]-4-cyclosporin | 0% | 0% | 0% |
| [(R)-3-(N-Morpholino)propylthio-Sar]-3-[(γ-hydroxy)-NMeLeu]-4-cyclosporin | 0% | 0% | 0% |

-continued

| Compounds | Epimerization % | | |
|---|---|---|---|
| | 29 hours | 77 hours | 125 hours |
| [(R)-3-(N-Morpholino)propylthio-Sar]-3-[(γ-methoxy)-NMeLeu]-4-cyclosporin | 0% | 0% | 0% |
| [(R)-2-(N,N-Diethylamino)ethylthio-Sar]-3-[NMeIle]-4-cyclosporin | ~4% | ~10% | ~16% |
| [(R)-3-(N,N-Diethylamino)propylthio-Sar]-3-[NMeIle]-4-cyclosporin | 0% | 0% | 0% |

-continued
| Compounds | Epimerization % | | |
|---|---|---|---|
| | 29 hours | 77 hours | 125 hours |
| 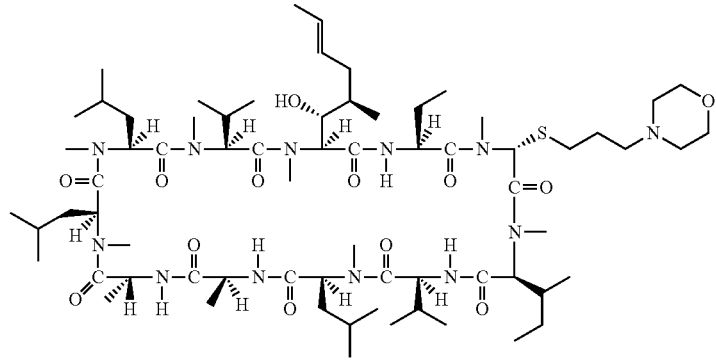 [SMILES: C/C=C/C[C@@H](C)[C@@H](O)[C@H]1C(=O)N[C@@H](CC)C(=O)N(C)[C@H](SCCCN2CCOCC2)C(=O)N(C)[C@@H](C(C)CC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N-Morpholino)propyl-Sar]-3-[NMeIle]-4-cyclosporin | 0% | 0% | 0% |
| 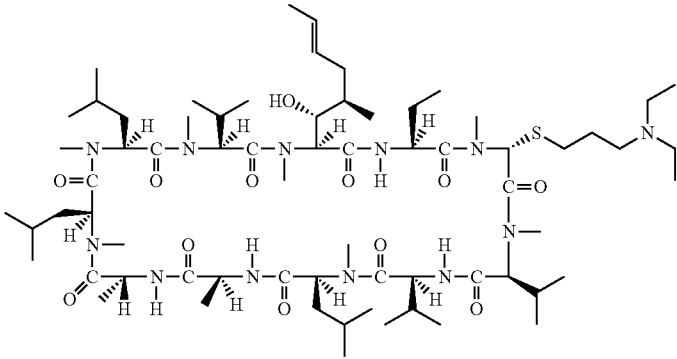 [SMILES: C/C=C/C[C@@H](C)[C@@H](O)[C@H]1C(=O)N[C@@H](CC)C(=O)N(C)[C@H](SCCCN(CC)CC)C(=O)N(C)[C@@H](C(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N,N-Diethylamino)propylthio-Sar]-3-[NMeVal]-4-cyclosporin | 0% | 0% | 0% |
| 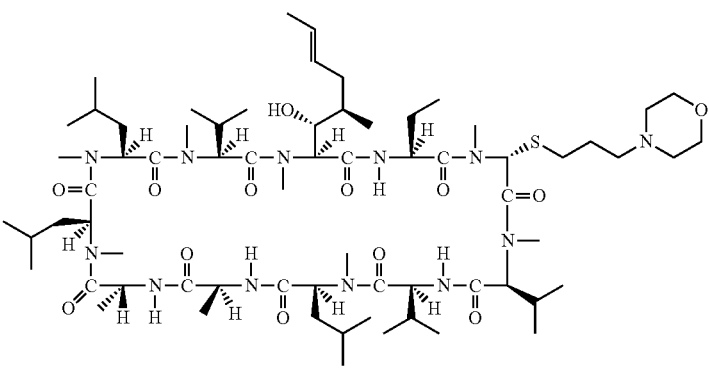 [SMILES: C/C=C/C[C@@H](C)[C@@H](O)[C@H]1C(=O)N[C@@H](CC)C(=O)N(C)[C@H](SCCCN2CCOCC2)C(=O)N(C)[C@@H](C(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N-Morpholino)propyl-Sar]-3-[NMeVal]-4-cyclosporin | 0% | 0% | 0% |
While not being bound by a particular theory, the inventors hypothesized that the epimerization occurred through the following pathway:

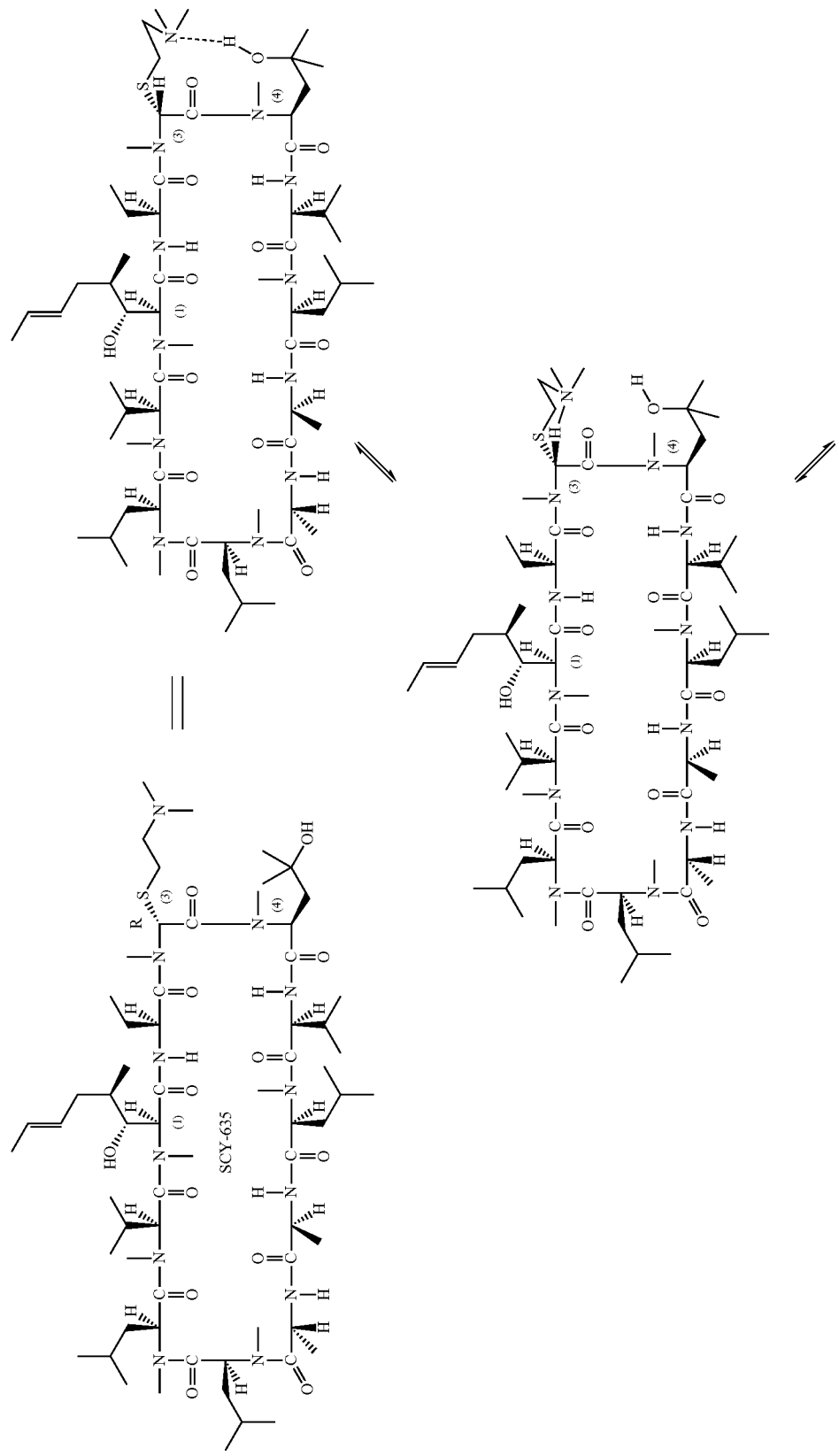

-continued
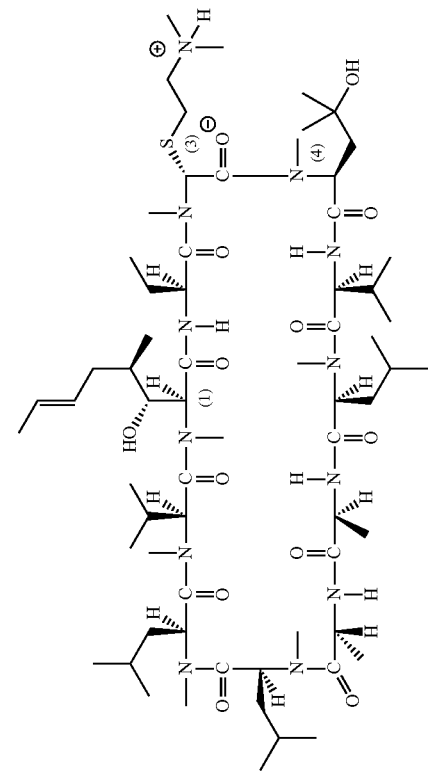
⇌
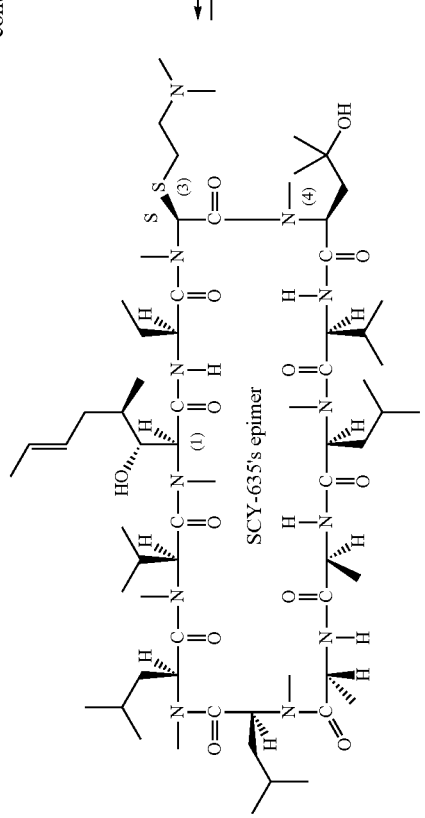
SCY-635's epimer

Thus, the two carbon side chain at position 3 of the sarcosine of cyclosporine contributes to the unstability, because it can form a six-membered ring transation state, and stimulate the epimerization. Additionally, the epimerization is accelerated by the γ-hydroxy group at the 4-position of leucine.

Accordingly, the inventors envisioned novel cyclosporine derivatives having enhanced stability while maintaining good cyclophilin binding activity. In particular, the inventors have surprisingly found that the masking the γ-hydroxy group on leucine at position 4, elongating side carbon chain (e.g., with 3 carbons or higher), and/or substituting the amine terminal at position 3 with a bulky side chain can prevent or minimize the epimerization.

Example 50

Anti HCV Activity of Cyclosporin Derivatives

The anti-HCV activity of cyclosporine derivatives were evaluated in the HCV subgenomic replicon assay. The assay use the cell line ET (luc-ubi-neo/ET), which is a Huh7 human hepatoma cell line harboring an HCV replicon with a stable luciferase (Luc) reporter. HCV RNA replication was assessed by quantifying HCV replicon-derived luciferase activity. The antiviral activity of cyclosporine analogs were evaluated after drug treatment, the EC 50 and EC 90 were determined in subsequent assessments by using the luciferase end point (Krieger, N., et al., 2001, *J. Virol.* 75, 4614-4624; Pietschmann, T., et al., 2002, *J. Virol.* 76, 4008-4021; each of which is incorporated herein by reference).

The results of certain compounds are as follows:

| Compounds | Antiviral activity IC$_{50}$ (µM) |
|---|---|
| Cyclosporin A | 0.41 |
| [N-Methylvaline]-4-cyclosporin (SDZ-220-384) | 0.17 |
| [N-Methylisoleucine]-4-cyclosporin (SDZ-NIM-811) | 0.15 |
| [(R)-2-(N,N-Diethylamino)ethylthio-Sar]-3-[NMeVal]-4-cyclosporin | 0.04 |
| [(S)-2-(N,N-Diethylamino)ethylthio-Sar]-3-[NMeVal]-4-cyclosporin | 3.66 |
| [(R)-2-(N,N-Diethylamino)ethylthio-Sar]-3-[NMeIle]-4-cyclosporin | 0.04 |
| [(S)-2-(N,N-Diethylamino)ethylthio-Sar]-3-[NMeIle]-4-cyclosporin | 1.87 |
| [(R)-3-(N-Morphlino)propylthio-Sar]-3-[(γ-Hydroxy)-NMeLeu]-4-cyclosporin (Example 1) | 0.04 |
| [(R)-3-(N,N-Diethylamino)propylthio-Sar]-3-[(γ-Hydroxy)-NMeLeu]-4-cyclosporin (Example 2) | 0.07 |
| [(R)-3-(N-Morphlino)propylthio-Sar]-3-[(γ-Methoxy)-NMeLeu]-4-Dihydrocyclosporin (Example 10) | 0.09 |
| [(R)-3-(N-Morphlino)propylthio-Sar]-3-[(γ-Methoxy)-NMeLeu]-4-cyclosporin (Example 12) | 0.06 |
| [(R)-3-(N-Morphlino)propylthio-Sar]-3-[(γ-Allyloxy)-NMeLeu]-4-cyclosporin (Example 26) | 0.08 |

Examples 51-210

The following compounds can be prepared according to a method analogous to those described herein.

TABLE 1

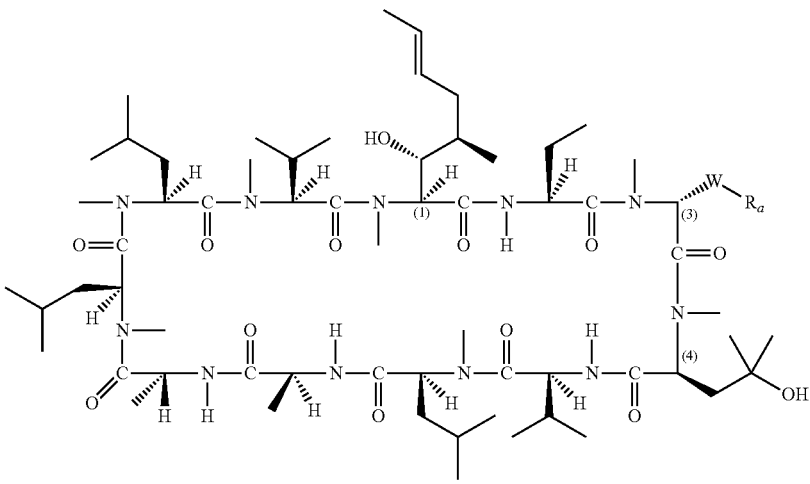

| Ex. No. | W | R$_a$ | Name |
|---|---|---|---|
| 51 | S | (CH$_2$)$_3$-N-pyrrolidinyl | [(R)-3-(N-Pyrrolidinyl)propylthio-Sar]-3-[(γ-hydroxy)-NMeLeu]-4-cyclosporin |
| 52 | S | (CH$_2$)$_3$-N-piperidinyl | [(R)-3-(N-Piperidinyl)propylthio-Sar]-3-[(γ-hydroxy)-NMeLeu]-4-cyclosporin |

TABLE 1-continued

| Ex. No. | W | $R_a$ | Name |
|---|---|---|---|
| 53 | S | (CH2)3-thiomorpholine | [(R)-3-(N-Thiomorpholino)propylthio-Sar]-3-[(γ-hydroxy)-NMeLeu]-4-cyclosporin |
| 54 | S | (CH2)3-N(CH3)2 | [(R)-3-(N,N-Dimethylamino)propylthio-Sar]-3-[(γ-hydroxy)-NMeLeu]-4-cyclosporin |
| 55 | S | (CH2)3-N(iPr)(CH3) | [(R)-3-(N-iso-Propyl-N-methylamino)propylthio-Sar]-3-[(γ-hydroxy)-NMeLeu]-4-cyclosporin |
| 56 | S | (CH2)4-pyrrolidine | [(R)-4-(N-Pyrrolidinyl)Butylthio-Sar]-3-[(γ-hydroxy)-NMeLeu]-4-cyclosporin |
| 57 | S | (CH2)4-piperidine | [(R)-4-(N-Piperidinyl)Butylthio-Sar]-3-[(γ-hydroxy)-NMeLeu]-4-cyclosporin |
| 58 | S | (CH2)4-morpholine | [(R)-4-(N-Morpholino)Butylthio-Sar]-3-[(γ-hydroxy)-NMeLeu]-4-cyclosporin |
| 59 | S | (CH2)4-thiomorpholine | [(R)-4-(N-Thiomorpholino)Butylthio-Sar]-3-[(γ-hydroxy)-NMeLeu]-4-cyclosporin |
| 60 | S | (CH2)4-N(CH3)2 | [(R)-4-(N,N-Dimethylamino)butylthio-Sar]-3-[(γ-hydroxy)-NMeLeu]-4-cyclosporin |

TABLE 1-continued

| Ex. No. | W | $R_a$ | Name |
|---|---|---|---|
| 61 | S | (CH2)4-N(Et)2 | [(R)-4-(N,N-Diethylamino)butylthio-Sar]-3-[(γ-hydroxy)-NMeLeu]-4-cyclosporin |
| 62 | S | (CH2)4-NH-iPr | [(R)-4-(N-iso-Propylamino)butylthio-Sar]-3-[(γ-hydroxy)-NMeLeu]-4-cyclosporin |
| 63 | S | (CH2)4-N(Me)(iPr) | [(R)-4-(N-iso-Propyl-N-methylamino)butylthio-Sar]-3-[(γ-hydroxy)-NMeLeu]-4-cyclosporin |
| 64 | S | (CH2)4-N(Et)(iPr) | [(R)-4-(N-iso-Propyl-N-ethylamino)butylthio-Sar]-3-[(γ-hydroxy)-NMeLeu]-4-cyclosporin |
| 65 | S | (4-methyl)pentyl | [(R)-(4-Methyl)pentylthio-Sar]-3-[(γ-hydroxy)-NMeLeu]-4-cyclosporin |
| 66 | S | (5-methyl)hexyl | [(R)-(5-Methyl)hexylthio-Sar]-3-[(γ-hydroxy)-NMeLeu]-4-cyclosporin |
| 67 | S | 2-methoxypropyl | [(R)-2-Methoxypropylthio-Sar]-3-[(γ-hydroxy)-NMeLeu]-4-cyclosporin |
| 68 | S | 2-(2-methoxypropyloxy)propyl | [(R)-2-(2-Methoxypropyloxy)propylthio-Sar]-3-[(γ-hydroxy)-NMeLeu]-4-cyclosporin |

TABLE 2

| Ex. No. | W | $R_a$ | Name |
|---|---|---|---|
| 69 | S | (pyrrolidine-propyl) | [(R)-3-(N-Pyrrolidinyl)propylthio-Sar]-3-[(γ-methylthio)methoxy-NMeLeu]-4-cyclosporin |
| 70 | S | (piperidine-propyl) | [(R)-3-(N-Piperidinyl)propylthio-Sar]-3-[(γ-methylthio)methoxy-NMeLeu]-4-cyclosporin |
| 71 | S | (thiomorpholine-propyl) | [(R)-3-(N-Thiomorpholino)propylthio-Sar]-3-[(γ-methylthio)methoxy-NMeLeu]-4-cyclosporin |
| 72 | S | (N,N-dimethylamino-propyl) | [(R)-3-(N,N-Dimethylamino)propylthio-Sar]-3-[(γ-methylthio)methoxy-NMeLeu]-4-cyclosporin |
| 73 | S | (N,N-diethylamino-propyl) | [(R)-3-(N,N-Diethylamino)propylthio-Sar]-3-[(γ-methylthio)methoxy-NMeLeu]-4-cyclosporin |
| 74 | S | (N-iso-propyl-N-ethylamino-propyl) | [(R)-3-(N-iso-Propyl-N-ethylamino)propylthio-Sar]-3-[(γ-methylthio)methoxy-NMeLeu]-4-cyclosporin |
| 75 | S | (4-methylpentyl) | [(R)-(4-Methyl)pentylthio-Sar]-3-[(γ-methylthio)methoxy-NMeLeu]-4-cyclosporin |
| 76 | S | (5-methylhexyl) | [(R)-(5-Methyl)hexylthio-Sar]-3-[(γ-methylthio)methoxy-NMeLeu]-4-cyclosporin |
| 77 | S | (2-methoxypropyl) | [(R)-2-Methoxypropylthio-Sar]-3-[(γ-methylthio)methoxy-NMeLeu]-4-cyclosporin |

TABLE 2-continued
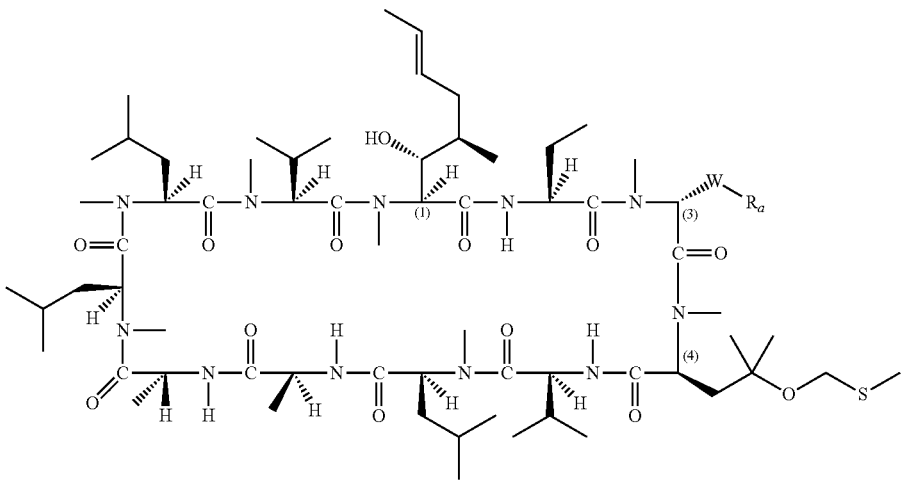
| Ex. No. | W | $R_a$ | Name |
|---|---|---|---|
| 78 | S | 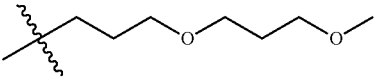 [SMILES: *CCCOCCCOC] | [(R)-2-(2-Methoxypropyloxy)propylthio-Sar]-3-[(γ-methylthio)methoxy-NMeLeu]-4-cyclosporin |
TABLE 3
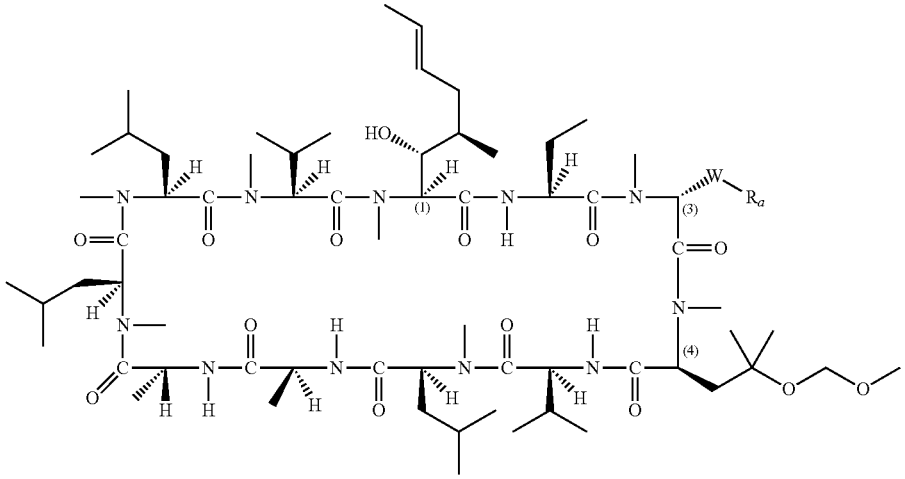
| Ex. No. | W | $R_a$ | Name |
|---|---|---|---|
| 79 | S | 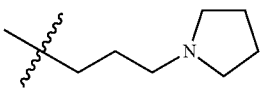 [SMILES: *CCCN1CCCC1] | [(R)-3-(N-Pyrrolidinyl)propylthio-Sar]-3-[(γ-methyloxy)methoxy-NMeLeu]-4-cyclosporin |
| 80 | S | 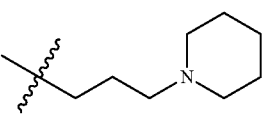 [SMILES: *CCCN1CCCCC1] | [(R)-3-(N-Piperidinyl)propylthio-Sar]-3-[(γ-methyloxy)methoxy-NMeLeu]-4-cyclosporin |

TABLE 3-continued

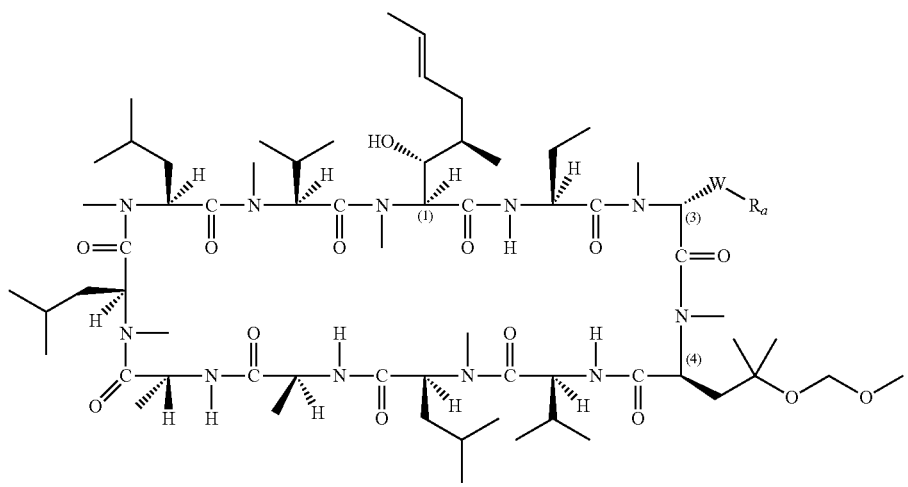

| Ex. No. | W | $R_a$ | Name |
|---|---|---|---|
| 81 | S | (morpholinopropyl) | [(R)-3-(N-Morpholino)propylthio-Sar]-3-[(γ-methyloxy)methoxy-NMeLeu]-4-cyclosporin |
| 82 | S | (N,N-dimethylaminopropyl) | [(R)-3-(N,N-Dimethylamino)propylthio-Sar]-3-[(γ-methyloxy)methoxy-NMeLeu]-4-cyclosporin |
| 83 | S | (N,N-diethylaminopropyl) | [(R)-3-(N,N-Diethylamino)propylthio-Sar]-3-[(γ-methyloxy)methoxy-NMeLeu]-4-cyclosporin |
| 84 | S | (N-iso-propyl-N-ethylaminopropyl) | [(R)-3-(N-iso-Propyl-N-ethylamino)propylthio-Sar]-3-[(γ-methyloxy)methoxy-NMeLeu]-4-cyclosporin |
| 85 | S | (4-methylpentyl) | [(R)-(4-Methyl)pentylthio-Sar]-3-[(γ-methyloxy)methoxy-NMeLeu]-4-cyclosporin |
| 86 | S | (5-methylhexyl) | [(R)-(5-Methyl)hexylthio-Sar]-3-[(γ-methyloxy)methoxy-NMeLeu]-4-cyclosporin |
| 87 | S | (2-methoxypropyl) | [(R)-2-Methoxypropylthio-Sar]-3-[(γ-methyloxy)methoxy-NMeLeu]-4-cyclosporin |
| 88 | S | (2-(2-methoxypropyloxy)propyl) | [(R)-2-(2-Methoxypropyloxy)propylthio-Sar]-3-[(γ-methyloxy)methoxy-NMeLeu]-4-cyclosporin |

TABLE 4

| Ex. No. | W | $R_a$ | Name |
|---|---|---|---|
| 89 | S | (CH₂)₂-N-thiomorpholine | [(R)-2-(N-Thiomorpholino)ethylthio-Sar]-3-[(γ-methoxy)-NMeLeu]-4-cyclosporin |
| 90 | S | (CH₂)₂-NH-iPr | [(R)-2-(N-iso-Propylamino)ethylthio-Sar]-3-[(γ-methoxy)-NMeLeu]-4-cyclosporin |
| 91 | S | (CH₂)₂-N(Me)-iPr | [(R)-2-(N-iso-Propyl-N-methylamino)ethylthio-Sar]-3-[(γ-methoxy)-NMeLeu]-4-cyclosporin |
| 92 | S | (CH₂)₃-N-thiomorpholine | [(R)-3-(N-Thiomorpholino)propylthio-Sar]-3-[(γ-methoxy)-NMeLeu]-4-cyclosporin |
| 93 | S | (CH₂)₃-N-4-methylpiperazine | [(R)-3-(N-4-Methylpiperazinyl)propylthio-Sar]-3-[(γ-methoxy)-NMeLeu]-4-cyclosporin |
| 94 | S | (CH₂)₃-NH-iPr | [(R)-3-(N-iso-Propylamino)propylthio-Sar]-3-[(γ-methoxy)-NMeLeu]-4-cyclosporin |
| 95 | S | (CH₂)₃-N(Me)-iPr | [(R)-3-(N-iso-Propyl-N-methylamino)propylthio-Sar]-3-[(γ-methoxy)-NMeLeu]-4-cyclosporin |
| 96 | S | (CH₂)₄-N-pyrrolidine | [(R)-4-(N-Pyrrolidinyl)butylthio-Sar]-3-[(γ-methoxy)-NMeLeu]-4-cyclosporin |

TABLE 4-continued

| Ex. No. | W | $R_a$ | Name |
|---|---|---|---|
| 97 | S | (piperidinyl-butyl) | [(R)-4-(N-Piperidinyl)butylthio-Sar]-3-[(γ-methoxy)-NMeLeu]-4-cyclosporin |
| 98 | S | (morpholino-butyl) | [(R)-4-(N-Morpholino)butylthio-Sar]-3-[(γ-methoxy)-NMeLeu]-4-cyclosporin |
| 99 | S | (thiomorpholino-butyl) | [(R)-4-(N-Thiomorpholino)butylthio-Sar]-3-[(γ-methoxy)-NMeLeu]-4-cyclosporin |
| 100 | S | (4-methylpiperazinyl-butyl) | [(R)-4-(N-4-Methylpiperazinyl)butylthio-Sar]-3-[(γ-methoxy)-NMeLeu]-4-cyclosporin |
| 101 | S | (dimethylamino-butyl) | [(R)-4-(N,N-Dimethylamino)butylthio-Sar]-3-[(γ-methoxy)-NMeLeu]-4-cyclosporin |
| 102 | S | (diethylamino-butyl) | [(R)-4-(N,N-Diethylamino)butylthio-Sar]-3-[(γ-methoxy)-NMeLeu]-4-cyclosporin |
| 103 | S | (iso-propylamino-butyl) | [(R)-4-(N-iso-Propylamino)butylthio-Sar]-3-[(γ-methoxy)-NMeLeu]-4-cyclosporin |
| 104 | S | (iso-propyl-N-methylamino-butyl) | [(R)-4-(N-iso-Propyl-N-methylamino)butylthio-Sar]-3-[(γ-methoxy)-NMeLeu]-4-cyclosporin |

TABLE 4-continued

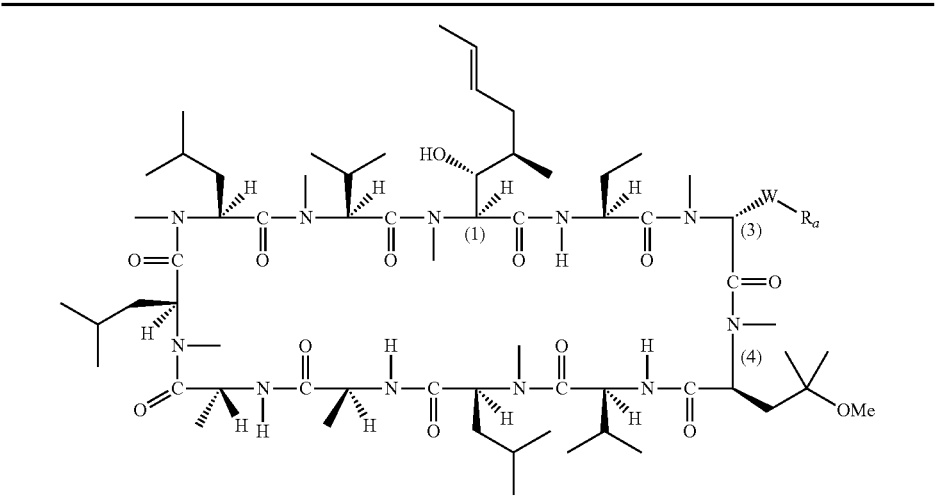

| Ex. No. | W | $R_a$ | Name |
|---|---|---|---|
| 105 | S |  | [(R)-4-(N-iso-Propyl-N-ethylamino)butylthio-Sar]-3-[(γ-methoxy)-NMeLeu]-4-cyclosporin |
| 106 | S |  | [(R)-n-Pentylthio-Sar]-3-[(γ-methoxy)-NMeLeu]-4-cyclosporin |
| 107 | S |  | [(R)-(4-Methyl)pentylthio-Sar]-3-[(γ-methoxy)-NMeLeu]-4-cyclosporin |
| 108 | S |  | [(R)-(5-Methyl)hexylthio-Sar]-3-[(γ-methoxy)-NMeLeu]-4-cyclosporin |
| 109 | S |  | [(R)-2-Methoxypropylthio-Sar]-3-[(γ-methoxy)-NMeLeu]-4-cyclosporin |
| 110 | S |  | [(R)-2-(2-Methoxypropyloxy)propylthio-Sar]-3-[(γ-methoxy)-NMeLeu]-4-cyclosporin |

TABLE 5

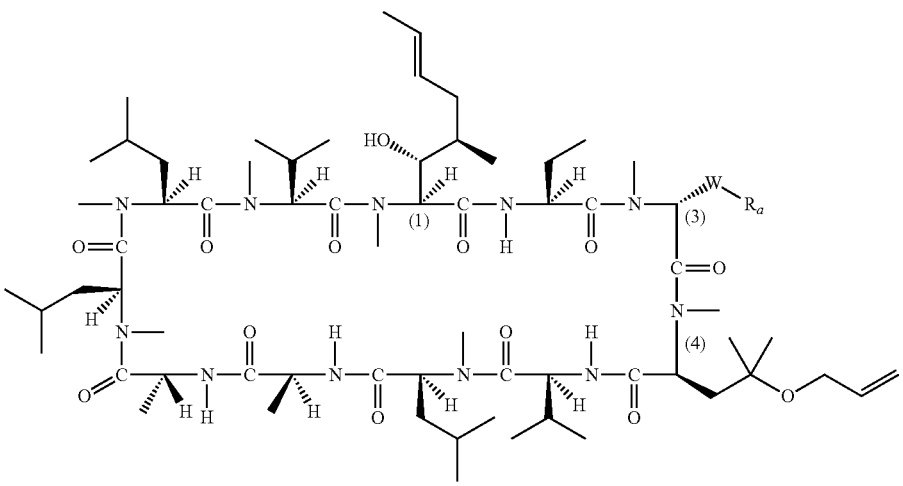

| Ex. No. | W | $R_a$ | Name |
|---|---|---|---|
| 111 | S | 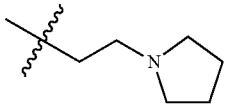 [SMILES: *CCN1CCCC1] | [(R)-2-(N-Pyrrolidinyl)ethylthio-Sar]-3-[(γ-allyloxy)-NMeLeu]-4-cyclosporin |
| 112 | S | 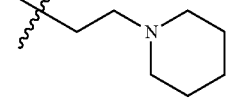 | [(R)-2-(N-Piperidinyl)ethylthio-Sar]-3-[(γ-allyloxy)-NMeLeu]-4-cyclosporin |
| 113 | S | 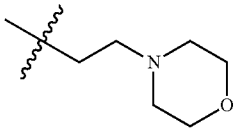 | [(R)-2-(N-Morpholino)ethylthio-Sar]-3-[(γ-allyloxy)-NMeLeu]-4-cyclosporin |
| 114 | S | 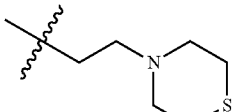 | [(R)-2-(N-Thiomorpholino)ethylthio-Sar]-3-[(γ-allyloxy)-NMeLeu]-4-cyclosporin |
| 115 | S | 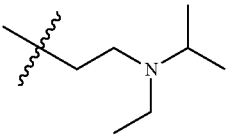 [SMILES: *CCN(CC)C(C)C] | [(R)-2-(N-iso-Propyl-N-ethylamino)ethylthio-Sar]-3-[(γ-allyloxy)-NMeLeu]-4-cyclosporin |
| 116 | S | 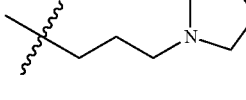 | [(R)-3-(N-Pyrrolidinyl)propylthio-Sar]-3-[(γ-allyloxy)-NMeLeu]-4-cyclosporin |
| 117 | S | 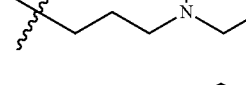 | [(R)-3-(N-Piperidinyl)propylthio-Sar]-3-[(γ-allyloxy)-NMeLeu]-4-cyclosporin |
| 118 | S | 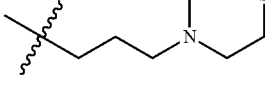 | [(R)-3-(N-Thiomorpholino)propylthio-Sar]-3-[(γ-allyloxy)-NMeLeu]-4-cyclosporin |

TABLE 5-continued

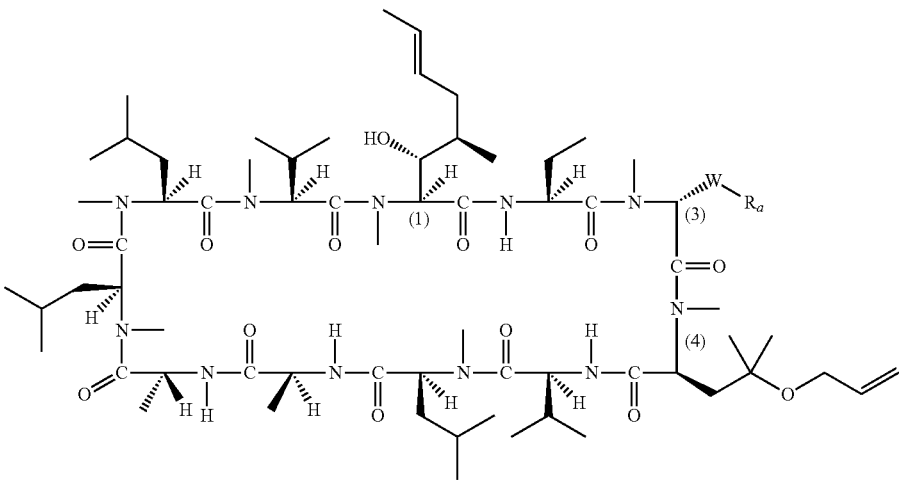

| Ex. No. | W | $R_a$ | Name |
|---|---|---|---|
| 119 | S |  | [(R)-3-(N-4-Methylpiperazinyl)propylthio-Sar]-3-[(γ-allyloxy)-NMeLeu]-4-cyclosporin |
| 120 | S | 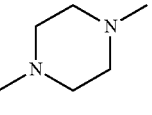 | [(R)-3-(N,N-Dimethylamino)propylthio-Sar]-3-[(γ-allyloxy)-NMeLeu]-4-cyclosporin |
| 121 | S | 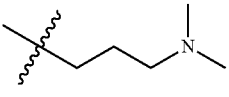 [SMILES: *CCCN(C)C] | [(R)-3-(N,N-Diethylamino)propylthio-Sar]-3-[(γ-allyloxy)-NMeLeu]-4-cyclosporin |
| 122 | S | 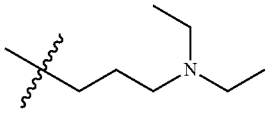 [SMILES: *CCCN(CC)CC] | [(R)-3-(N-iso-Propylamino)propylthio-Sar]-3-[(γ-allyloxy)-NMeLeu]-4-cyclosporin |
| 123 | S | 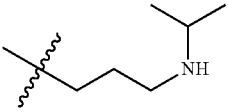 [SMILES: *CCCNC(C)C] | [(R)-3-(N-iso-Propyl-N-methylamino)propylthio-Sar]-3-[(γ-allyloxy)-NMeLeu]-4-cyclosporin |
| 124 | S | 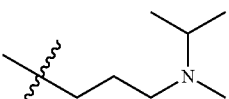 | [(R)-3-(N-iso-Propyl-N-ethylamino)propylthio-Sar]-3-[(γ-allyloxy)-NMeLeu]-4-cyclosporin |
| 125 | S | 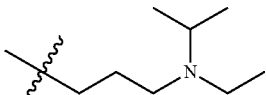 | [(R)-4-(N-Pyrrolidinyl)butylthio-Sar]-3-[(γ-allyloxy)-NMeLeu]-4-cyclosporin |

TABLE 5-continued
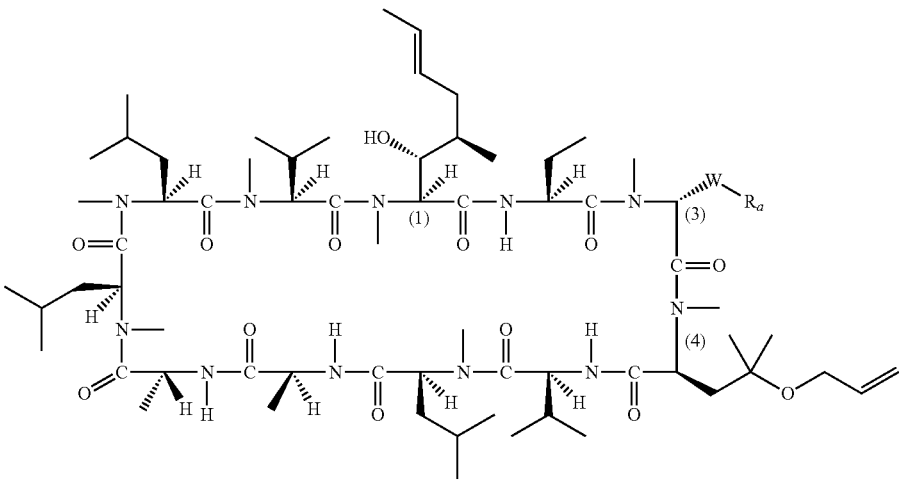
| Ex. No. | W | $R_a$ | Name |
|---|---|---|---|
| 126 | S | 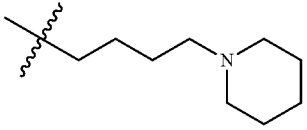 [SMILES: *CCCCN1CCCCC1] | [(R)-4-(N-Piperidinyl)butylthio-Sar]-3-[(γ-allyloxy)-NMeLeu]-4-cyclosporin |
| 127 | S | 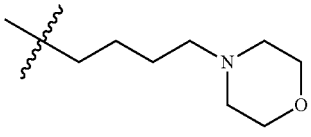 [SMILES: *CCCCN1CCOCC1] | [(R)-4-(N-Morpholino)butylthio-Sar]-3-[(γ-allyloxy)-NMeLeu]-4-cyclosporin |
| 128 | S | 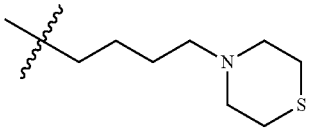 [SMILES: *CCCCN1CCSCC1] | [(R)-4-(N-Thiomorpholino)butylthio-Sar]-3-[(γ-allyloxy)-NMeLeu]-4-cyclosporin |
| 129 | S | 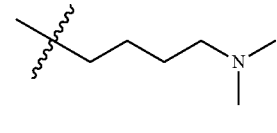 [SMILES: *CCCCN(C)C] | [(R)-4-(N,N-Dimethylamino)butylthio-Sar]-3-[(γ-allyloxy)-NMeLeu]-4-cyclosporin |

TABLE 5-continued

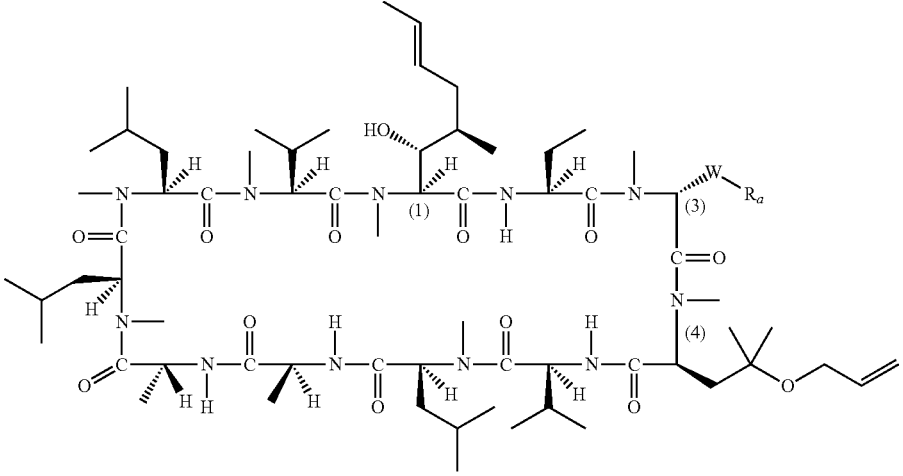

| Ex. No. | W | $R_a$ | Name |
|---|---|---|---|
| 130 | S |  | [(R)-4-(N,N-Diethylamino)butylthio-Sar]-3-[(γ-allyloxy)-NMeLeu]-4-cyclosporin |
| 131 | S |  | [(R)-4-(N-iso-Propylamino)butylthio-Sar]-3-[(γ-allyloxy)-NMeLeu]-4-cyclosporin |
| 132 | S |  | [(R)-4-(N-iso-Propyl-N-methylamino)butylthio-Sar]-3-[(γ-allyloxy)-NMeLeu]-4-cyclosporin |
| 133 | S |  | [(R)-4-(N-iso-Propyl-N-ethylamino)butylthio-Sar]-3-[(γ-allyloxy)-NMeLeu]-4-cyclosporin |
| 134 | S | 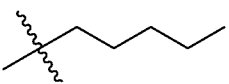 [SMILES: *CCCCC] | [(R)-n-Pentylthio-Sar]-3-[(γ-allyloxy)-NMeLeu]-4-cyclosporin |
| 135 | S | 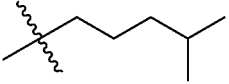 [SMILES: *CCCC(C)C] | [(R)-(4-Methyl)pentylthio-Sar]-3-[(γ-allyloxy)-NMeLeu]-4-cyclosporin |

TABLE 5-continued
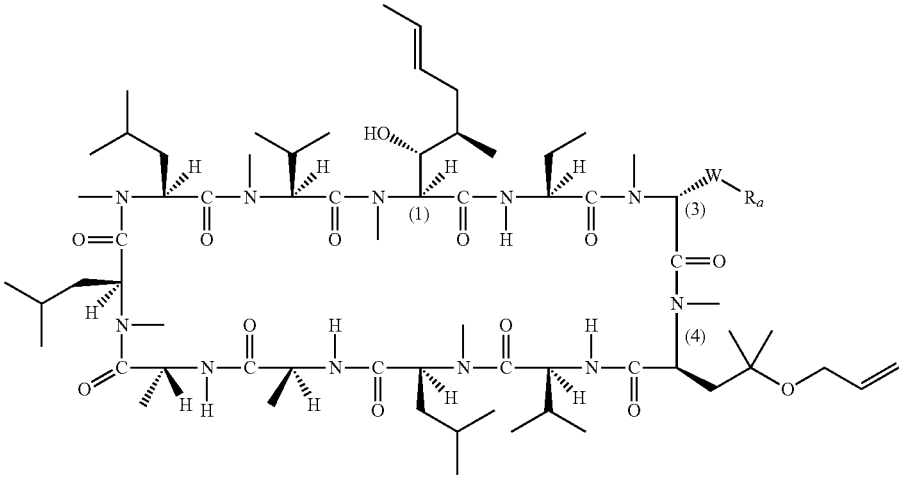
| Ex. No. | W | $R_a$ | Name |
|---|---|---|---|
| 136 | S | 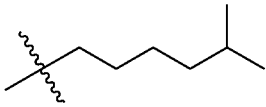 [SMILES: *CCCCC(C)C] | [(R)-(5-Methyl)hexylthio-Sar]-3-[(γ-allyloxy)-NMeLeu]-4-cyclosporin |
| 137 | S | 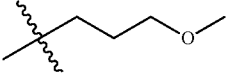 [SMILES: *CCCOC] | [(R)-2-Methoxypropylthio-Sar]-3-[(γ-allyloxy)-NMeLeu]-4-cyclosporin |
| 138 | S | 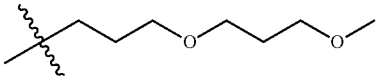 [SMILES: *CCCOCCCOC] | [(R)-2-(2-Methoxypropyloxy)propylthio-Sar]-3-[(γ-allyloxy)-NMeLeu]-4-cyclosporin |
TABLE 6
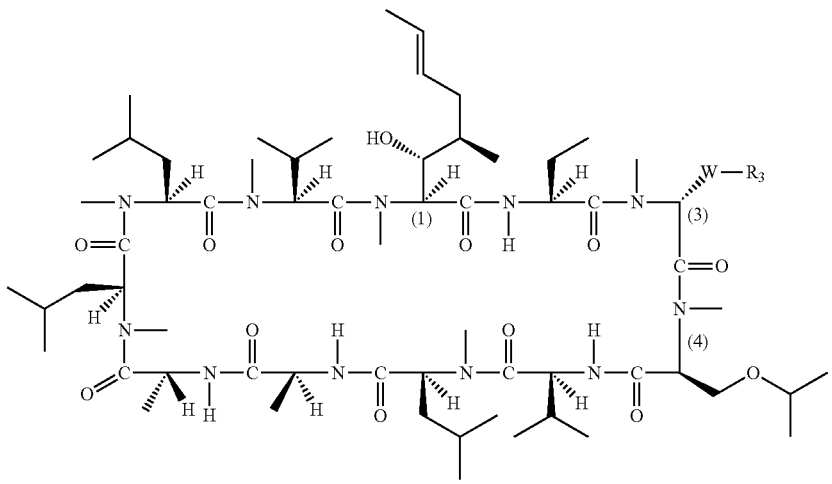
| Ex. No. | W | $R_3$ | Name |
|---|---|---|---|
| 139 | S | 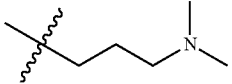 [SMILES: *CCCN(C)C] | [(R)-3-(N,N-Dimethylamino)propylthio-Sar]-3-[(β-isopropoxy)-NMeSer]-4-cyclosporin |

TABLE 6-continued

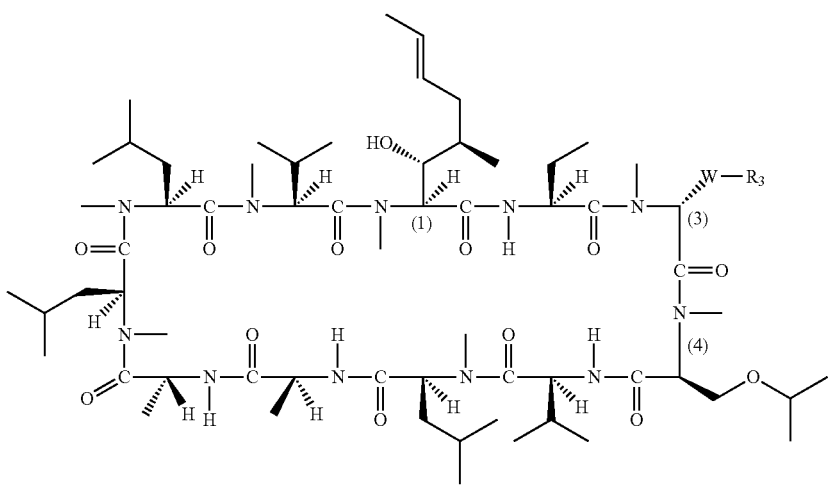

| Ex. No. | W | R₃ | Name |
|---|---|---|---|
| 140 | S | (CH₂)₃N(Et)₂ | [(R)-3-(N,N-Diethylamino)propylthio-Sar]-3-[(β-iso-propoxy)-NMeSer]-4-cyclosporin |
| 141 | S | (CH₂)₃N(iPr)(Et) | [(R)-3-(N-iso-Prapyl-N-ethylamino)propylthio-Sar]-3-[(β-iso-propoxy)-NMeSer]-4-cyclosporin |
| 142 | S | (CH₂)₃-pyrrolidinyl | [(R)-3-(N-Pyrrolidinyl)propylthio-Sar]-3-[(β-iso-propoxy)-NMeSer]-4-cyclosporin |
| 143 | S | (CH₂)₃-piperidinyl | [(R)-3-(N-Piperidinyl)propylthio-Sar]-3-[(β-iso-propoxy)-NMeSer]-4-cyclosporin |
| 144 | S | (CH₂)₃-morpholino | [(R)-3-(N-Morpholino)propylthio-Sar]-3-[(β-iso-propoxy)-NMeSer]-4-cyclosporin |

TABLE 7

| Ex. No. | W | R₃ | Name |
|---|---|---|---|
| 145 | S | -CH₂CH₂CH₂-N(CH₃)₂ | [(R)-3-(N,N-Dimethylamino)propylthio-Sar]-3-[(β-pentan-3-yloxy)-NMeSer]-4-cyclosporin |
| 146 | S | -CH₂CH₂CH₂-N(Et)₂ | [(R)-3-(N,N-Diethylamino)propylthio-Sar]-3-[(β-pentan-3-yloxy)-NMeSer]-4-cyclosporin |
| 147 | S | -CH₂CH₂CH₂-N(iPr)(Et) | [(R)-3-(N-iso-Propyl-N-ethylamino)propylthio-Sar]-3-[(β-pentan-3-yloxy)-NMeSer]-4-cyclosporin |
| 148 | S | -CH₂CH₂CH₂-pyrrolidinyl | [(R)-3-(N-Pyrrolidinyl)propylthio-Sar]-3-[(β-pentan-3-yloxy)-NMeSer]-4-cyclosporin |
| 149 | S | -CH₂CH₂CH₂-piperidinyl | [(R)-3-(N-Piperidinyl)propylthio-Sar]-3-[(β-pentan-3-yloxy)-NMeSer]-4-cyclosporin |
| 150 | S | -CH₂CH₂CH₂-morpholino | [(R)-3-(N-Morpholino)propylthio-Sar]-3-[(β-pentan-3-yloxy)-NMeSer]-4-cyclosporin |

TABLE 8

| Ex. No. | W | R₃ | Name |
|---|---|---|---|
| 151 | S | -(CH₂)₃-N(CH₃)₂ | [(R)-3-(N,N-Dimethylamino)propylthio-Sar]-3-[(β-iso-butoxy)-NMeSer]-4-cyclosporin |
| 152 | S | -(CH₂)₃-N(Et)₂ | [(R)-3-(N,N-Diethylamino)propylthio-Sar]-3-[(β-iso-butoxy)-NMeSer]-4-cyclosporin |
| 153 | S | -(CH₂)₃-N(iPr)(Et) | [(R)-3-(N-iso-Propyl-N-ethylamino)propylthio-Sar]-3-[(β-iso-butoxy)-NMeSer]-4-cyclosporin |
| 154 | S | -(CH₂)₃-pyrrolidinyl | [(R)-3-(N-Pyrrolidinyl)propylthio-Sar]-3-[(β-iso-butoxy)-NMeSer]-4-cyclosporin |
| 155 | S | -(CH₂)₃-piperidinyl | [(R)-3-(N-Piperidinyl)propylthio-Sar]-3-[(β-iso-butoxy)-NMeSer]-4-cyclosporin |
| 156 | S | -(CH₂)₃-morpholino | [(R)-3-(N-Morpholino)propylthio-Sar]-3-[(β-iso-butoxy)-NMeSer]-4-cyclosporin |

TABLE 9

| Ex. No. | W | R₃ | Name |
|---|---|---|---|
| 157 | S | (CH₂)₃-N(CH₃)₂ | [(R)-3-(N,N-Dimethylamino)propylthio-Sar]-3-[(β-2-ethylbutoxy)-NMeSer]-4-cyclosporin |
| 158 | S | (CH₂)₃-N(C₂H₅)₂ | [(R)-3-(N,N-Diethylamino)propylthio-Sar]-3-[(β-2-ethylbutoxy)-NMeSer]-4-cyclosporin |
| 159 | S | (CH₂)₃-N(iPr)(Et) | [(R)-3-(N-iso-Propyl-N-ethylamino)propylthio-Sar]-3-[(β-2-ethylbutoxy)-NMeSer]-4-cyclosporin |
| 160 | S | (CH₂)₃-pyrrolidinyl | [(R)-3-(N-Pyrrolidinyl)propylthio-Sar]-3-[(β-2-ethylbutoxy)-NMeSer]-4-cyclosporin |
| 161 | S | (CH₂)₃-piperidinyl | [(R)-3-(N-Piperidinyl)propylthio-Sar]-3-[(β-2-ethylbutoxy)-NMeSer]-4-cyclosporin |
| 162 | S | (CH₂)₃-morpholino | [(R)-3-(N-Morpholino)propylthio-Sar]-3-[(β-2-ethylbutoxy)-NMeSer]-4-cyclosporin |

TABLE 10
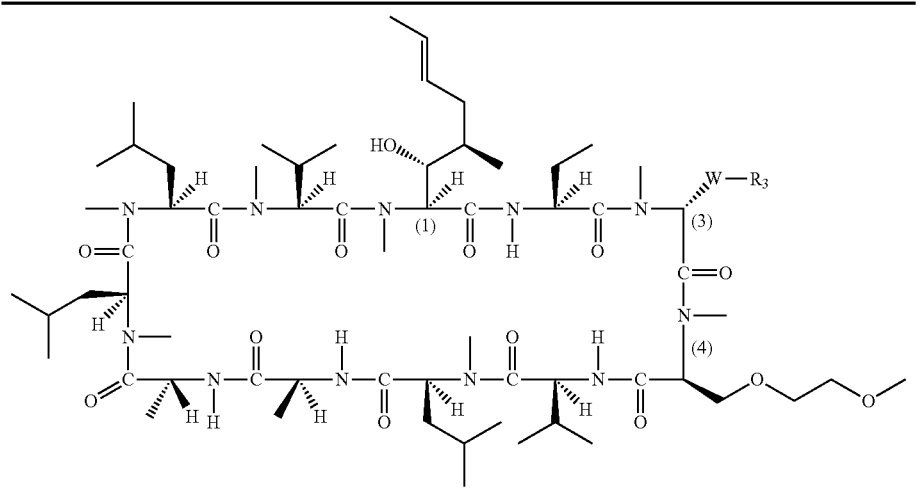
| 163 | S | 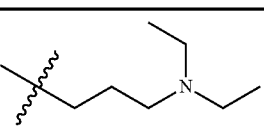 | [(R)-3-(N,N-Diethylamino)propylthio-Sar]-3-[β-(2-methoxyethoxy)-NMeSer]-4-cyclosporin |
| 164 | S | 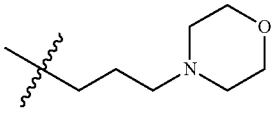 [SMILES: *CCCN1CCOCC1] | [(R)-3-(N-Morpholino)propylthio-Sar]-3-[β-(2-methoxyethoxy)-NMeSer]-4-cyclosporin |
TABLE 11
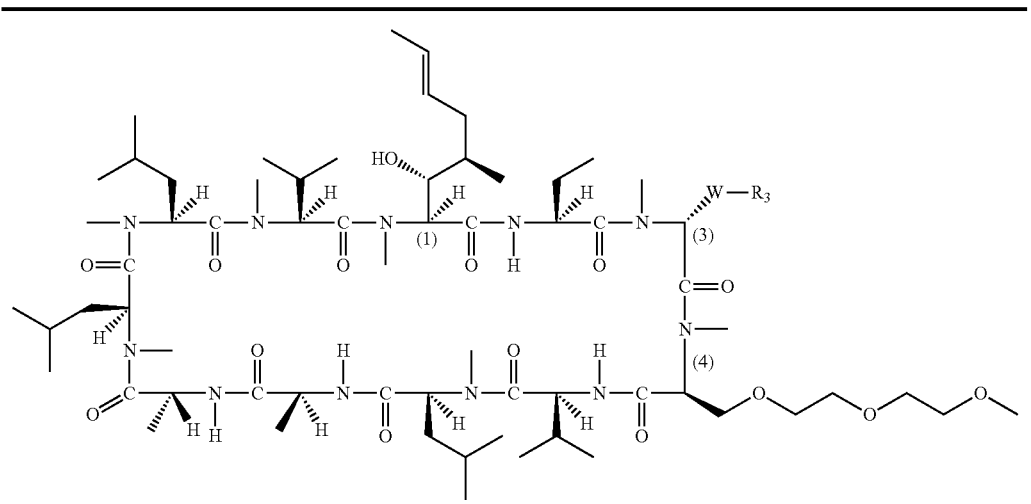
| 165 | S | 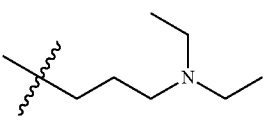 [SMILES: *CCCN(CC)CC] | [(R)-3-(N,N-Diethylamino)propylthio-Sar]-3-[β-[2-(2-methoxyethoxy)ethoxy]-NMeSer]-4-cyclosporin |
| 166 | S | 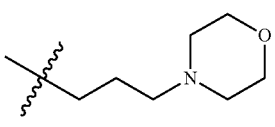 [SMILES: *CCCN1CCOCC1] | [(R)-3-(N-Morpholino)propylthio-Sar]-3-[β-[2-(2-methoxyethoxy)ethoxy]-NMeSer]-4-cyclosporin |

TABLE 12

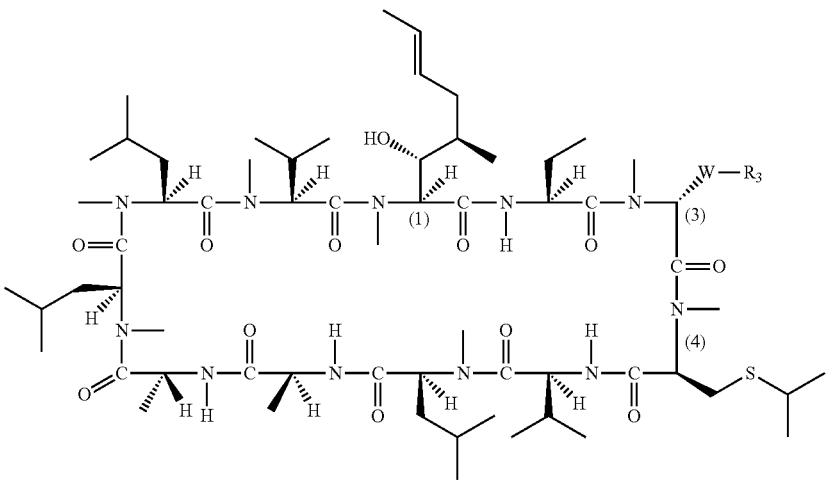

| Ex. No. | W | R₃ | Name |
|---|---|---|---|
| 167 | S | 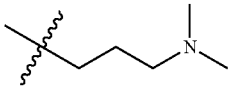 [SMILES: *CCCN(C)C] | [(R)-3-(N,N-Dimethylamino)propylthio-Sar]-3-[(β-iso-propylthio)-NMeCys]-4-cyclosporin |
| 168 | S | 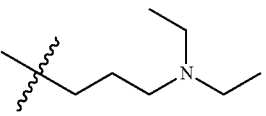 [SMILES: *CCCN(CC)CC] | [(R)-3-(N,N-Diethylamino)propylthio-Sar]-3-[(β-iso-propylthio)-NMeCys]-4-cyclosporin |
| 169 | S | 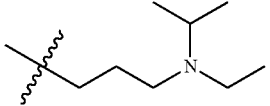 [SMILES: *CCCN(CC)C(C)C] | [(R)-3-(N-iso-Propyl-N-ethylamino)propylthio-Sar]-3-[(β-iso-propylthio)-NMeCys]-4-cyclosporin |
| 170 | S | 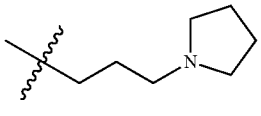 [SMILES: *CCCN1CCCC1] | [(R)-3-(N-Pyrrolidinyl)propylthio-Sar]-3-[(β-iso-propylthio)-NMeCys]-4-cyclosporin |
| 171 | S | 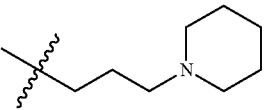 [SMILES: *CCCN1CCCCC1] | [(R)-3-(N-Piperidinyl)propylthio-Sar]-3-[(β-iso-propylthio)-NMeCys]-4-cyclosporin |
| 172 | S | 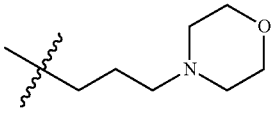 | [(R)-3-(N-Morpholino)propylthio-Sar]-3-[(β-iso-propylthio)-NMeCys]-4-cyclosporin |

TABLE 13

| Ex. No. | W | R₃ | Name |
|---------|---|-----|------|
| 173 | S | (CH₂)₃N(CH₃)₂ | [(R)-3-(N,N-Dimethylamino)propylthio-Sar]-3-[(β-pentan-3-ylthio)-NMeCys]-4-cyclosporin |
| 174 | S | (CH₂)₃N(Et)₂ | [(R)-3-(N,N-Diethylamino)propylthio-Sar]-3-[(β-pentan-3-ylthio)-NMeCys]-4-cyclosporin |
| 175 | S | (CH₂)₃N(iPr)(Et) | [(R)-3-(N-iso-Propyl-N-ethylamino)propylthio-Sar]-3-[(β-pentan-3-ylthio)-NMeCys]-4-cyclosporin |
| 176 | S | (CH₂)₃-pyrrolidinyl | [(R)-3-(N-Pyrrolidinyl)propylthio-Sar]-3-[(β-pentan-3-ylthio)-NMeCys]-4-cyclosporin |
| 177 | S | (CH₂)₃-piperidinyl | [(R)-3-(N-Piperidinyl)propylthio-Sar]-3-[(β-pentan-3-ylthio)-NMeCys]-4-cyclosporin |
| 178 | S | (CH₂)₃-morpholino | [(R)-3-(N-Morpholino)propylthio-Sar]-3-[(β-pentan-3-ylthio)-NMeCys]-4-cyclosporin |

TABLE 14

| Ex. No. | W | R₃ | Name |
|---|---|---|---|
| 179 | S | (CH₂)₃N(CH₃)₂ | [(R)-3-(N,N-Dimethylamino)propylthio-Sar]-3-[(β-iso-butylthio)-NMeCys]-4-cyclosporin |
| 180 | S | (CH₂)₃N(Et)₂ | [(R)-3-(N,N-Diethylamino)propylthio-Sar]-3-[(β-iso-butylthio)-NMeCys]-4-cyclosporin |
| 181 | S | (CH₂)₃N(iPr)(Et) | [(R)-3-(N-iso-Propyl-N-ethylamino)propylthio-Sar)-3-[(β-iso-butylthio)-NMeCys]-4-cyclosporin |
| 182 | S | (CH₂)₃-pyrrolidinyl | [(R)-3-(N-Pyrrolidinyl)propylthio-Sar]-3-[(β-iso-butylthio)-NMeCys]-4-cyclosporin |
| 183 | S | (CH₂)₃-piperidinyl | [(R)-3-(N-Piperidinyl)propylthio-Sar]-3-[(β-iso-butylthio)-NMeCys]-4-cyclosporin |
| 184 | S | (CH₂)₃-morpholino | [(R)-3-(N-Morpholino)propylthio-Sar]-3-[(β-iso-butylthio)-NMeCys]-4-cyclosporin |

TABLE 15

| Ex. No. | W | R₃ | Name |
|---|---|---|---|
| 185 | S | —CH₂CH₂CH₂N(CH₃)₂ | [(R)-3-(N,N-Dimethylamino)propylthio-Sar]-3-[(β-2-ethylbutylthio)-NMeCys]-4-cyclosporin |
| 186 | S | —CH₂CH₂CH₂N(CH₂CH₃)₂ | [(R)-3-(N,N-Diethylamino)propylthio-Sar]-3-[(β-2-ethylbutylthio)-NMeCys]-4-cyclosporin |
| 187 | S | —CH₂CH₂CH₂N(iPr)(Et) | [(R)-3-(N-iso-Propyl-N-ethylamino)propylthio-Sar]-3-[(β-2-ethylbutylthio)-NMeCys]-4-cyclosporin |
| 188 | S | —CH₂CH₂CH₂-(N-pyrrolidinyl) | [(R)-3-(N-Pyrrolidinyl)propylthio-Sar]-3-[(β-2-ethylbutylthio)-NMeCys]-4-cyclosporin |
| 189 | S | —CH₂CH₂CH₂-(N-piperidinyl) | [(R)-3-(N-Piperidinyl)propylthio-Sar]-3-[(β-2-ethylbutylthio)-NMeCys]-4-cyclosporin |
| 190 | S | —CH₂CH₂CH₂-(N-morpholino) | [(R)-3-(N-Morpholino)propylthio-Sar]-3-[(β-2-ethylbutylthio)-NMeCys]-4-cyclosporin |

TABLE 16
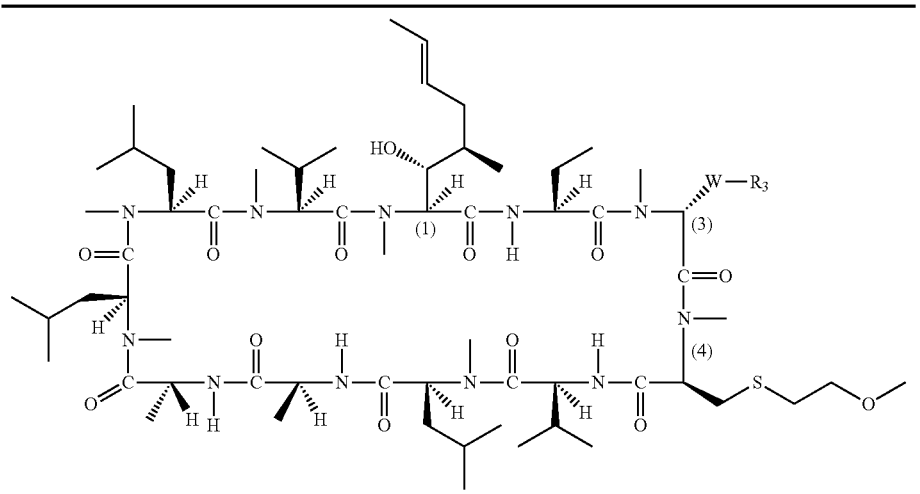
| 191 | S | 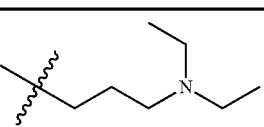 | [(R)-3-(N,N-Diethylamino)propylthio-Sar]-3-[β-(2-methoxyethylthio)-NMeCys]-4-cyclosporin |
| --- | --- | --- | --- |
| 192 | S | 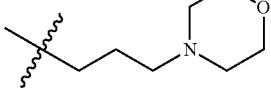 | [(R)-3-(N-Morpholino)propylthio-Sar]-3-[β-(2-methoxyethylthio)-NMeCys]-4-cyclosporin |
TABLE 17
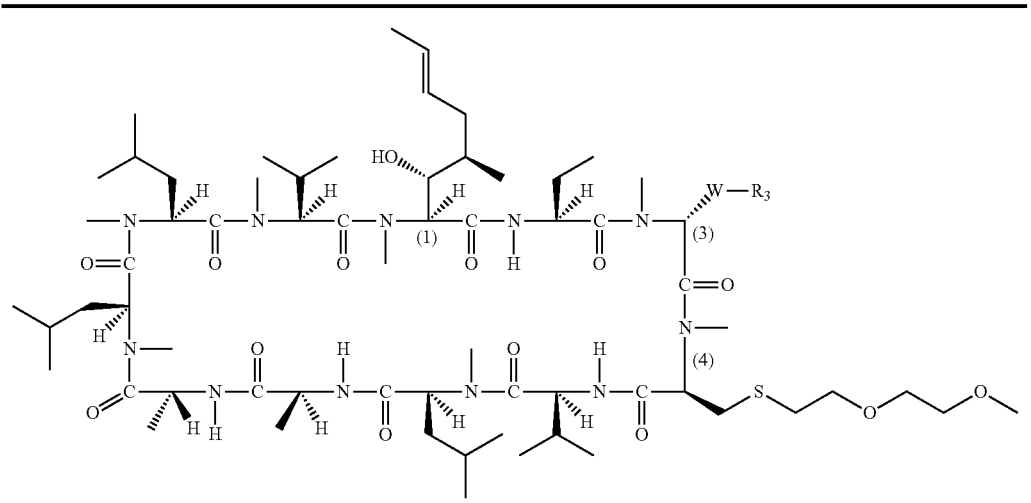
| 193 | S | 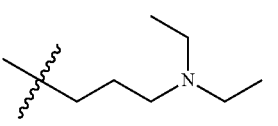 [SMILES: *CCCN(CC)CC] | [(R)-3-(N,N-Diethylamino)propylthio-Sar]-3-[β-[2-(2-methoxyethoxy)ethylthio]-NMeCys]-4-cyclosporin |
| --- | --- | --- | --- |
| 194 | S | 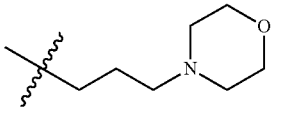 [SMILES: *CCCN1CCOCC1] | [(R)-3-(N-Morpholino)propylthio-Sar]-3-[β-[2-(2-methoxyethoxy)ethylthiol-NMeCys]-4-cyclosporin |

TABLE 18

| Ex. No. | R₅ | Name |
|---|---|---|
| 195 | —CH₂—O—CH₃ | [(β-Methoxy-NMeSer]-4-cyclosporin |
| 196 | —CH₂—O—CH(CH₃)₂ | [(β-iso-Propoxy)-NMeSer]-4-cyclosporin |
| 197 | —CH₂—O—CH(CH₂CH₃)₂ | [(β-Pentan-3-yloxy)-NMeSer]-4-cyclosporin |
| 198 | —CH₂—O—CH₂CH(CH₃)₂ | [(β-iso-Butoxy)-NMeSer]-4-cyclosporin |
| 199 | —CH₂—O—CH₂CH(CH₂CH₃)₂ | [(β-2-Ethylbutoxy)-NMeSer]-4-cyclosporin |
| 200 | —CH₂—O—CH₂CH₂—N(CH₂CH₃)₂ | [(β-2-(N,N-Diethylamino)ethoxy)-NMeSer]-4-cyclosporin |
| 201 | —CH₂—O—CH₂CH₂—O—CH₃ | [(β-(2-Methoxyethoxy)-NMeSer]-4-cyclosporin |
| 201 | —CH₂—O—CH₂CH₂—O—CH₂CH₂—O—CH₃ | [(β-[2-(2-Methoxyethoxy)ethoxy]-NMeSer]-4-cyclosporin |
| 203 | —CH₂—S—CH₃ | [(β-Methylthio)-NMeCys]-4-cyclosporin |

TABLE 18-continued

| Ex. No. | R₅ | Name |
|---|---|---|
| 204 | (CH₂-S-iPr) | [(β-iso-Propylthio)-NMeCys]-4-cyclosporin |
| 205 | (CH₂-S-CH(Et)₂) | [(β-Pentan-3-ylthio)-NMeCys]-4-cyclosporin |
| 206 | (CH₂-S-iBu) | [(β-iso-Butylthio)-NMeCys]-4-cyclosporin |
| 207 | (CH₂-S-CH₂CH(Et)₂) | [(β-2-Ethylbutylthio)-NMeCys]-4-cyclosporin |
| 208 | (CH₂-S-CH₂CH₂NEt₂) | [(β-2-(N,N-Diethylamino)ethylthio)-NMeCys]-4-cyclosporin |
| 209 | (CH₂-S-CH₂CH₂OMe) | [β-(2-Methoxyethylthio)-NMeCys]-4-cyclosporin |
| 210 | (CH₂-S-CH₂CH₂OCH₂CH₂OMe) | [β-2-(2-Methoxyethoxy)ethylthio]-NMeCys]-4-cyclosporin |

What is claimed is:
1. A compound of the formula (II):

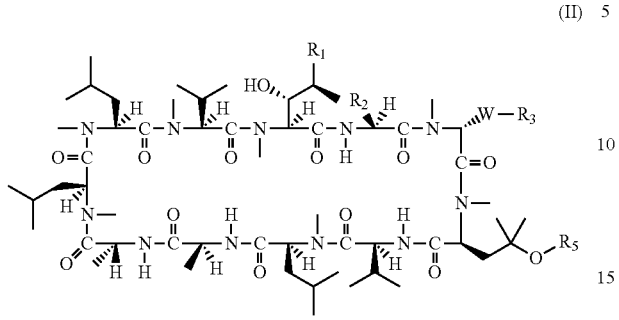

or pharmaceutically acceptable salt thereof, wherein the symbols have the following meanings and are, for each occurrence, independently selected:

$R_1$ is n-butyl or (E)-but-2-enyl;
$R_2$ is ethyl, 1-hydroxyethyl, isopropyl or n-propyl;
W is O, or S;
each occurrence of $R_3$ is:
  ($C_3$-$C_6$)alkyl substituted by one or more groups $R_4$ each occurrence of which is independently selected from the group consisting of $OR_a$, $SR_a$, $O(CH_2)_mOH$, $O(CH_2O_m(CH_2)_mOH$, $C(=O)(C_1$-$C_6)$alkyl, $C(=O)OH$, $C(=O)O(C_1$-$C_6)$alkyl, $-NR_AR_B$, and $-NR_C(CH_2)_mNR_AR_B$; wherein each occurrence $R_a$ is independently H or alkyl;
  ($C_3$-$C_6$)alkynyl substituted by one or more groups which may be the same or different selected from the group consisting of hydroxy, amino, monoalkylamino and dialkylamino; or
  ($C_3$-$C_6$)alkenyl substituted by one or more groups which may be the same or different selected from the group consisting of hydroxy, amino, monoalkylamino and dialkylamino;
each occurrence of $R_5$ is H, alkyl or substituted alkyl, alkenyl or substituted alkenyl, alkynyl or substituted alkynyl, cycloalkyl or substituted cycloalkyl, cycloalkenyl or substituted cycloalkenyl, or aryl or substituted aryl;
each occurrence of $R_A$ and $R_B$ is independently:
  hydrogen;
  ($C_1$-$C_6$)alkyl, optionally substituted by one or more groups $R_D$ which may be the same or different;
  ($C_2$-$C_6$)alkenyl or ($C_2$-$C_6$)alkynyl;
  ($C_3$-$C_7$)cycloalkyl optionally substituted with ($C_1$-$C_6$) alkyl;
  phenyl optionally substituted with from one to five groups which may be the same or different selected from halogen, $-O(C_1$-$C_6)$alkyl, $-C(=O)O(C_1$-$C_6)$alkyl, amino, alkylamino and dialkylamino;
  or a heterocyclic ring which may be saturated or unsaturated containing five or six ring atoms and from one to three heteroatoms which may the same or different selected from nitrogen, sulfur and oxygen;
  or $R_A$ and $R_B$, together with the nitrogen atom to which the are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;
each occurrence of $R_C$ is independently hydrogen or ($C_1$-$C_6$)alkyl;
each occurrence of $R_D$ is independently halogen, hydroxy, $O(C_1$-$C_4)$alkyl, $C(=O)(C_1$-$C_4)$alkyl, $C(=O)O(C_1$-$C_4)$alkyl; and
m is an integer of 1, 2, 3, 4 or 5.

2. The compound of claim 1, wherein:
$R_5$ is:
  ($C_1$-$C_6$)alkyl, optionally substituted by one or more groups $R_6$ which may be the same or different;
  ($C_2$-$C_6$)alkenyl, optionally substituted by one or more groups which may be the same or different selected from hydroxy, ($C_1$-$C_6$)alkyl, aryl, $(CH_2)_pOR_A$, $O(CH_2)_mOH$, $O(CH_2)_mO(CH_2)_mOH$, $O(CH_2)_mNR_AR_B$, $O(CH_2)_mO(CH_2)_mNR_AR_B$, $(CH_2)_pNR_AR_B$, $(CH_2)_pNR_C(CH_2)_mNR_AR_B$, $(CH_2)_pNR_C(CH_2)_mNR_C(CH_2)_mNR_AR_B$, $(CH_2)_pC(=O)NR_AR_B$, $(CH_2)_pC(=O)OR_A$;
  ($C_2$-$C_6$)alkynyl, optionally substituted by one or one or more groups which may be the same or different selected from halogen, hydroxy, amino, monoalkylamino and dialkylamino;
  ($C_3$-$C_7$)cycloalkyl, optionally substituted by one or more groups which may be the same or different selected from halogen, hydroxy, amino, monoalkylamino and dialkylamino;
  phenyl or $CH_2$-phenyl, optionally substituted by one or more groups which may be the same or different selected from halogen, hydroxy, ($C_1$-$C_6$)alkyl, $(CH_2)_p$ $OR_A$, $(CH_2)_pNR_AR_B$, $(CH_2)_pC(=O)NR_AR_B$, $(CH_2)_p$ $C(=O)OR_A$;
each occurrence of $R_6$ is independently halogen, hydroxy, aryl, $S(C_1$-$C_6)$alkyl, $SR_A$, $OR_A$, $O(CH_2)_mOH$, $O(CH_2)_m(CH_2)_mOH$, $C(=O)OR_A$, $C(=O)NR_AR_B$, $NR_AR_B$, $O(CH_2)_mNR_AR_B$, $O(CH_2)_mO(CH_2)_mNR_AR_B$, $NR_C(CH_2)_mNR_AR_B$, or $NR_C(CH_2)_mNR_C(CH_2)_mNR_AR_B$, wherein said aryl or phenyl is optionally substituted by one or more groups which may be the same or different selected from halogen, hydroxy, ($C_1$-$C_6$)alkyl, $(CH_2)_p$ $OR_A$, $(CH_2)_pNR_AR_B$, $(CH_2)_pC(=O)NR_AR_B$ and $(CH_2)_p$ $C(=O)OR_A$;
each occurrence of $R_A$ and $R_B$ is independently:
  hydrogen;
  ($C_1$-$C_6$)alkyl, optionally substituted by one or more groups $R_D$ which may be the same or different;
  ($C_2$-$C_6$)alkenyl or ($C_2$-$C_6$)alkynyl;
  ($C_3$-$C_7$)cycloalkyl optionally substituted with ($C_1$-$C_6$) alkyl;
  phenyl optionally substituted with from one to five groups which may be the same or different selected from halogen, $-O(C_1$-$C_6)$alkyl, $-C(=O)O(C_1$-$C_6)$ alkyl, amino, alkylamino and dialkylamino;
  or a heterocyclic ring which may be saturated or unsaturated containing five or six ring atoms and from one to three heteroatoms which may the same or different selected from nitrogen, sulfur and oxygen;
  or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;
each occurrence of $R_C$ is independently hydrogen or $(C_1$-$C_6)$alkyl;
p is an integer of 0, 1, 2, 3, 4, or 5; and
m is an integer of 1, 2, 3, 4 or 5.

3. The compound of claim 1, wherein $R_1$ is n-butyl.

4. The compound of claim 1, wherein $R_1$ is (E)-but-2-enyl.

5. The compound of claim 1, wherein $R_2$ is ethyl.

6. The compound of claim 1, wherein W is O.

7. The compound of claim 1, wherein W is S.

8. The compound of claim 1, wherein $R_3$ is —$(CH_2)_n$NR$_A$R$_B$, wherein n is an integer of 3, 4, 5 or 6; and wherein each occurrence of $R_A$ and $R_B$ is independently hydrogen; $(C_1$-$C_4)$alkyl, optionally substituted by one or more groups $R_D$ which may be the same or different, in which each occurrence of $R_D$ is independently halogen, hydroxy, O$(C_1$-$C_4)$alkyl, C(=O)$(C_1$-$C_4)$alkyl, C(=O)O$(C_1$-$C_4)$alkyl; or $R_A$ and $R_B$, together with the nitrogen atom to which they are attached, form a saturated or unsaturated heterocyclic ring containing from three to seven ring atoms, which ring may optionally contain another heteroatom selected from the group consisting of nitrogen, oxygen and sulfur and may be optionally substituted by from one to four groups which may be the same or different selected from $(C_1$-$C_4)$alkyl, phenyl and benzyl.

9. The compound of claim 1, wherein $R_3$ is —$(CH_2)_n$NR$_A$R$_B$, wherein n is an integer of 3, 4, 5 or 6; and wherein $R_A$ and $R_B$, together with the nitrogen atom to which they are attached, form a saturated or unsaturated heterocyclic ring containing from three to seven ring atoms, which ring may optionally contain another heteroatom selected from nitrogen, oxygen and sulfur and may be optionally substituted by from one to four groups which may be the same or different selected from $(C_1$-$C_4)$alkyl, phenyl and benzyl.

10. The compound of claim 1, wherein $R_3$ is 3-aminobutyl, 3 monoalkylaminobutyl, or 3-dialkylaminobutyl, and wherein said alkyl is $(C_1$-$C_4)$alkyl.

11. The compound of claim 1, wherein $R_5$ is H or methyl.

12. The compound of claim 1, wherein $R_3$ is

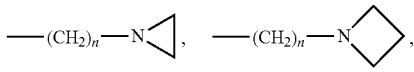

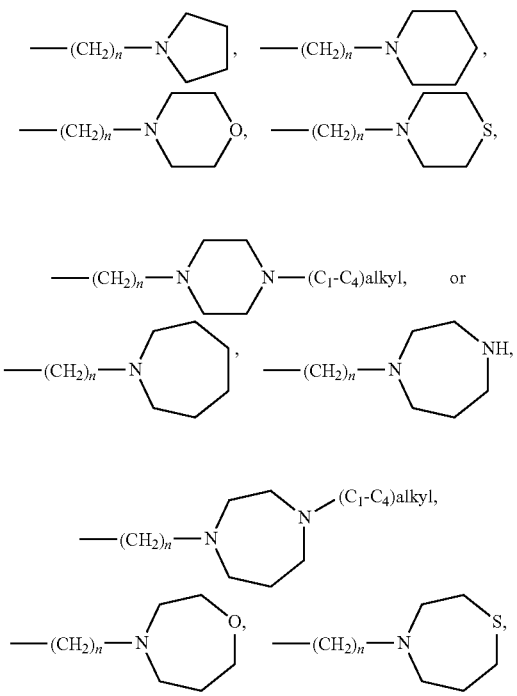

in which n is an integer of 3, 4, 5 or 6.

13. The compound of claim 1, wherein $R_5$ is $CH_2$—S—$(C_1$-$C_6)$alky, $CH_2$—O—$(C_1$-$C_6)$alkyl, $(C_2$-$C_6)$alkenyl, benzyl, $(C_2$-$C_6)$OH, $(C_1$-$C_6)$-monoalkyl amine, $(C_1$-$C_6)$-dialkyl amine, or $(C_1$-$C_6)$-cyclic amine.

14. The compound of claim 1, wherein each occurrence $R_{a'}$ is independently H, Me or Et.

15. The compound of claim 1, wherein $R_3$ is $(C_3$-$C_6)$alkyl substituted by one or more groups $R_4$ each occurrence of which is independently selected from the group consisting of O$R_{a'}$ and S$R_{a''}$.

16. The compound of claim 1, having the following chemical structure:

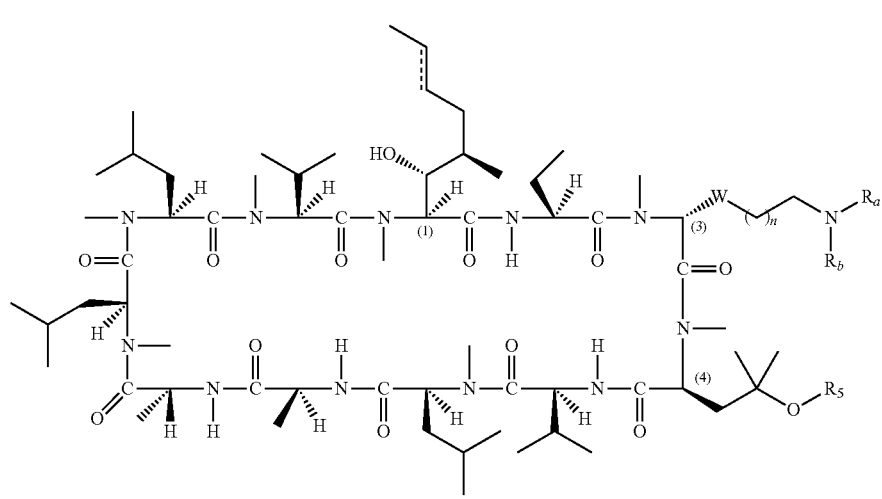

(XV)

wherein ∥ represents a single bond or a double bond;

W is O or S;

$R_5$ is methyl, ethyl, n-propyl, i-propyl, n-butyl, i-butyl, t-butyl, $CH_2CMe_3$, phenyl, $CH_2$-phenyl,

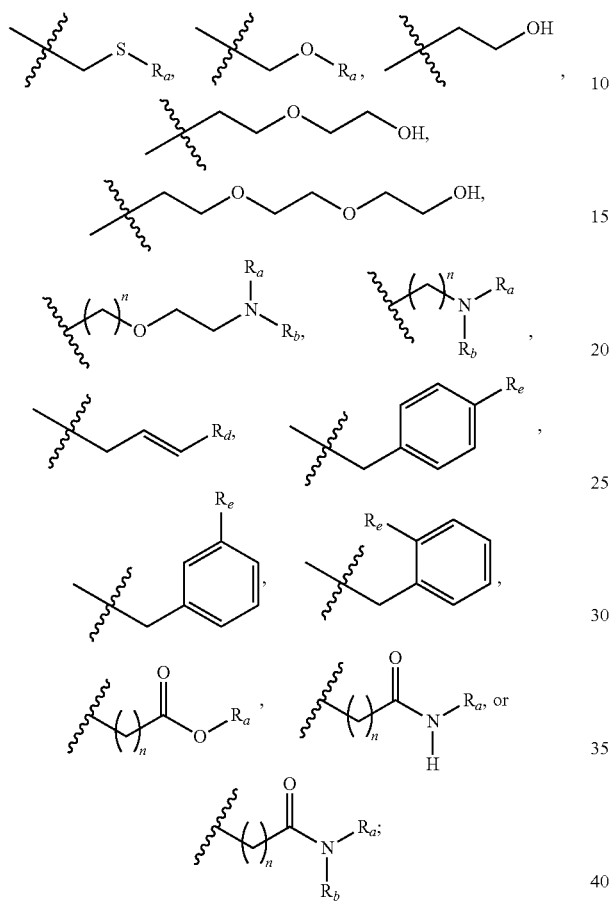

each $R_d$ is independently $R_a$, $OR_a$, $CH_2OR_a$,

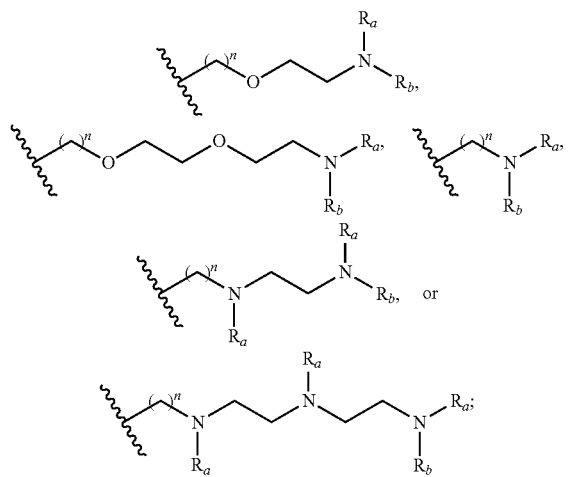

each $R_e$ is independently H, Me, Et, $OR_a$, $CH_2OR_a$, $CH_2CH_2OR_a$,

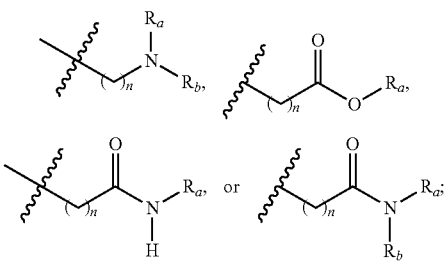

each of $R_a$ and $R_b$ is independently H, methyl, ethyl, n-propyl, propyl, n-butyl, i-butyl, t-butyl, $CH_2CMe_3$, phenyl, $CH_2$-phenyl,

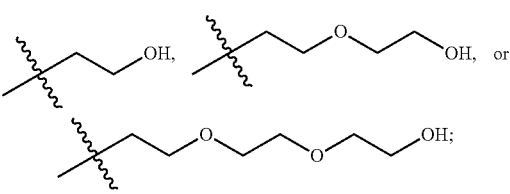

or $R_a$ and $R_b$, together with the nitrogen atom to which they are attached

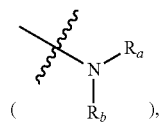

form a heterocycle selected from

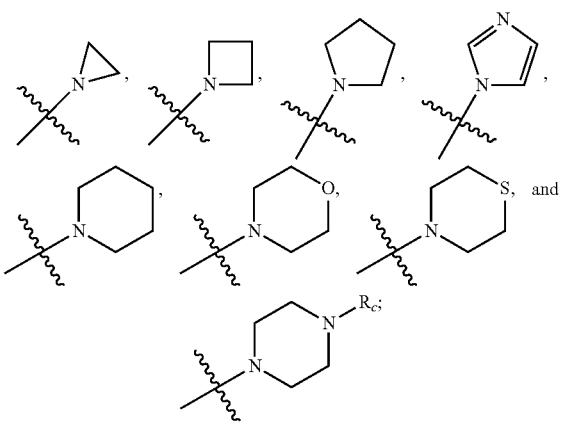

$R_c$ is H, methyl, ethyl, n-propyl, i-propyl, n-butyl, i-butyl, t-butyl, $CH_2CMe_3$, phenyl, or $CH_2$-phenyl; and each n is independently 2, 3, 4, 5 or 6.

17. The compound of claim 16, wherein n is 2, 3 or 4.

18. The compound of claim 16, wherein each of $R_a$ and $R_b$ is independently H, methyl, ethyl, n-propyl, i-propyl, n-butyl, i-butyl, or t-butyl, provided that when $R_a$ is H or methyl, then $R_b$ is n-propyl, i-propyl, n-butyl, i-butyl, or t-butyl; or

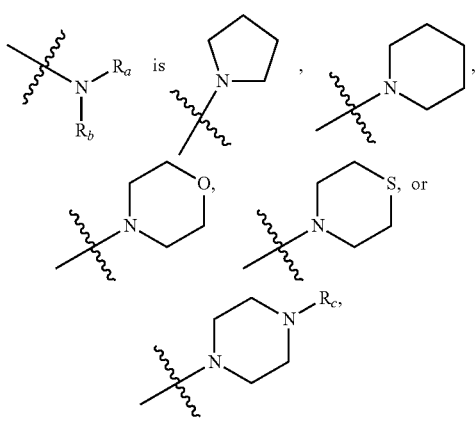

in which $R_c$ is H, methyl, ethyl, n-propyl, i-propyl, n-butyl, i-butyl, or t-butyl.

19. The compound of claim 1, wherein $R_5$ is H.

20. The compound of claim 1, having the following chemical structure:

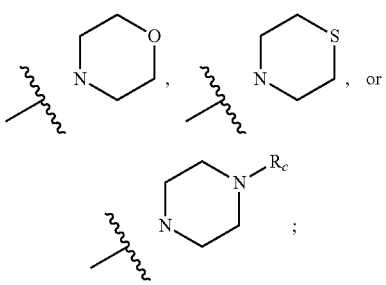

$R_c$ is H, methyl, ethyl, n-propyl, i-propyl, n-butyl, i-butyl, t-butyl, $CH_2CMe_3$, phenyl, or $CH_2$-phenyl; and each n is independently 2, 3, 4, 5 or 6.

21. The compound of claim 20, wherein n is 2, 3 or 4.

22. The compound of claim 20, wherein each of $R_a$ and $R_b$ is independently H, methyl, ethyl, n-propyl, i-propyl, n-butyl, i-butyl, or t-butyl, provided that when $R_a$ is H or methyl, then $R_b$ is n-propyl, i-propyl, n-butyl, i-butyl, or t-butyl; or (XVII)

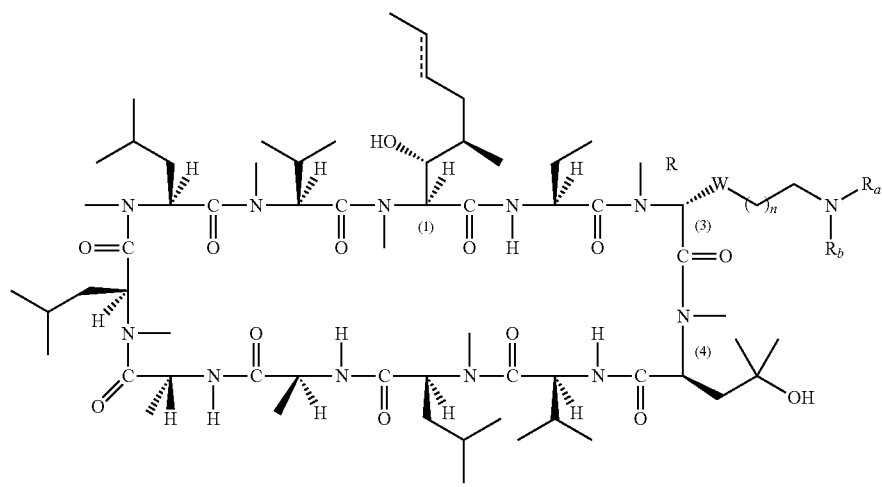

wherein ∥ represents a single bond or a double bond;
W is S or O;
each of $R_a$ and $R_b$ is independently H, methyl, ethyl, n-propyl, propyl, n-butyl, i-butyl, t-butyl, $CH_2CMe_3$, phenyl, or $CH_2$-phenyl, or

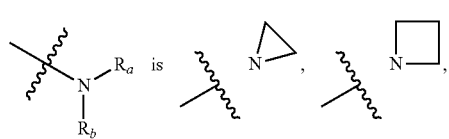

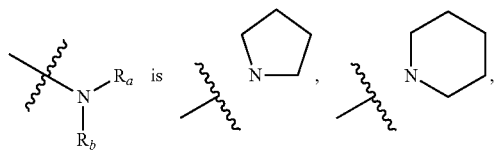

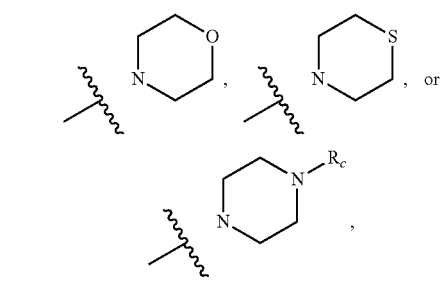

in which $R_c$ is H, methyl, ethyl, n-propyl, i-propyl, n-butyl, i-butyl, or t-butyl.

23. The compound of claim 1, having the following chemical structure:

(XVIII)

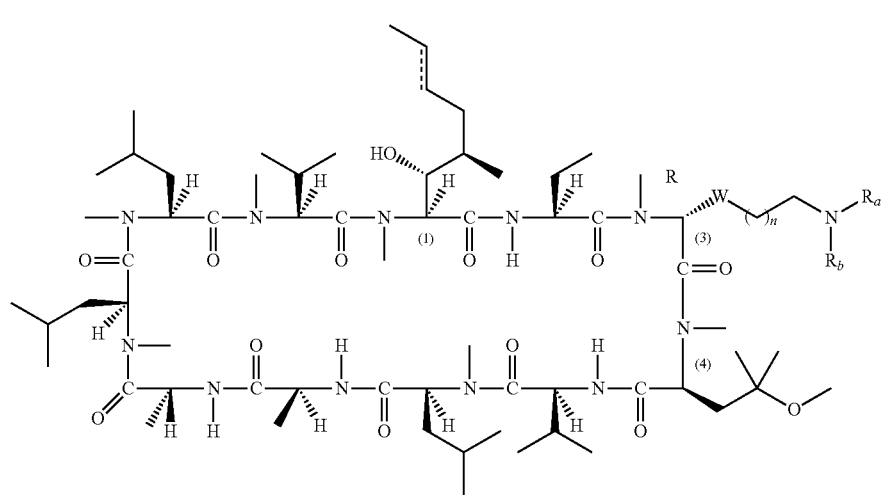

wherein ‖ represents a single bond or a double bond;
W is S or O;
each of $R_a$ and $R_b$ is independently H, methyl, ethyl, n-propyl, propyl, n-butyl, i-butyl, t-butyl, $CH_2CMe_3$, phenyl, or $CH_2$-phenyl; or $R_a$ and $R_b$, together with the nitrogen atom to which they are attached

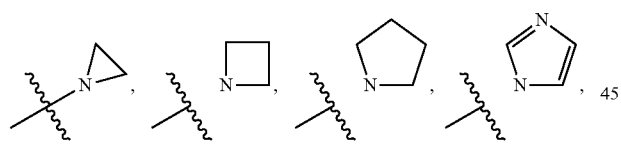

form a heterocycle selected from

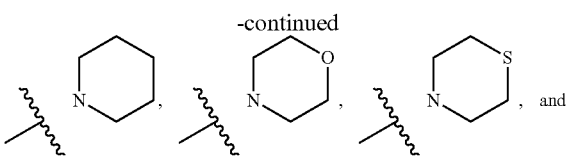

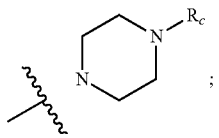

$R_c$ is H, methyl, ethyl, n-propyl, i-propyl, n-butyl, i-butyl, t-butyl, $CH_2CMe_3$, phenyl, or $CH_2$-phenyl; and
each n is independently 2, 3, 4, 5 or 6.

24. The compound of claim 1, having the following chemical structure:

(XIX)

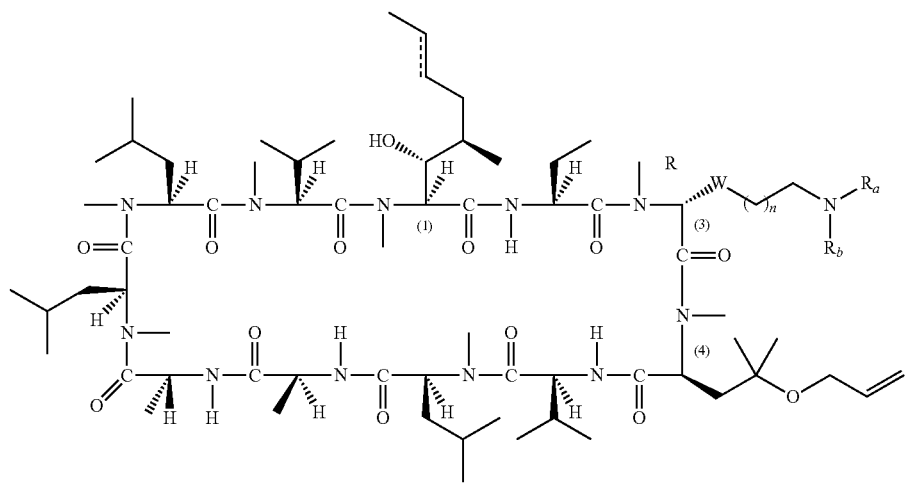

wherein ∥ represents a single bond or a double bond;
W is S or O;
each of $R_a$ and $R_b$ is independently H, methyl, ethyl, n-propyl, propyl, n-butyl, i-butyl, t-butyl, $CH_2CMe_3$, phenyl, or $CH_2$-phenyl; or $R_a$ and $R_b$, together with the nitrogen atom to which they are attached

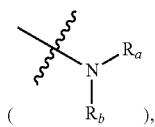

form a heterocycle selected from

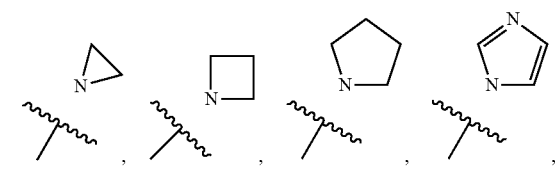

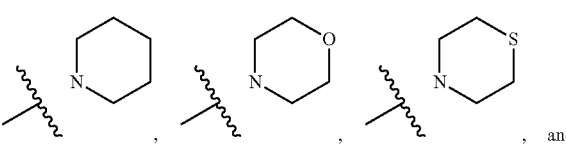

, and

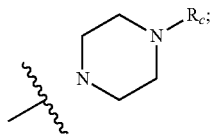

$R_c$ is H, methyl, ethyl, n-propyl, i-propyl, n-butyl, i-butyl, t-butyl, $CH_2CMe_3$, phenyl, or $CH_2$-phenyl; and
each n is independently 2, 3, 4, 5 or 6.

25. The compound of claim 1, having the following chemical structure:

wherein ∥ represents a single bond or a double bond;
W is S or O;
each of $R_a$ and $R_b$ is independently H, methyl, ethyl, n-propyl, propyl, n-butyl, i-butyl, t-butyl, $CH_2CMe_3$, phenyl, or $CH_2$-phenyl; or $R_a$ and $R_b$, together with the nitrogen atom to which they are attached

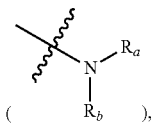

form a heterocycle selected from

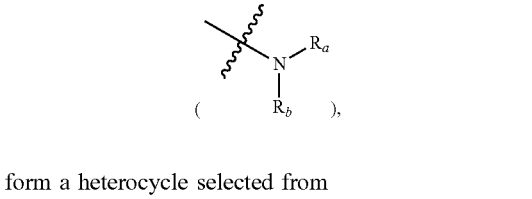

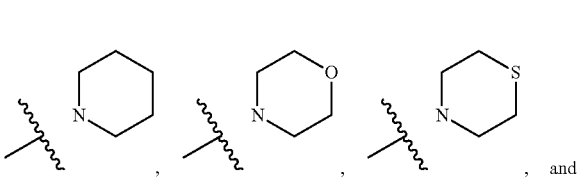

, and

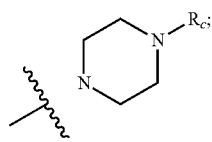

$R_c$ is H, methyl, ethyl, n-propyl, i-propyl, n-butyl, i-butyl, t-butyl, $CH_2CMe_3$, phenyl, or $CH_2$-phenyl; and
each n is independently 2, 3, 4, 5 or 6.

(XX)

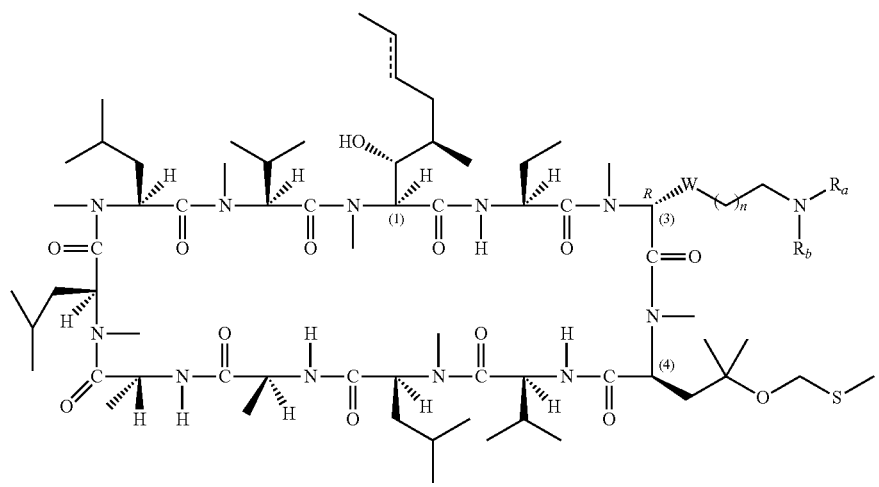

26. The compound of claim 1, having the following chemical structure:

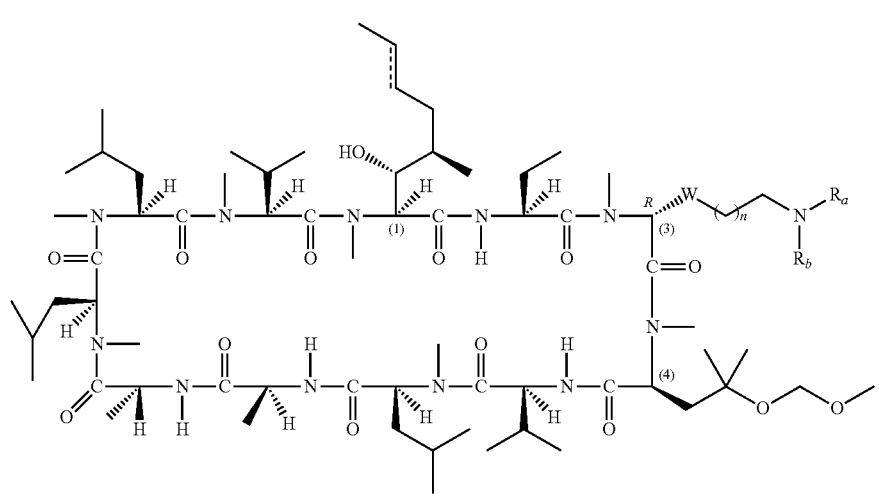

(XXI)

wherein ∥ represents a single bond or a double bond;
W is S or O;
each of $R_a$ and $R_b$ is independently H, methyl, ethyl, n-propyl, propyl, n-butyl, i-butyl, t-butyl, $CH_2CMe_3$, phenyl, or $CH_2$-phenyl; or $R_a$ and $R_b$, together with the nitrogen atom to which they are attached

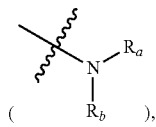

form a heterocycle selected from

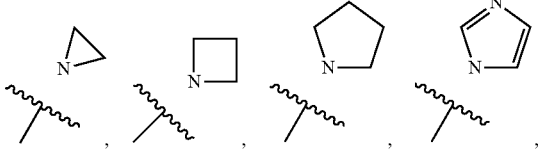

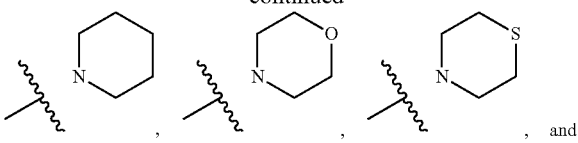

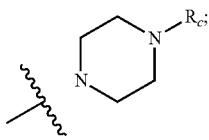

$R_c$ is H, methyl, ethyl, n-propyl, i-propyl, n-butyl, i-butyl, t-butyl, $CH_2CMe_3$, phenyl, or $CH_2$-phenyl; and each n is independently 2, 3, 4, 5 or 6.

27. The compound of claim 1, having the following chemical structure:

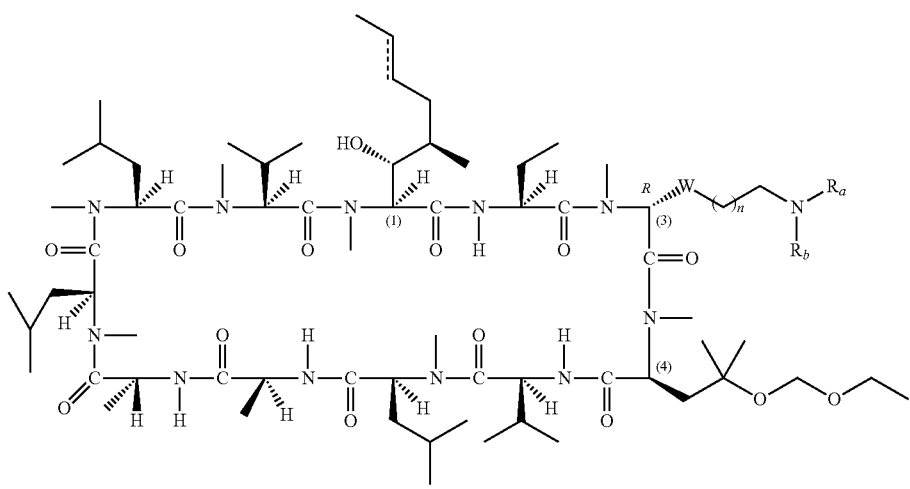

(XXII)

wherein ∥ represents a single bond or a double bond;
W is S or O;
each of $R_a$ and $R_b$ is independently H, methyl, ethyl, n-propyl, propyl, n-butyl, i-butyl, t-butyl, $CH_2CMe_3$, phenyl, or $CH_2$-phenyl; or $R_a$ and $R_b$, together with the nitrogen atom to which they are attached

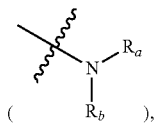

form a heterocycle selected from

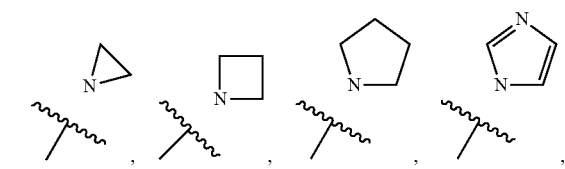

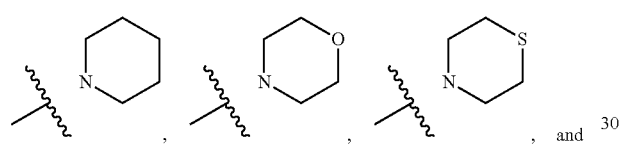
, and

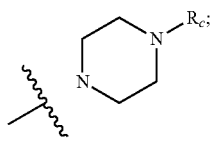

$R_c$ is H, methyl, ethyl, n-propyl, i-propyl, n-butyl, i-butyl, t-butyl, $CH_2CMe_3$, phenyl, or $CH_2$-phenyl; and
each n is independently 2, 3, 4, 5 or 6.

28. The compound of claim 1, having the following chemical structure:

wherein ∥ represents a single bond or a double bond;
W is S or O;
each of $R_a$ and $R_b$ is independently H, methyl, ethyl, n-propyl, propyl, n-butyl, i-butyl, t-butyl, $CH_2CMe_3$, phenyl, or $CH_2$-phenyl; or $R_a$ and $R_b$, together with the nitrogen atom to which they are attached

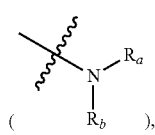

form a heterocycle selected from

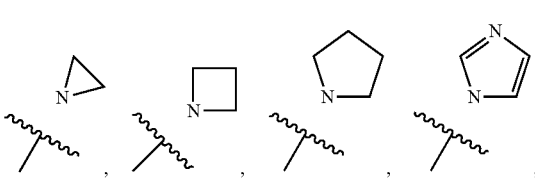

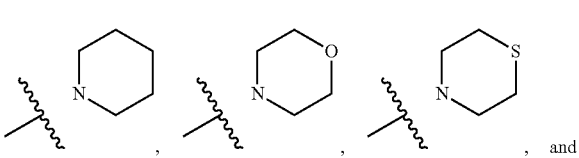
, and

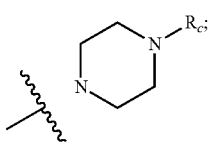

$R_c$ is H, methyl, ethyl, n-propyl, i-propyl, n-butyl, i-butyl, t-butyl, $CH_2CMe_3$, phenyl, or $CH_2$-phenyl;
$R_f$ is H or OMe; and
each n is independently 2, 3, 4, 5 or 6.

(XXIII)

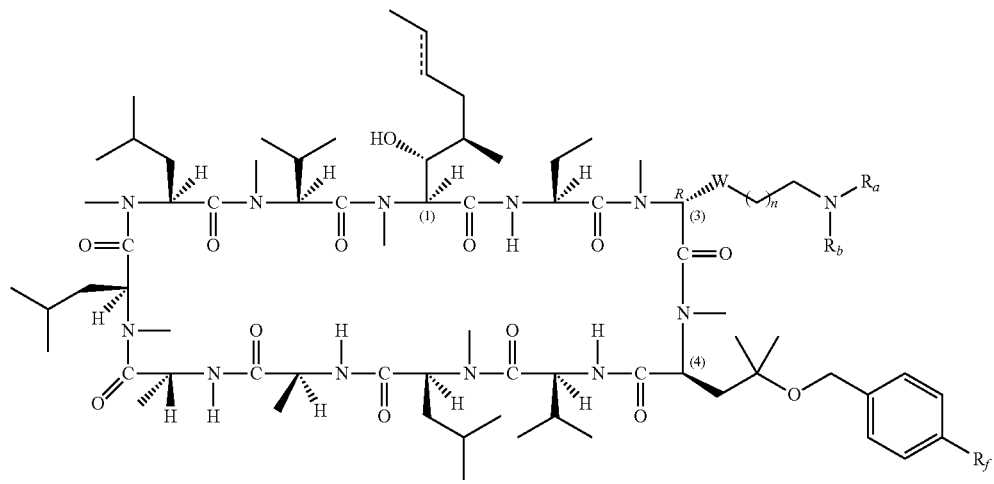

29. A compound of claim 1 selected from the group consisting of:
[(R)-3-(N-Pyrrolidinyl)propylthio-Sar]-3-[(γ-hydroxy)-NMeLeu]-4-cyclosporin
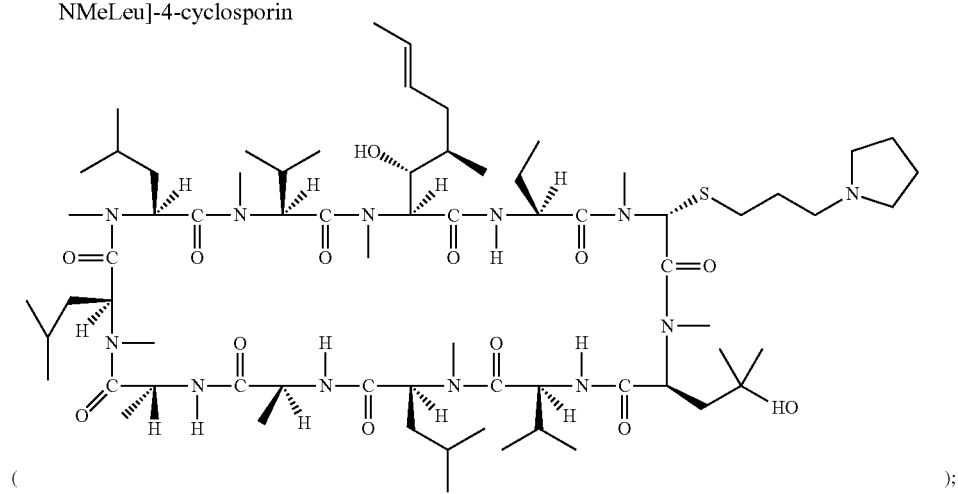
[(R)-3-(N-Piperidinyl)propylthio-Sar]-3-[(γ-hydroxy)-NMeLeu]-4-cyclosporin
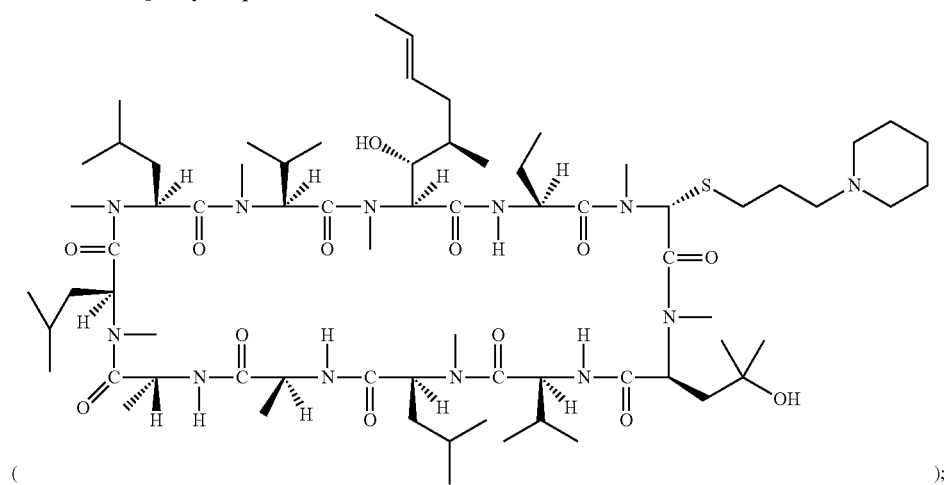
[(R)-3-(N-Thiomorpholino)propylthio-Sar]-3-[(γ-hydroxy)-NMeLeu]-4-cyclosporin
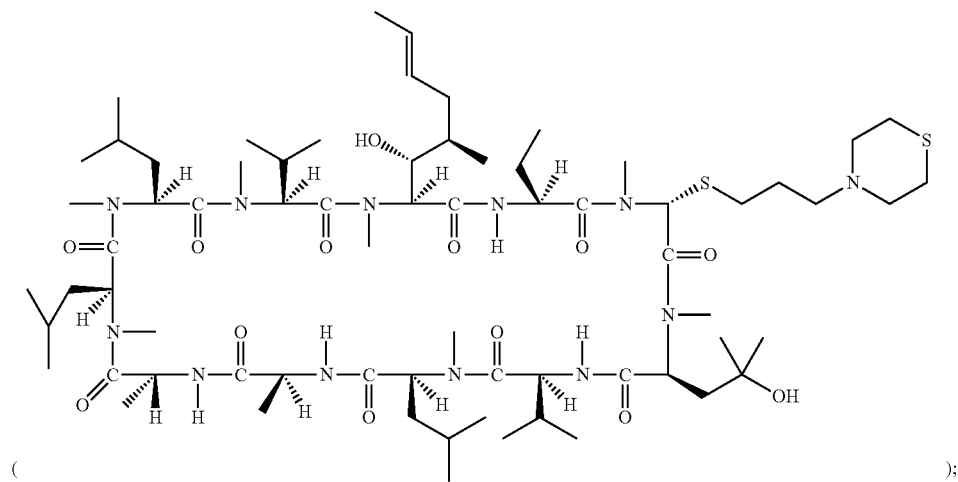 [SMILES: C/C=C/C[C@@H](C)[C@@H](O)[C@H]1C(=O)N[C@@H](CC)C(=O)N(C)[C@H](SCCCN2CCSCC2)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

[(R)-3-(N,N-Dimethylamino)propylthio-Sar]-3-[(γ-hydroxy)-NMeLeu]-4-cyclosporin
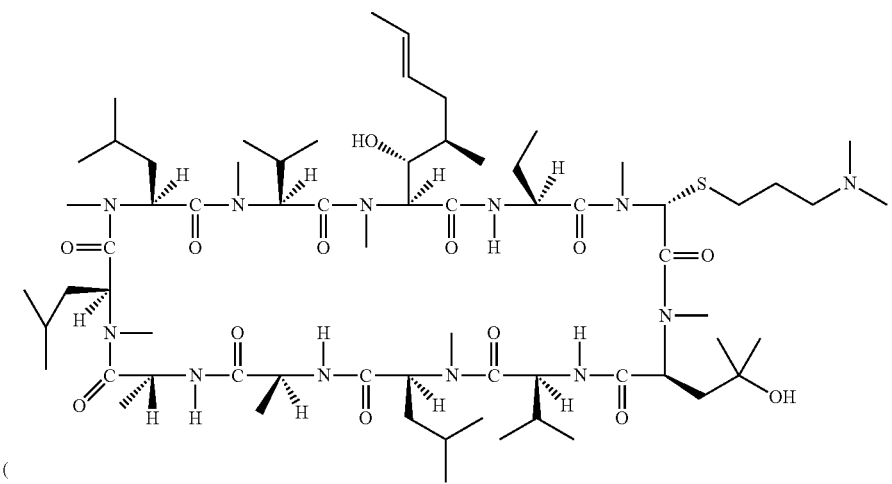
( );
[(R)-3-(N-iso-Propyl-N-methylamino)propylthio-Sar]-3-[(γ-hydroxy)-NMeLeu]-4-cyclosporin
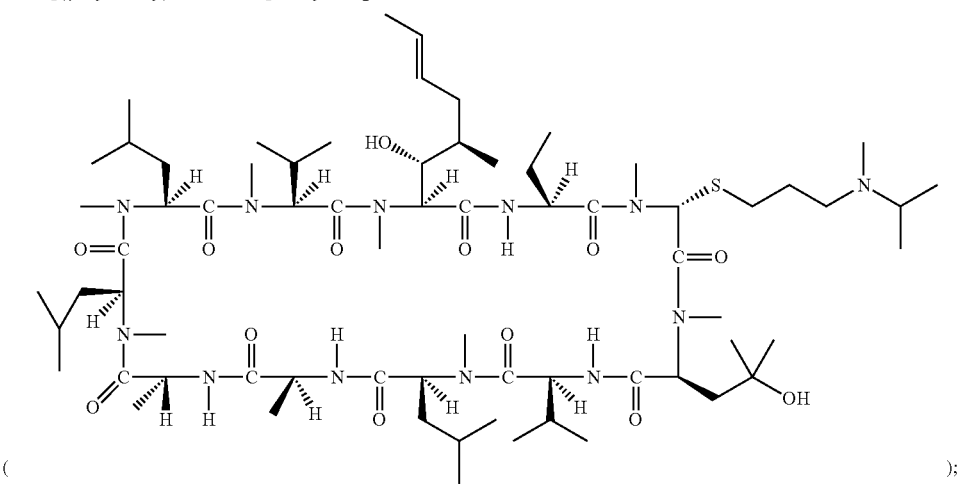
( );
[(R)-4-(N-Pyrrolidinyl)Butylthio-Sar]-3-[(γ-hydroxy)-NMeLeu]-4-cyclosporin
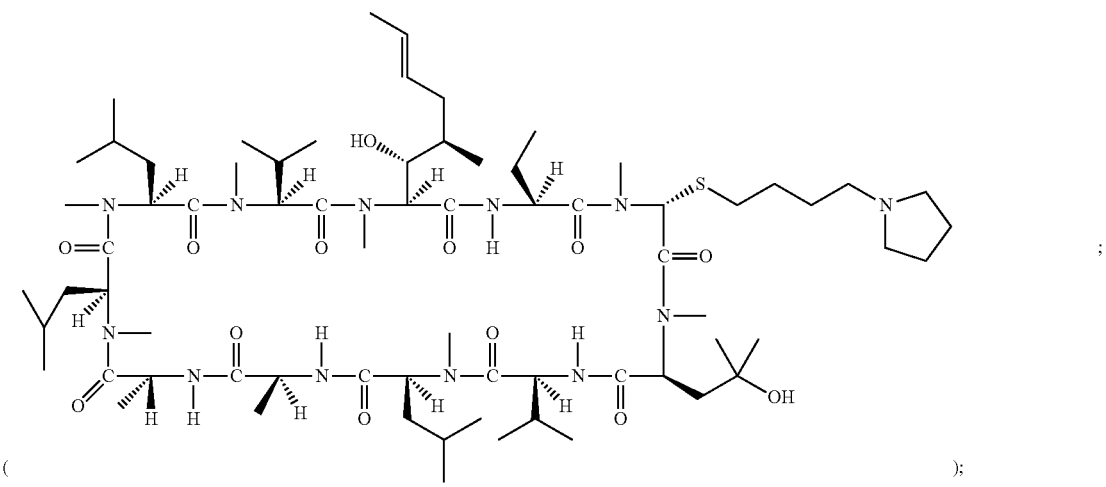 [SMILES: C/C=C/C[C@@H](C)[C@@H](O)[C@H]1C(=O)N[C@@H](CC)C(=O)N(C)[C@H](SCCCCN2CCCC2)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );

[(R)-4-(N-Piperidinyl)Butylthio-Sar]-3-[(γ-hydroxy)-
NMeLeu]-4-cyclosporin
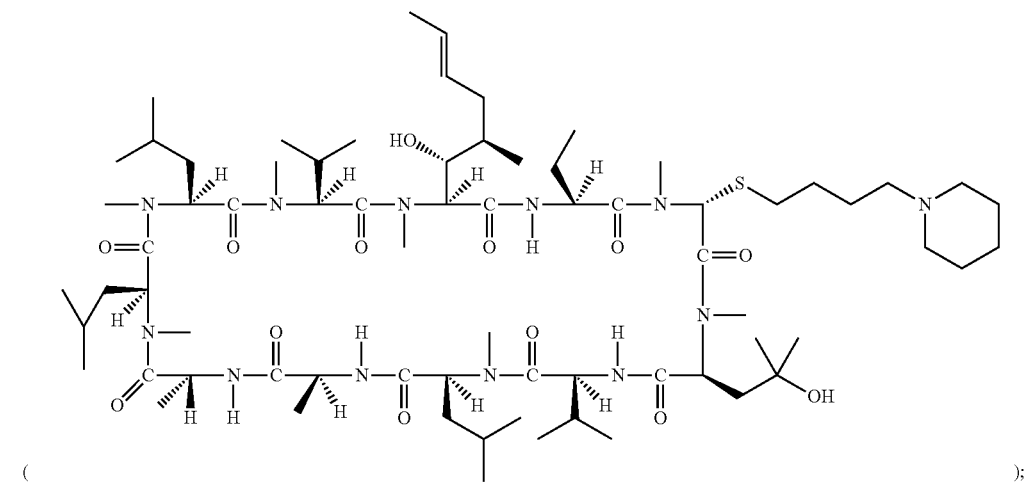 [SMILES: C/C=C/C[C@@H](C)[C@@H](O)[C@H]1C(=O)N[C@@H](CC)C(=O)N(C)[C@H](SCCCCN2CCCCC2)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-4-(N-Morpholino)Butylthio-Sar]-3-[(γ-hydroxy)-
NMeLeu]-4-cyclosporin
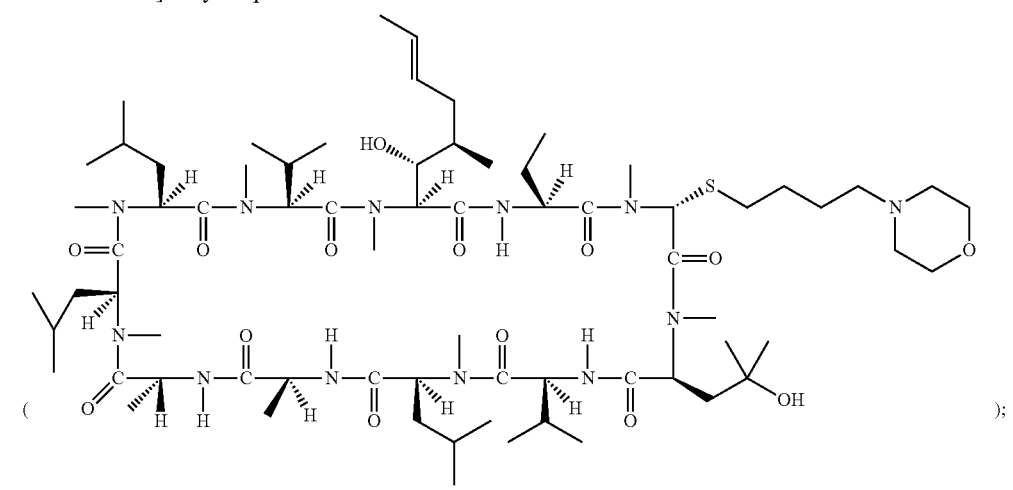
[(R)-4-(N-Thiomorpholino)Butylthio-Sar]-3-[(γ-hydroxy)-NMeLeu]-4-cyclosporin
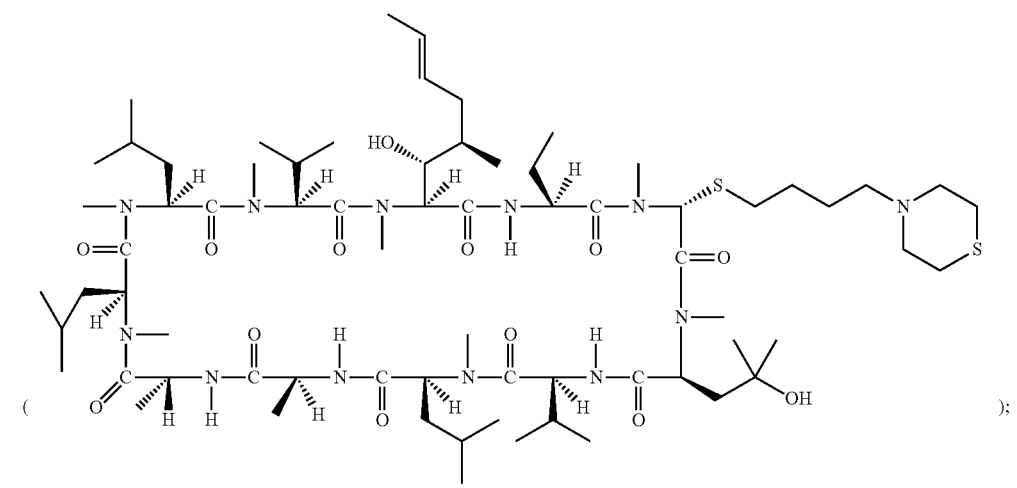 [SMILES: C/C=C/C[C@@H](C)[C@@H](O)[C@H]1C(=O)N[C@@H](CC)C(=O)N(C)[C@H](SCCCCN2CCSCC2)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

[(R)-4-(N,N-Dimethylamino)butylthio-Sar]-3-[(γ-hydroxy)-NMeLeu]-4-cyclosporin
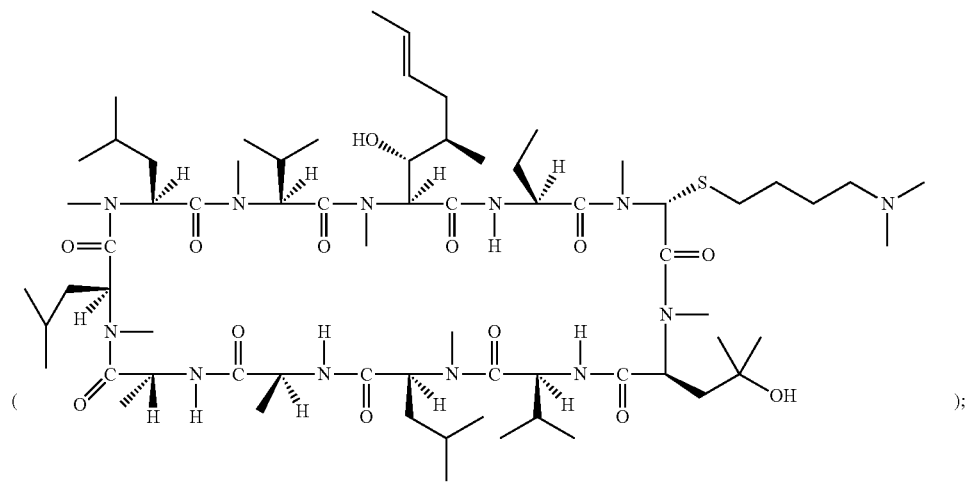 [SMILES: C/C=C/C[C@@H](C)[C@@H](O)[C@H]1C(=O)N[C@@H](CC)C(=O)N(C)[C@H](SCCCCN(C)C)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-4-(N,N-Diethylamino)butylthio-Sar]-3-[(γ-hydroxy)-NMeLeu]-4-cyclosporin
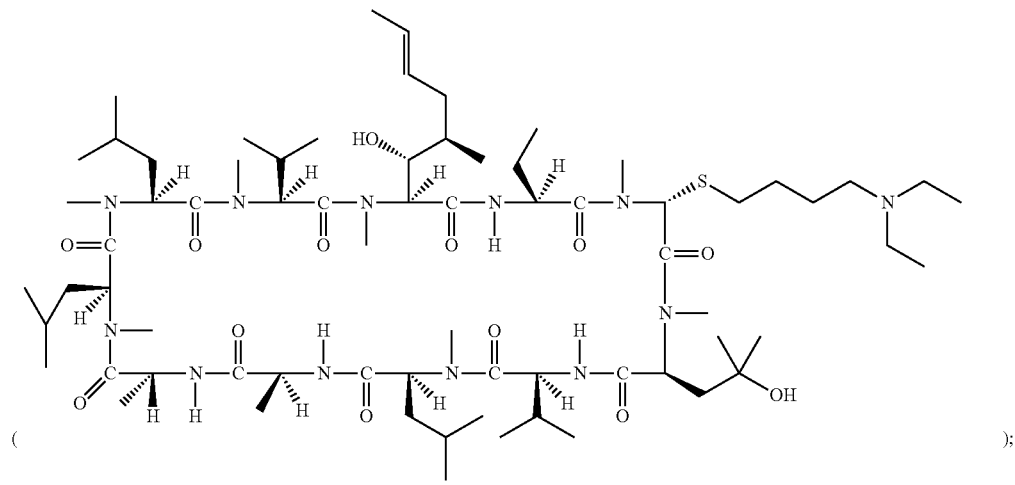 [SMILES: C/C=C/C[C@@H](C)[C@@H](O)[C@H]1C(=O)N[C@@H](CC)C(=O)N(C)[C@H](SCCCCN(CC)CC)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-4-(N-iso-Propylamino)butylthio-Sar]-3-[(γ-hydroxy)-NMeLeu]-4-cyclosporin
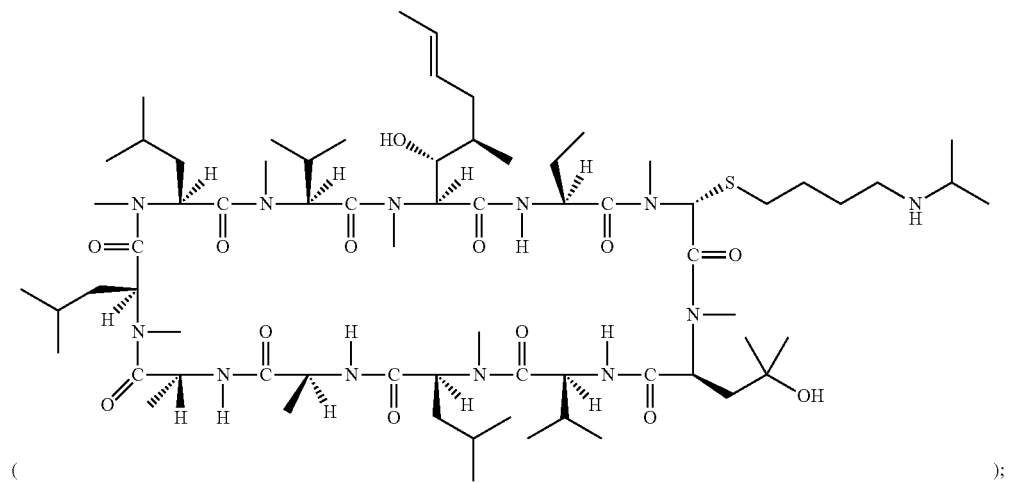 [SMILES: C/C=C/C[C@@H](C)[C@@H](O)[C@H]1C(=O)N[C@@H](CC)C(=O)N(C)[C@H](SCCCCNC(C)C)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

[(R)-4-(N-iso-Propyl-N-methylamino)butylthio-Sar]-3-[(γ-hydroxy)-NMeLeu]-4-cyclosporin
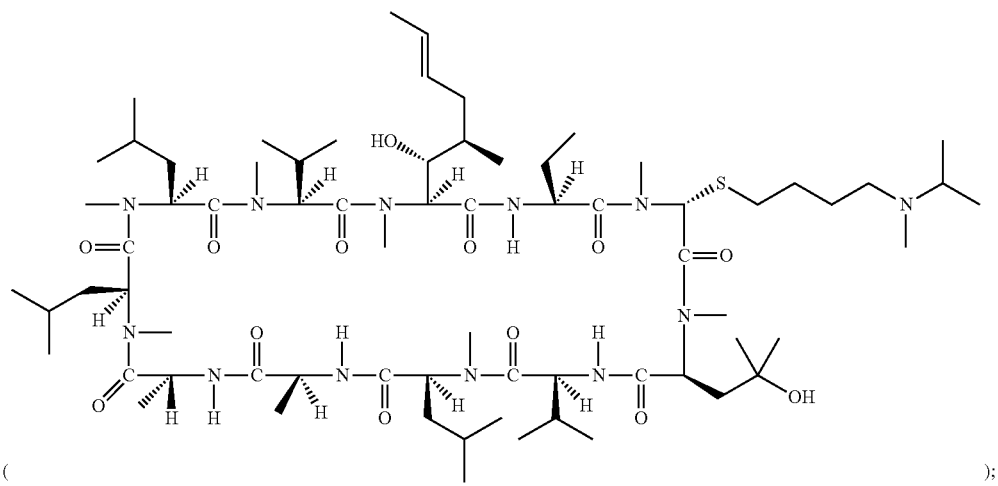 [SMILES: C/C=C/C[C@@H](C)[C@@H](O)[C@H]1C(=O)N[C@@H](CC)C(=O)N(C)[C@H](SCCCCN(C)C(C)C)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-4-(N-iso-Propyl-N-ethylamino)butylthio-Sar]-3-[(γ-hydroxy)-NMeLeu]-4-cyclosporin
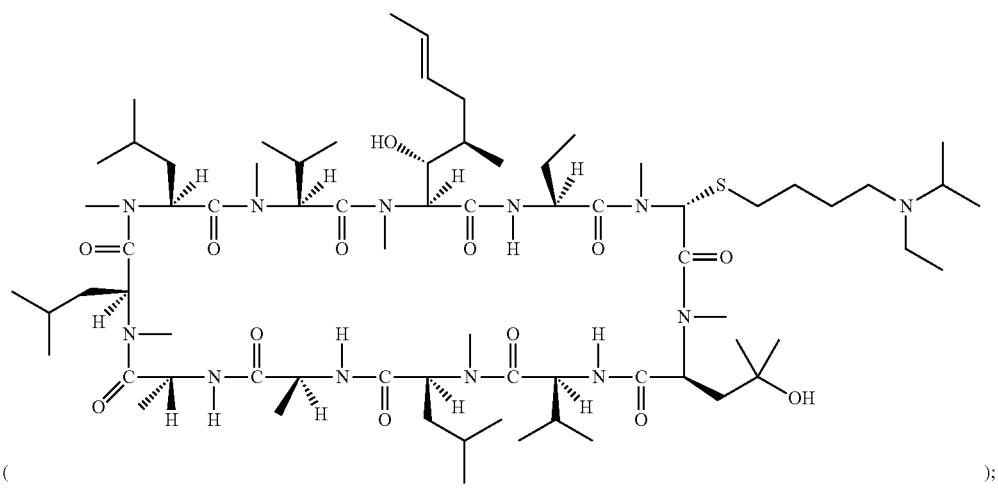 [SMILES: C/C=C/C[C@@H](C)[C@@H](O)[C@H]1C(=O)N[C@@H](CC)C(=O)N(C)[C@H](SCCCCN(CC)C(C)C)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-Pyrrolidinyl)propylthio-Sar]-3-[(γ-methylthio)methoxy-NMeLeu]-4-cyclosporin
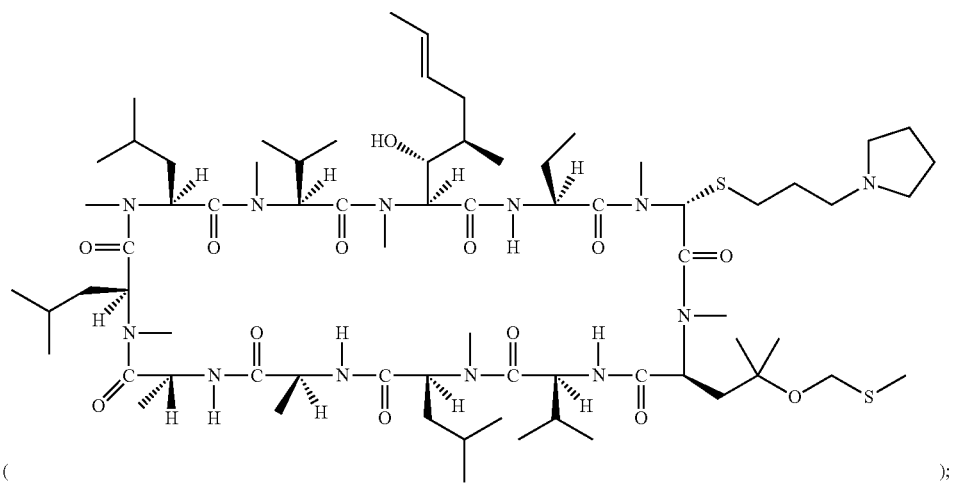
( );

[(R)-3-(N-Piperidinyl)propylthio-Sar]-3-[(γ-methylthio)methoxy-NMeLeu]-4-cyclosporin
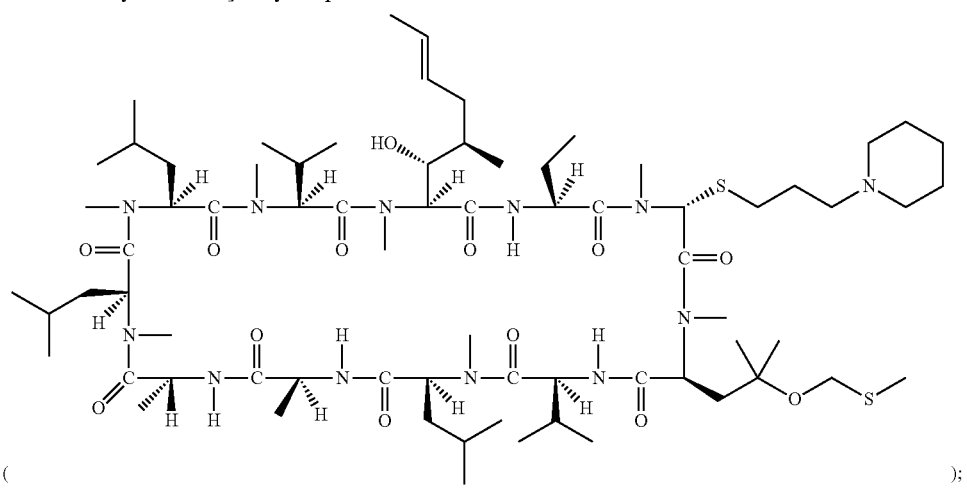
[(R)-3-(N-Thiomorpholino)propylthio-Sar]-3-[(γ-methylthio)methoxy-NMeLeu]-4-cyclosporin
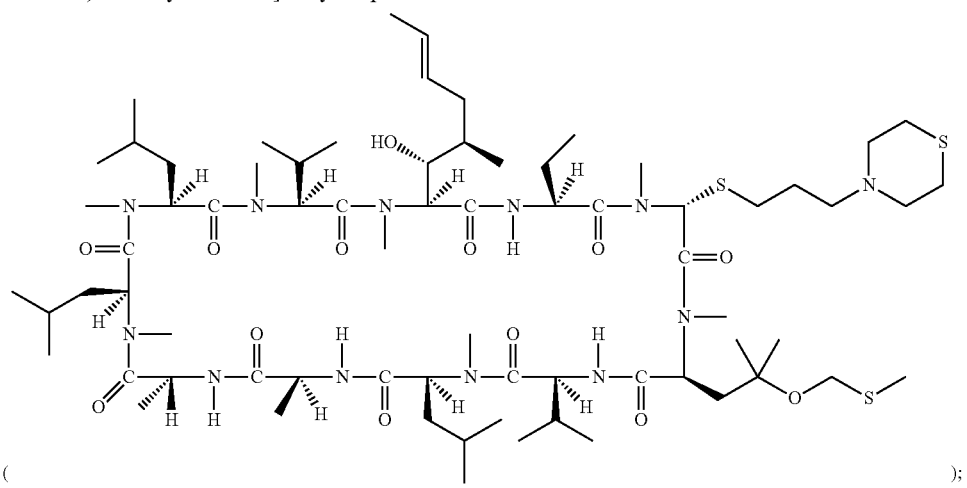
[(R)-3-(N,N-Dimethylamino)propylthio-Sar]-3-[(γ-methylthio)methoxy-NMeLeu]-4-cyclosporin
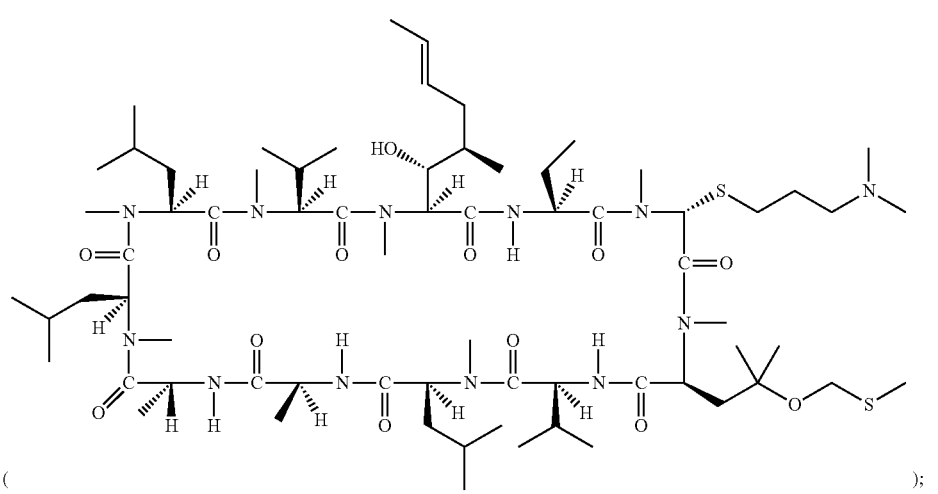 [SMILES: C/C=C/C[C@@H](C)[C@@H](O)[C@H]1C(=O)N[C@@H](CC)C(=O)N(C)[C@H](SCCCN(C)C)C(=O)N(C)[C@@H](CC(C)(C)OCSC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

[(R)-3-(N,N-Diethylamino)propylthio-Sar]-3-[(γ-methyl-thio)methoxy-NMeLeu]-4-cyclosporin
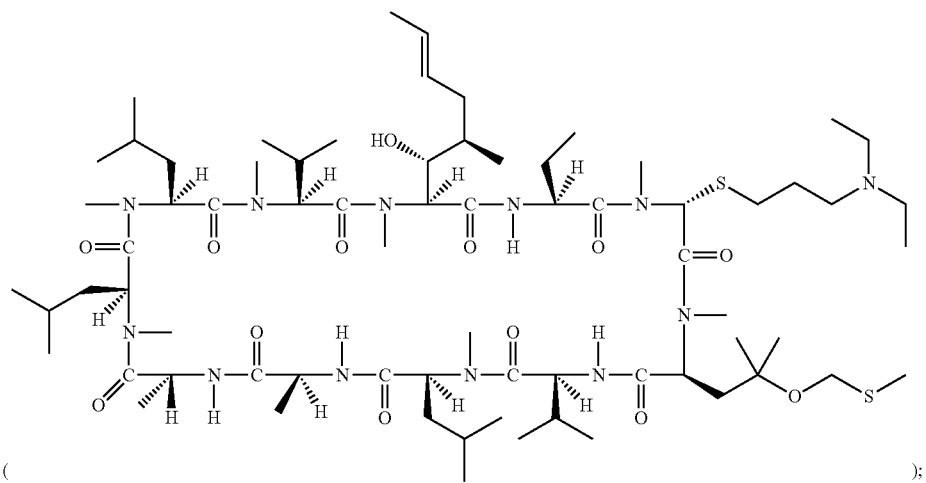 [SMILES: C/C=C/C[C@@H](C)[C@@H](O)[C@H]1C(=O)N[C@@H](CC)C(=O)N(C)[C@H](SCCCN(CC)CC)C(=O)N(C)[C@@H](CC(C)(C)OCSC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-iso-Propyl-N-ethylamino)propylthio-Sar]-3-[(γ-methylthio)methoxy-NMeLeu]-4-cyclosporin
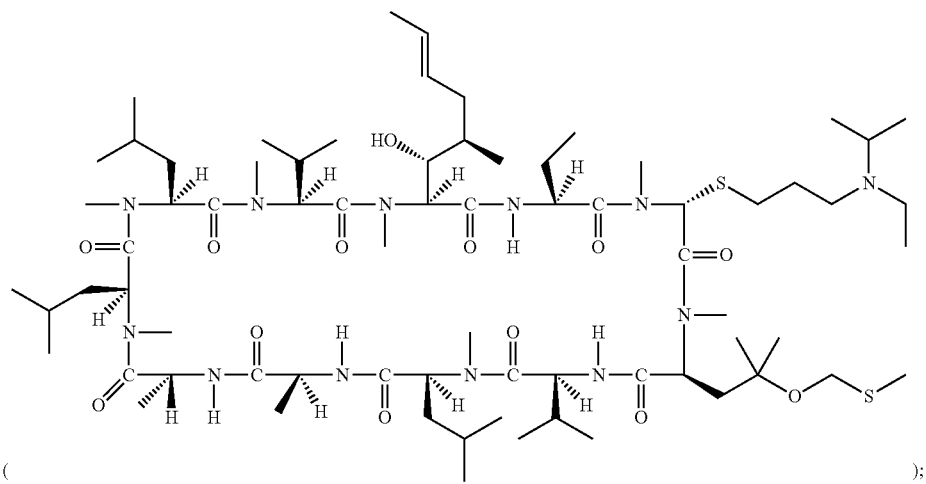 [SMILES: C/C=C/C[C@@H](C)[C@@H](O)[C@H]1C(=O)N[C@@H](CC)C(=O)N(C)[C@H](SCCCN(CC)C(C)C)C(=O)N(C)[C@@H](CC(C)(C)OCSC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-Pyrrolidinyl)propylthio-Sar]-3-[(γ-methyloxy)methoxy-NMeLeu]-4-cyclosporin
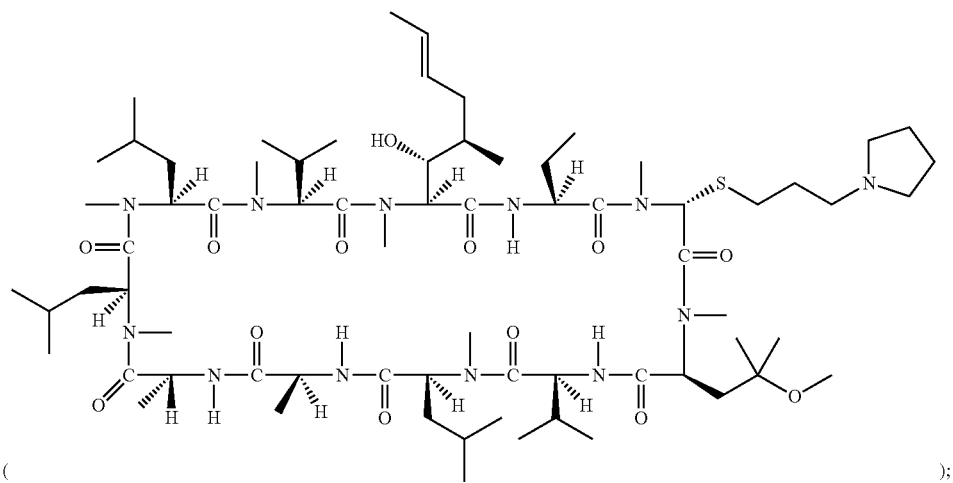 [SMILES: C/C=C/C[C@@H](C)[C@@H](O)[C@H]1C(=O)N[C@@H](CC)C(=O)N(C)[C@H](SCCCN2CCCC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );

[(R)-3-(N-Piperidinyl)propylthio-Sar]-3-[(γ-methyloxy)methoxy-NMeLeu]-4-cyclosporin
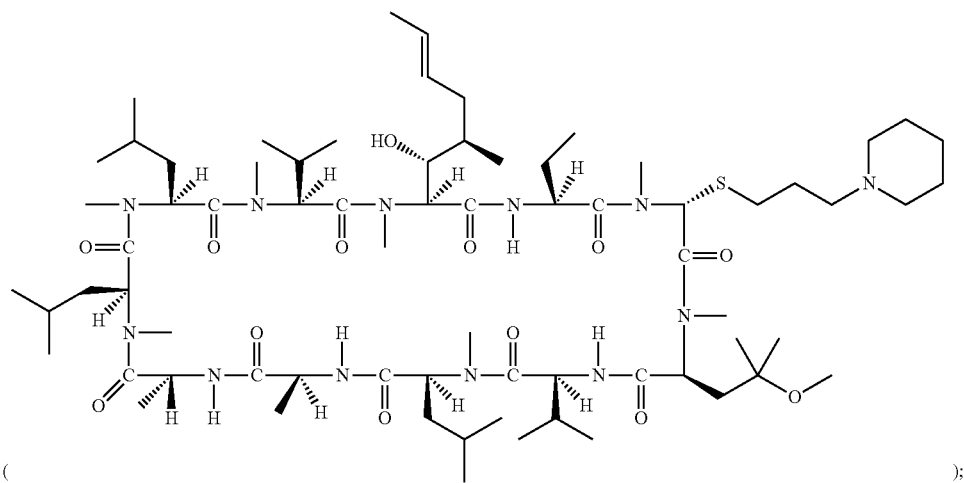
( );
[(R)-3-(N-Morpholino)propylthio-Sar]-3-[(γ-methyloxy)methoxy-NMeLeu]-4-cyclosporin
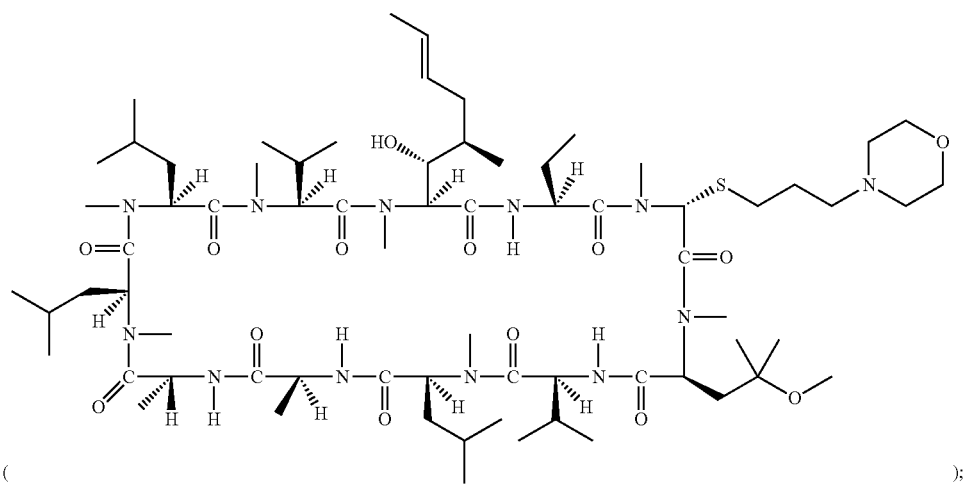 [SMILES: C/C=C/C[C@@H](C)[C@@H](O)[C@H]1C(=O)N[C@@H](CC)C(=O)N(C)[C@H](SCCCN2CCOCC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N,N-Dimethylamino)propylthio-Sar]-3-[(γ-methyloxy)methoxy-NMeLeu]-4-cyclosporin
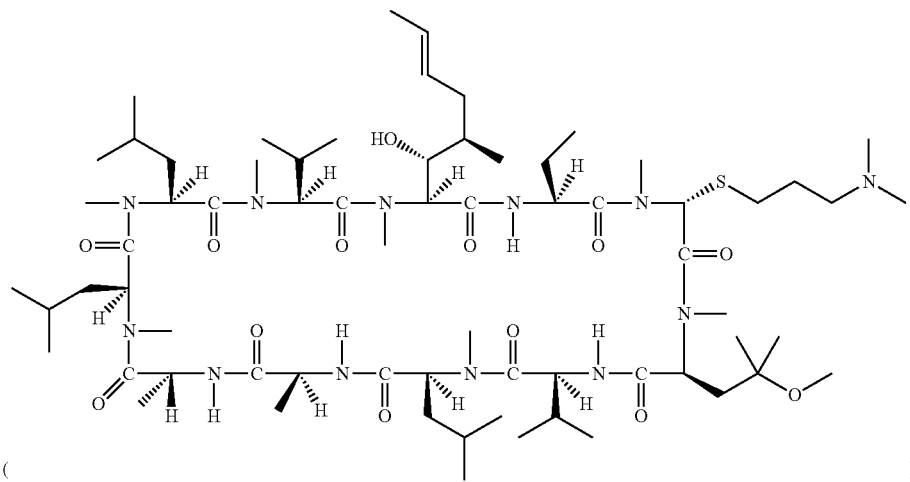
( );

[(R)-3-(N,N-Diethylamino)propylthio-Sar]-3-[(γ-methyl-oxy)methoxy-NMeLeu]-4-cyclosporin
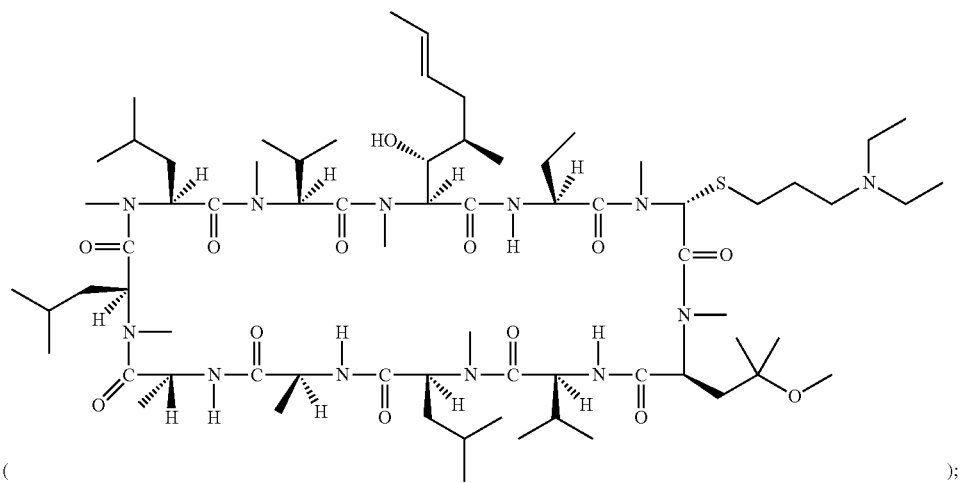 [SMILES: C/C=C/C[C@@H](C)[C@@H](O)[C@H]1C(=O)N[C@@H](CC)C(=O)N(C)[C@H](SCCCN(CC)CC)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-iso-Propyl-N-ethylamino)propylthio-Sar]-3-[(γ-methyloxy)methoxy-NMeLeu]-4-cyclosporin
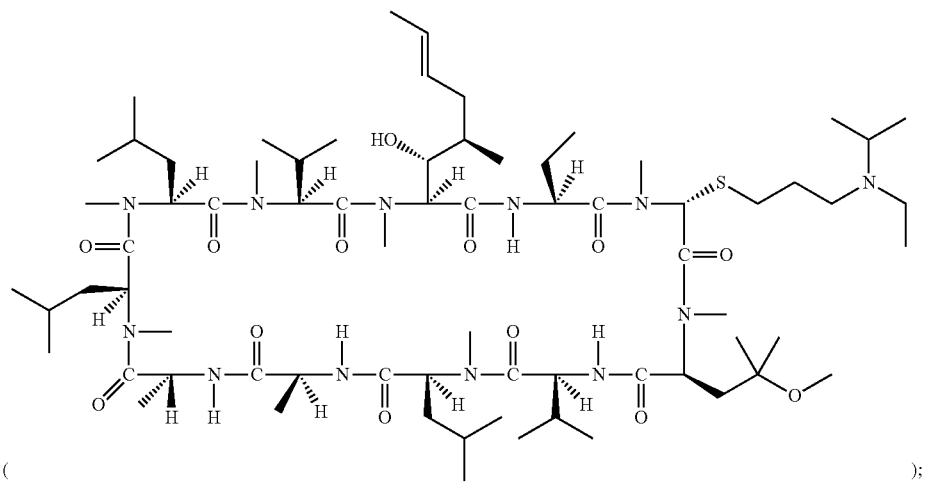 [SMILES: C/C=C/C[C@@H](C)[C@@H](O)[C@H]1C(=O)N[C@@H](CC)C(=O)N(C)[C@H](SCCCN(CC)C(C)C)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-Thiomorpholino)propylthio-Sar]-3-[(γ-methoxy)-NMeLeu]-4-cyclosporin
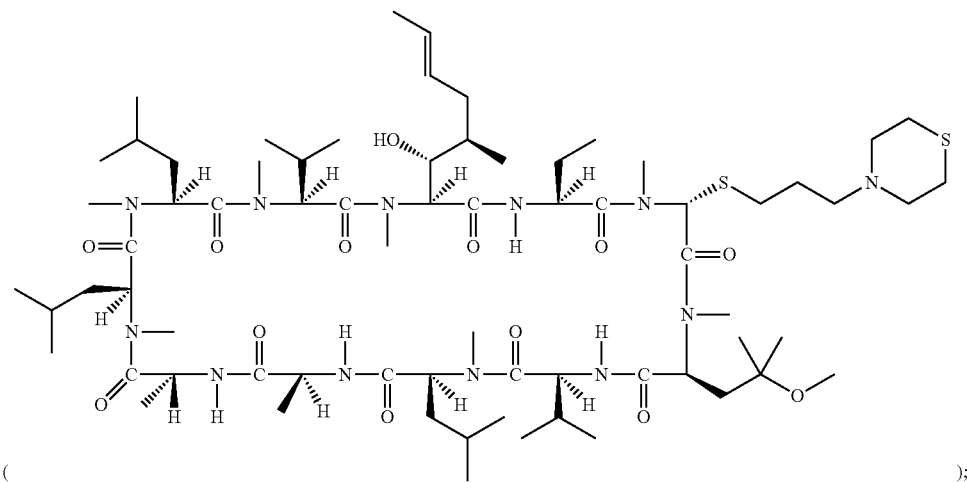 [SMILES: C/C=C/C[C@@H](C)[C@@H](O)[C@H]1C(=O)N[C@@H](CC)C(=O)N(C)[C@H](SCCCN2CCSCC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );

[(R)-3-(N-4-Methylpiperazinyl)propylthio-Sar]-3-[(γ-methoxy)-NMeLeu]-4-cyclosporin
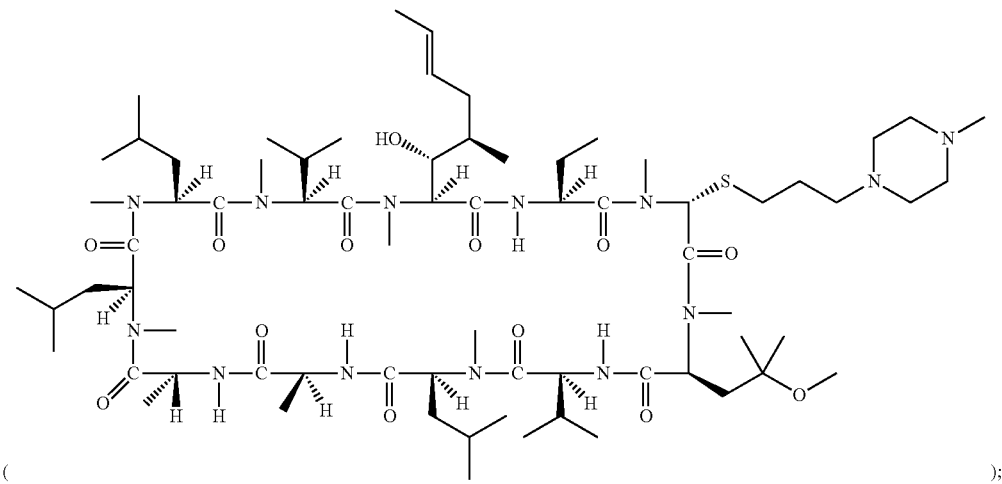 [SMILES: C/C=C/C[C@@H](C)[C@@H](O)[C@H]1C(=O)N[C@@H](CC)C(=O)N(C)[C@H](SCCCN2CCN(C)CC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-iso-Propylamino)propylthio-Sar]-3-[(γ-methoxy)-NMeLeu]-4-cyclosporin
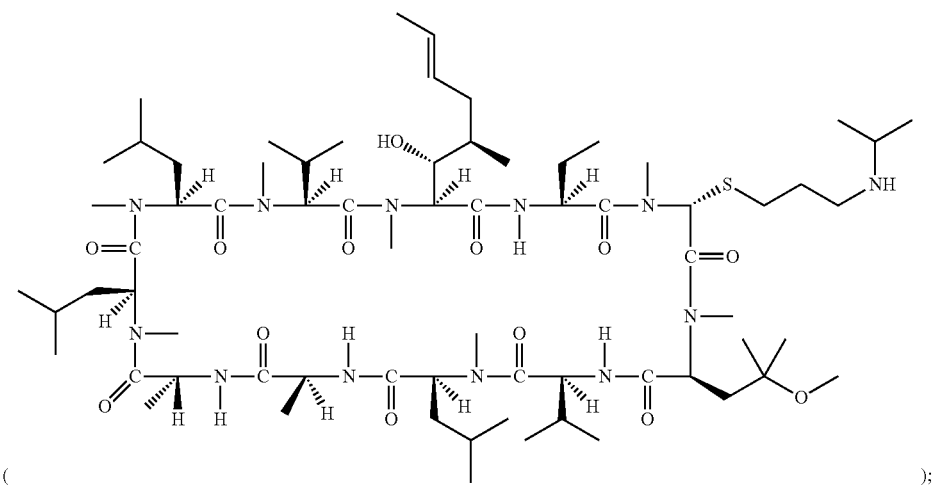 [SMILES: C/C=C/C[C@@H](C)[C@@H](O)[C@H]1C(=O)N[C@@H](CC)C(=O)N(C)[C@H](SCCCNC(C)C)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-iso-Propyl-N-methylamino)propylthio-Sar]-3-[(γ-methoxy)-NMeLeu]-4-cyclosporin
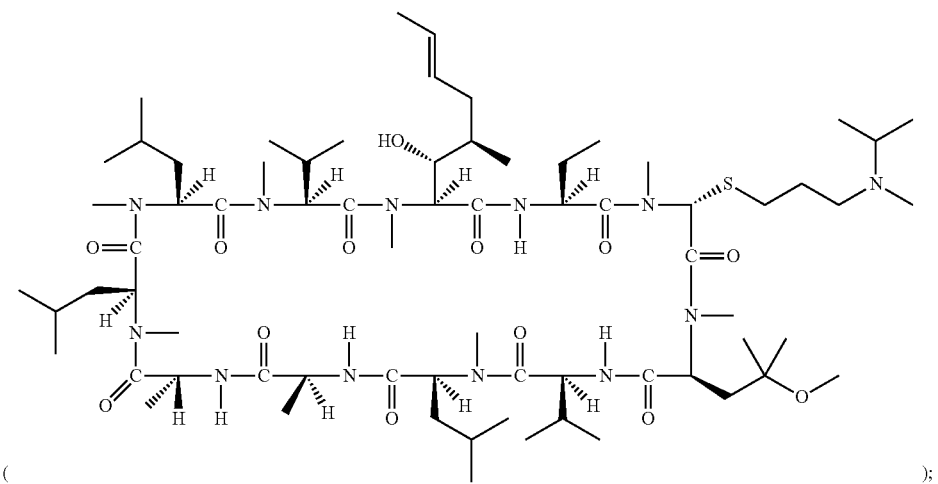 [SMILES: C/C=C/C[C@@H](C)[C@@H](O)[C@H]1C(=O)N[C@@H](CC)C(=O)N(C)[C@H](SCCCN(C)C(C)C)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );

[(R)-4-(N-Pyrrolidinyl)butylthio-Sar]-3-[(γ-methoxy)-NMeLeu]-4-cyclosporin
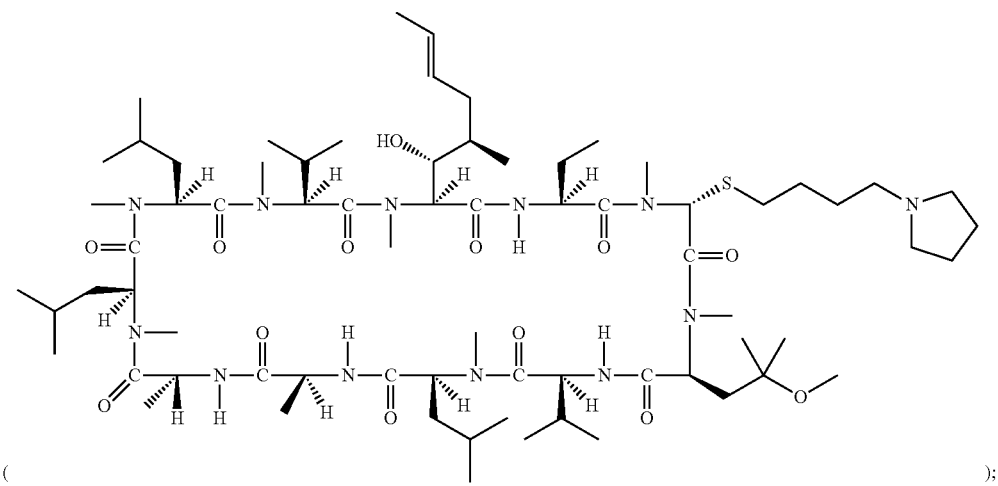 [SMILES: C/C=C/C[C@@H](C)[C@@H](O)[C@H]1C(=O)N[C@@H](CC)C(=O)N(C)[C@H](SCCCCN2CCCC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-4-(N-Piperidinyl)butylthio-Sar]-3-[(γ-methoxy)-NMeLeu]-4-cyclosporin
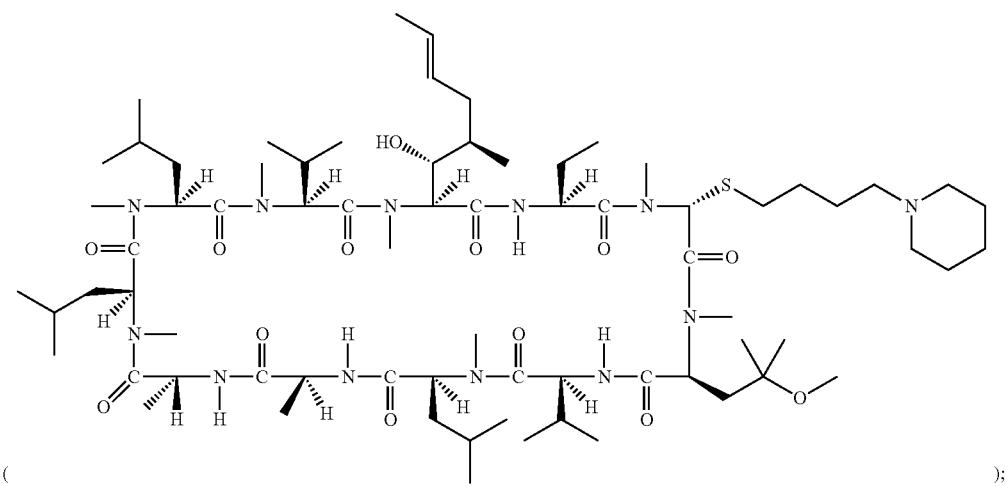 [SMILES: C/C=C/C[C@@H](C)[C@@H](O)[C@H]1C(=O)N[C@@H](CC)C(=O)N(C)[C@H](SCCCCN2CCCCC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-4-(N-Morpholino)butylthio-Sar]-3-[(γ-methoxy)-NMeLeu]-4-cyclosporin
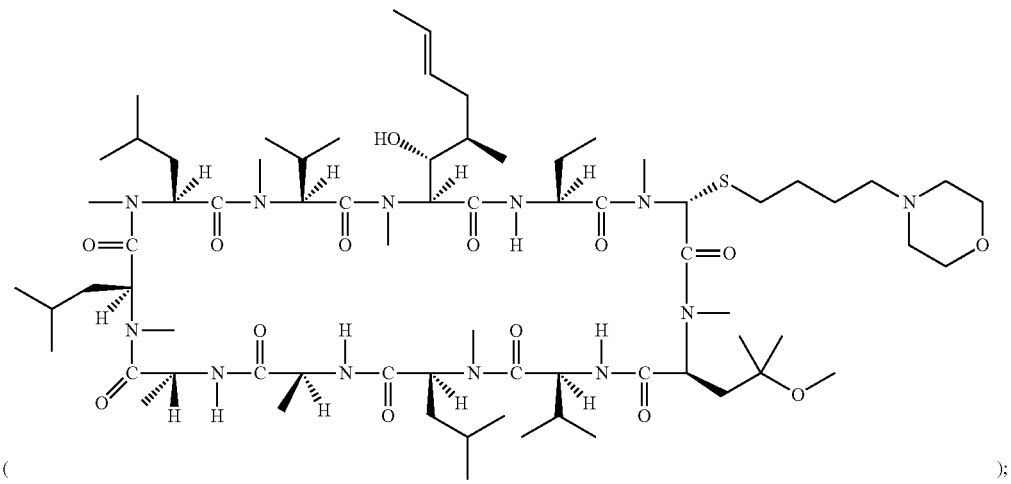 [SMILES: C/C=C/C[C@@H](C)[C@@H](O)[C@H]1C(=O)N[C@@H](CC)C(=O)N(C)[C@H](SCCCCN2CCOCC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

[(R)-4-(N-Thiomorpholino)butylthio-Sar]-3-[(γ-methoxy)-NMeLeu]-4-cyclosporin
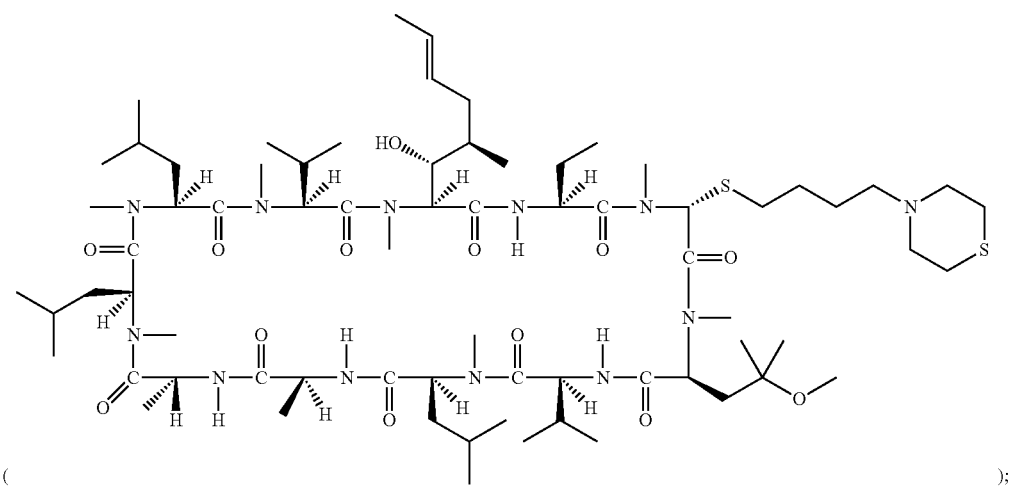 [SMILES: C/C=C/C[C@@H](C)[C@@H](O)[C@H]1C(=O)N[C@@H](CC)C(=O)N(C)[C@H](SCCCCN2CCSCC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-4-(N-4-Methylpiperazinyl)butylthio-Sar]-3-[(γ-methoxy)-NMeLeu]-4-cyclosporin
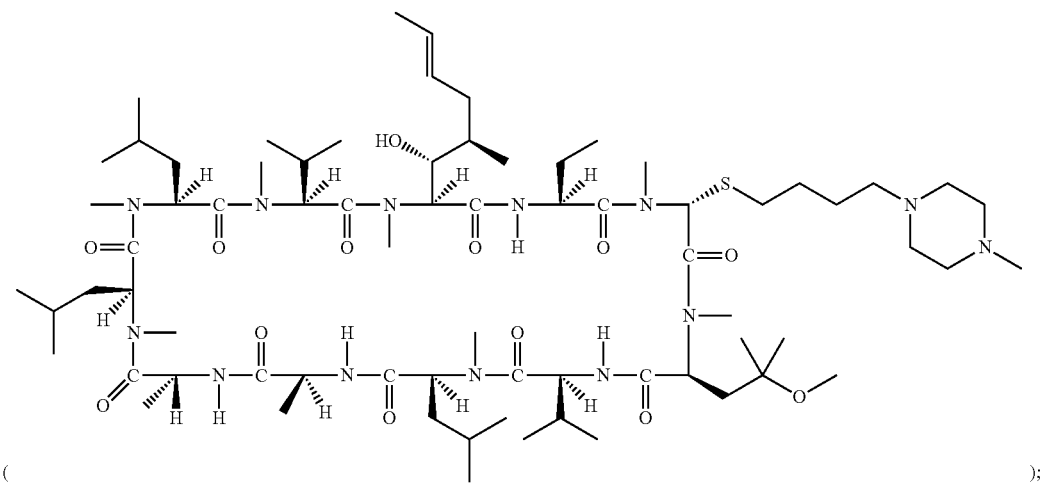 [SMILES: C/C=C/C[C@@H](C)[C@@H](O)[C@H]1C(=O)N[C@@H](CC)C(=O)N(C)[C@H](SCCCCN2CCN(C)CC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-4-(N,N-Dimethylamino)butylthio-Sar]-3-[(γ-methoxy)-NMeLeu]-4-cyclosporin
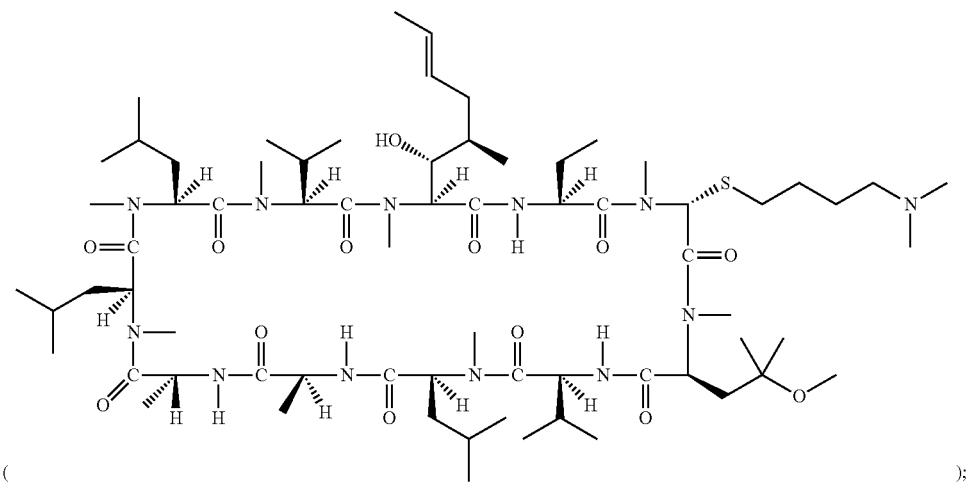 [SMILES: C/C=C/C[C@@H](C)[C@@H](O)[C@H]1C(=O)N[C@@H](CC)C(=O)N(C)[C@H](SCCCCN(C)C)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

[(R)-4-(N,N-Diethylamino)butylthio-Sar]-3-[(γ-methoxy)-NMeLeu]-4-cyclosporin
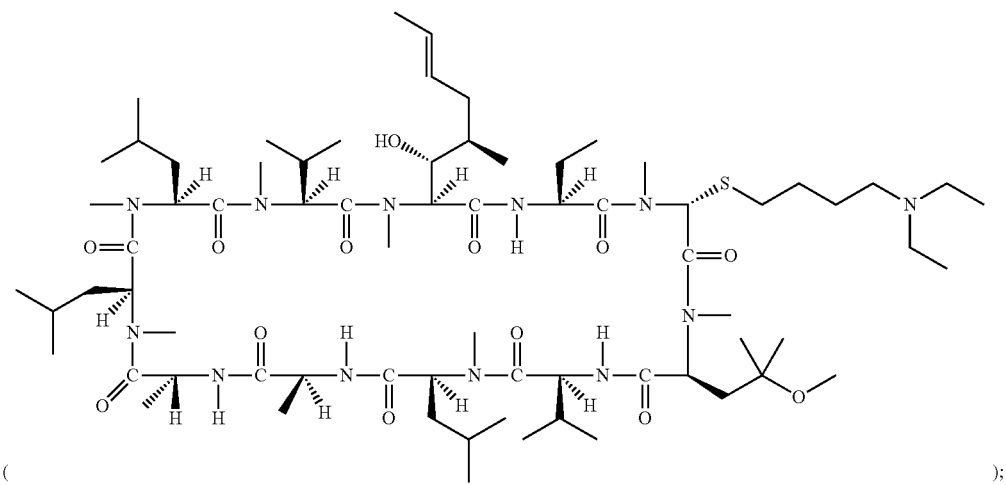 [SMILES: C/C=C/C[C@@H](C)[C@@H](O)[C@H]1C(=O)N[C@@H](CC)C(=O)N(C)[C@H](SCCCCN(CC)CC)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-4-(N-iso-Propylamino)butylthio-Sar]-3-[(γ-methoxy)-NMeLeu]-4-cyclosporin
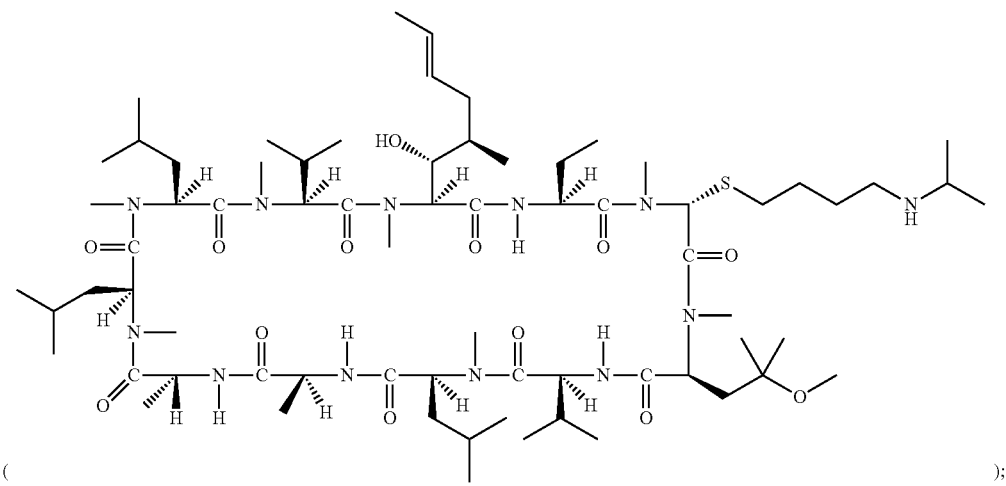 [SMILES: C/C=C/C[C@@H](C)[C@@H](O)[C@H]1C(=O)N[C@@H](CC)C(=O)N(C)[C@H](SCCCCNC(C)C)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-4-(N-iso-Propyl-N-methylamino)butylthio-Sar]-3-[(γ-methoxy)-NMeLeu]-4-cyclosporin
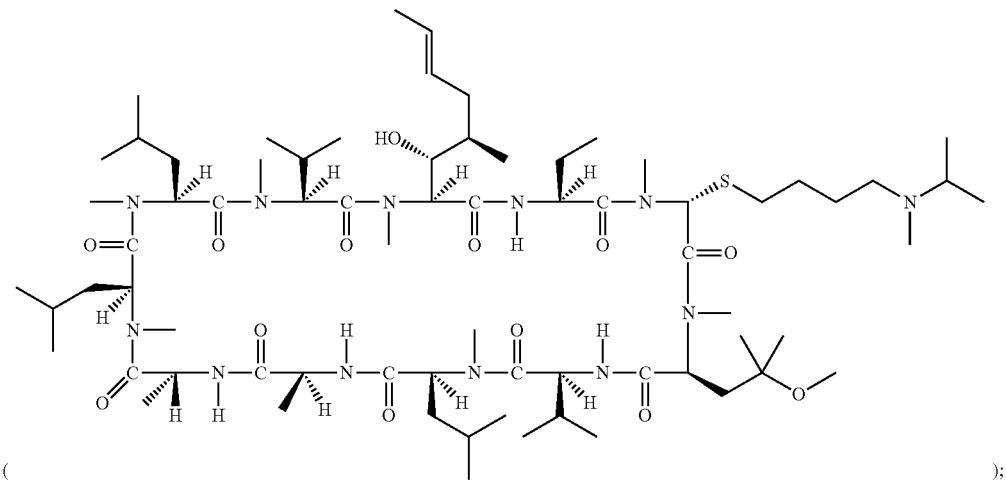 [SMILES: C/C=C/C[C@@H](C)[C@@H](O)[C@H]1C(=O)N[C@@H](CC)C(=O)N(C)[C@H](SCCCCN(C)C(C)C)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );

[(R)-4-(N-iso-Propyl-N-ethylamino)butylthio-Sar]-3-[(γ-methoxy)-NMeLeu]-4-cyclosporin
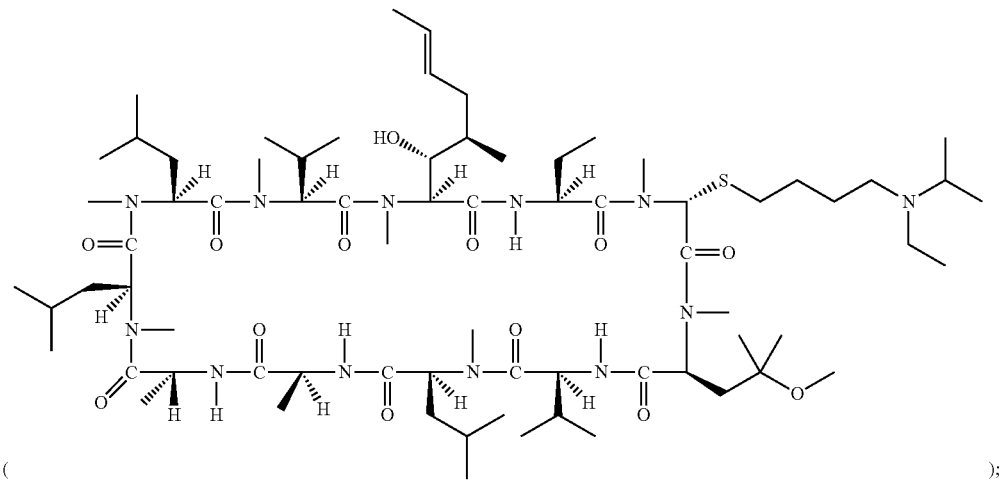 [SMILES: C/C=C/C[C@@H](C)[C@@H](O)[C@H]1C(=O)N[C@@H](CC)C(=O)N(C)[C@H](SCCCCN(CC)C(C)C)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-Pyrrolidinyl)propylthio-Sar]-3-[(γ-allyloxy)-NMeLeu]-4-cyclosporin
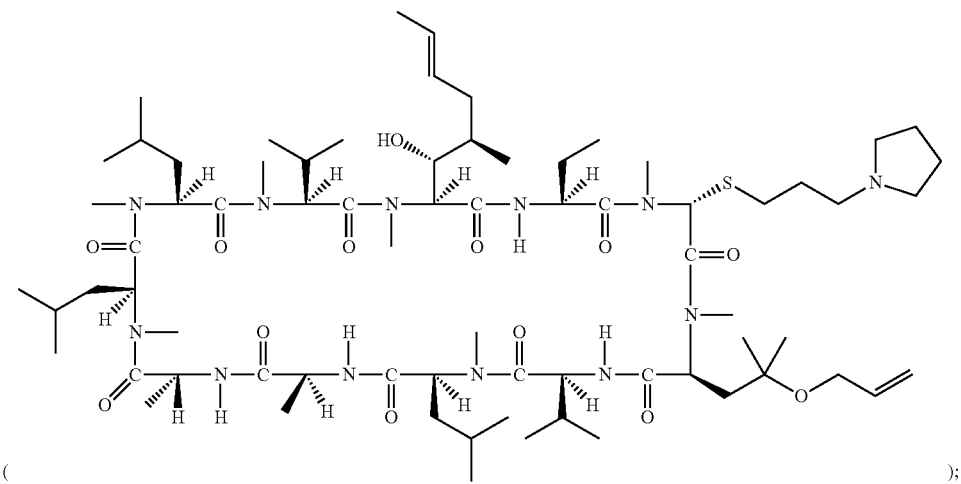 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCN2CCCC2)C(=O)N1C]
( );
[(R)-3-(N-Piperidinyl)propylthio-Sar]-3-[(γ-allyloxy)-NMeLeu]-4-cyclosporin
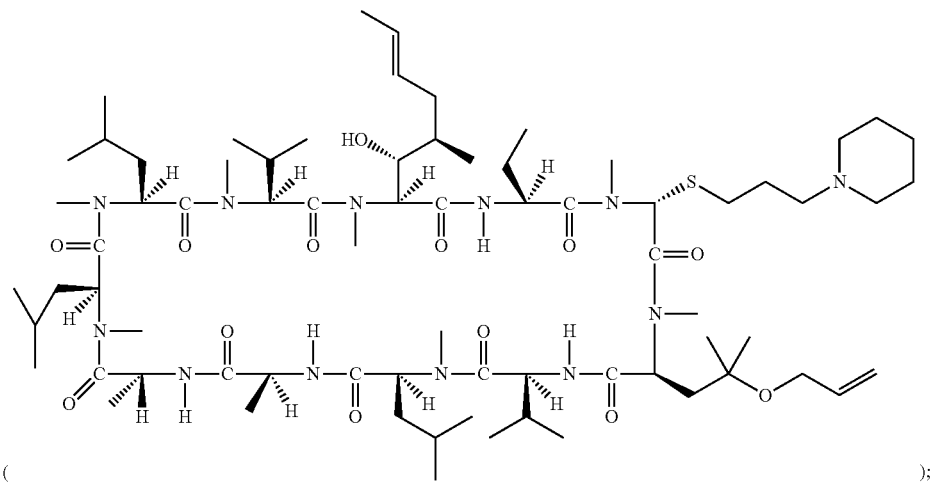 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCN2CCSCC2)C(=O)N1C]
( );

[(R)-3-(N-Thiomorpholino)propylthio-Sar]-3-[(γ-allyloxy)-NMeLeu]-4-cyclosporin
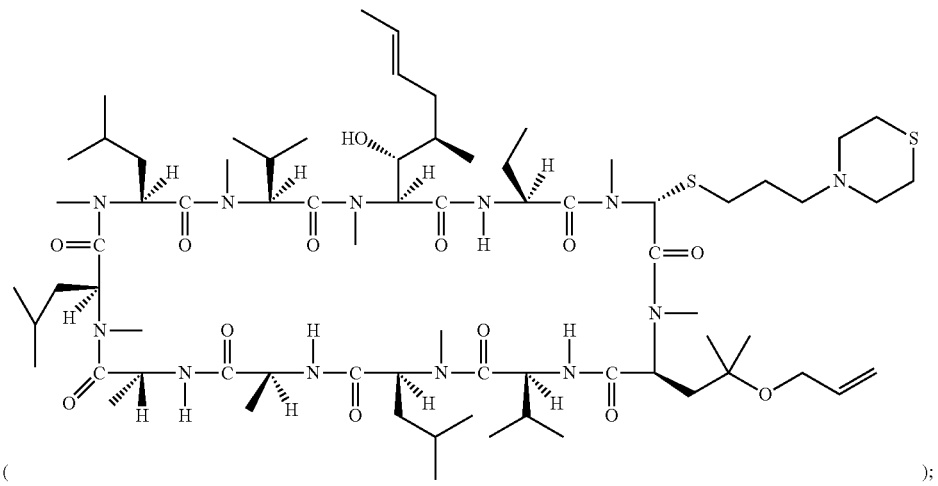
[(R)-3-(N-4-Methylpiperazinyl)propylthio-Sar]-3-[(γ-allyloxy)-NMeLeu]-4-cyclosporin
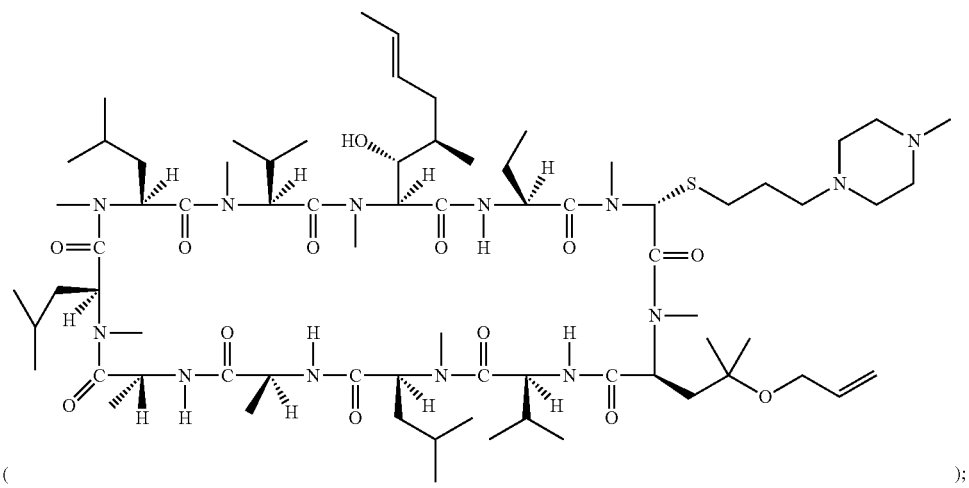 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCN2CCN(C)CC2)C(=O)N1C]
[(R)-3-(N,N-Dimethylamino)propylthio-Sar]-3-[(γ-allyloxy)-NMeLeu]-4-cyclosporin
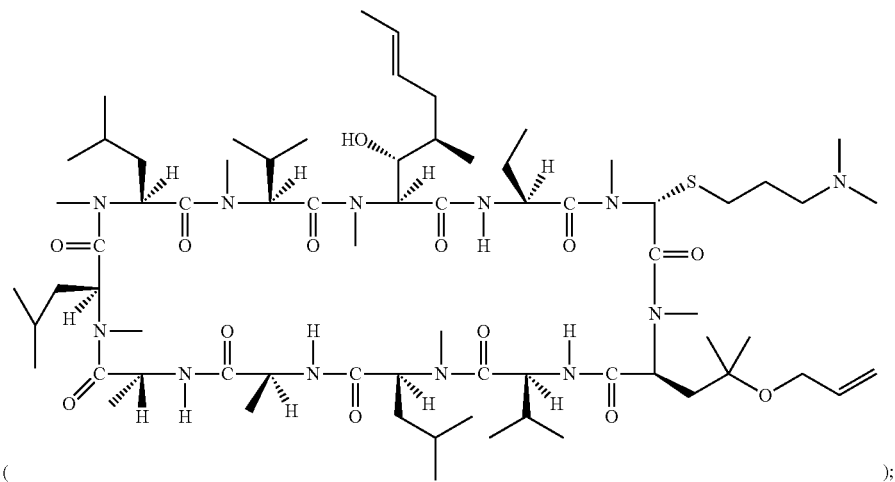 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCN(C)C)C(=O)N1C]

[(R)-3-(N,N-Diethylamino)propylthio-Sar]-3-[(γ-allyloxy)-NMeLeu]-4-cyclosporin
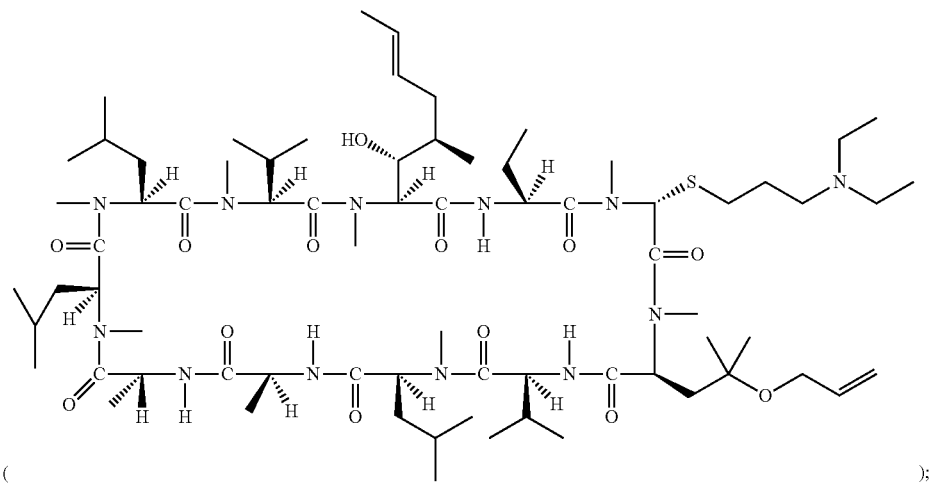 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCN(CC)CC)C(=O)N1C]
( );
[(R)-3-(N-iso-Propylamino)propylthio-Sar]-3-[(γ-allyloxy)-NMeLeu]-4-cyclosporin
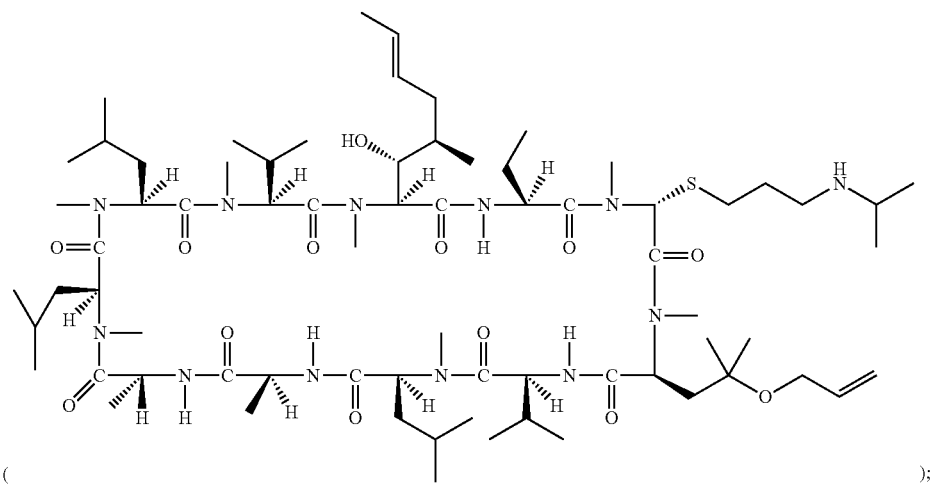 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCNC(C)C)C(=O)N1C]
( );
[(R)-3-(N-iso-Propyl-N-methylamino)propylthio-Sar]-3-[(γ-allyloxy)-NMeLeu]-4-cyclosporin
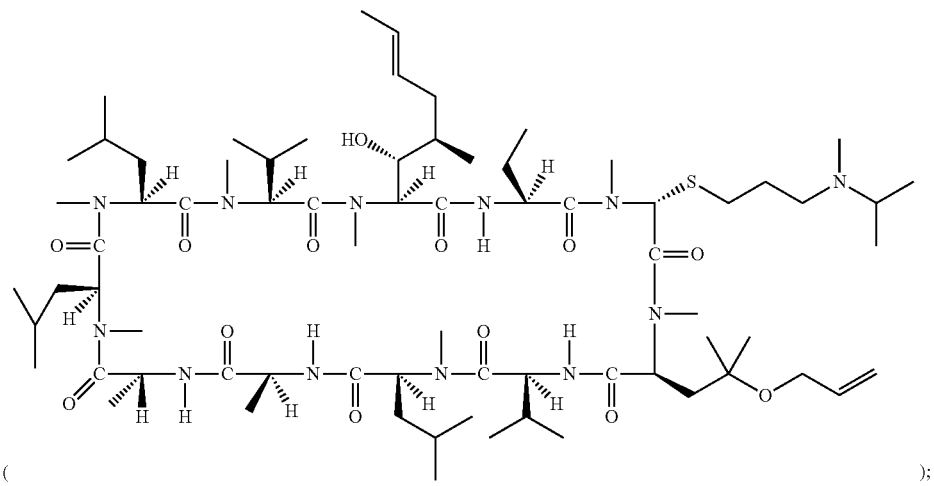 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCN(C)C(C)C)C(=O)N1C]
( );

[(R)-3-(N-iso-Propyl-N-ethylamino)propylthio-Sar]-3-[(γ-allyloxy)-NMeLeu]-4-cyclosporin
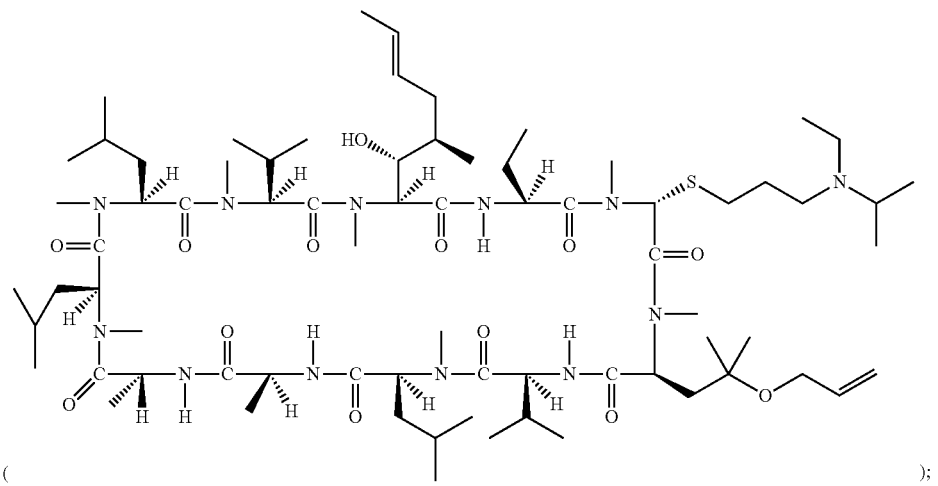 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCN(CC)C(C)C)C(=O)N1C]
( );
[(R)-4-(N-Pyrrolidinyl)butylthio-Sar]-3-[(γ-allyloxy)-NMeLeu]-4-cyclosporin
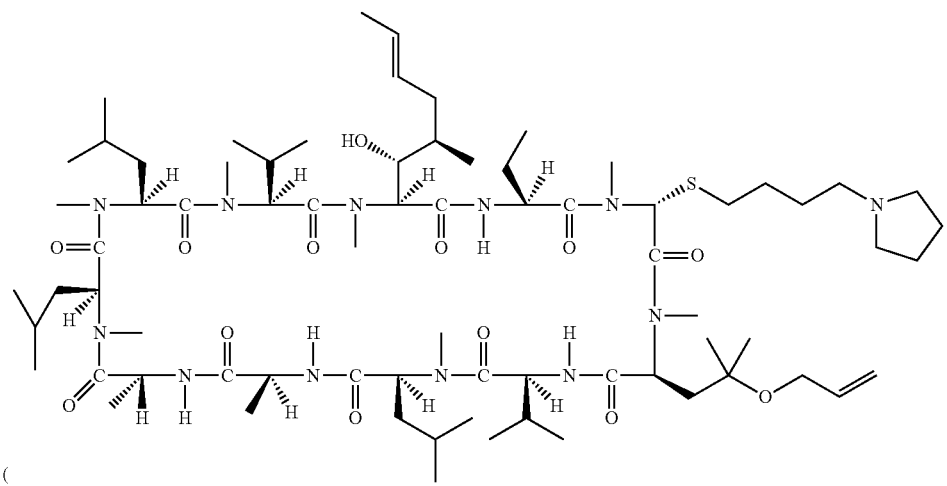
( );
[(R)-4-(N-Piperidinyl)butylthio-Sar]-3-[(γ-allyloxy)-NMeLeu]-4-cyclosporin
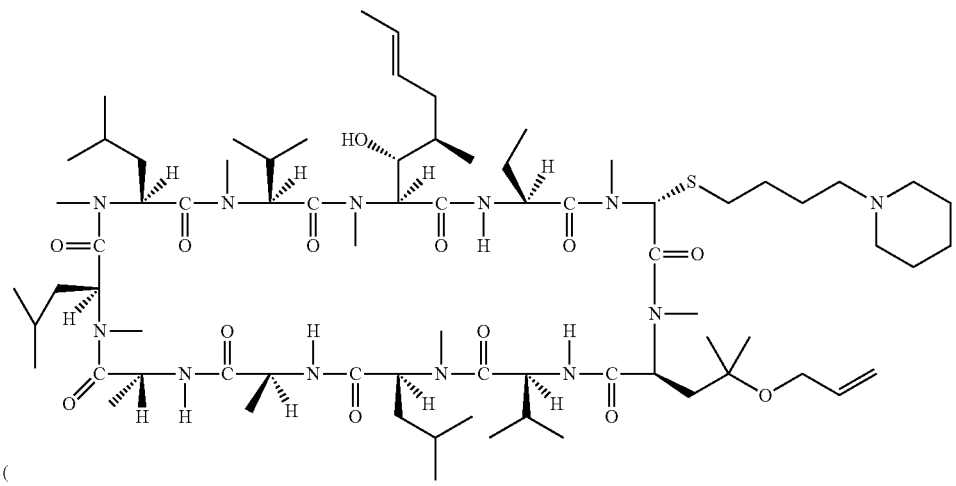
( );

[(R)-4-(N-Morpholino)butylthio-Sar]-3-[(γ-allyloxy)-NMeLeu]-4-cyclosporin
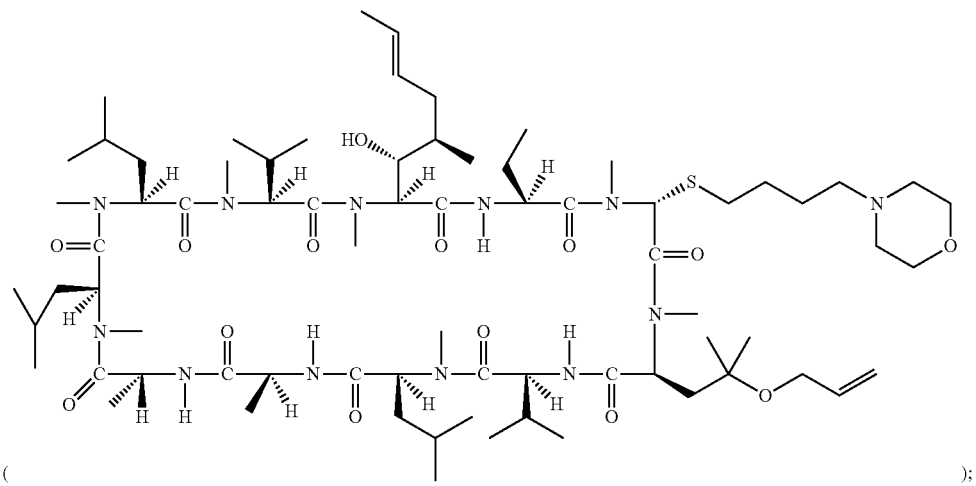 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCCN2CCSCC2)C(=O)N1C]
( );
[(R)-4-(N-Thiomorpholino)butylthio-Sar]-3-[(γ-allyloxy)-NMeLeu]-4-cyclosporin
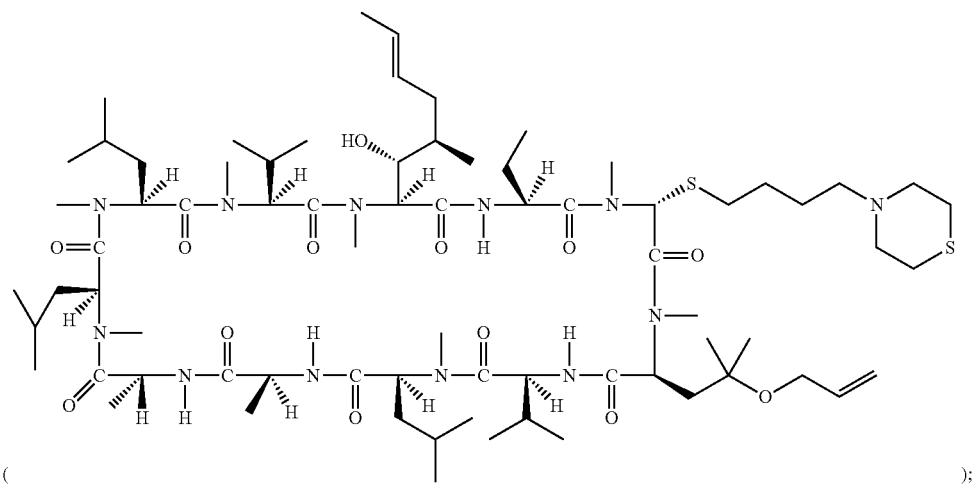
( );
[(R)-4-(N,N-Dimethylamino)butylthio-Sar]-3-[(γ-allyloxy)-NMeLeu]-4-cyclosporin
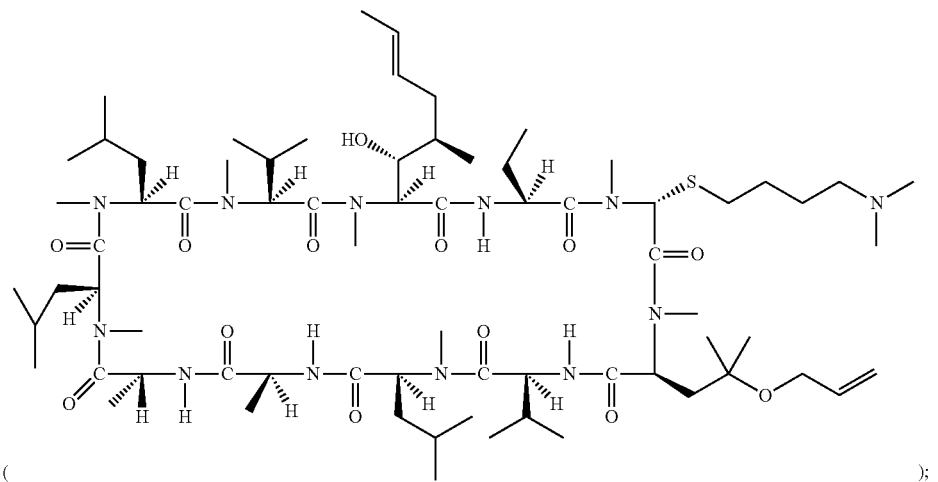 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCCN(C)C)C(=O)N1C]
( );

[(R)-4-(N,N-Diethylamino)butylthio-Sar]-3-[(γ-allyloxy)-NMeLeu]-4-cyclosporin
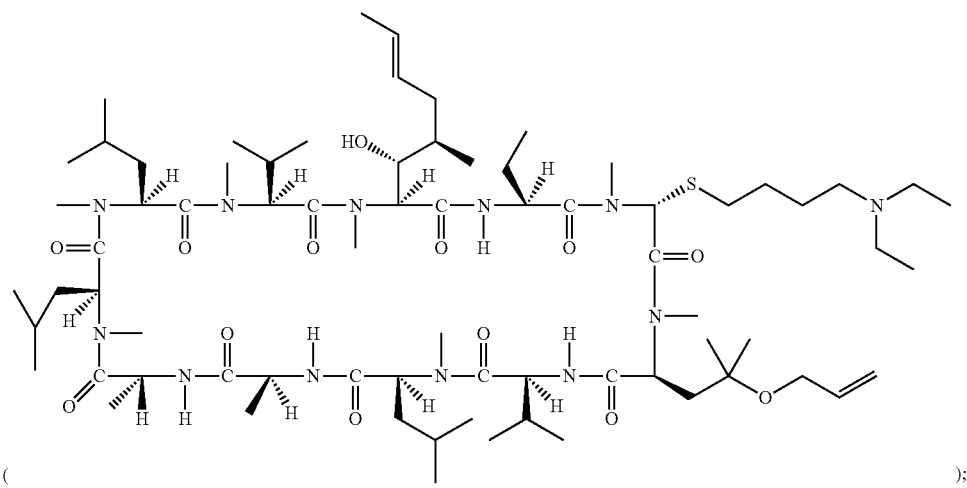 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCCN(CC)CC)C(=O)N1C]
[(R)-4-(N-iso-Propylamino)butylthio-Sar]-3-[(γ-allyloxy)-NMeLeu]-4-cyclosporin
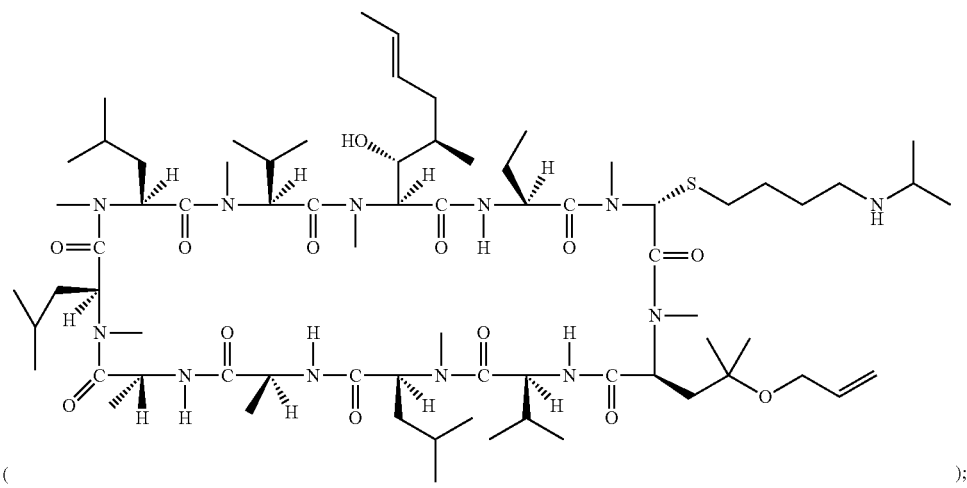 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCCNC(C)C)C(=O)N1C]
[(R)-4-(N-iso-Propyl-N-methylamino)butylthio-Sar]-3-[(γ-allyloxy)-NMeLeu]-4-cyclosporin
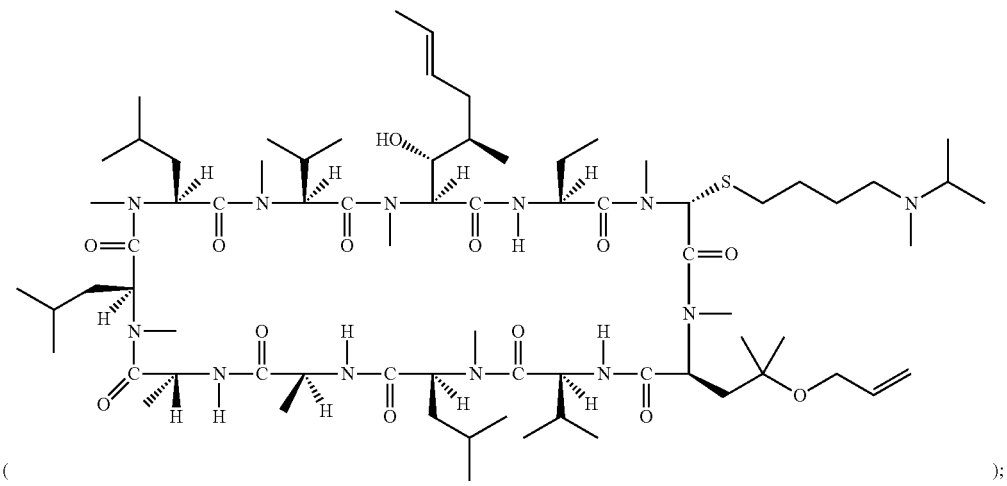 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCCN(C)C(C)C)C(=O)N1C]

[(R)-4-(N-iso-Propyl-N-ethylamino)butylthio-Sar]-3-[(γ-allyloxy)-NMeLeu]-4-cyclosporin
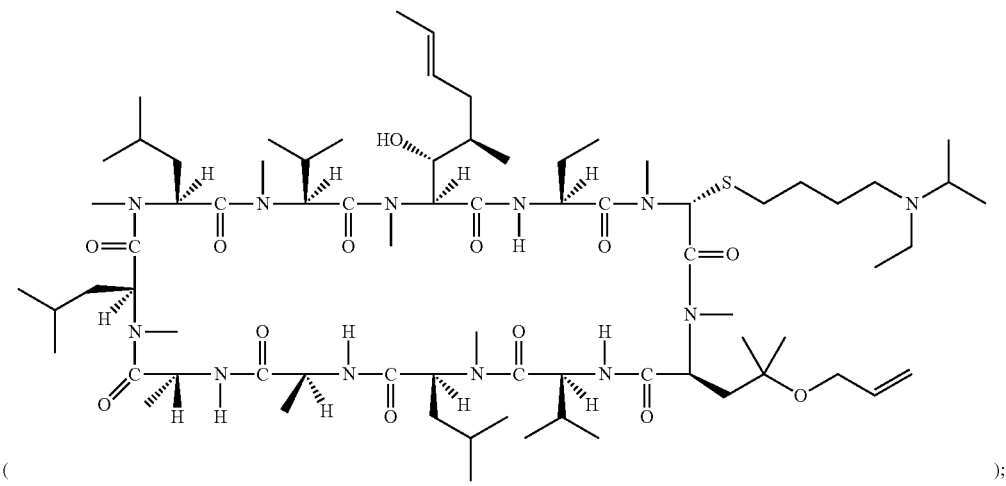 [SMILES: C=CCOC(C)(C)C[C@H]1C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)[C@H](SCCCCN(CC)C(C)C)C(=O)N1C]
( );
[(R)-3-(N,N-Dimethylamino)propylthio-Sar]-3-[(β-iso-propoxy)-NMeSer]-4-cyclosporin
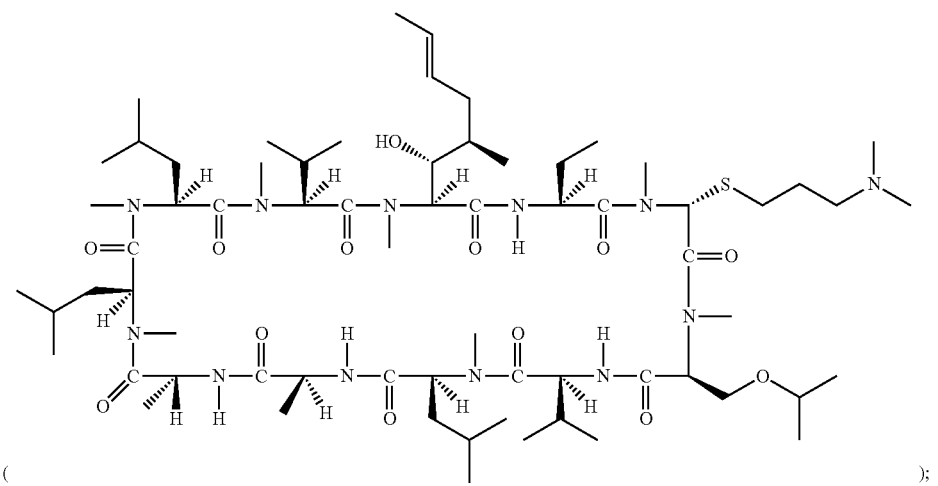 [SMILES: C/C=C/C[C@@H](C)[C@@H](O)[C@H]1C(=O)N[C@@H](CC)C(=O)N(C)[C@H](SCCCN(C)C)C(=O)N(C)[C@@H](COC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N,N-Diethylamino)propylthio-Sar]-3-[(β-iso-propoxy)-NMeSer]-4-cyclosporin
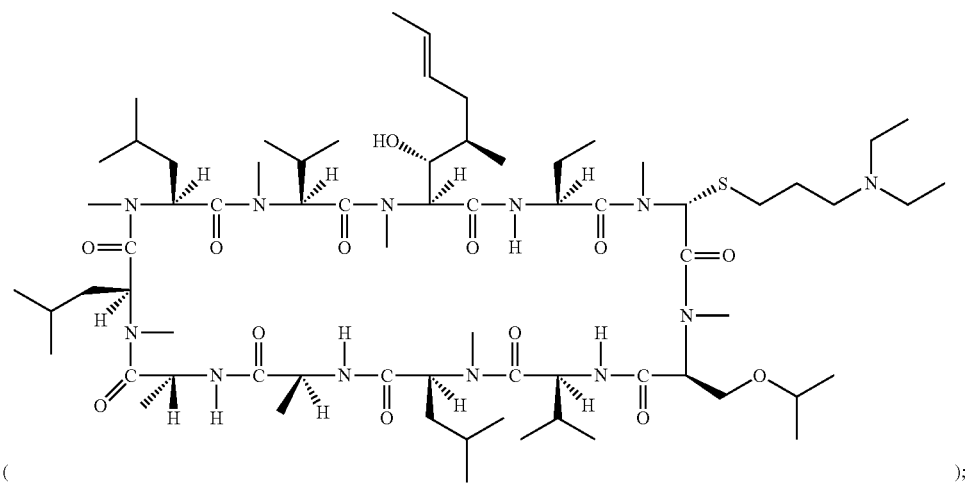 [SMILES: C/C=C/C[C@@H](C)[C@@H](O)[C@H]1C(=O)N[C@@H](CC)C(=O)N(C)[C@H](SCCCN(CC)CC)C(=O)N(C)[C@@H](COC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );

[(R)-3-(N-iso-Propyl-N-ethylamino)propylthio-Sar]-3-
[(β-iso-propoxy)-NMeSer]-4-cyclosporin
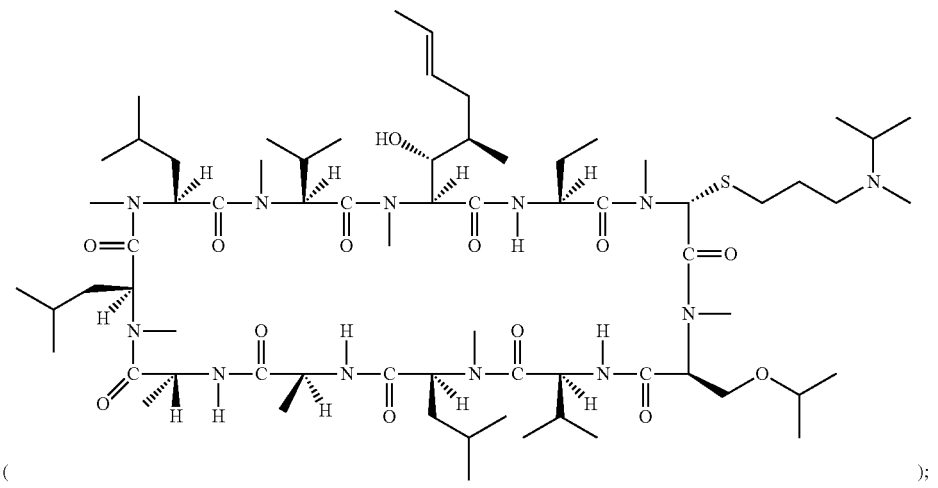 [SMILES: C/C=C/C[C@@H](C)[C@@H](O)[C@H]1C(=O)N[C@@H](CC)C(=O)N(C)[C@H](SCCCN(C)C(C)C)C(=O)N(C)[C@@H](COC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-Pyrrolidinyl)propylthio-Sar]-3-[(β-iso-
propoxy)-NMeSer]-4-cyclosporin
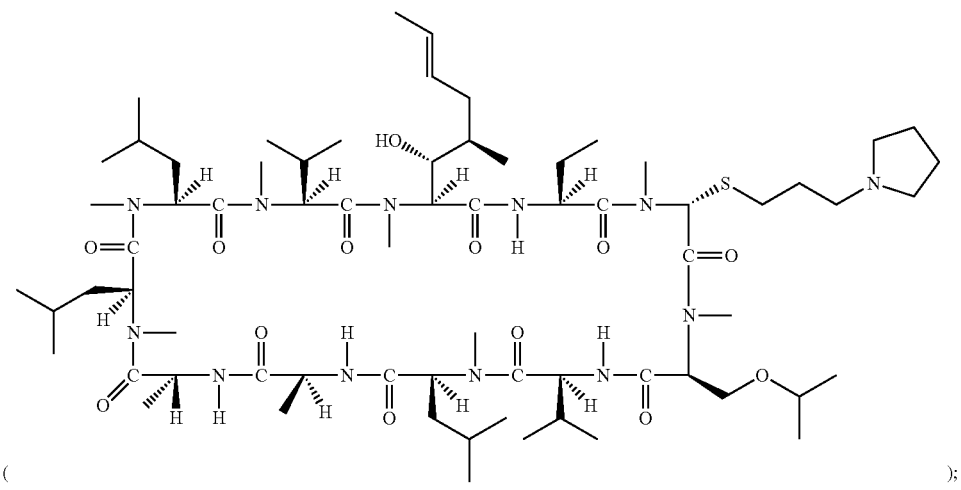
( );
[(R)-3-(N-Piperidinyl)propylthio-Sar]-3-[(β-iso-
propoxy)-NMeSer]-4-cyclosporin
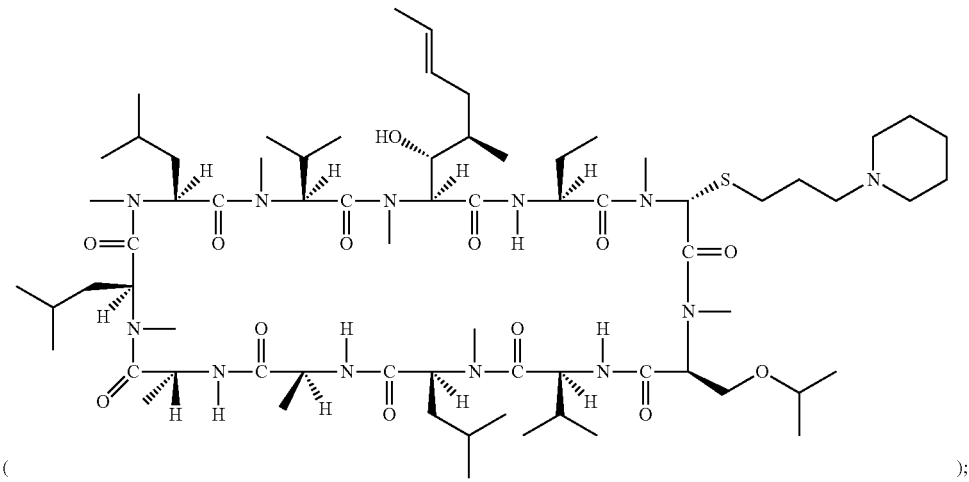 [SMILES: C/C=C/C[C@@H](C)[C@@H](O)[C@H]1C(=O)N[C@@H](CC)C(=O)N(C)[C@H](SCCCN2CCCCC2)C(=O)N(C)[C@@H](COC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );

[(R)-3-(N-Morpholino)propylthio-Sar]-3-[(β-iso-propoxy)-NMeSer]-4-cyclosporin
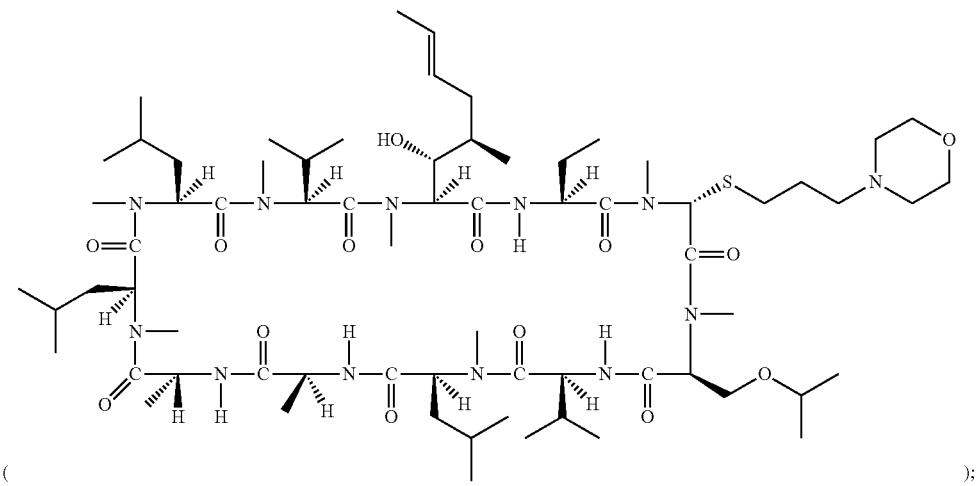 [SMILES: C/C=C/C[C@@H](C)[C@@H](O)[C@H]1C(=O)N[C@@H](CC)C(=O)N(C)[C@H](SCCCN2CCOCC2)C(=O)N(C)[C@@H](COC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N,N-Dimethylamino)propylthio-Sar]-3-[(β-pentan-3-yloxy)-NMeSer]-4-cyclosporin
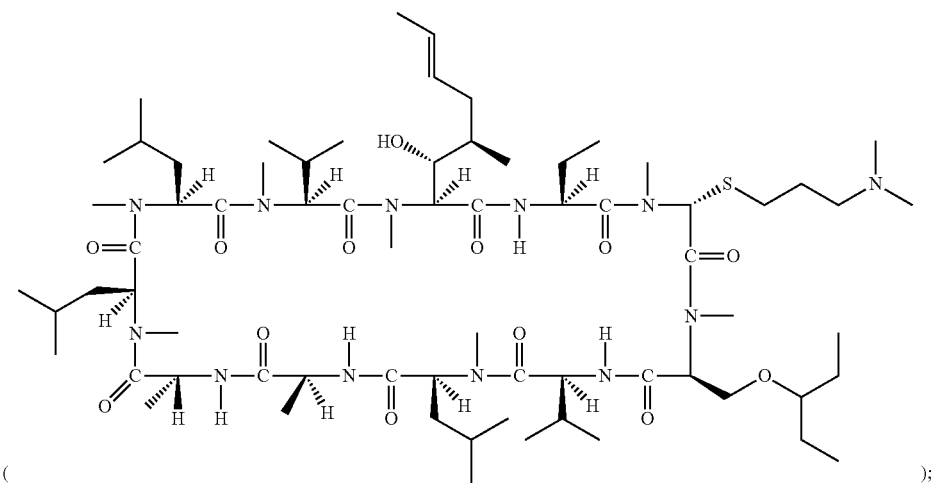 [SMILES: C/C=C/C[C@@H](C)[C@@H](O)[C@H]1C(=O)N[C@@H](CC)C(=O)N(C)[C@H](SCCCN(C)C)C(=O)N(C)[C@@H](COC(CC)CC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N,N-Diethylamino)propylthio-Sar]-3-[(β-pentan-3-yloxy)-NMeSer]-4-cyclosporin
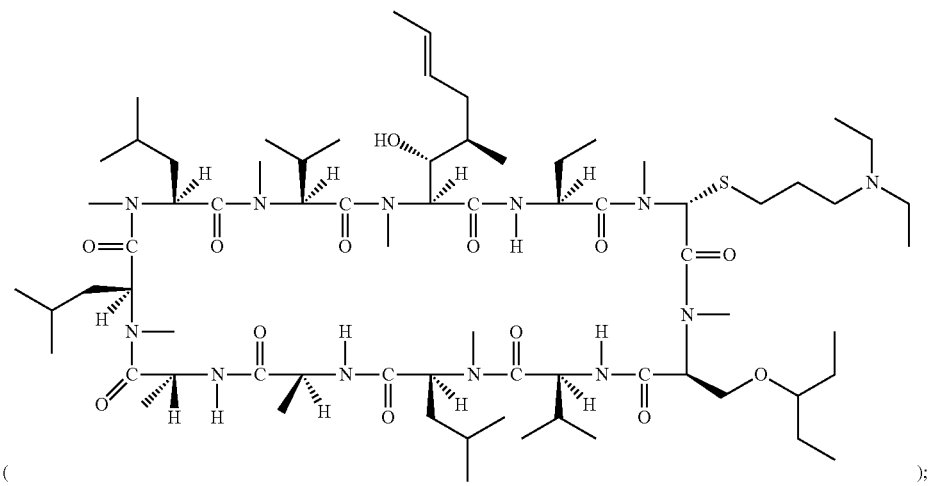 [SMILES: C/C=C/C[C@@H](C)[C@@H](O)[C@H]1C(=O)N[C@@H](CC)C(=O)N(C)[C@H](SCCCN(CC)CC)C(=O)N(C)[C@@H](COC(CC)CC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

[(R)-3-(N-iso-Propyl-N-ethylamino)propylthio-Sar]-3-
[(β-pentan-3-yloxy)-NMeSer]-4-cyclosporin
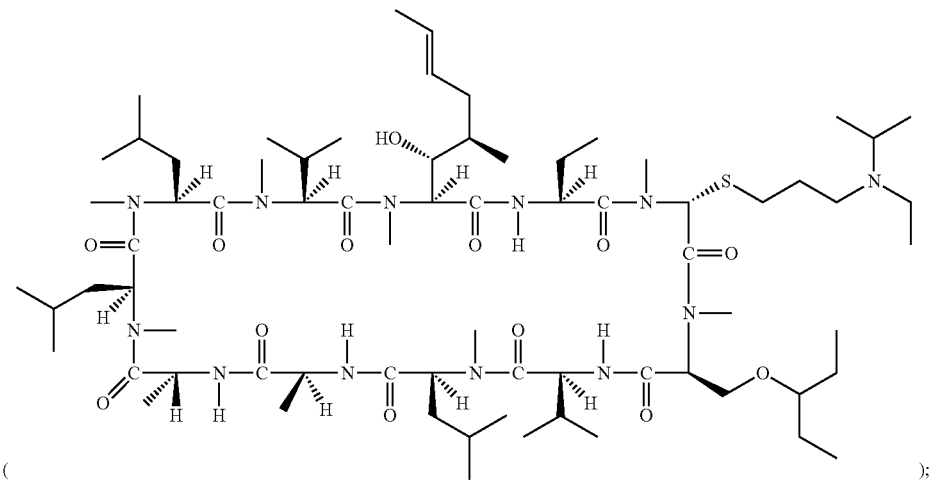 [SMILES: C/C=C/C[C@@H](C)[C@@H](O)[C@H]1C(=O)N[C@@H](CC)C(=O)N(C)[C@H](SCCCN(CC)C(C)C)C(=O)N(C)[C@@H](COC(CC)CC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-Pyrrolidinyl)propylthio-Sar]-3-[(β-pentan-3-
yloxy)-NMeSer]-4-cyclosporin
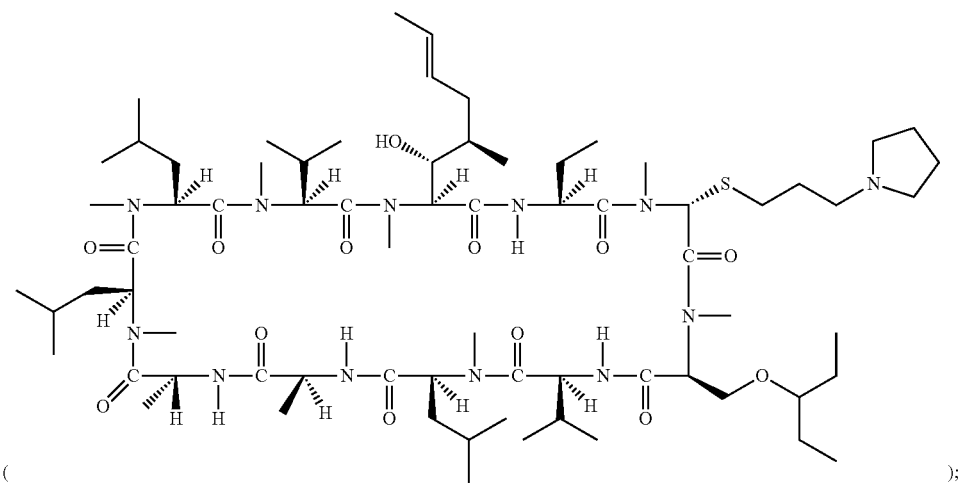 [SMILES: C/C=C/C[C@@H](C)[C@@H](O)[C@H]1C(=O)N[C@@H](CC)C(=O)N(C)[C@H](SCCCN2CCCC2)C(=O)N(C)[C@@H](COC(CC)CC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-Piperidinyl)propylthio-Sar]-3-[(β-pentan-3-
yloxy)-NMeSer]-4-cyclosporin
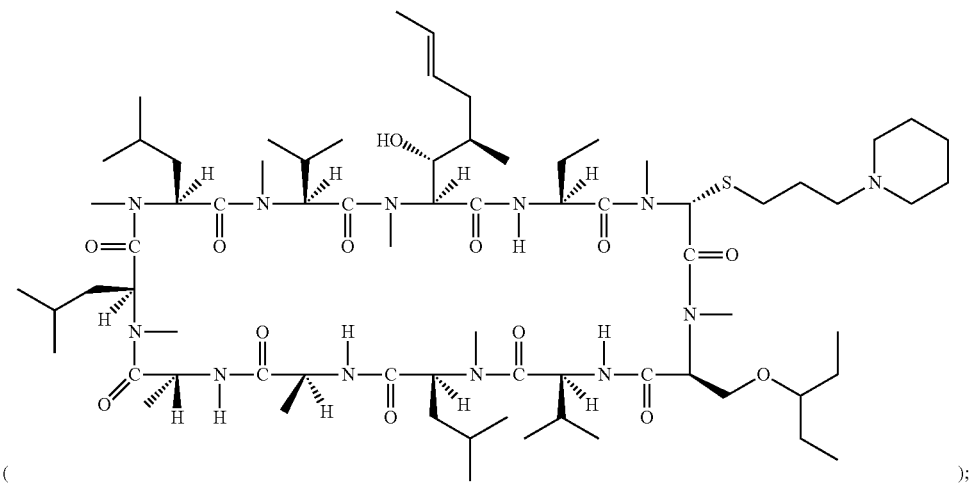
( );

[(R)-3-(N-Morpholino)propylthio-Sar]-3-[(β-pentan-3-yloxy)-NMeSer]-4-cyclosporin
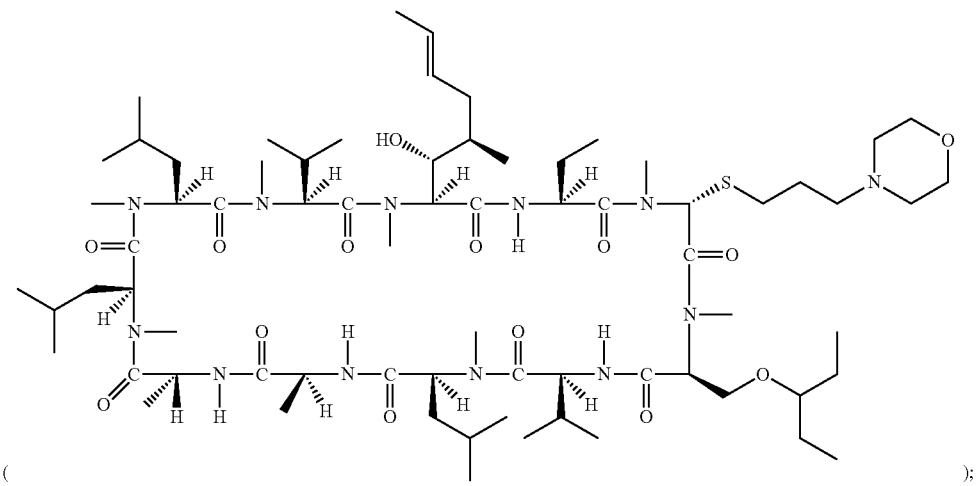 [SMILES: C/C=C/C[C@@H](C)[C@@H](O)[C@H]1C(=O)N[C@@H](CC)C(=O)N(C)[C@H](SCCCN2CCOCC2)C(=O)N(C)[C@@H](COC(CC)CC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N,N-Dimethylamino)propylthio-Sar]-3-[(β-iso-butoxy)-NMeSer]-4-cyclosporin
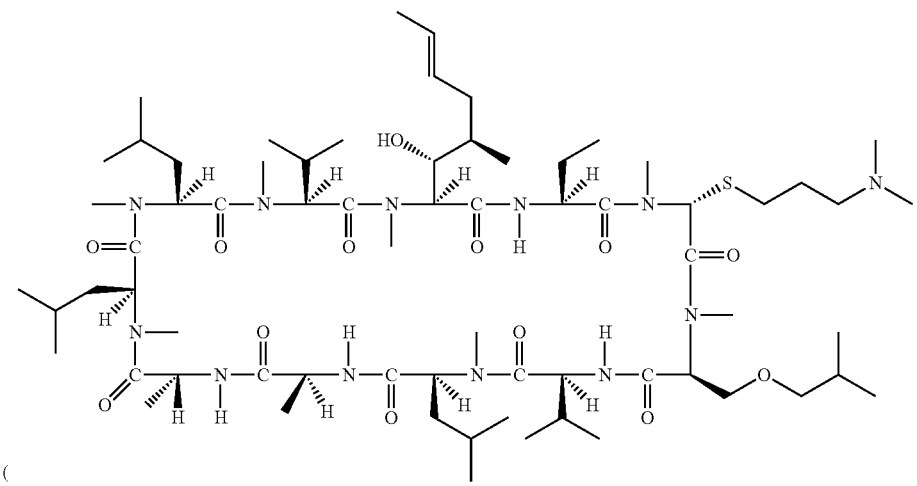
[(R)-3-(N,N-Diethylamino)propylthio-Sar]-3-[(β-iso-butoxy)-NMeSer]-4-cyclosporin
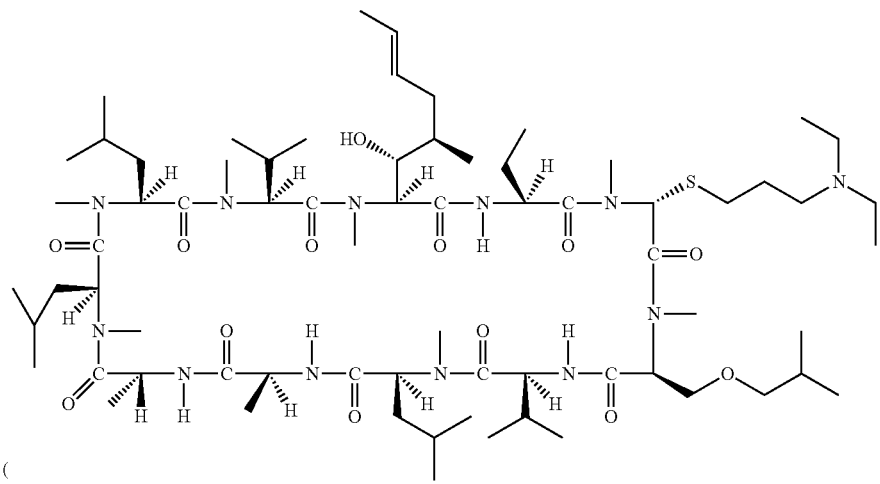

[(R)-3-(N-iso-Propyl-N-ethylamino)propylthio-Sar]-3-[(β-iso-butoxy)-NMeSer]-4-cyclosporin
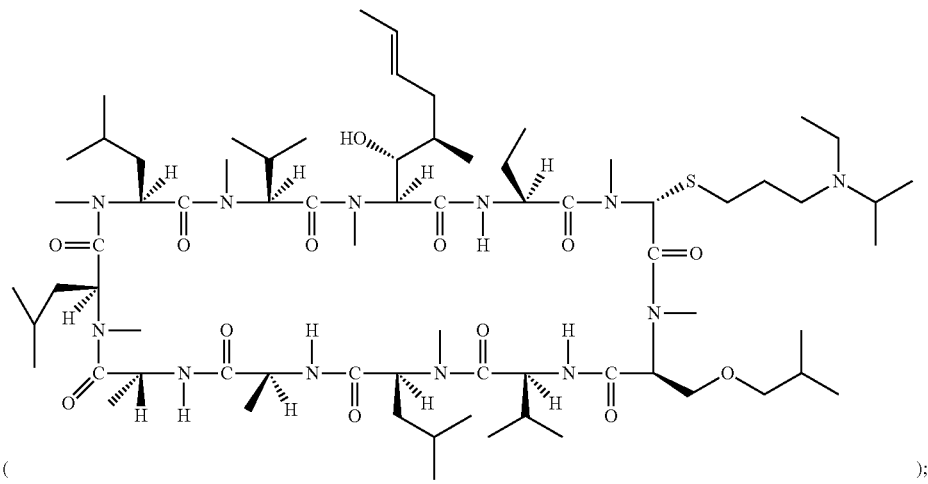 [SMILES: C/C=C/C[C@@H](C)[C@@H](O)[C@H]1C(=O)N[C@@H](CC)C(=O)N(C)[C@H](SCCCN(CC)C(C)C)C(=O)N(C)[C@@H](COCC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N-Pyrrolidinyl)propylthio-Sar]-3-[(β-iso-butoxy)-NMeSer]-4-cyclosporin
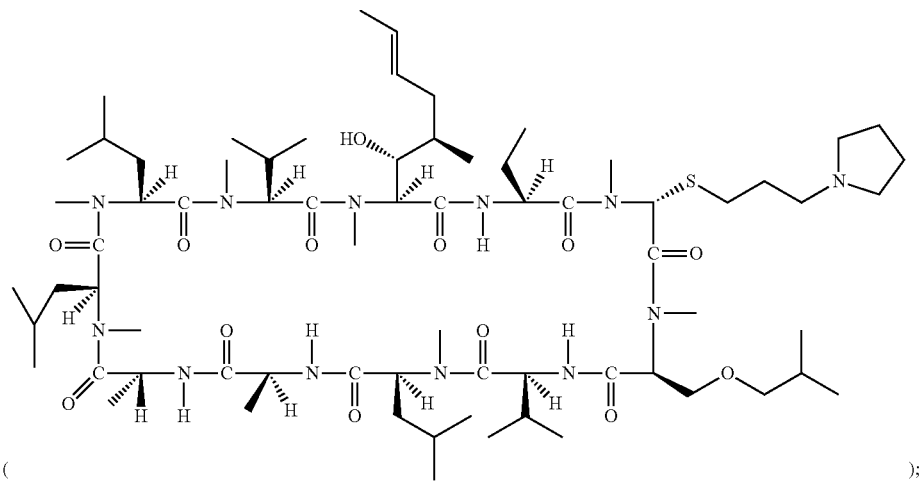 [SMILES: C/C=C/C[C@@H](C)[C@@H](O)[C@H]1C(=O)N[C@@H](CC)C(=O)N(C)[C@H](SCCCN2CCCC2)C(=O)N(C)[C@@H](COCC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N-Piperidinyl)propylthio-Sar]-3-[(β-iso-butoxy)-NMeSer]-4-cyclosporin
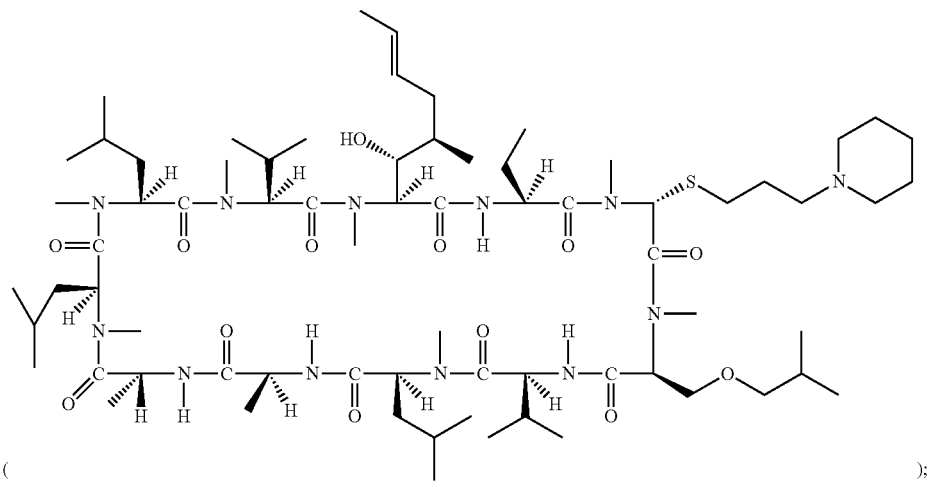 [SMILES: C/C=C/C[C@@H](C)[C@@H](O)[C@H]1C(=O)N[C@@H](CC)C(=O)N(C)[C@H](SCCCN2CCCCC2)C(=O)N(C)[C@@H](COCC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

[(R)-3-(N-Morpholino)propylthio-Sar]-3-[(β-iso-butoxy)-NMeSer]-4-cyclosporin
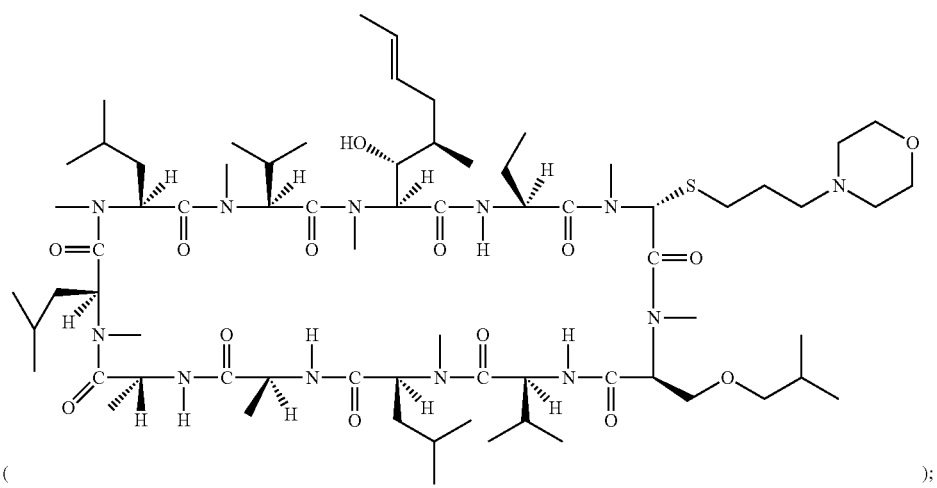 [SMILES: C/C=C/C[C@@H](C)[C@@H](O)[C@H]1C(=O)N[C@@H](CC)C(=O)N(C)[C@H](SCCCN2CCOCC2)C(=O)N(C)[C@@H](COCC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N,N-Dimethylamino)propylthio-Sar]-3-[(β-2-ethylbutoxy)-NMeSer]-4-cyclosporin
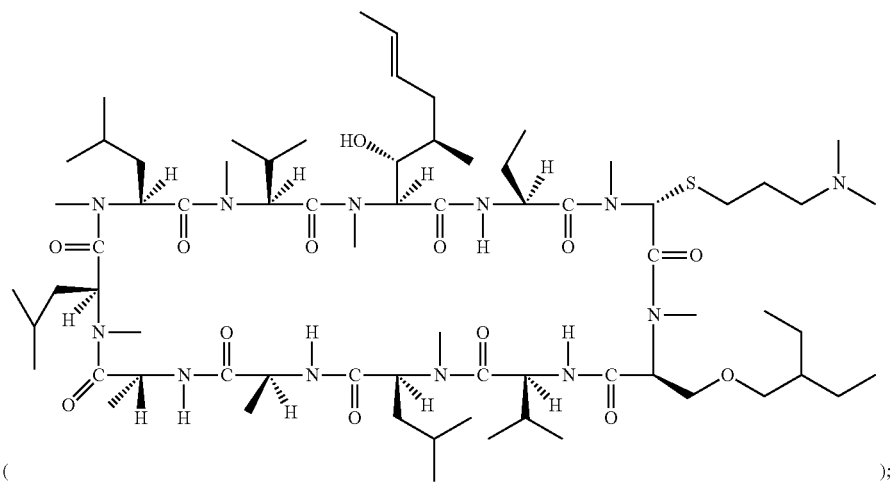
[(R)-3-(N,N-Diethylamino)propylthio-Sar]-3-[(β-2-ethylbutoxy)-NMeSer]-4-cyclosporin
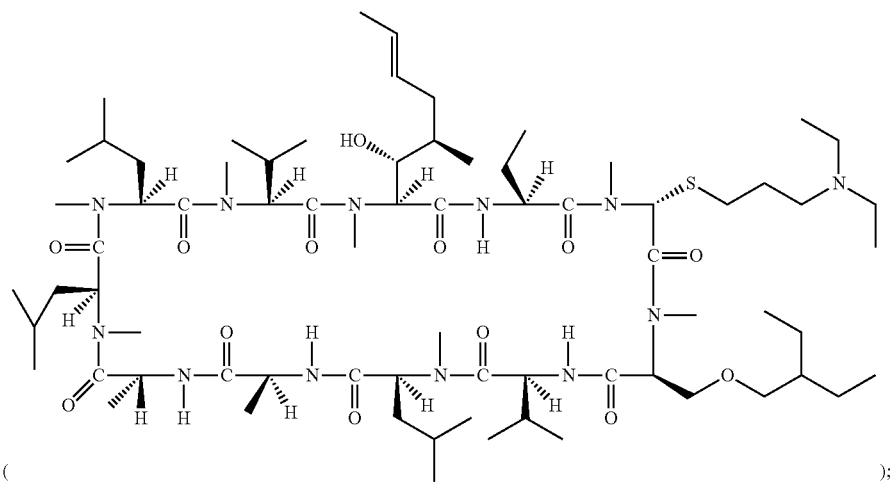 [SMILES: C/C=C/C[C@@H](C)[C@@H](O)[C@H]1C(=O)N[C@@H](CC)C(=O)N(C)[C@H](SCCCN(CC)CC)C(=O)N(C)[C@@H](COCC(CC)CC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

[(R)-3-(N-iso-Propyl-N-ethylamino)propylthio-Sar]-3-[(β-2-ethylbutoxy)-NMeSer]-4-cyclosporin
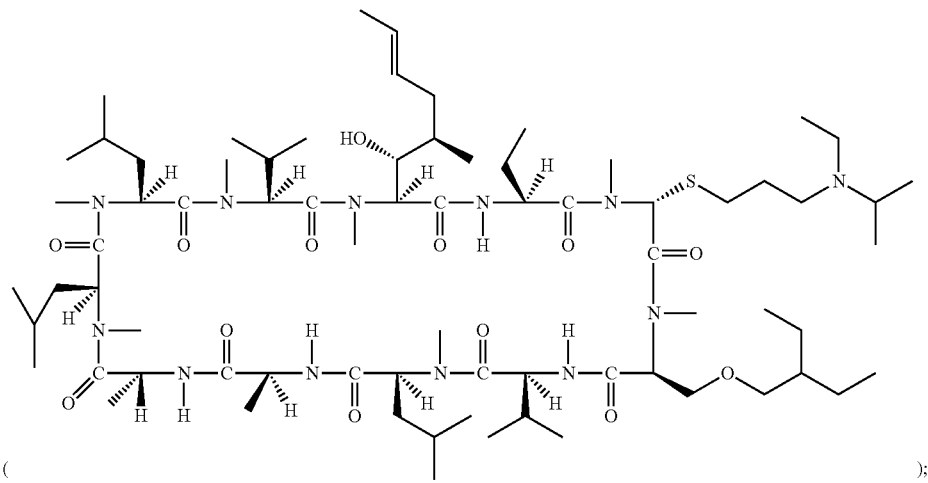 [SMILES: C/C=C/C[C@@H](C)[C@@H](O)[C@H]1C(=O)N[C@@H](CC)C(=O)N(C)[C@H](SCCCN(CC)C(C)C)C(=O)N(C)[C@@H](COCC(CC)CC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-Pyrrolidinyl)propylthio-Sar]-3-[(β-2-ethylbutoxy)-NMeSer]-4-cyclosporin
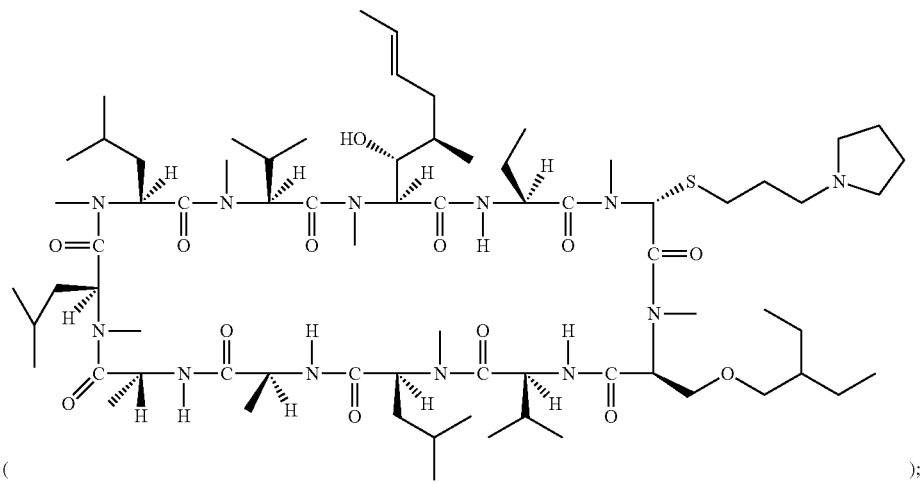 [SMILES: C/C=C/C[C@@H](C)[C@@H](O)[C@H]1C(=O)N[C@@H](CC)C(=O)N(C)[C@H](SCCCN2CCCC2)C(=O)N(C)[C@@H](COCC(CC)CC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-Piperidinyl)propylthio-Sar]-3-[(β-2-ethylbutoxy)-NMeSer]-4-cyclosporin
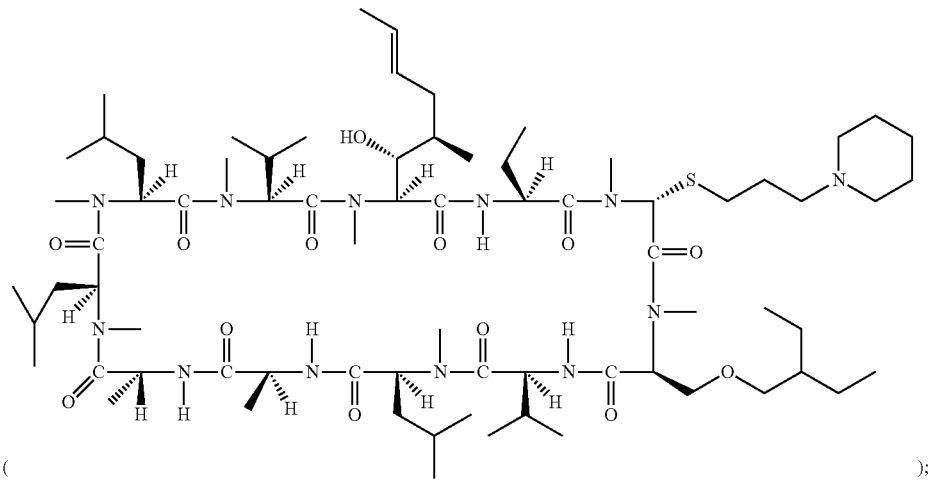 [SMILES: C/C=C/C[C@@H](C)[C@@H](O)[C@H]1C(=O)N[C@@H](CC)C(=O)N(C)[C@H](SCCCN2CCCCC2)C(=O)N(C)[C@@H](COCC(CC)CC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );

[(R)-3-(N-Morpholino)propylthio-Sar]-3-[(β-2-ethylbu-
toxy)-NMeSer]-4-cyclosporin
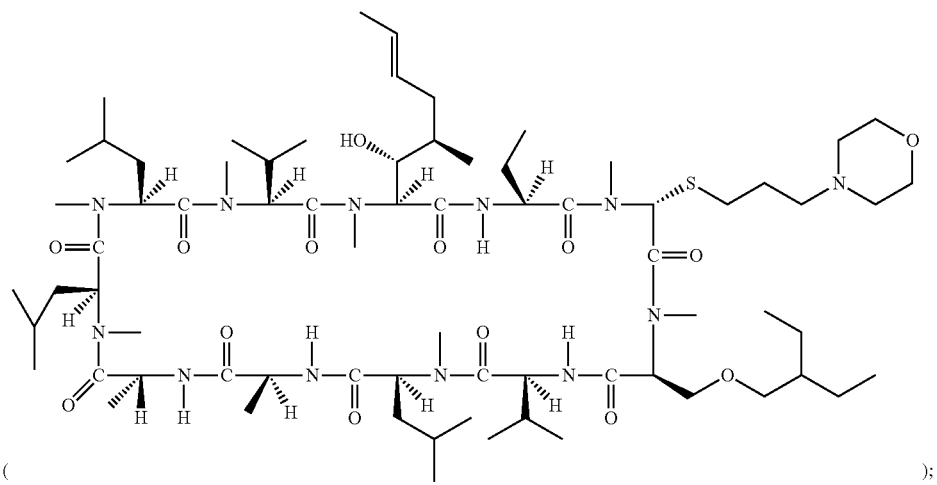 [SMILES: C/C=C/C[C@@H](C)[C@@H](O)[C@H]1C(=O)N[C@@H](CC)C(=O)N(C)[C@H](SCCCN2CCOCC2)C(=O)N(C)[C@@H](COCC(CC)CC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N,N-Diethylamino)propylthio-Sar]-3-[β-(2-
methoxyethoxy)-NMeSer]-4-cyclosporin
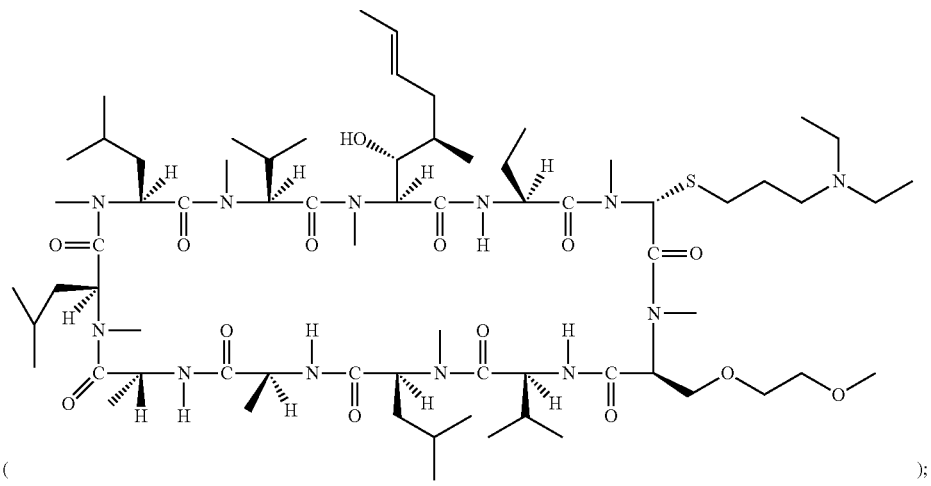 [SMILES: C/C=C/C[C@@H](C)[C@@H](O)[C@H]1C(=O)N[C@@H](CC)C(=O)N(C)[C@H](SCCCN(CC)CC)C(=O)N(C)[C@@H](COCCOC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N-Morpholino)propylthio-Sar]-3-[β-(2-methoxy-
ethoxy)-NMeSer]-4-cyclosporin
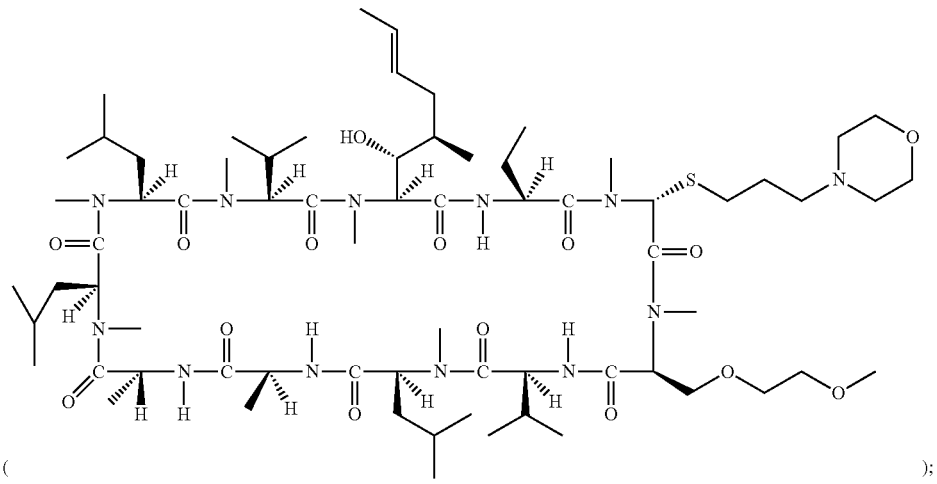 [SMILES: C/C=C/C[C@@H](C)[C@@H](O)[C@H]1C(=O)N[C@@H](CC)C(=O)N(C)[C@H](SCCCN2CCOCC2)C(=O)N(C)[C@@H](COCCOC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

[(R)-3-(N,N-Diethylamino)propylthio-Sar]-3-[β-[2-(2-methoxyethoxy)ethoxy]-NMeSer]-4-cyclosporin
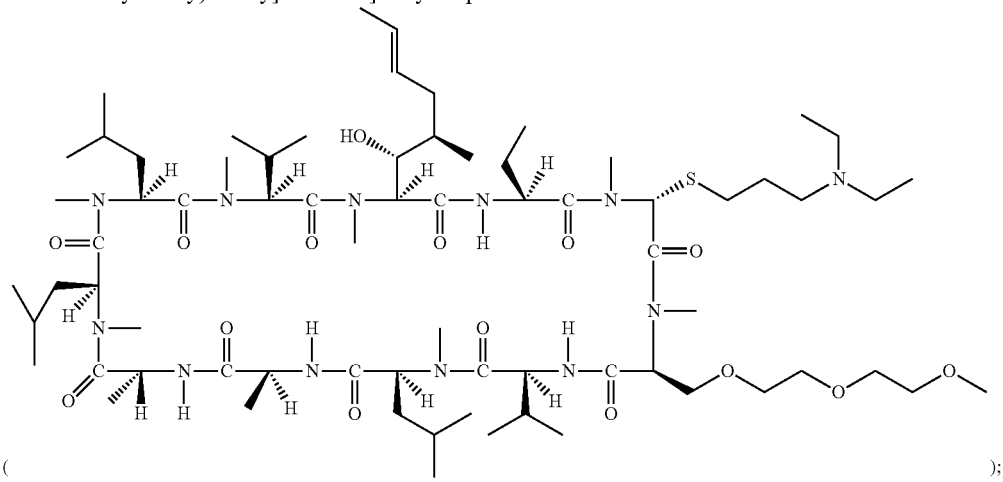
and
[(R)-3-(N-Morpholino)propylthio-Sar]-3-[β-[2-(2-methoxyethoxy)ethoxy]-NMeSer]-4-cyclosporin
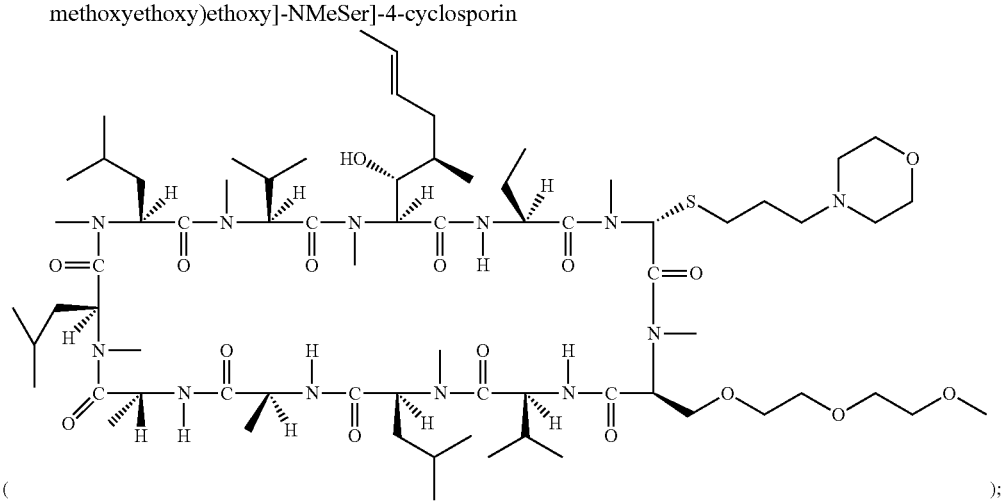
or a pharmaceutically acceptable salt thereof.
30. A compound of claim 1 selected from the group consisting of:
[(R)-3-(N,N-Diethylamino)propylthio-Sar]-3-[(γ-hydroxy)-NMeLeu]-4-cyclosporin
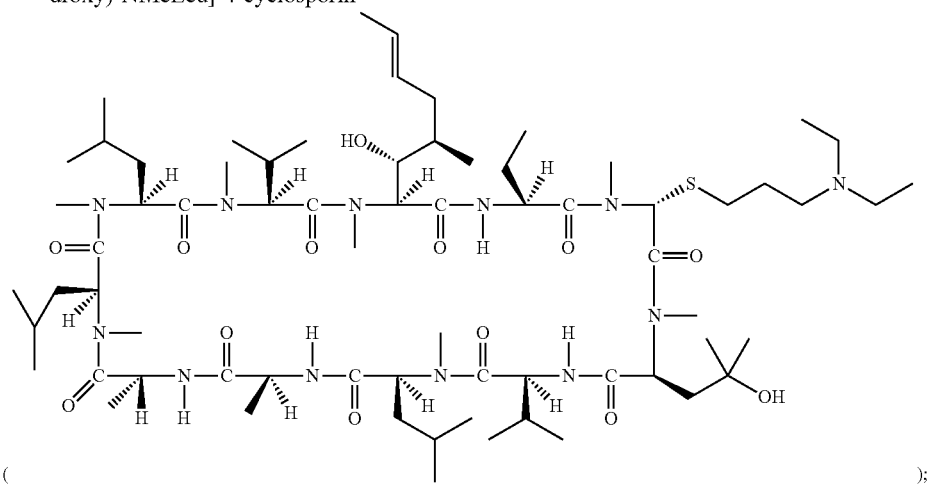

[(R)-3-(N-iso-Propyl-N-ethylamino)propylthio-Sar]-3-[(γ-hydroxy)-NMeLeu]-4-cyclosporin
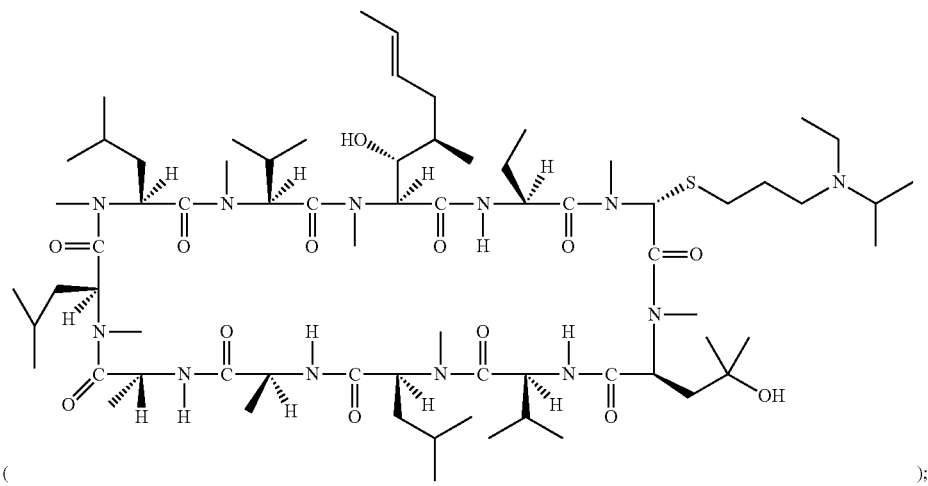 [SMILES: C/C=C/C[C@@H](C)[C@@H](O)[C@H]1C(=O)N[C@@H](CC)C(=O)N(C)[C@H](SCCCN(CC)C(C)C)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
);
[(R)-3-(N-Pyrrolidinyl)propylthio-Sar]-3-[(γ-hydroxy)-NMeLeu]-4-cyclosporin
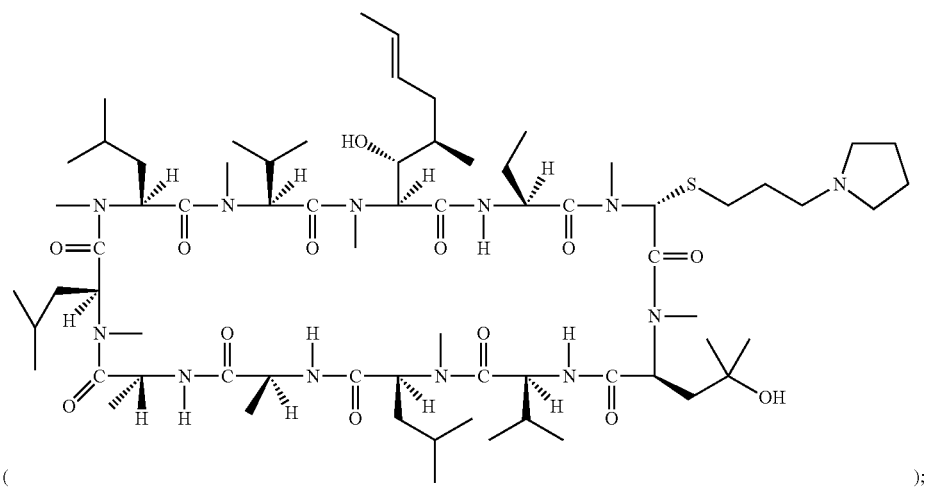 [SMILES: C/C=C/C[C@@H](C)[C@@H](O)[C@H]1C(=O)N[C@@H](CC)C(=O)N(C)[C@H](SCCCN2CCCC2)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
);
[(R)-3-(N-Piperidinyl)propylthio-Sar]-3-[(γ-hydroxy)-NMeLeu]-4-cyclosporin
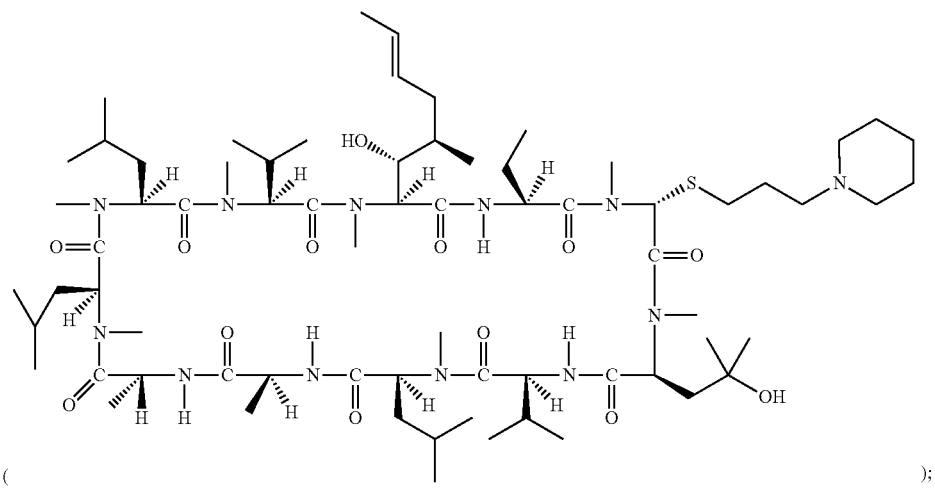
);

[(R)-3-(N-Morphlino)propylthio-Sar]-3-[(γ-hydroxy)-
NMeLeu]-4-cyclosporin
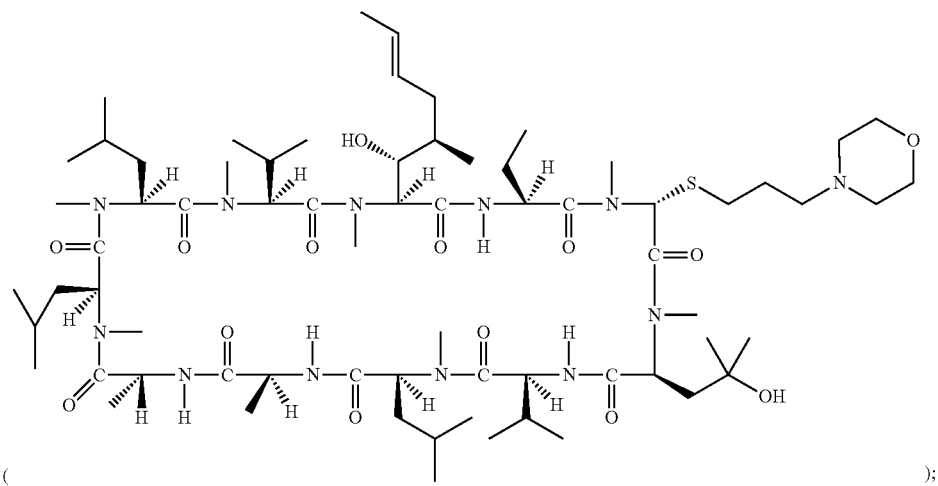 [SMILES: C/C=C/C[C@@H](C)[C@@H](O)[C@H]1C(=O)N[C@@H](CC)C(=O)N(C)[C@H](SCCCN2CCOCC2)C(=O)N(C)[C@@H](CC(C)(C)O)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N,N-Dimethylamino)propylthio-Sar]-3-[(γ-
methoxy)-NMeLeu]-4-cyclosporin
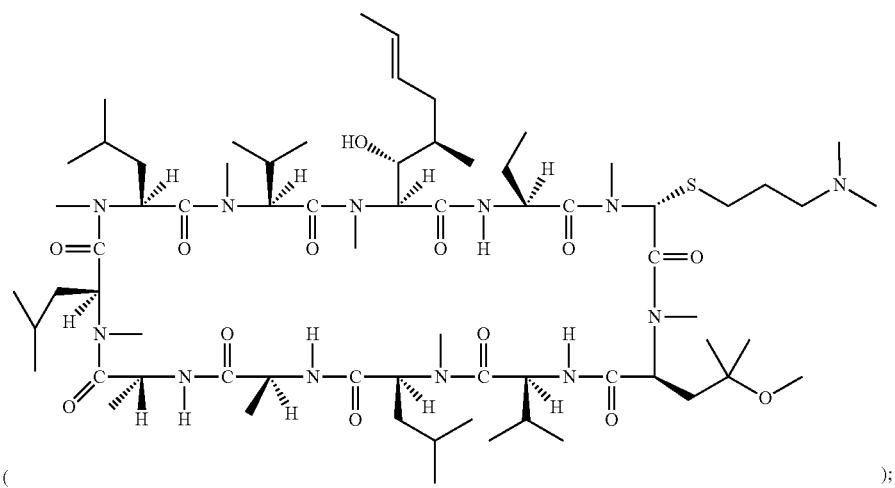 [SMILES: C/C=C/C[C@@H](C)[C@@H](O)[C@H]1C(=O)N[C@@H](CC)C(=O)N(C)[C@H](SCCCN(C)C)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N,N-Diethylamino)propylthio-Sar]-3-[(γ-
methoxy)-NMeLeu]-4-cyclosporin
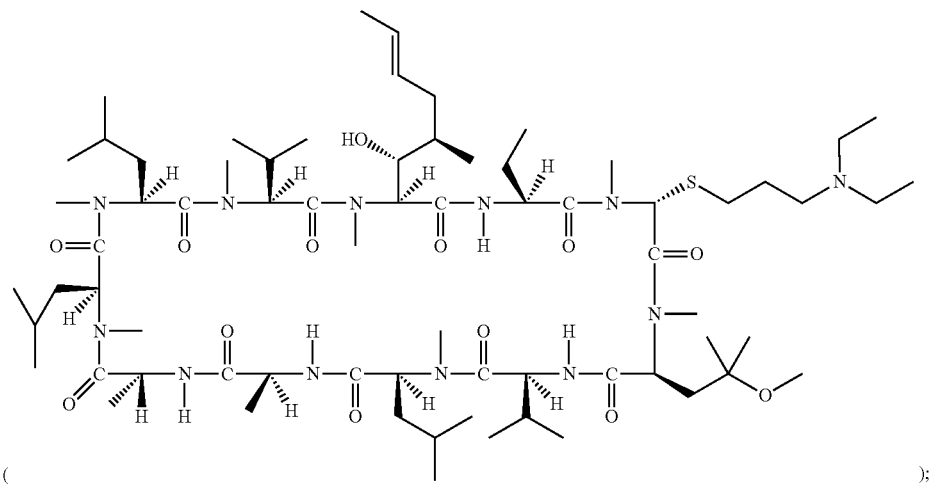 [SMILES: C/C=C/C[C@@H](C)[C@@H](O)[C@H]1C(=O)N[C@@H](CC)C(=O)N(C)[C@H](SCCCN(CC)CC)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );

[(R)-3-(N-iso-Propylamino)propylthio-Sar]-3-[(γ-methoxy)-NMeLeu]-4-cyclosporin
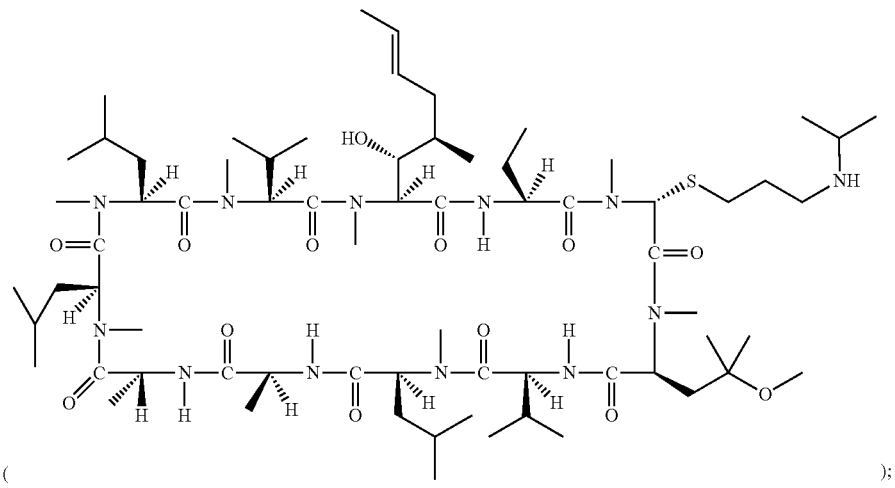 [SMILES: C/C=C/C[C@@H](C)[C@@H](O)[C@H]1C(=O)N[C@@H](CC)C(=O)N(C)[C@H](SCCCNC(C)C)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N-iso-Propyl-N-methylamino)propylthio-Sar]-3-[(γ-methoxy)-NMeLeu]-4-cyclosporin
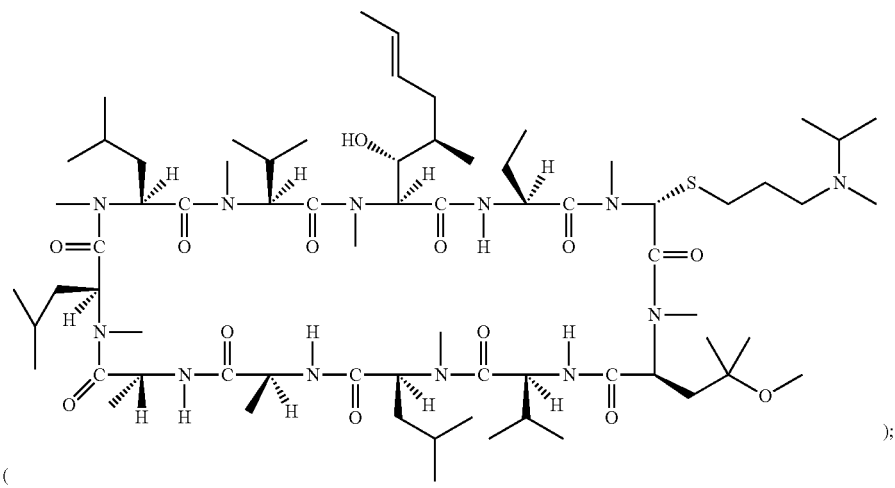 [SMILES: C/C=C/C[C@@H](C)[C@@H](O)[C@H]1C(=O)N[C@@H](CC)C(=O)N(C)[C@H](SCCCN(C)C(C)C)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
[(R)-3-(N-iso-Propyl-N-ethylamino)propylthio-Sar]-3-[(γ-methoxy)-NMeLeu]-4-cyclosporin
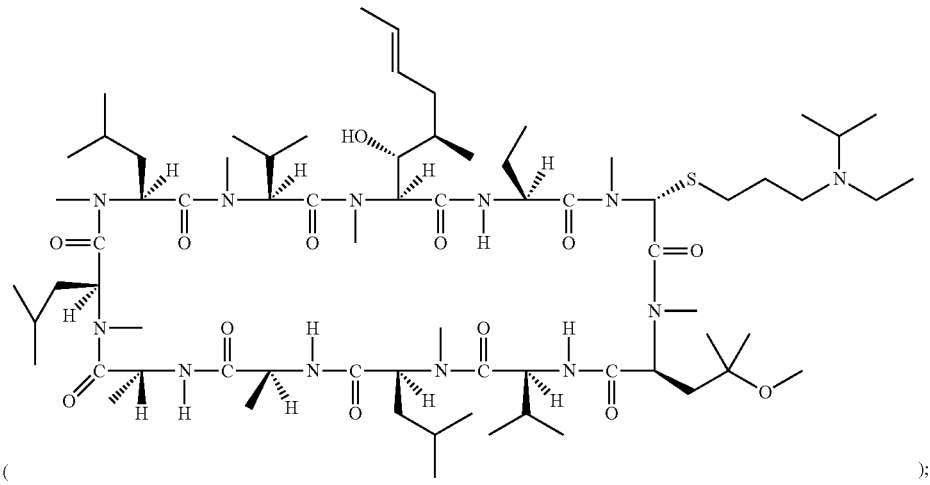 [SMILES: C/C=C/C[C@@H](C)[C@@H](O)[C@H]1C(=O)N[C@@H](CC)C(=O)N(C)[C@H](SCCCN(CC)C(C)C)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

[(R)-3-(N-Pyrrolidinyl)propylthio-Sar]-3-[(γ-methoxy)-NMeLeu]-4-cyclosporin
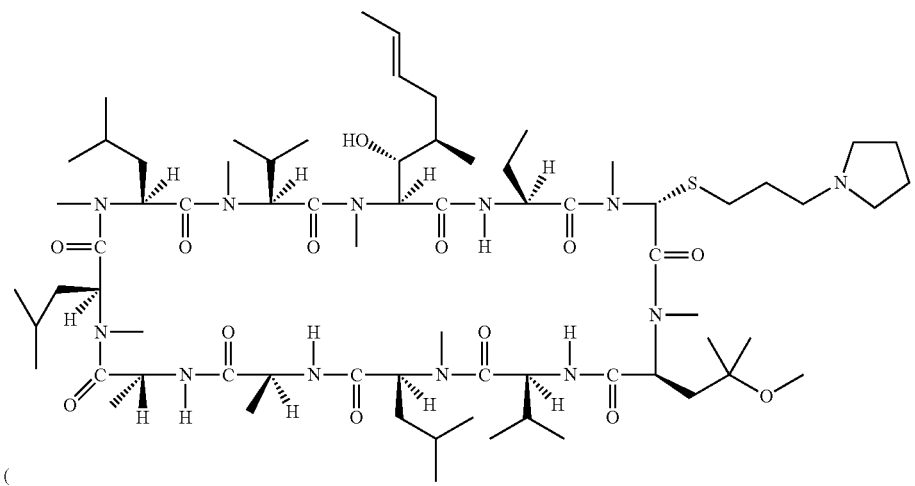
( );
[(R)-3-(N-Piperidinyl)propylthio-Sar]-3-[(γ-methoxy)-NMeLeu]-4-cyclosporin
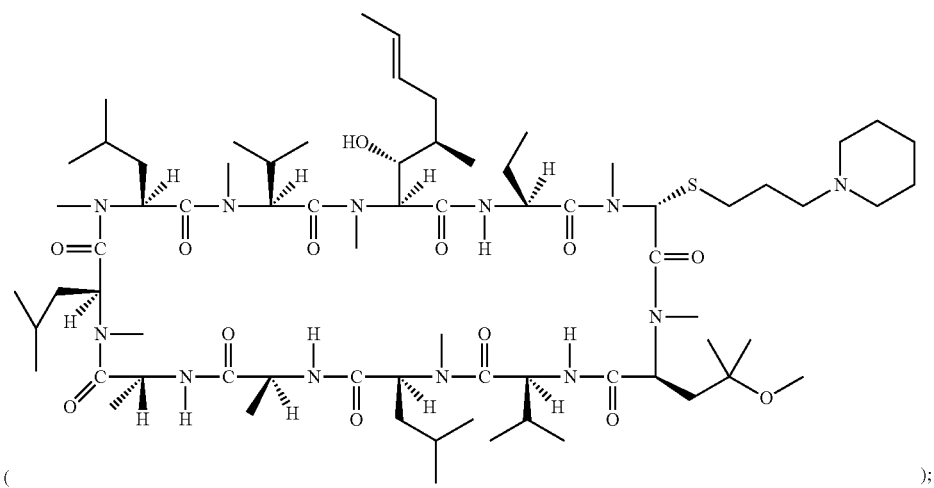 [SMILES: C/C=C/C[C@@H](C)[C@@H](O)[C@H]1C(=O)N[C@@H](CC)C(=O)N(C)[C@H](SCCCN2CCCCC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
( );
[(R)-3-(N-Morphlino)propylthio-Sar]-3-[(γ-methoxy)-NMeLeu]-4-cyclosporin
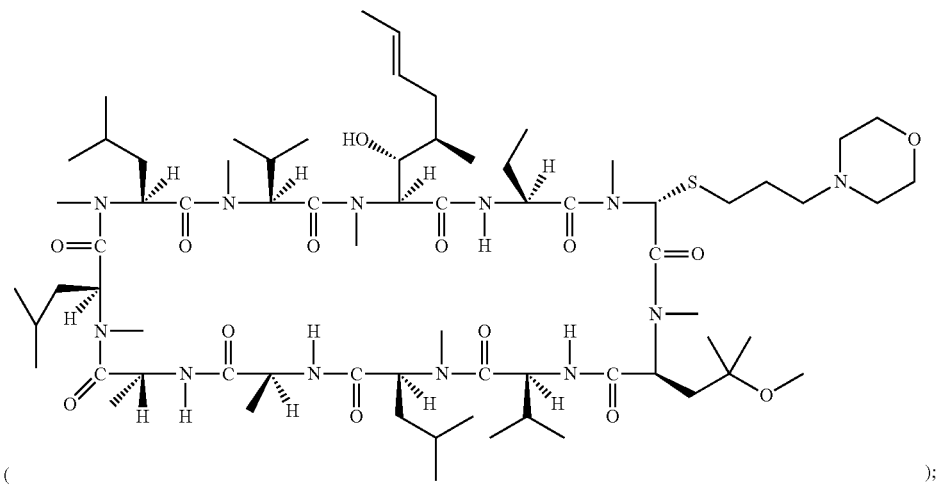
( );

[(R)-3-(N-Thiomorpholino)propylthio-Sar]-3-[(γ-methoxy)-NMeLeu]-4-cyclosporin

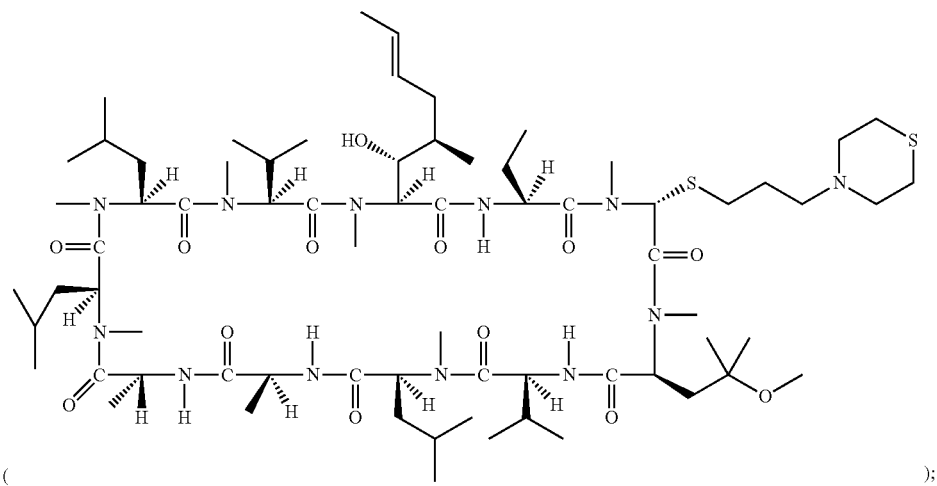 [SMILES: C/C=C/C[C@@H](C)[C@@H](O)[C@H]1C(=O)N[C@@H](CC)C(=O)N(C)[C@H](SCCCN2CCSCC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

and

[(R)-3-(N-4-Methylpiperazinyl)propylthio-Sar]-3-[(γ-methoxy)-NMeLeu]-4-cyclosporin

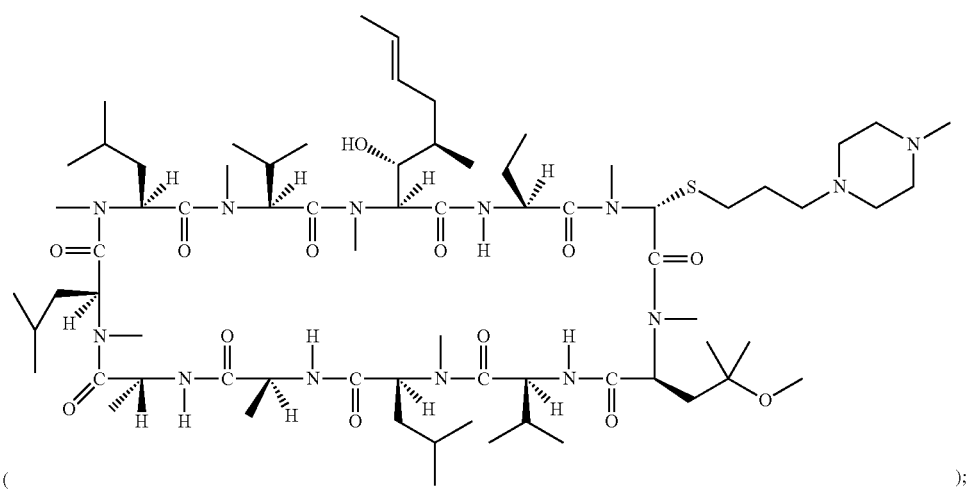 [SMILES: C/C=C/C[C@@H](C)[C@@H](O)[C@H]1C(=O)N[C@@H](CC)C(=O)N(C)[C@H](SCCCN2CCN(C)CC2)C(=O)N(C)[C@@H](CC(C)(C)OC)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

or a pharmaceutically acceptable salts thereof.

31. A pharmaceutical composition comprising at least one compound according to claim 1 and a pharmaceutically-acceptable carrier or diluent.

32. A method for treating a viral infection in a mammalian species in need thereof, the method comprising administering to the mammalian species a therapeutically effective amount of at least one compound according to claim 1.

33. A method for treating hepatitis C virus infection in a mammalian species in need thereof, the method comprising administering to the mammalian species a therapeutically effective amount of at least one compound according to claim 1.

34. A method for treating hepatitis B virus infection in a mammalian species in need thereof, the method comprising administering to the mammalian species a therapeutically effective amount of at least one compound according to claim 1.

35. A method for treating HIV virus infection in a mammalian species in need thereof, the method comprising administering to the mammalian species a therapeutically effective amount of at least one compound according to claim 1.

* * * * *